US008461303B2

(12) United States Patent
Smith et al.

(10) Patent No.: US 8,461,303 B2
(45) Date of Patent: *Jun. 11, 2013

(54) LOX AND LOXL2 INHIBITORS AND USES THEREOF

(75) Inventors: Victoria Smith, Burlingame, CA (US); Scott Ogg, San Francisco, CA (US); Peter Van Vlasselaer, Portola Valley, CA (US); Vivian E. Barry, Foster City, CA (US); Derek Marshall, Pacifica, CA (US); Alison Kay Holzer, Redwood City, CA (US); Hector Rodriguez, Brisbane, CA (US); Miho Oyasu, San Mateo, CA (US); Scott Alan McCauley, Brisbane, CA (US); Carlos Aurelio Garcia, San Lorenzo, CA (US); Donna Hiroko Tokuoka Biermann, San Mateo, CA (US)

(73) Assignee: Gilead Biologics, Inc., Foster City, CA (US)

( * ) Notice: Subject to any disclaimer, the term of this patent is extended or adjusted under 35 U.S.C. 154(b) by 789 days.

This patent is subject to a terminal disclaimer.

(21) Appl. No.: 12/185,050

(22) Filed: Aug. 1, 2008

(65) Prior Publication Data

US 2009/0053224 A1 Feb. 26, 2009

Related U.S. Application Data

(60) Provisional application No. 60/963,282, filed on Aug. 2, 2007, provisional application No. 60/963,249, filed on Aug. 2, 2007, provisional application No. 60/963,214, filed on Aug. 2, 2007, provisional application No. 60/963,248, filed on Aug. 2, 2007, provisional application No. 60/963,246, filed on Aug. 2, 2007.

(51) Int. Cl.
*C07K 16/00* (2006.01)
*C12P 21/08* (2006.01)

(52) U.S. Cl.
USPC ............... 530/387.1; 530/388.1; 530/387.3; 530/391.3; 530/391.7

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,996,345 A | 12/1976 | Ullman et al. |
| 4,034,074 A | 7/1977 | Miles |
| 4,098,876 A | 7/1978 | Piasio et al. |
| 4,485,088 A | 11/1984 | Chvapil |
| 4,545,382 A | 10/1985 | Higgins et al. |
| 4,637,403 A | 1/1987 | Garcia et al. |
| 4,666,828 A | 5/1987 | Gusella |
| 4,683,202 A | 7/1987 | Mullis |
| 4,731,374 A | 3/1988 | Griss et al. |
| 4,748,116 A | 5/1988 | Simonsson et al. |
| 4,801,531 A | 1/1989 | Frossard |
| 4,816,567 A | 3/1989 | Cabilly et al. |
| 4,843,086 A | 6/1989 | Griss et al. |
| 4,879,219 A | 11/1989 | Wands et al. |
| 4,886,812 A | 12/1989 | Griss et al. |
| 4,943,593 A | 7/1990 | Palfreyman et al. |
| 4,946,778 A | 8/1990 | Ladner et al. |
| 4,965,288 A | 10/1990 | Palfreyman et al. |
| 4,997,854 A | 3/1991 | Kagan et al. |
| 5,011,771 A | 4/1991 | Bellet et al. |
| 5,021,404 A | 6/1991 | Folkman et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,192,659 A | 3/1993 | Simons |
| 5,252,608 A | 10/1993 | Palfreyman et al. |
| 5,262,035 A | 11/1993 | Gregg et al. |
| 5,272,057 A | 12/1993 | Smulson et al. |
| 5,281,521 A | 1/1994 | Trojanowski et al. |
| 5,545,806 A | 8/1996 | Lonberg et al. |
| 5,545,807 A | 8/1996 | Surani et al. |
| 5,625,126 A | 4/1997 | Lonberg et al. |

(Continued)

FOREIGN PATENT DOCUMENTS

| | | |
|---|---|---|
| EP | 0186087 | 8/1989 |
| EP | 0375408 | 6/1990 |

(Continued)

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Freshney , Culture of Animal Cells, A Manual of Basic Technique, Alan R. Liss, Inc., 1983, New York, p. 4.*
Dermer, Bio/Technology, 1994, 12:320.*
Akiri, et al. Lysyl oxidase-related protein-1 promotes tumor fibrosis and tumor progression in vivo. Cancer Res. Apr. 1, 2003;63(7):1657-66.
Bouez, et al. The lysyl oxidase LOX is absent in basal and squamous cell carcinomas and its knockdown induces an invading phenotype in a skin equivalent model. Clinical Cancer Res. Mar. 12, 2006(5);1463-9.
Burbelo, et al. Monoclonal antibodies to human lysyl oxidase. Coll Relat Res. Jun. 1986;6(2):153-62.
Database GENESEQ (Derwent, London, UK), Accession No. ABB07649, Feb. 14, 2002, 99.9% identical to SEQ ID No. 2.
Database Issued Patents (United States Patent & Trademark Office, Alexandria, VA) US Patent No. 6,300,092. Oct. 9, 2001 99.9% identical to SEQ ID No. 2.

(Continued)

*Primary Examiner* — Hong Sang
(74) *Attorney, Agent, or Firm* — Morrison & Foerster LLP

(57) ABSTRACT

The present application relates to anti-LOX and anti-LOXL2 antibodies and their use in purification, diagnostic and therapeutic methods. Antibodies include monoclonal antibodies, humanized antibodies and functional fragments thereof. Anti-LOX and anti-LOXL2 antibodies can be used to identify and treat conditions such as a fibrotic condition, angiogenesis, or to prevent a transition from an epithelial cell state to a mesenchymal cell state.

30 Claims, 18 Drawing Sheets

U.S. PATENT DOCUMENTS

| | | | |
|---|---|---|---|
| 5,633,425 A | 5/1997 | Lonberg et al. | |
| 5,641,484 A | 6/1997 | Hung et al. | |
| 5,661,016 A | 8/1997 | Lonberg et al. | |
| 5,721,138 A | 2/1998 | Lawn | |
| 6,015,562 A * | 1/2000 | Hinman et al. | 424/181.1 |
| 6,140,056 A * | 10/2000 | Khodadoust | 435/6 |
| 6,225,118 B1 | 5/2001 | Grant et al. | |
| 6,277,622 B1 | 8/2001 | Weiss | |
| 6,300,092 B1 | 10/2001 | Khodadoust et al. | |
| 6,303,318 B1 | 10/2001 | O'Brien | |
| 6,316,416 B1 | 11/2001 | Patierno et al. | |
| 6,326,174 B1 | 12/2001 | Joyce et al. | |
| 6,391,602 B1 | 5/2002 | Khodadoust | |
| 6,534,261 B1 | 3/2003 | Cox, III et al. | |
| 6,808,707 B2 | 10/2004 | Ensley | |
| 7,112,668 B2 | 9/2006 | Rastelli et al. | |
| 7,208,300 B2 | 4/2007 | Evans et al. | |
| 7,255,856 B2 | 8/2007 | Li et al. | |
| 7,255,857 B2 | 8/2007 | Li et al. | |
| 7,335,294 B2 | 2/2008 | Heller et al. | |
| 7,348,170 B2 | 3/2008 | Yuuki et al. | |
| 7,396,920 B2 * | 7/2008 | Hemmings et al. | 536/23.1 |
| 7,445,920 B2 | 11/2008 | Evans et al. | |
| 7,585,634 B2 | 9/2009 | Kim et al. | |
| 8,163,494 B2 | 4/2012 | Neufeld et al. | |
| 8,168,180 B2 | 5/2012 | Neufeld et al. | |
| 2001/0005581 A1 | 6/2001 | Grant et al. | |
| 2001/0012890 A1 | 8/2001 | Thompson | |
| 2002/0072089 A1 | 6/2002 | Holtzman et al. | |
| 2002/0123476 A1 | 9/2002 | Emanuele et al. | |
| 2002/0128218 A1 | 9/2002 | Emanuele et al. | |
| 2002/0151007 A1 | 10/2002 | Khodadoust et al. | |
| 2002/0156263 A1 | 10/2002 | Chen | |
| 2003/0008023 A1 | 1/2003 | Lu | |
| 2003/0017068 A1 | 1/2003 | Larrain et al. | |
| 2003/0092037 A1 | 5/2003 | Matsuzaki et al. | |
| 2003/0096980 A1 | 5/2003 | Froehler et al. | |
| 2003/0099213 A1 | 5/2003 | Lee et al. | |
| 2003/0114410 A1 | 6/2003 | Neufeld et al. | |
| 2003/0129672 A1 | 7/2003 | Dyer et al. | |
| 2003/0149997 A1 | 8/2003 | Hageman | |
| 2003/0152926 A1 | 8/2003 | Murray et al. | |
| 2003/0211076 A1 | 11/2003 | Li et al. | |
| 2004/0009154 A1 | 1/2004 | Khan et al. | |
| 2004/0029114 A1 | 2/2004 | Mack et al. | |
| 2004/0156854 A1 | 8/2004 | Mulligan et al. | |
| 2004/0171110 A1 | 9/2004 | Evans et al. | |
| 2004/0176296 A1 | 9/2004 | Holtzman et al. | |
| 2004/0197328 A1 | 10/2004 | Young et al. | |
| 2004/0213756 A1 | 10/2004 | Michal et al. | |
| 2004/0248871 A1 | 12/2004 | Farjanel et al. | |
| 2004/0253220 A1 * | 12/2004 | Perrier et al. | 424/94.4 |
| 2004/0253606 A1 | 12/2004 | Aziz et al. | |
| 2004/0258676 A1 | 12/2004 | Perrier et al. | |
| 2004/0265230 A1 | 12/2004 | Martinez et al. | |
| 2005/0020521 A1 | 1/2005 | Rana et al. | |
| 2005/0079538 A1 | 4/2005 | Griffin et al. | |
| 2005/0119202 A1 | 6/2005 | Kreutzer et al. | |
| 2005/0181375 A1 | 8/2005 | Aziz et al. | |
| 2005/0259483 A1 | 11/2005 | Nakamura et al. | |
| 2005/0260639 A1 | 11/2005 | Nakamura et al. | |
| 2006/0019256 A1 | 1/2006 | Clarke et al. | |
| 2006/0083736 A1 * | 4/2006 | Law et al. | 424/133.1 |
| 2006/0088532 A1 | 4/2006 | Alitalo et al. | |
| 2006/0088882 A1 | 4/2006 | Jain et al. | |
| 2006/0127402 A1 | 6/2006 | Neufeld et al. | |
| 2006/0127902 A1 | 6/2006 | Madden et al. | |
| 2006/0134172 A1 | 6/2006 | Shepard et al. | |
| 2006/0134801 A1 | 6/2006 | Chada et al. | |
| 2006/0216722 A1 | 9/2006 | Betoltz et al. | |
| 2006/0223760 A1 | 10/2006 | Li et al. | |
| 2007/0010469 A1 | 1/2007 | Chan et al. | |
| 2007/0021365 A1 * | 1/2007 | Erler et al. | 514/44 |
| 2007/0037203 A1 | 2/2007 | Kapeller-libermann et al. | |
| 2007/0054278 A1 | 3/2007 | Cargill | |
| 2007/0059745 A1 | 3/2007 | Sharp et al. | |
| 2007/0154481 A1 | 7/2007 | Gelinas et al. | |
| 2007/0184439 A1 | 8/2007 | Guilford et al. | |
| 2007/0197424 A1 | 8/2007 | Friedman et al. | |
| 2007/0225242 A1 | 9/2007 | Erler et al. | |
| 2007/0231323 A1 | 10/2007 | Phillips | |
| 2007/0243214 A1 | 10/2007 | Schiemann et al. | |
| 2008/0031817 A1 | 2/2008 | Mazar et al. | |
| 2008/0118928 A1 | 5/2008 | Hageman | |
| 2008/0137893 A1 | 6/2008 | Ross et al. | |
| 2008/0181896 A1 | 7/2008 | Khan et al. | |
| 2008/0187523 A1 | 8/2008 | Zhang et al. | |
| 2008/0220424 A1 | 9/2008 | Haber et al. | |
| 2008/0248477 A1 | 10/2008 | Holtzman et al. | |
| 2008/0261870 A1 | 10/2008 | Trackman et al. | |
| 2008/0274453 A1 | 11/2008 | Hageman | |
| 2008/0279857 A1 | 11/2008 | Skerry et al. | |
| 2008/0286808 A1 | 11/2008 | Schellenberger et al. | |
| 2008/0292547 A1 | 11/2008 | Tolleshaug et al. | |
| 2008/0305965 A1 | 12/2008 | Moorhouse et al. | |
| 2009/0022703 A1 | 1/2009 | Li et al. | |
| 2009/0023149 A1 | 1/2009 | Knudsen et al. | |
| 2009/0035348 A1 | 2/2009 | Zadini et al. | |
| 2009/0053224 A1 | 2/2009 | Smith et al. | |
| 2009/0104201 A1 | 4/2009 | Smith et al. | |
| 2009/0142301 A1 | 6/2009 | Bevec et al. | |
| 2009/0232773 A1 | 9/2009 | Kato et al. | |
| 2009/0233270 A9 | 9/2009 | St. Croix et al. | |
| 2009/0239947 A1 | 9/2009 | Dai et al. | |
| 2009/0275633 A1 | 11/2009 | Esteller | |
| 2010/0119515 A1 | 5/2010 | Neufeld et al. | |
| 2010/0144603 A1 | 6/2010 | Watnick | |
| 2010/0203062 A1 | 8/2010 | Stalmans et al. | |
| 2010/0209415 A1 | 8/2010 | Smith et al. | |
| 2010/0317721 A1 | 12/2010 | Neufeld | |
| 2011/0044907 A1 | 2/2011 | Marshall et al. | |
| 2011/0044981 A1 | 2/2011 | Spangler et al. | |
| 2011/0076272 A1 | 3/2011 | Smith et al. | |
| 2011/0076285 A1 | 3/2011 | Stalmans et al. | |
| 2011/0076739 A1 | 3/2011 | McCauley et al. | |
| 2011/0200606 A1 | 8/2011 | McCauley et al. | |
| 2011/0207144 A1 | 8/2011 | Marshall et al. | |
| 2012/0087917 A1 | 4/2012 | Smith et al. | |
| 2012/0165398 A1 | 6/2012 | Neufeld et al. | |
| 2012/0202206 A1 | 8/2012 | Neufeld et al. | |
| 2012/0309020 A1 | 12/2012 | Smith et al. | |
| 2013/0017207 A1 | 1/2013 | Smith et al. | |

FOREIGN PATENT DOCUMENTS

| | | |
|---|---|---|
| EP | 0799891 | 10/1997 |
| EP | 0960192 | 12/1999 |
| EP | 1149169 | 10/2001 |
| EP | 1 616 881 | 1/2006 |
| EP | 1690932 | 8/2006 |
| EP | 1693448 | 8/2006 |
| EP | 1715035 A2 | 10/2006 |
| EP | 2078531 | 7/2009 |
| EP | 1315519 | 12/2010 |
| WO | WO-89-12060 | 12/1989 |
| WO | WO-92-20702 | 11/1992 |
| WO | WO 9600614 | 1/1996 |
| WO | WO 96/40746 A1 | 12/1996 |
| WO | WO 9700441 | 1/1997 |
| WO | WO 98/06830 A1 | 2/1998 |
| WO | WO 99/65928 A2 | 12/1999 |
| WO | WO 00/44910 A1 | 3/2000 |
| WO | WO 01/83702 A2 | 8/2001 |
| WO | WO-01-83792 | 11/2001 |
| WO | WO 01/92495 A2 | 12/2001 |
| WO | WO 02/11667 A2 | 2/2002 |
| WO | WO 01/92495 A3 | 5/2002 |
| WO | WO 02/061092 A2 | 8/2002 |
| WO | WO 02/086443 A2 | 10/2002 |
| WO | WO 02079492 | 10/2002 |
| WO | WO 02/11667 A3 | 3/2003 |
| WO | 03031939 | 4/2003 |
| WO | WO 02/061092 A3 | 8/2003 |
| WO | 03100016 | 12/2003 |
| WO | 2004023973 | 3/2004 |
| WO | WO 2004/047720 A2 | 6/2004 |
| WO | WO-2004-061423 | 7/2004 |
| WO | WO 2004091655 A2 * | 10/2004 |

| WO | WO 01/83702 A3 | 3/2005 |
| WO | 2005100604 | 10/2005 |
| WO | WO 2004/047720 A3 | 2/2006 |
| WO | WO 2006/128740 A2 | 7/2006 |
| WO | WO 2007/045927 A2 | 4/2007 |
| WO | WO 2007/045927 A3 | 8/2007 |
| WO | WO 2007/126457 A2 | 11/2007 |
| WO | 2008063479 | 5/2008 |
| WO | 2008070616 | 6/2008 |
| WO | 2008132453 | 11/2008 |
| WO | 2008138578 | 11/2008 |
| WO | 2009010974 | 1/2009 |
| WO | WO-2009/017833 | 2/2009 |
| WO | WO-2009/035791 | 3/2009 |
| WO | WO-2010/080769 | 7/2010 |
| WO | WO-2010/091279 | 8/2010 |
| WO | WO-2011/022667 | 2/2011 |
| WO | WO-2011/022670 | 2/2011 |
| WO | WO-2011/022706 | 2/2011 |
| WO | WO-2011/022709 | 2/2011 |
| WO | WO-2011/022710 | 2/2011 |
| WO | WO-2011/041309 | 4/2011 |
| WO | WO-2011/097513 | 8/2011 |
| WO | WO-2012/139045 | 10/2012 |
| WO | WO-2012/167181 | 12/2012 |

OTHER PUBLICATIONS

Decitre, et al. Lysyl oxidase-like protein localizes to sites of de novo fibrinogenesis in fibrosis and in the early stromal reaction of ductal breast carcinomas. Lab. Invest. Feb. 1998;78(2):143-51.

Erler, et al. Hypoxia promotes invasion and metastasis of breast cancer cells by increasing lysyl oxidase expression. Breast Cancer Res. Jun. 17, 2005;7(Suppl 2):P5.05.

Erler, et al. Lysyl oxidase is essential for hypoxia-induced metastasis. Nature Apr. 27, 2006;1222-6.

Erler, et al. Lysyl oxidase mediates hypoxic control of metastasis. Cancer Res. Nov. 1, 2006;66(21):10238-41.

Fogelgren, et al. Cellular fibronectin binds to lysyl oxidase with high affinity and is critical for its proteolytic activation. J Biol Chem. Jul. 1, 2005;280(26):24690-7.

Giampuzzi, et al. Down-regulation of lysyl oxidase-induced tumorigenic transformation in NRK-49F cells characterized by constitutive activation of ras proto-oncogene. J Biol Chem. Aug. 3, 2001;276(31):29226-32.

Higgins, et al. Hypoxia promotes a fibrogenesis in vivo via HIF-1 stimulation of epithelial-to-mesenchymal transition. Journal Clinical Investigation. Dec. 2007;117(12):3810-20.

Hockel, et al. Tumor Hypoxia: Definitions and Current Clinical, Biologic and Molecular Aspects. Journal of the National Cancer Institute. Feb. 2001;(93)4:266-276.

Kagan, et al. Lysyl oxidase: properties, specificity, and biological roles inside and outside of the cell. J. Cell. Biochem. 2003;88:660-72.

Kirschmann, et al. A molecular role for lysyl oxidase in breast cancer invasion. Cancer Res. Aug. 2002;62:4478-83.

Kirschmann, et al. Differentially expressed genes associated with the metastatic phenotype in breast cancer. Breast Cancer Res Treat. May 1999;55(2):127-36.

Li, et al. Localization and activity of lysyl oxidase within nuclei of fibrogenic cells. Proc. Natl. Acad. Sci. 1997;94: 12817-12822.

Mbeunkui, et al. Identification of differentially secreted biomarkers using LC-MS/MS in isogenic cell lines representing a progression of breast cancer. Journal Proteome Res. 2007;6:2993-3002.

Palamakumbura, et al. The propeptide domain of lysyl oxidase induces phenotypic reversion of ras-transformed cells. J. Biol. Chem. Sep. 2004;279(39):40593-600.

Panchenko, et al. Metalloproteinase activity secreted by fibrogenic cells in the processing of prolysyl oxidase. Potential role of procollagen C-proteinase. J Biol Chem. Mar. 22, 1996;271(12):7113-9.

Payne, et al. Lysyl oxidase regulates breast cancer cell migration and adhesion through a hydrogen peroxide-mediated mechanism. Cancer Res. Dec. 15, 2005;65(24):11429-36.

Peyrol, et al. Lysyl oxidase gene expression in the stromal reaction to in situ and invasive ductal breast carcinoma. Am J Pathol. Feb. 1997;150(2):497-507.

Ren, et al. Reduced lysyl oxidase messenger RNA levels in experimental and human prostate cancer. Cancer Res. Mar. 15, 1998;58:1285-90.

Rost, et al. Reduction of LOX- and LOXL2-mRNA expression in head and neck squamous cell carcinomas. Anticancer Res. Mar.-Apr. 2003;23(2B):1565-1573.

Rucker, et al. Copper, lysyl oxidase, and extracellular matrix protein cross-linking. Am J Clin Nutr. 1998;67(suppl):996S-1002S.

Saito, et al. Regulation of a novel gene encoding a lysyl oxidase-related protein in cellular adhesion and senescence. J Biol Chem. Mar. 28, 1997;272(13):8157-60.

Sevil, et al. Pharmacokinetic analysis of beta-aminopropionitrile in rabbits. Vet Res. 1996;27(2):117-23. (Abstract only).

Shieh, et al. Association of expression aberrances and genetic polymorphisms of lysyl oxidase with areca-associated oral tumorigenesis. Clinical Cancer Res. Aug. 1, 2007;13(15):4378-4385.

Trivedy, et al. The upregulation of lysyl oxidase in oral submucous fibrosis and squamous cell carcinoma. J Oral Pathol. Med. Jul. 1999;28(6):246-51.

Atabani, et al. (1997) "Identification of an Immunodominant Neutralizing and Protective Epitope from Measles Virus Fusion Protein by Using Human Sera from Acute Infection" J. Virology 71(10):7240-7245.

Betakova, et al. (1998) "Monoclonal Anti-Idiotypic Antibodies Mimicking the Immunodominant Epitope of Influenza Virus Haemagglutinin Elicit Biologically Significant Immune Responses" J. Gen. Virology 79(Pt.3):461-470.

Berithaupt, et al. (2008) "Demyelinating Myelin Oligodendrocyte Glycoprotein-Specific Autoantibody Response Is Focused on one Dominant Conformational Epitope Region in Rodents" J. Immunology 181(2):1255-1263.

Ferrari, et al. (1991) "Identification of Immunodominant T Cell Epitopes of the Hepatitis B Virus Nucleocapsid Antigen" J. Clin. Invest. 88(1):214-222.

Kang, et al. (2009) "Prosaposin Inhibits Tumor Metastasis Via Paracrine and Endocrine Stimulation of Stromal p53 and Tsp-1" Proc. Natl. Acad. Sci. U.S.A. 106(29):12115-12120.

Saito, et al. (1997) "Regulation of a Novel Gene Encoding a Lysyl Oxidase-Related Protein in Cellular Adhesion and Senescence" J. Biol. Chem. 272(13):8157-8160.

Albini et al., "The chemoinvasion assay: a tool to study tumor and endothelial cell invasion of basement membranes," Int. J. Dev. Biol. 48:563-571 (2004).

Brown et al., "Exploting Tumour Hypoxia in Cancer Treatment," Nature Reviews 4:437-447 (2004).

Cairns et al., "Acute Hypoxia Enhances Spontaneous Lymph Node Metastasis in an Orthotopic Murine Model of Human zcervical Carcinoma," Cancer Res. 64:2054-2061 (2004).

Csiszar, "Somatic Mutation of the Lysyl Oxidase Gene on Chromosome SO23.1 in Colorectal Tumors," Int. J. Cancerw 97:636-642 (2002).

Csiszar, "Lysyl Oxidases: A Novel Multifunctional Amine Oxidase Family," Progress in Nucleic Acid Research and Molecular Biology 7:1-32 (2001).

Denko et al., "Investigating hypoxic tumor phsyiology through gene expression patterns," Oncogene 22:5907-5914 (2003).

Fodstad et al., "A New Experimental Metastasis Model in Athymic Nude Mice, the Human Malignant Melanoma Lox," Intl. J. Cancer 41:442-449 (1988) (Abstract).

Fong et al., "Lysyl oxidase-like 2 expression is increased in colon and esophageal tumors and associated with less differentiated colon tumors," Genes, Chromosomes and Cancer vol. 46(7):644-655, 2007.

Kagan, H.M., "Intra- and extracellular enzymes of collagen biosynthesis as biological and chemical targets in the control of fibrosis," Acta Tropica 77(1):147-152 (2000).

Kaneda et al., "Lysyl Oxidase is a Tumor Suppressor Gene Inactivated by Methylation and Loss of Heterozygosity in Human Gastric Cancers," Cancer Res. 64:5410-5415 (2004).

Kenyon et al., "Lysyl Oxidase and mg Messenger RNA," Science 253:802 (1991).

Kim et al., "A new gene with sequence and structural similarity to the gene encoding human lysyl oxidase," J. Biol. Chem. 270(13):7176-7182 (1995).

Le et al., "Expression and Prognostic Significance of a Panel of Tissue Hypoxia Markers in Head-and-Neck Squamous Cell Carcinoma," Int. J. Radiation Oncology Biol. Phys. 69(1):157-175 (2007).

Levene et al., "Possibilities for the therapeutic control of fibrosis," Br.J. Dermatol. 112(3):363-371 (1985).

Maki et al., "Cloning and characterization of a fourth human lysyl oxidase isoenzyme," Biochem. J. 355:381-387 (2001).

Molnar et al., "Structural and functional diversity of lysyl oxidase and the LOX-like proteins," Biochimica Biohphysica Acta 1547:220-224 (2003).

Murawaki et al., "Serum lysyl oxidase activity in chronic liver disease in comparison with serum levels of prolyl hydrozylase and laminin," Hepatology 14(6):1167-1173 (1991).

Palamakumbura et al., "A Fluorometric Assay for Detection of Lysyl Oxidase Enzyme Activity in Biological Samples," Analytical Biochem. 300:245-251 (2002).

Riechmann et al., "Reshaping human antibodies for therapy," Nature 332(6162):323-327 (1988).

Satoh et al., "Inhibition of local adhesion kinase by antisense oligonucleotides enhances the sensitivity of breast cancer cells to camptothecins," Biocell 27(1):47-55 (2003).

Sommer et al., "Transient expression of lysyl oxidase by liver myofibroblasts in murine schistosomiasis," Laboratory Investigation 69(4):46-470 (1993).

Sorensen et al., "Hypoxia-induced expression of endogenous markers in vitro is highly influenced by pH," Radiotherapy and Oncology 83:362-366 (2007).

Stassar et al., "Identification of human renal cell carcinoma associated genes by suppression subtractive hybridization," Br. J. Cancer 85(9):1372-1382 (2001).

Tamura et al., "Inhibition of Cell Migration, Spreading, and Focal Adhesions by Tumor Suppressor PTEN," Science 280:1614-1617 (1998) (Abstract).

Tockman et al., "Consideration in bringing a cancer biomarker to clinical application," Cancer Res. 52:2711s-2718s (1992).

Trackman et al., "Cloning of rat aorta lysyl oxidase cDNA: Complete codons and predicted amino acid sequence," Biochem. 29(20)4863-4870 (1990 and Corrected Page: Biochem. 30(33):8282 (1991).

Van Lancker et al., "Patterns of axillary lymph node metastasis in breast cancer," Am. J. Clin. Oncol. 18(3):267-272 (1995) (Abstract).

Van Roy et al., "Invasiveness and Metastatic Capability of Rat Fibroblast-like Cells before and after Transfection with Immortalizing and Transforming Genes," Cancer Res. 46:4787-4795 (1986).

Walling et al., "Aggressive basal cell carcinoma: Presentation, pathogenesis, and management," Cancer and Metastasis Reviews 23:389-402 (2004) (Abstract).

Zhang et al., "Hypoxia Enhances Metastatic Efficiency in HT-1060 Fibrosarcoma Cells by Increasing Cell Survival in Lungs Not Cell Adhesion and Invasion," Cancer Res. 67(18):7789-7797 (2007).

EP 08020752 Search Report dated May 20, 2009.

EP 08020753 Search Report dated May 26, 2009.

Examination Report for NZ 598456, mailed Nov. 6, 2012.

Supplementary European Search Report for EP 10810673.3, mailed Nov. 26, 2012.

Supplementary European Search Report for EP 10810675.8, mailed Dec. 4, 2012.

Patent Examination Report No. 1 for AU 2008299784, mailed Dec. 12, 2012.

Non-Final Office Action for U.S. Appl. No. 12/860,834, mailed Jan. 10, 2013.

GenBank Public DNA Database, Accession No. AAA59525.1 "Lysyl Oxidase [*Homo sapiens*]", Jan. 7, 1995.

GenBank Public DNA Database Accession No. AAA59541.1 "Lysyl Oxidase [*Homo sapiens*]", Jan. 7, 1995.

GenBank Public DNA Database Accession No. AAB21243.1 "Lysyl Oxidase [*Homo sapiens*]", May 7, 1993.

GenBank Public DNA Database Accession No. AAB23549.1 "Lysyl Oxidase [*Homo sapiens*]", May 8, 1993.

GenBank Public DNA Database Accession No. AAD02130.1 "Lysyl Oxidase [*Homo sapiens*]", May 6, 1999.

GenBank Public DNA Database Accession No. AAH15090.1 "Lysyl Oxidase-Like 1 [*Homo sapiens*]", Jul. 15, 2006.

GenBank Public DNA Database Accession No. AAH74820.1 "Lysyl Oxidase [*Homo sapiens*]", Jul. 15, 2006.

GenBank Public DNA Database Accession No. AAH74872.1 "Lysyl Oxidase [*Homo sapiens*]", Jul. 15, 2006.

GenBank Public DNA Database Accession No. AAK51671.1 "Lysyl Oxidase-Like 3 Protein [*Homo sapiens*]", May 9, 2001.

GenBank Public DNA Database Accession No. AAK71934.1 "Lysyl Oxidase-Related Protein C [*Homo sapiens*]", Jul. 11, 2001.

GenBank Public DNA Database Accession No. AF039291 "*Homo sapiens* Lysyl Oxidase mRNA, Complete cds", May 6, 1999.

GenBank Public DNA Database Accession No. AF282619 "*Homo sapiens* Lysyl Oxidase-like 3 Protein mRNA, Complete cds", May 9, 2001.

GenBank Public DNA Database Accession No. AF338441 "*Homo sapiens* Lysyl Oxidase-Related Protein C (LOXC) mRNA, Complete cds", Jul. 11, 2001.

GenBank Public DNA Database Accession No. BC015090 "*Homo sapiens* Lysyl Oxidase-Like 1, mRNA (cDNA Clone MGC:16541 Image:4040510), Complete cds", Jul. 15, 2006.

GenBank Public DNA Database Accession No. BC018439 "*Mus musculus* Lysyl Oxidase, mRNA (cDNA Clone MGC:11525 Image:2655752), Complete cds", Jul. 15, 2006.

GenBank Public DNA Database Accession No. BC074820 "*Homo sapiens* Lysyl Oxidase, mRNA (cDNA Clone MGC:104085 Image:30915536), complete cds", Jul. 15, 2006.

GenBank Public DNA Database Accession No. BC074872 "*Homo sapiens* Lysyl Oxidase, mRNA (cDNA Clone MGC:103851 Image:30915233), Complete cds", Jul. 15, 2006.

GenBank Public DNA Database Accession No. M84150 "Human Lysyl Oxidase Gene, Partial cds", Jan. 7, 1995.

GenBank Public DNA Database Accession No. M94054 "Human Lysyl Oxidase (LOX) mRNA, Complete cds", Jan. 7, 1995.

GenBank Public DNA Database Accession No. NM_002317 "*Homo sapiens* Lysyl Oxidase (LOX), Transcript Variant 1, mRNA", Mar. 13, 2011.

GenBank Public DNA Database Accession No. NM_033325 "*Mus musculus* Lysyl Oxidase-Like 2 (Loxl2), mRNA", Mar. 10, 2011.

GenBank Public DNA Database Accession No. NP_002308 "Protein-Lysine 6-Oxidase Isoform 1 Preproprotein [*Homo sapiens*]", Mar. 13, 2011.

GenBank Public DNA Database Accession No. NP_002309 "Lysyl Oxidase 2 Precursor [*Homo sapiens*]", Mar. 27, 2011.

GenBank Public DNA Database Accession No. NP_005567 "Lysyl Oxidase Homolog 1 Preproprotein [*Homo sapiens*]", Mar. 27, 2011.

GenBank Public DNA Database Accession No. NP_034858 "Protein-Lysine 6-Oxidase Precursor [*Mus musculus*]", Mar. 11, 2011.

GenBank Public DNA Database Accession No. NP_034859 "Lysyl Oxidase Homolog 1 Precursor [*Mus musculus*]", Mar. 12, 2011.

GenBank Public DNA Database Accession No. NP_115587 "Lysyl Oxidase Homolog 4 Precursor [*Homo sapiens*]", Mar. 13, 2011.

GenBank Public DNA Database Accession No. NP_115882 "AP-1 Complex Subunit mu-1 Isoform 2 [*Homo sapiens*]", Mar. 13, 2011.

GenBank Public DNA Database Accession No. NP_201582 "Lysyl Oxidase Homolog 2 Precursor [*Mus musculus*]", Mar. 10, 2011.

GenBank Public DNA Database Accession No. S45875 "Lysyl Oxidase [Human, Skin Fibroblasts, mRNA Partial, 1254 nt]", May 8, 1993.

GenBank Public DNA Database Accession No. S78694 "Lysyl Oxidase [Human, mRNA, 1780 nt]", May 7, 1993.

GenBank Public DNA Database Accession No. U89942 "Human Lysyl Oxidase-Related Protein (WS9-14) mRNA, Complete cds", Aug. 18, 2003.

Portolano, et al. (1993). "Lack of Promiscuity in Autoantigen-Specific H and L Chain Combinations as Revealed by Human H and L Chain 'Roulette'". J Immunol 150(3):880-887.

Understanding Cancer Series: Cancer Slide 8: Invasion and Metastasis, www.cancer.gov/cancertopics/understandingcancer/cancer/slide8, posted Jan. 28, 2005, reviewed Sep. 30, 2009.

Office Action for U.S. Appl. No. 13/204,336, mailed Nov. 26, 2012.

Office Action for U.S. Appl. No. 13/204,336, mailed Jan. 7, 2013.

Office Action for U.S. Appl. No. 12/185,054, mailed Jan. 28, 2013.

Akagawa, et al. (2007). "Systematic Screening of lysyl Oxidase-Like (LOXL) Family Genes Demonstrates that LOXL2 Is a Susceptibility Gene to Intracranial Aneurysms." Hum Genet 121(3-4): 377-87.

Asuncion et al. (2001) "A Novel Human Lysyl Oxidase-Like Gene (LOXL4) on Chromosome 10q24 Has an Altered Scavenger Receptor Cysteine Rich Domain" Matrix Biol. 20(7):487-491.

Atsawasuwan, et al. (2005). "Expression of Lysyl Oxidase Isoforms in MC3T3-E1 Osteoblastic Cells." Biochem Biophys Res Commun 327(4): 1042-6.

Atsawasuwan, et al. (2008). "Lysyl Oxidase Binds Transforming Growth Factor-β and Regulates Its Signaling via Amine Oxidase Activity." J Biol Chem 283(49): 34229-40.

Borel et al. (2001) "Lysyl Oxidase-Like Protein from Bovine Aorta. Isolation and Maturation to an Active Form by Bone Morphogenetic Protein-1" J. Biol. Chem.276(52):48944-48949.

Bronson et al. (2005) "LOXL Null Mice Demonstrate Selective Dentate Structural Changes but Maintain Dentate Granule Cell and CA1 Pyramidal Cell Potentiation in the Hippocampus" Neurosci. Lett. 390(2):118-122.

Chanoki, et al. (1995) "Increased Expression of Lysyl Oxidase in Skin with Scleroderma" Br. J. Dermatol. 133(5):710-5.

Chichester, et al. (1981). "Lung Lysyl Oxidase and Prolyl Hydroxylase: Increases Induced by Cadmium Chloride Inhalation and the Effect of β-Aminopropionitrile in Rats." Am Rev Respir Dis 124(6): 709-13.

Chioza, et al. (2001). "Mutations in the lysyl oxidase gene are not associated with amyotrophic lateral sclerosis." Amyotroph Lateral Scler Other Motor Neuron Disord 2(2): 93-7.

Csiszar, et al. (1996). "Functional analysis of the promoter and first intron of the human lysyl oxidase gene." Mol Biol Rep 23(2): 97-108.

Erler, et al. (2009). "Hypoxia-induced lysyl oxidase is a Critical mediator of bone marrow cell recruitment to form the premetastatic niche." Cancer Cell 15(1): 35-44.

Gacheru, et al. (1997). "Transcriptional and post-transcriptional control of lysyl oxidase expression in vascular smooth muscle cells: effects of TGF-β1 and serum deprivation." J Cell Biochem 65(3): 395-407.

Giampuzzi et al. (2000) "Lysyl Oxidase Activates the Transcription Activity of Human Collagene III Promoter. Possible Involvement of Ku Antigen" J. Biol. Chem. 275(46):36341-36349.

Görögh et al. (2007) "Selective Upregulation and Amplification of the Lysyl Oxidase Like-4 (LOXL4) Gene in Head and Neck Squamous cell Carcinoma" J. Pathol. 212(1):74-82.

Görögh, et al. (2008). "Functional analysis of the 5' flanking domain of the LOXL4 gene in head and neck squamous cell carcinoma cells." Int J Oncol 33(5): 1091-8.

Harris et al. (1974) "Connective Tissue Amine Oxidase. II. Purification and Partial Characterization of Lysyl Oxidase from Chick Aorta" Biochim. Biophys. Acta 341(2):332-344.

Hayashi, et al. (2004). "Comparative immunocytochemical localization of lysyl oxidase (LOX) and the lysyl oxidase-like (LOXL) proteins: changes in the expression of LOXL during development and growth of mouse tissues." J Mol Histol 35(8-9): 845-55.

Hein, et al. (2001). "Lysyl oxidases: expression in the fetal membranes and placenta." Placenta 22(1): 49-57.

Hollosi, et al. (2009). "Lysyl oxidase-like 2 promotes migration in noninvasive breast cancer cells but not in normal breast epithelial cells." Int J Cancer 125(2):318-327.

Hornstra et al. (2003) "Lysyl Oxidase is Required for Vascular and Diaphragmatic Development in Mice" J. Biol. Chem. 278(16):14387-14393.

Huang et al. (2001) "Cloning and Characterization of a Human Lysyl Oxidase-Like 3 Gene (hLOXL3)" Matrix Biol. 20(2):153-157.

Ito et al. (2001) "Molecular Cloning and Biological Activity of a Novel Lysyl Oxidase-Related Gene Expressed in Cartilage" J. Biol. Chem. 276(26):24023-24029.

Jansen & Csiszar (2007). "Intracellular localization of the matrix enzyme lysyl oxidase in polarized epithelial cells." Matrix Biol 26(2): 136-9.

Jourdan Le-Saux et al. (1994) "Lysyl Oxidase cDNA of Myofibroblast from Mouse Fibrotic Liver" Biochem. Biophys. Res. Comm. 199(2):587-592.

Jourdan Le-Saux et al. (1999) "The LOXL2 Gene Encodes a New Lysyl Oxidase-Like Protein and Is Expressed at High Levels in Reproductive Tissues" J. Biol. Chem. 274(18):12939-12944.

Jourdan Le-Saux et al. (2001) "Central Nervous System, Uterus, Heart, and Leukocyte Expression of the LOXL3 Gene, Encoding a Novel Lysyl Oxidase-Like Protein" Genomics 74(2):211-218.

Jourdan-Le Saux, et al. (1998). "The human lysyl oxidase-related gene (LOXL2) maps between markers D8S280 and D8S278 on chromosome 8p21.2-p21.3." Genomics 51(2): 305-7.

Jourdan-Le Saux, et al. (2000). "The mouse lysyl oxidase-like 2 gene (mLOXL2) maps to chromosome 14 and is highly expressed in skin, lung and thymus." Matrix Biol 19(2): 179-83.

Jung, et al. (2003). "Purification of Enzymatically Active Human Lysyl Oxidase and Lysyl Oxidase-Like Protein from Escherichia coli Inclusion Bodies." Protein Expr Purif 31(2): 240-6.

Kagan (1994) "Lysyl Oxidase: Mechanism, Regulation and Relationship to Liver Fibrosis" Pathol. Res. Pract. 190(9-10):910-919.

Kagan et al. (1982) "Lysyl Oxidase: Preparation and Role in Elastin Biosynthesis" Meth. Enzymol. 82(A):637-649.

Kagan, et al. (1995) "Expression of Lysyl Oxidase from cDNA Constructs in Mammalian Cells: The Propeptide Region Is Not Essential to the Folding and Secretion of the Functional Enzyme" J. Cell Biochem. 59(3):329-38.

Kagan, et al. (1995). "Catalytic Properties and Structural Components of Lysyl Oxidase." Novartis Foundation Symp. 192: 100-15; discussion 115-21.

Khakoo, et al. (1997) "Congenital Cutis Laxa and Lysyl Oxidase Deficiency" Clin. Genet. 51(2):109-14.

Kim et al. (1999) "Coexpression of the Lysyl Oxidase-Like Gene (LOXL) and the Gene Encoding Type III Procollagen in Induced Liver Fibrosis" J. Cell Biochem. 72(2):181-188.

Kim et al. (2003) "Expression and Purification of Enzymatically Active Forms of the Human Lysyl Oxidase-Like Protein 4" J. Biol. Chem. 278(52):52071-52074.

Kim, et al. (1997). "A Highly Polymorphic (CA) Repeat Sequence in the Human Lysyl Oxidase-Like Gene." Clin Genet 51(2): 131-2.

Krebs & Krawetz (1993) "Lysyl Oxidase Copper-Talon Complex: A Model" Biochim. Biophys. Acta 1202(1):7-12.

Laczko, et al. (2007). "Active lysyl oxidase (LOX) correlates with focal adhesion kinase (FAK)/paxillin activation and migration in invasive astrocytes." Neuropathol Appl Neurobiol 33(6): 631-43.

Lazarus et al. (1995) "Induction of Human Monocyte Motility by Lysyl Oxidase" Matrix Biol. 14(9):727-731.

Lelievre, et al. (2008). "VE-statin/egfl7 Regulates Vascular Elastogenesis by Interacting with Lysyl Oxidases." EMBO J 27(12): 1658-70.

Lucero & Kagan (2006). "Lysyl Oxidase: an Oxidative Enzyme and Effector of Cell Function." Cell Mol Life Sci 63(19-20): 2304-16.

Mäki, et al. (2001). "Cloning and Characterization of a Fifth Human Lysyl Oxidase Isoenzyme: the Third Member of the Lysyl Oxidase-Related Subfamily with Four Scavenger Receptor Cysteine-Rich Domains." Matrix Biol 20(7): 493-6.

Molnar, et al. (2005). "Drosophila lysyl oxidases Dmloxl-1 and Dmloxl-2 are differentially expressed and the active DmLOXL-1 influences gene expression and development." J Biol Chem 280(24): 22977-85.

Ooshima & Midorikawa (1977) "Increased lysyl Oxidase Activity in Blood Vessels of Hypertensive Rats and Effect of beta-Aminopropionitrile on Arteriosclerosis" Jpn. Circ. J. 41(12):1337-40.

Payne, et al. (2007). "Paradoxical roles for lysyl oxidases in cancer—a prospect." J Cell Biochem 101(6): 1338-54.

Peinado, et al. (2005). "Switching on-off Snail: LOXL2 versus GSK3β." Cell Cycle 4(12): 1749-52.

Polgar, et al. (2007). "Lysyl oxidase interacts with hormone placental lactogen and synergistically promotes breast epithelial cell proliferation and migration." J Biol Chem 282(5): 3262-72.

Postovit, et al. (2008). "Hypoxia/reoxygenation: a dynamic regulator of lysyl oxidase-facilitated breast cancer migration." J Cell Biochem 103(5): 1369-78.

Rayton et al. (1979) "Induction of Lysyl Oxidase with Copper. Properties of an In Vitro System" J. Biol. Chem. 254(3):621-626.

Rodriguez et al. (2010) "Modulation of lysyl oxidase-like 2 enzymatic activity by an allosteric antibody inhibitor" *J. Biol. Chem.* 285:20964-20974.

Royce, et al. (1980) "Reduced Lysyl Oxidase Activity in Skin Fibroblasts from Patients with Menkes' Syndrome" Biochem. J. 192(2):579-86.

Schlotzer-Schrehardt, et al. (2008). "Genotype-correlated expression of lysyl oxidase-like 1 in ocular tissues of patients with pseudoexfoliation syndrome/glaucoma and normal patients." Am J Pathol 173(6): 1724-35.

Sebban, et al. (2009). "Lysyl Oxidase-Like 4 Is Alternatively Spliced in an Anatomic Site-Specific Manner in Tumors Involving the Serosal Cavities." Virchows Arch 454(1): 71-9.

Siegel et al. (1978) "Biochemical and Immunochemical Study of Lysyl Oxidase in Experimental Hepatic Fibrosis in the Rat" *Proc. Natl. Acad. Sci. USA* 75(6):2945-2949.

Smith-Mungo & Kagan (1998) "Lysyl Oxidase: Properties, Regulation and Multiple Functions in Biology" Matrix Biol. 16: 387-98.

Stassen (1976) "Properties of Highly Purified Lysyl Oxidase from Embryonic Chick Cartilage" *Biophys. Acta* 438(1):49-60.

Szabo, et al. (1997). "The Human Lysyl Oxidase-Like Gene Maps between STS Markers D15S215 and GHLC.GCT7C09 on Chromosome 15." Hum Genet 101(2): 198-200.

Szauter, et al. (2005). "Lysyl Oxidase in Development, Aging and Pathologies of the Skin." Pathol Biol (Paris) 53(7): 448-56.

Tang, et al. (1983). "Reaction of Aortic Lysyl Oxidase with β-Aminopropionitrile." J Biol Chem 258(7): 4331-8.

Tang, et al. (1984). "β-substituted Ethylamine Derivatives as Suicide Inhibitors of Lysyl Oxidase." J Biol Chem 259(2): 975-9.

Thomassin, et al. (2005) "The Pro-Regions of Lysyl Oxidase and Lysyl Oxidase-Like 1 Are Required for Deposition onto Elastic Fibers" J Biol. Chem. Dec. 30, 2005; 280(52):42848-55.

Trackman & Kagan (1979). "Nonpeptidyl Amine Inhibitors Are Substrates of Lysyl Oxidase." J Biol Chem 254(16): 7831-6.

Trackman et al. (1981) "Development of a Peroxidase-Coupled Fluorometric Assay for Lysyl Oxidase" *Anal. Biochem.* 113(2):336-342.

Vadasz, et al. (2005). "Abnormal Deposition of Collagen around Hepatocytes in Wilson's Disease Is Associated with Hepatocyte Specific Expression of Lysyl Oxidase and Lysyl Oxidase like protein-2." J Hepatol 43(3): 499-507.

Weise, et al. (2008). "LOXL4 is a Selectively Expressed Candidate Diagnostic Antigen in Head and Neck Cancer." Eur J Cancer 44(9): 1323-31.

Wu et al. (2007) "LOXL1 and LOXL4 are Epigenetically Silenced and Can Inhibit Ras/Extracellular Signal-Regulated Kinase Signaling Pathway in Human Bladder Cancer" *Cancer Res.* 67(9):4123-4129.

Akhtar et al. (2002) "The sponge/Matrigel angiogenesis assay" *Angiogenesis* 5(1-2):75-80.

Arguello et al.(1992) "Incidence and Distribution of Experimental Metastases in Mutant Mice with Defective Organ Microenvironments (Genotypes Sl/Sld and W/Wv)" *Cancer Research* 52(8):2304-2309.

Auerbach et al. (1974) "A simple procedure for the long-term cultivation of chicken embryos" *Devel. Biol.* 41(2):391-394.

Auerbach et al. (2003) "Angiogenesis Assays: A Critical Overview" *Clinical Chemistry* 49(1):32-40.

Barzu, et al. "Characterization of B-Cell Epitopes on IpaB, an Invasion-Associated Antigen of *Shigella flexneri*: Identification of an Immunodominant Domain Recognized during Natural Infection" Infection and Immunity, Sep. 1993, vol. 61, No. 9, pp. 3825-3831.

Bedogni et al. (2004) "Topical treatment with inhibitors of the phosphatidylinositol 3'-kinase/Akt and Raf/mitogen-activated protein kinase kinase/extracellular signal-regulated kinase pathways reduces melanoma development in severe combined immunodeficient mice" *Cancer Res.* 64(7):2552-2560.

Beilmann et al. (2004) "Human primary co-culture angiogenesis assay reveals additive stimulation and different angiogenic properties of VEGF and HGF" *Cytokine* 26(4):178-185.

Berger et al. (2004) "A murine model of ex vivo angiogenesis using aortic disks grown in fibrin clot" *Microvascular Res.* 68(3):179-187.

Bhowmick, et al. (2004). "Stromal fibroblasts in cancer initiation and progression." Nature 432(7015): 332-7.

Blacher et al. (2001) "Improved quantification of angiogenesis in the rat aortic ring assay" *Angiogenesis*4(2):133-142.

Brody, et al. (1976) "Lung lysyl oxidase and elastin synthesis during compensatory lung growth" *Chest* 69(2 Suppl):271-272.

Brown et al. (1996) "A novel in vitro assay for human angiogenesis" *Laboratory Investigation* 75(4):539-555.

Bruns, et al. "Vascular Endothelial Growth Factor Is an In Vivo Survival Factor for Tumor Endothelium in a Murine Model of Colorectal Carcinoma Liver Metastases" *Cancer*, 2000 vol. 89, No. 3, pp. 488-499.

Cancer Reference Information; Detailed guide: Breast cancer, how is breast cancer diagnosed? www.cancer.org/docroot/CRI_2_4_3X_How_is_breast_cancer_diagnosed, Nov. 16, 2009.

Cardone, et al. (1997). "Prognostic value of desmoplastic reaction and lymphocytic infiltration in the management of breast cancer." Panminerva Med 39(3): 174-7.

Chang & Werb (2001) "The Many Faces of Metalloproteases: Cell Growth, Invasion, Angiogenesis and Metastasis" Trends Cell. Biol. 11(11):S37-43.

Chen (2005) "Boyden chamber assay" *Methods Mol. Biol.* 294:15-22.

Chow, et al. "Identification and Expression of an Allergen Asp f 13 from *Aspergillus fumigatus* and Epitope Mapping Using Human IgE Antibodies and Rabbit Polyclonal Antibodies," Biochem. J, 2000, vol. 346, pp. 423-431.

Christiansen & Rajasekaran (2006) "Reassessing Epithelial to Mesenchymal Transition as a Prerequisite for Carcinoma Invasion and Metastasis" Cancer Res., 66(17):8319-26.

Christiansen, et al. (2004) "Biological Impediments to Monoclonal Antibody-Based Cancer Immunotherapy" Mol. Cancer Ther. 3(11):1493-1501.

Chu & Peters (2008). "Serial analysis of the vascular endothelial transcriptome under static and shear stress conditions." Physiol Genomics 34(2): 185-92.

Chu, et al. (2008). "Glycogen synthase kinase-3β regulates DeltaNp63 gene transcription through the β-catenin signaling pathway." J Cell Biochem 105(2): 447-53.

Conti, et al. (2008). "The desmoplastic reaction surrounding hepatic colorectal adenocarcinoma metastases aids tumor growth and survival via alphav integrin ligation." Clin Cancer Res 14(20): 6405-13.

De Eguileor et al. (2004) "Hirudo medicinalis: avascular tissues for clear-cut angiogenesis studies?" *Current Pharmaceutical Design* 10(16):1979-1998.

Dillman, (1989) "Monoclonal antibodies for treating cancer" Ann. Intern. Med. 111(7):592-603.

Entrez Gene data base searching result in National Library of Medicine. 2010.

Erler, et al. (2004) "627 The role of Hypoxia-Induced Lysyl Oxidase in Cancer Progression, Tumor Response to Therapy and Patient Prognosis" Eur. J. Cancer Suppl. 2(8):190.

Erler, et al. (2004) "Lysyl Oxidase is Essential for Hypoxia-Induced Metastasis" Pro. Amer. Assoc. Cancer Res. 47:570.

Erler, et al. (2006) "12 LOX is Essential for Hypoxia-Induced Metastasis" Radiother. Oncol. 78:S5.

Evans et al. (1999) "Vaccine Therapy for Cancer—Fact or Fiction?" QJM. 92(6):299-307.

Example from Wikipedia, the free encyclopedia, "Monoclonal Antibody Therapy," (http://en.wikipedia.org/wiki/Antibody_therapy), accessed on Oct. 4, 2010.

Example of the USPTO's Written Description Training Materials, Revision 1, Mar. 25, 2008, 84 pages in length.

Fidler, et al. (1994) "The implications of angiogenesis for the biology and therapy of cancer metastasis" Cell 79(2):185-188.

Go & Owen (2003) "The rat aortic ring assay for in vitro study of angiogenesis" *Methods Mol. Med.* 85:59-64.

González-Iriate et al. (2003) "A modified chorioallantoic membrane assay allows for specific detection of endothelial apoptosis induced by antiangiogenic substances" *Angiogenesis* 6(3):251-254.

Guedez et al. (2003) "Quantitative assessment of angiogenic responses by the directed in vivo angiogenesis assay" *Am. J. Pathol.* 162(5):1431-1439.

Gulec & Woltering (2004) "A new in vitro assay for human tumor angiogenesis: three-dimensional human tumor angiogenesis assay" *Ann. Surgical Oncology* 11(1):99-104.

Gura (1997) "Systems for Identifying New Drugs Are Often Faulty" Science 278(5347):1041-1042.

Ham, et al. (2008) "144 Inhibition of an Extracellular Matrix Protein Increases Survival in Orthotopic Nude Mouse Models" J. Surg. Res. 144(2):239-240.

Harrison & Lazo (1987) "High Dose Continuous Infusion of Bleomycin in Mice: A New Model for Drug-Induced Pulmonary Fibrosis" *J. Pharmacol. Exp. Ther*. 243(3):1185-1194.

Hartwell (1998) "Angiogenesis in P- and E-selectin-deficient mice" *Microcirculation* 5(2-3):173-178.

Herrington et al., Principles and basic methodology of DNA/RNA detection by in situ hybridization. Chapter 4, pp. 69-102, Diagnostic Molecular Pathology vol. 1, Phenotyping and genotyping of intact cells, IRL Press, Oxford University Press, 1992.

Hohenester et al. (1999) "Crystal Structure of a Scavenger Receptor Cysteine-Rich Domain Sheds Light on an Ancient Superfamily" *Nat. Struct. Biol*. 6(3):228-232.

Jain (1994) "Barriers to Drug Delivery in Solid Tumors" Scientific American 271(1):58-65.

Jakobsson et al .(1994) "A Morphometric Method to Evaluate Angiogenesis Kinetics in the Rat Mesentry" *Intl. J. Exp. Pathol*. 75(3):214-219.

Kaku, et al. (2007). "Post-translational modifications of collagen upon BMP-induced osteoblast differentiation." Biochem Biophys Res Commun 359(3): 463-8.

Kamath et al. (2001) "Signaling from Protease-Activated Receptor-1 Inhibits Migration and Invasion of Breast Cancer Cells" *Cancer Res*. 61(15):5933-5940.

Klutke, et al. (2008). "Decreased endopelvic fascia elastin content in uterine prolapse." Acta Obstet Gynecol Scand 87(1): 111-5.

Kragh et al. (2003) "In vivo chamber angiogenesis assay: an optimized Matrigel plug assay for fast assessment of anti-angiogenic activity" *Intl. J. Oncology* 22(2):305-311.

Kragh et al. (2004) "A versatile in vivo chamber angiogenesis assay for measuring anti-angiogenic activity in mice" *Oncology Reports* 11(2):303-307.

Kresse, et al. (2008). "DNA copy number changes in high-grade malignant peripheral nerve sheath tumors by array CGH." Mol Cancer 7: 48.

Li, et al. (2007). "Tumor microenvironment: the role of the tumor stroma in cancer." J Cell Biochem 101(4): 805-15.

Lichtenberg et al. (1999) "The rat Subcutaneous Air Sac model: a quantitative assay of antiangiogenesis in induced vessels" *Am. J. Pharmacol. Toxicology* 84(1):34-40.

Luo, et al. "Significant expression of vascular endothelial growth factor/vascular permeability factor in mouse ascites tumors" *Cancer Res.*, 1998, vol. 58, No. 12, pp. 2652-2660.

Macartney-Coxson, et al. (2008). "Metastatic susceptibility locus, an 8p hot-spot for tumour progression disrupted in colorectal liver metastases: 13 candidate genes examined at the DNA, mRNA and protein level." BMC Cancer 8:187.

Madakamutil, et al. "Immunodominance in the TCR Repertoire of α TCR Peptide-Specific CD4+ Treg Population that Controls Experimental Autoimmune Encephalomyelitis" J. Immunology 2008, vol. 180, pp. 4577-4585.

Masson et al. (2002) "Mouse Aortic Ring Assay: A New Approach of the Molecular Genetics of Angiogenesis" *Biol. Proc. Online* 4:24-31.

Mattioli, et al. "Mimicry of the Immunodominant Conformation-Dependent Antigenic Site of Hepatitis A Virus by Motifs Selected from Synthetic Peptide Libraries" Journal of Virology, Sep. 1995, vol. 69, No. 9, pp. 5294-5299.

Miller et al. (2004) "A novel technique for quantifying changes in vascular density, endothelial cell proliferation and protein expression in response to modulators of angiogenesis using the chick chorioallantoic membrane (CAM) assay" *J. Translational Med*. 2(1):4.

Monticone, et al. (2004). "Gene expression profile of human bone marrow stromal cells determined by restriction fragment differential display analysis." J Cell Biochem 92(4): 733-44.

Morbidelli & Ziche (2004) "The rabbit corneal pocket assay for the study of angiogenesis" *Cancer Treatment Res*. 117:147-151.

Müller, et al. (2006). "Lung fibroblasts from patients with emphysema show markers of senescence in vitro." Respir Res 7: 32.

Nagaoka, et al. (2008). "1,25(OH)2D3 regulates collagen quality in an osteoblastic cell culture system." Biochem Biophys Res Commun 377(2): 674-8.

Nakken, et al. (2007). "Multiple inflammatory-, tissue remodelling- and fibrosis genes are differentially transcribed in the livers of Abcb4 (-/ -) mice harbouring chronic cholangitis." Scand J Gastroenterol 42(10): 1245-55.

National Cancer Institute; Staging: Questions and answers, www.cancer.gov/cancertopics/factsheet/detection/staging, Nov. 6, 2009.

Nehls & Drenckhahn (1995) "A novel, microcarrier-based in vitro assay for rapid and reliable quantification of three-dimensional cell migration and angiogenesis" *Microvascular Res*. 50(3):311-322.

Nelson et al. (1988) "Effect of β-Aminopropionitrile and Ascorbate on Fibroblast Migration" *Proc. Soc. Exp. Biol. Med*. 188(3):346-352.

Nguyen et al. (1994) "Quantitation of angiogenesis and antiangiogenesis in the chick embryo chorioallantoic membrane" *Microvascular Res*. 47(1):31-40.

Nicosia & Ottinetti (1990) "Growth of microvessels in serum-free matrix culture of rat aorta. A quantitative assay of angiogenesis in vitro" *Laboratory Investig*. 63(1):115-122.

Nissanov et al. (1995) "Automatic vessel segmentation and quantification of the rat aortic ring assay of angiogenesis" *Laboratory Investig*. 73(5):734-739.

Norrby (1992) "On the quantitative rat mesenteric-window angiogenesis assay" *EXS* 61:282-286.

Norrby (2006) "In vivo models of angiogenesis" *J. Cell. Mol. Med*. 10(3):588-612.

Okada et al. (1995) "A quantative in vivo method of analyzing human tumor-induced angiogenesis in mice using agarose microencapsulation and hemoglobin enzyme-linked immunosorbent assay" *Japan. J. Cancer Res*. 86(12):1182-1188.

Orimo & Weinberg (2006). "Stromal fibroblasts in cancer: a novel tumor-promoting cell type." Cell Cycle 5(15): 1597-601.

Orimo, et al. (2001). "Cancer-associated myofibroblasts possess various factors to promote endometrial tumor progression." Clin Cancer Res 7(10): 3097-105.

Parsons-Wingerter et al. (2000) "Fibroblast growth factor-2 selectively stimulates angiogenesis of small vessels in arterial tree" *Arteriosclerosis Thrombosis Vasc. Biol*. 20(5):1250-1256.

Pascal, et al. (2005). "Comparison of replicative senescence and stress-induced premature senescence combining differential display and low-density DNA arrays." FEBS Lett 579(17): 3651-9.

Pinnell (1982) "Molecular Defects in the Ehlers-Danlos Syndrome" J. Invest. Dermatol. 79(Supp 1):90S-92S.

Pires Martins, et al. (2001). "Whole-body gene expression by data mining." Genomics 72(1): 34-42.

Presta et al. (1999) "Purine analogue 6-methylmercaptopurine riboside inhibits early and late phases of the angiogenesis process" *Cancer Res*. 59(10):2417-2424.

R&D Systems. Ordering Information: Catalog No. MAB2639. Anti-human lysyl oxidase homolog 2 monoclonal antibody. Apr. 18, 2005.

Radisky, et al. (2001) "Tumors Are Unique Organs Defined by Abnormal Signaling and Context" Semin. Cancer Bio. 11(2):87-95.

Rakic et al. (2003) "Placental Growth Factor, a Member of the VEGF Family, Contributes to the Development of Choroidal Neovascularization" *Invest. Ophthalmol. Vis. Sci*. 44(7):3186-3193.

Reed et al. (2007) "Culture of murine aortic explants in 3-dimensional extracellular matrix: a novel, miniaturized assay of angiogenesis in vitro" *Microvascular Res*. 73(3):248-252.

Resnick, et al. (1994) "The SRCR Superfamily: A Family Reminiscent of The Ig Superfamily" Trends Biochem. Sci. 19(1):5-8.

Ribatti (2004) "The first evidence of the tumor-induced angiogenesis in vivo by using the chorioallantoic membrane assay dated 1913" *Leukemia* 18(8):1350-1351.

Ribatti et al. (1996) "The chick embryo chorioallantoic membrane as a model for in vivo research on angiogenesis" *Intl. J. Devel. Biol*. 40(6):1189-1197.

Ribatti et al. (1997) "New model for the study of angiogenesis and antiangiogenesis in the chick embryo chorioallantoic membrane: the gelatin sponge/chorioallantoic membrane assay" *J. Vascular Res*. 34(6):455-463.

Ribatti et al. (2000) "The Chick Embryo Chorioallantoic Membrane as a Model for In Vivo Research on Anti-Angiogenesis" *Curr. Pharmacol. Biotechnol.* 1(1):73-82.

Richardson & Singh (2003) "Observations on the use of the avian chorioallantoic membrane (CAM) model in investigations into angiogenesis" *Curr. Drug Targets Cardiovasc. Hematol. Disorders* 3(2):155-185.

Rozalski, et al. "Epitope Specificities of Murine Monoclonal and Rabbit Polyclonal Antibodies against Enterobacterial Lipopolysaccharides of the Re Chemotype" Infection and Immunity, Sep. 1989, vol. 57, No. 9, pp. 2645-2652.

Salnikow, et al. (2008). "Regulation of hypoxia-inducible genes by ETS1 transcription factor." Carcinogenesis 29(8): 1493-9.

Sasaki et al. (1998) "Mac-2 Binding Protein is a Cell-Adhesive Protein of the Extracellular Matrix Which Self-Assembles into Ring-Like Structures and Binds β1 Integrins, Collagens and Fibronectin" *EMBO J.* 17(6):1606-1613.

Schmidt, et al. (2007). "[Mapping of a deletion interval on 8p21-22 in prostate cancer by gene dosage PCR]." Verh Dtsch Ges Pathol 91: 302-7.

Sequence search result (Neufeld) 2010.

Stapleton, et al. "Neutralization Escape Mutants Define a Dominant Immunogenic Neutralization Site on Hepatitis A Virus" Journal of Virology, Feb. 1987, vol. 61, No. 2, pp. 491-498.

Stiffey-Wilusz et al. (2001) "An ex vivo angiogenesis assay utilizing commercial porcine carotid artery: modification of the rat aortic ring assay" *Angiogenesis* 4(1):3-9.

Tarp, et al. "Identifi cation of a Novel Cancer-Specific Immunodominant Glycopeptide Epitope in the MUC1 Tandem Repeat" *Glycobiology*, 2007, vol. 17, No. 2, pp. 197-209.

Thiery, et al. (2003) "Epithelial-Mesenchymal Transitions in Development and Pathologies" Curr. Opin. Cell. Biol. 15(6):740-6.

Topp, et al. (1998) "Antibody Transport in Cultured Tumor Cell Layers" J. Control. Release 53(1-3):15-23.

Vautherot, et al. "Bovine Coronavirus Spike Glycoprotein: Localization of an Immunodominant Region at the Amino-Terminal End of S2" *Journal of General Virology*, 1992, vol. 73, pp. 3289-3294.

Waldmann (2003) "Immunotherapy: Past, Present and Future" *Nat. Med.* 9(3):269-277.

Walters & Kleeberger (2008) "Mouse Models of Bleomycin-Induced Pulmonary Fibrosis" *Current Protocols Pharmacol.* 40:5.46.1-5.46.17.

Weiner, (1999) "An Overview of Monoclonal Antibody Therapy of Cancer" Seminars Oncology 26(4):41-50.

Zhu & Nicosia (2002) "The thin prep rat aortic ring assay: a modified method for the characterization of angiogenesis in whole mounts" *Angiogenesis* 5(1-2):81-86.

"The role of the Extracellular Matrix in Cancer" Mar. 2001, U.S. Department of Energy: http:www.science.doe.gov/Accomplishments_Awards/Decades_Discovery/85.html.

Adamson, et al. (1974) "The Pathogenesis of Bleomycin-Induced Pulmonary Fibrosis in Mice" Am. J. Pathol. 77(2):185-189.

Barker, et al. (2011) "LOXL2-mediated matrix remodeling in metastasis and mammary gland involution" Cancer Res., 71(5):1561-1572.

Barry-Hamilton, et al. (2010) "Allosteric inhibition of lysyl oxidase-like-2 impedes the development of a pathologic microenvironment" Nat.Med., 19(9):1009-1017.

Boneberg, et. al. (2009) "Angiogenesis and lymphangiogenesis are downregulated in primary breast cancer" Br. J. Cancer, 101(4):605-614.

Brukamp, et al. (2007) "Hypoxia and Podocyte-Specific Vhlh Deletion Confer Risk of Glomerular Disease" Am. J. Physiol. Renal. Physiol. 293(4):F1397-F1407.

Butcher, et al. (2009) "A Tense Situation: Forcing Tumour Progression" Nat. Rev. Cancer 9(2):108-122.

Chan, et al. (2007) "Hypoxia, Gene Expression, and Metastasis" Cancer Metastasis Rev. 26(2):333-339.

Chang, et al. (2004) "Gene expression signature of fibroblast serum response predicts human cancer progression: similarities between tumors and wounds" PLoS Biol. 2(2):206-213.

Gross, et al. (2001)"Idiopathic Pulmonary Fibrosis" N. Engl. J. Med. 345(7):517-525.

Noblesse, et al. (2004) "Lsyl oxidase-like and lysysl oxidase are present in the dermis and epidermis of a skin equivalent and in himan skin and are associate to elastic fibers" J. Investig. Dermatol., 122:621-630.

Peroutka, et al. (2008) "Enhanced Protein Expression in Mammalian Cells Using Engineered SUMO Fusions: Secreted phospholipase A2" Protein Sci. 17(9):1586-1595.

Postlethwaite, et al. (1987) "Stimulation of the chemotactic migration of human fibroblasts by transforming growth factor β" J. Exp. Med. 165(1):251-256.

Pouysségur, et al. (2006) "Hypoxia Signalling in Cancer and Approaches to Enforce Tumour Regression" Nature 441(7092):437-443.

Sappino, et al. (1988) "Smooth-Muscle Differentiation in Stromal Cells of Malignant and Non-Malignant Breast Tissues" Int. J. Cancer 41(5):707-712. Abstract Only.

Selman, et al. (2006) "Gene Expression Profiles Distinguish Idiopathic Pulmonary Fibrosis from Hypersensitivity Pneumonitis" Am. J. Respir. Crit.Care Med. 173(2):188-198.

Sheppard (2006) "Transforming Growth Factor β: A Central Modulator of Pulmonary and Airway Inflammation and Fibrosis" Proc. Am. Thorac. Soc. 3(5):413-417.

Siegers, et al. (1986) "Hepatoprotection by Malotilate against Carbon Tetrachloride-Alcohol Induced Liver Fibrosis" Inflammation Res. 18(5-6):600-603. Abstract Only.

Sion, et al. (2006) "Lysyl oxidase (lox) and hypoxia-induced metastases" Cancer Biology & Therapy, 5(8):909-911.

Trentham, et al. (1977) "Autoimmunity to Type II Collagen: An Experimental Model of Arthritis" J. Experimental Medicine 146:857-868.

Watters, et al. (1987) "Idiopathic Pulmonary Fibrosis. Pretreatment Bronchoalveolar Lavage Cellular Constituents and Their Relationships with Lung Histopathology and Clinical Response to Therapy" Am. Rev. Respir. Dis. 135(3):696-704. Abstract Only.

U.S. Appl. No. 12/860,632, filed Aug. 20, 2010, Marshall, et al.
U.S. Appl. No. 13/021,555, filed Feb. 4, 2011, McCauley, et al.
Office Action mailed Sep. 23, 2010 in U.S. Appl. No. 12/185,054.
Office Action mailed Feb. 15, 2011 in U.S. Appl. No. 12/185,054.
International Preliminary Report on Patentability Chapter I issued Feb. 2, 2010, in PCT/US2008/009354.
Written Opinion of the ISA mailed Apr. 29, 2009, in PCT/US2008/009354.
International Search Report mailed Apr. 29, 2009, in PCT/US2008/009354.
Invitation to Pay Additional Fees mailed Jan. 14, 2009 (including Annex "Communication Relating to the Results of Partial International Search"), in PCT/US2008/009354.
Communication pursuant to Article 94(3) EPC dated Jun. 8, 2010, in EP 08795003.6-1222.
Communication pursuant to Article 94(3) EPC dated Jul. 19, 2011, in EP 08795003.6-1222.
Communication under Rule 71(3) EPC dated Jul. 23, 2012, in EP 08795003.6-1222.
Office Action mailed Jun. 29, 2007, in U.S. Appl. No. 10/536,440.
Office Action mailed Mar. 28, 2008, in U.S. Appl. No. 10/536,440.
Office Action mailed Nov. 14, 2008, in U.S. Appl. No. 10/536,440.
Office Action mailed Jun. 26, 2009, in U.S. Appl. No. 10/536,440.
Office Action mailed Dec. 30, 2009, in U.S. Appl. No. 10/536,440.
Office Action mailed Jun. 28, 2010, in U.S. Appl. No. 10/536,440.
Office Action mailed Jul. 5, 2011, in U.S. Appl. No. 10/536,440.
Office Action mailed May 14, 2010, in U.S. Appl. No. 12/571,167.
Office Action mailed Nov. 5, 2010, in U.S. Appl. No. 12/571,167.
Office Action mailed Mar. 24, 2011, in U.S. Appl. No. 12/571,167.
Office Action mailed Jul. 28, 2011, in U.S. Appl. No. 12/571,167.
International Preliminary Examination Report mailed Dec. 8, 2003, in PCT/IL01/00728.
Written Opinion mailed Jun. 6, 2003, in PCT/IL01/00728.
International Search Report mailed Dec. 17, 2002, in PCT/IL01/00728.
Invitation to Pay Additional Fees mailed May 23, 2002, in PCT/IL01/00728.

International Search Report mailed Jan. 5, 2006, in PCT/IL03/01008.
Invitation to Pay Additional Fees mailed Jun. 13, 2005, in PCT/IL03/01008.
European Search Report mailed Jul. 29, 2005, in EP 01958338.4-2406.
Communication pursuant to Article 96(2) EPC mailed Nov. 14, 2005, in EP 01958338.4-2406.
Communication pursuant to Article 96(2) EPC mailed Jun. 25, 2007, in EP 01958338.4-2406.
Communication pursuant to Article 94(3) EPC mailed Feb. 10, 2009, in EP 01958338.4-2406.
European Search Report mailed Feb. 29, 2008, in EP 03777136.7-1222.
Communication pursuant to Article 94(3) EPC mailed May 29, 2008, in EP 03777136.7-1222.
European Search Report mailed Dec. 21, 2009, in EP 08020754.1-2402.
European Search Opinion mailed Dec. 21, 2009, in EP 08020754.1-2402.
Communication pursuant to Article 94(3) EPC mailed Oct. 22, 2010, in EP 08020754.1-2402.
Communication pursuant to Article 94(3) EPC mailed Mar. 15, 2011, in EP 08020754.1-2402.
European Search Opinion mailed Jun. 3, 2009, in EP 08020752.5-1222.
Communication pursuant to Article 94(3) EPC mailed Feb. 8, 2010, in EP 08020752.5-1222.
Communication pursuant to Article 94(3) EPC mailed Dec. 27, 2011, in EP 08020752.5-1222.
European Search Opinion mailed Jun. 3, 2009, in EP 08020753.3-1222.
Communication pursuant to Article 94(3) EPC mailed Dec. 27, 2011, in EP 08020753.3-1222.
European Search Report mailed Jul. 13, 2011, in EP 10012458.5-2406.
European Search Opinion mailed Jul. 13, 2011, in EP 10012458.5-2406.
European Search Report mailed Jun. 27, 2011, in EP 10012457.7-2406.
European Search Opinion mailed Jun. 27, 2011, in EP 10012457.7-2406.
International Preliminary Report on Patentability Chapter I issued May 11, 2010, in PCT/US2008/072039.
Written Opinion of the ISA mailed Jan. 13, 2009, in PCT/US2008/072039.
International Search Report mailed Jan. 13, 2009, in PCT/US2008/072039.
Communication pursuant to Article 94(3) EPC mailed Jun. 8, 2010, in EP 08830207.0-1222.
Communication pursuant to Article 94(3) EPC mailed Jul. 20, 2011, in EP 08830207.0-1222.
Communication pursuant to Article 94(3) EPC mailed Jul. 4, 2012, in EP 08830207.0-1222.
Office Action mailed Jun. 14, 2011, in U.S. Appl. No. 12/652,687.
Office Action mailed Dec. 13, 2011, in U.S. Appl. No. 12/652,687.
Office Action mailed Mar. 30, 2012, in U.S. Appl. No. 12/652,687.
Advisory Action mailed Feb. 23, 2012, in U.S. Appl. No. 12/652,687.
Notice of Allowance mailed Sep. 18, 2012, in U.S. Appl. No. 12/652,687.
International Preliminary Report on Patentability Chapter I issued Jul. 12, 2011, in PCT/US2010/020159.
Written Opinion of the ISA mailed Sep. 9, 2010, in PCT/US2010/020159.
International Search Report mailed Sep. 9, 2010, in PCT/US2010/020159.
Office Action mailed Jan. 17, 2012, in U.S. Appl. No. 12/701,289.
Office Action mailed Jun. 15, 2012, in U.S. Appl. No. 12/701,289.
Office Action mailed Sep. 24, 2012, in U.S. Appl. No. 12/701,289.
Advisory Action mailed Aug. 30, 2012, in U.S. Appl. No. 12/701,289.
International Preliminary Report on Patentability Chapter I issued Aug. 9, 2011, in PCT/US2010/023359.
Written Opinion of the ISA mailed Apr. 15, 2010, in PCT/US2010/023359.
International Search Report mailed Apr. 15, 2010, in PCT/US2010/023359.
International Preliminary Report on Patentability Chapter I issued Feb. 21, 2012, in PCT/US2010/046192.
Written Opinion of the ISA mailed Feb. 17, 2011, in PCT/US2010/046192.
International Search Report mailed Feb. 17, 2011, in PCT/US2010/046192.
Invitation to Pay Additional Fees mailed Nov. 18, 2010, in PCT/US2010/046192.
Office Action mailed Jul. 13, 2012, in U.S. Appl. No. 12/860,838.
International Preliminary Report on Patentability Chapter I issued Feb. 21, 2012, in PCT/US2010/046248.
Written Opinion of the ISA mailed Jan. 7, 2011, in PCT/US2010/046248.
International Search Report mailed Jan. 7, 2011, in PCT/US2010/046248.
Office Action mailed Jul. 12, 2012, in U.S. Appl. No. 12/860,693.
International Preliminary Report on Patentability Chapter I issued Feb. 21, 2012, in PCT/US2010/046196.
Written Opinion of the ISA mailed Oct. 1, 2010, in PCT/US2010/046196.
International Search Report mailed Oct. 1, 2010, in PCT/US2010/046196.
Office Action mailed May 29, 2012, in U.S. Appl. No. 12/860,632.
Office Action mailed Sep. 11, 2012, in U.S. Appl. No. 12/860,632.
International Preliminary Report on Patentability Chapter I issued Feb. 21, 2012, in PCT/US2010/046247.
Written Opinion of the ISA mailed Sep. 24, 2010, in PCT/US2010/046247.
International Search Report mailed Sep. 24, 2010, in PCT/US2010/046247.
Office Action mailed Dec. 22, 2011, in U.S. Appl. No. 12/892,574.
Office Action mailed Jun. 18, 2012, in U.S. Appl. No. 12/892,574.
Office Action mailed Aug. 31, 2012, in U.S. Appl. No. 12/892,574.
International Preliminary Report on Patentability Chapter I issued Apr. 3, 2012, in PCT/US2010/050542.
Written Opinion of the ISA mailed Nov. 29, 2010, in PCT/US2010/050542.
International Search Report mailed Nov. 29, 2010, in PCT/US2010/050542.
International Preliminary Report on Patentability Chapter I issued Aug. 7, 2012, in PCT/US2011/023791.
Written Opinion of the ISA mailed May 17, 2011, in PCT/US2011/023791.
International Search Report mailed May 17, 2011, in PCT/US2011/023791.
International Preliminary Report on Patentability Chapter I issued Feb. 21, 2012, in PCT/US2010/046244.
Written Opinion of the ISA mailed Feb. 8, 2011, in PCT/US2010/046244.
International Search Report mailed Feb. 8, 2011, in PCT/US2010/046244.
Invitation to Pay Additional Fees mailed Dec. 3, 2010, in PCT/US2010/046244.
Written Opinion of the ISA mailed Jun. 14, 2012, in PCT/US2012/032600.
International Search Report mailed Jun. 14, 2012, in PCT/US2012/032600.
Written Opinion of the ISA mailed Aug. 10, 2012, in PCT/US2012/037580.
International Search Report mailed Aug. 10, 2012, in PCT/US2012/037580.
Written Opinion of the ISA mailed Sep. 10, 2012, in PCT/US2012/040585.
International Search Report mailed Sep. 10, 2012, in PCT/US2012/040585.
Albini et al. (1987) "A Rapid In Vitro Assay for Quantitating the Invasive Potential of Tumor Cells" Cancer Res. 47(12):3239-3245.

Aplin et al. (1998) "Signal transduction and signal modulation by cell adhesion receptors: the role of integrins, cadherins, immunoglobulin-cell adhesion molecules, and selectins" Pharmacol Rev. 50(2):197-263.

Armstrong et al. (1999) "Changes in Collagen Turnover in Early Acute Respiratory Distress Syndrome," Am. J. Respir. Crit. Care Med. 160:1910-1915.

BLAST 2 Sequences (LOR-1 and LOR-2) results version BLASTP 2.2.14, Apr. 9, 2006.

Castera (2011) "Invasive and Non-Invasive Methods for the Assessment of Fibrosis and Disease Progression in Chronic Liver Disease," Best Pract. Res. Clin. Gastroent. 25:291-303.

Chua et al. (2005) "Pulmonary Fibrosis Searching for Model Answers," Am J. Respir. Cell. Mol. Biol. 33:9-13.

Database EMBL [Online] Oct. 28, 2008, "Sequence 15133 from Patent WO2004061423", retrieved from EBI accession No. EMBL:FB530075, Database accession No. FB530075.

Gelatt (1977) "Animal models for glaucoma" Invest. Ophthalmol. Visual Sci. 16(7):592-596.

Grant et al. (2001) "Overview: Rational Integration of Agents Directed at Novel Therapeutic Targets into Combination Chemotherapeutic Regimens" Curr. Opin. Investig Drugs 2(11):1600-1605.

Greenbaum et al. (2003) "Comparing protein abundance and mRNA expression levels on a genomic scale", Genome Biology 40 (9):117.01-117.08.

Grigorescu (2006) "Noninvasive Biochemical Markers of Liver Fibrosis," J. Gastrointestin. Liver Dis. 15(2):149-159.

Ishak et al. (1995) "Histological Grading and Staging of Chronic Hepatitis," J. Hepatol. 22:696-699.

Julien et al. (2008) "A reproducible and quantifiable model of choroidal neovascularization induced by VEGF A after subretinal adenoviral gene transfer in the rabbit" Molecular Vision 14:1358-1372.

Kaiser et al. (2006) "Cancer. First pass at cancer genome reveals complex landscape" Science 313(5792):1370.

Knodell et al. (1981) "Formulation and Application of a Numerical Scoring System for Assessing Histological Activity in Asymptomatic Chronic Active Hepatitis," Hepatol. 1(5):431-435.

Li et al. (1999) "Liver Fibrogenesis and the Role of Hepatic Stellate Cells: New Insights and Prospects for Therapy," J. of Gastroentero. and Hepatol. 14:618-633.

Lugassy et al. (2012) "The Enzymatic Activity of Lysyl Oxidas-like-2 (LOXL2) Is Not Required for LOXL2-induced Inhibition of Keratinocyte Differentiation", Journal of Biological Chemistry 287(5):3541-3549.

Luo et al. (1998) "Differential Inhibition of Fluid Accumulation and Tumor Growth in Two Mouse Ascites Tumors by an Antivascular Endothelial Growth Factor/Permeability Factor Neutralizing Antibody" Cancer Res. 58(12):2594-2600.

Maier et al. "Correlation of mRNA and protein in complex biological samples", FEBS Letters 583 (24):3966-3973, 2009.

Manns et al. (2011) "A Phase-2B Trial to Evaluate the Safety, Tolerability and Efficacy of a Caspase Inhibitor, GS-9450, in Adults Failing PEG/RBV Therapy for Chronic HCV Infection," J Hepatology. (2011) 54 Supplement 1: S55-S56.

McKechnie et al. (2003) "Hr44 Secreted wtih exosomes: Loss from ciliary epithelium in response to inflammation" IOVS 44(6): 2650-2656.

Mehal et al. (2011) "Expressway to the Core of Fibrosis," Nat. Med. 17(5):552-553.

NCBI dbSNP record for LOXL2, available at http://www.ncbi.nlm.nih.gov/projects/SNP/snp_ref.cqi?locusId=4017, retrived Apr. 19, 2012.

Ogata et al. (1996) "Changes in alveolar capilary formation in growing rat lung by repeated injections of a lathyrogen" Growth, Development and Aging 60:153-160.

Roskoski (2007) "Vascular endothelial growth factor (VEGF) signaling in tumor progression" Critical Reviews in Oncology/Hematology 62: 179-213.

Ruckert et al. (2009) "Functional analysis of LOXL2 in pancreatic carcinoma" International Journal of Colorectal Disease; Clinical and Molecular Gastroenterology and Surgery, Springer,Berlin, DE, 25(3):303-311.

Schena et al. (2005) "Pathogenic Mechanisms of Diabetic Nephropathy," J. Am. Soc. Nephrol. 16:S30-S33.

Scheuer (1991) "Classification of Chronic Viral Hepatitis: A Need for Reassessment," J. Hepatol. 13:372-374.

Siemann et al. "Tumor Vasculature: a Target for Anticancer Therapies" in: "Vascular-Targeted Therapies in Oncology", Mar. 10, 2006, John Wiley & Sons. Ltd. Chichester, UK.

Tzortzaki et al. (2006) "Active Remodeling in Idiopathic Interstitial Pneumonias: Evaluation of Collagen Types XII and XIV," J. Histochem. & Cytochem. 54(6):693-700.

Van Bergen et al. "The role of LOXa nd LOXL2 in wound healing after glaucoma filtration surgery", European association for vision and eye research, Oct. 8, 2010, Retrieved from the Internet: URL:http://www.ever.be/view_abstract.php?abs_id=5411.

Watanabe et al. (2010) "Nucleolin as cell surface receptor for tumor necrosis factor-alpha inducing protein: a carcinogenic factor of *Helicobacter pylori*", Journal of Cancer Research and Clinical Oncology 136(6):911-921.

Whaley-Connell et al. (2006) "Chronic Kidney Disease and the Cardiometabolic Syndrome," J. Clin. Hypert. 8(8):546-548.

Communication pursuant to Rules 70(2) and 70a(2) EPC for EP 10739181.5, mailed Nov. 5, 2012.

Examination Report for NZ 598464, mailed Nov. 5, 2012.

Examination Report for NZ 598466, mailed Nov. 5, 2012.

Final Office Action for U.S. Appl. No. 12/860,693, mailed Nov. 15, 2012.

Patent Examination Report No. 1 for AU 2008282739, issued Nov. 19, 2012.

Communication pursuant to Article 94(3) EPC for EP 08 830 207.0, mailed Nov. 22, 2012.

Notice on the Second Office Action (translation) for CN 200880101321.3, mailed Nov. 23, 2012.

Notice of Allowance for U.S. Appl. No. 12/860,625, mailed Nov. 23, 2012.

Partial European Search Report for EP 12172214.4, mailed Nov. 28, 2012, 10 pages.

European Search Report for EP 12172222.7, mailed Nov. 28, 2012, 15 pages.

Jansen, et al. Lysyl oxidase regulates kidney epithelial cell phenotype. ASMB Meeting Abstract/Matrix Biology. 2006; 25:S92.

Kenyon, et al. TGF-beta1 causes airway fibrosis and increased collagen I and III mRNA in mice. Thorax. Sep. 2003;58(9):772-7.

Peinado, et al. A molecular role for lysyl oxidase-like 2 enzyme in Snail regulation and tumor progression. EMBO J. Oct. 5, 2005; 24(19): 3446-3458.

Peinado, et al. Lysyl oxidase-like 2 as a new poor prognosis marker of squamous cell carcinomas. Cancer Res. Jun. 15, 2008;68(12):4541-50.

Rodriguez, et al. Regulation of lysyl oxidase in vascular cells: lysyl oxidase as a new player in cardiovascular diseases. Cardiovasc Res. Jul. 1, 2008;79(1):7-13.

Sheridan, et al. Increased lysyl oxidase activity in aortas of hypertensive rats and effect of beta-aminopropionitrile. Exp Mol Pathol. Apr. 1979;30(2):315-24.

Sivakumar, et al. Upregulation of lysyl oxidase and MMPs during cardiac remodeling in human dilated cardiomyopathy. Mol Cell Biochem. Jan. 2008;307(1-2):159-167.

Wang, et al. Lysyl oxidase inhibition reduces rat liver fibrosis after bile duct ligation. Gastroenterology & Digestive Disease Week Meeting—108th Annual Meeting of the American-Gastroenterological-Association. Washington, DC. May 19-24, 2007. 2007; 132(4):A827.

Notice of Reasons for Rejection (translation) for JP 2010-519263, mailed Feb. 1, 2013.

* cited by examiner

Lysyl Oxidase Enzymology
LOX/L enzymes act via a ping-pong mechanism which can be described by Michaelis-Menten kinetics $$E + S \overset{K_M}{\Leftrightarrow} ES \overset{k_{cat}}{\rightarrow} E + P$$

FIGURE 2
Common Modes of Enzymatic Inhibition

Competitive inhibition
• Inhibitor typically bears structural similarity to substrate
• Inhibition noticeable at low substrate concentrations but can be overcome at high substrate concentrations Uncompetitive inhibition
• Inhibitor binds at site that becomes available after substrate is bound at the active site
• Inhibition most noticeable at high substrate concentration Non-competitive inhibition
• Inhibitor binds at site away from substrate binding site
• Relative inhibition is the same at all substrate concentrations

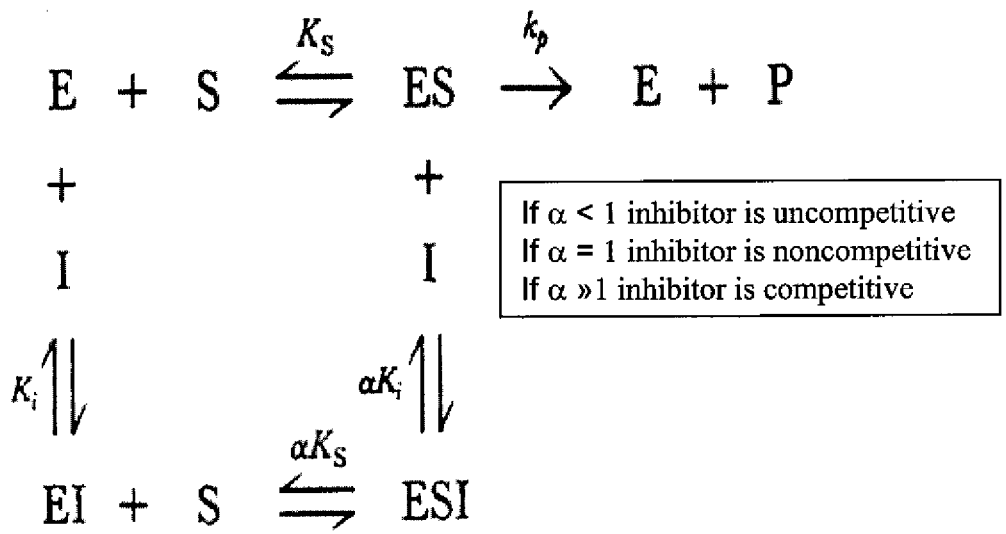

If $\alpha < 1$ inhibitor is uncompetitive
If $\alpha = 1$ inhibitor is noncompetitive
If $\alpha \gg 1$ inhibitor is competitive

FIGURE 3
βAPN is a Competitive Inhibitor of LOXL2
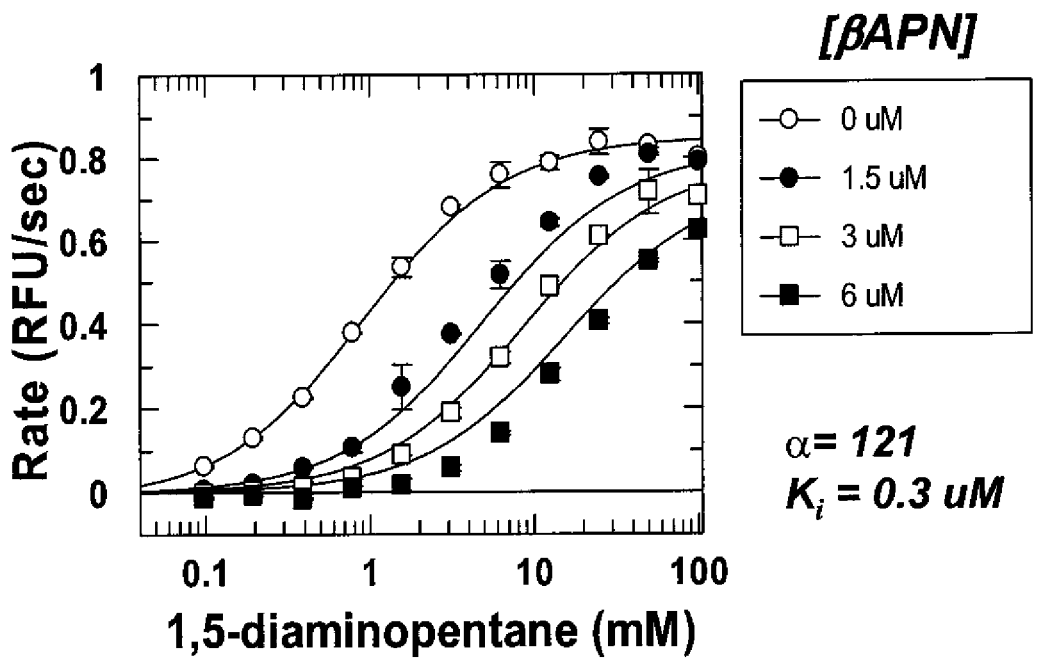
$\alpha = 121$
$K_i = 0.3\ uM$
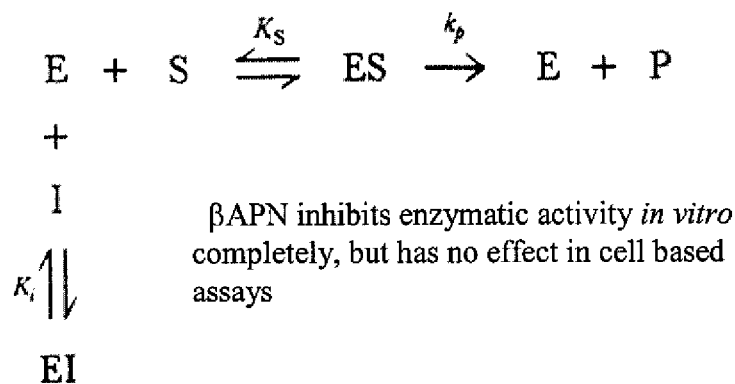
βAPN inhibits enzymatic activity *in vitro* completely, but has no effect in cell based assays Modes of Enzymatic Inhibition: LOXL2

Extracellular LOXL2: Localization and Function

At high cell density, LOXL2 is secreted and detected bound to the matrix and, in conditioned media, a blocking antibody will, ideally, bind all states and inhibit all activities Cell invasion/migration
Cell adhesion
(some EMT?)

EMT
Cell invasion/migration (?)

Figure 6
Murine Monoclonal Anti-LOXL2 Antibody

A. Variable Heavy Chain

*MEWSRVFIFLLSVTAGVHS*QVQLQQSGAELVRPGTSVKVSCKAS<u>GYAFTYYLIE</u>WVKQRPGQGLEWIG<u>VINPGSGGTNYNEKFKG</u>KATLTADKSSSTAYMQLSSLTSDDSAVYFCAR<u>NWMNFDY</u>WGQGTTLTVSS
(SEQ ID NO: 1)

B. Variable Light Chain

*MRCLAEFLGLLVLWIPGAIG*DIVMTQAAPSVSVTPGESVSISC<u>RSSKSLLHSNGNTYLY</u>WFLQRPGQSPQFLIY<u>RMSNLAS</u>GVPDRFSGSGSGTAFTLRISRVEAEDVGVYYC<u>MQHLEYPYT</u>FGGGTKLEIK
(SEQ ID NO: 2)

Figure 7
Anti-LOX antibody

A. <u>Variable Heavy Chain</u>

*MGWSWVFLFLLSVTAGVHS*QVQLQQSGAELVKPGASVKLSC
KAS<u>GYTFRSYDIN</u>WVRQRPEQGLEWIG<u>WIFPGDGSTKYNEK
FKG</u>KAILTTDKSSSTAYMQLSRLTSEDSAVYFCAR<u>VYYAMD
Y</u>WGQGTSVTVSS...(SEQ ID NO: 3)

B. <u>Variable Light Chain 1</u>

*MKLPVRLLVMFWIPASSS*DVLLTQTPLSLPVSLGDQASISC<u>RSS
QSIVHSNGNTYLE</u>WYLQKPGQSPKLLIY<u>KVSNRFS</u>GVPDRF
GGSGSGTDFTLKINRVEAEDLGIYYC<u>FQSSHIPLT</u>FGAGTKLE
LKRAD...(SEQ ID NO: 4)

C. <u>Variable Light Chain 2</u>

*MKLPVRLLVMFWIPASSS*DVLLTQTPLSLPVSLGDQASISC<u>RSS
QSIVHSNGNTYLE</u>WYLQKPGQSPKLLIY<u>KVSIRFS</u>GVPDRFG
GSGSGTDFTLKINRVEAEDLGIYYC<u>FQSSHIPLT</u>FGAGTKLEL
KRAD...(SEQ ID NO: 5)

Anti-LOXL2 Antibodies: Protein Screen B Update
Assessment of LOXL2 Enzymatic Activity Anti-LOXL2 Antibody designated AB0023
- α-LOXL2 antibodies repeated inhibitory activity observed in 10 ml prep material in enzymatic assay
- Inhibition also repeated in cell-based assays
- Sequence analysis confirmed that M01, M16, M19, M20 are identical Anti-LOXL2 Antibody AB0023 and Enzymatic Activity AB0023 is a partial inhibitor of LOXL2 enzymatic activity with an apparent IC50 of ~ 30 nM

Figure 10
Anti-LOXL2 Antibody AB0023: A Non-Competitive Inhibitor
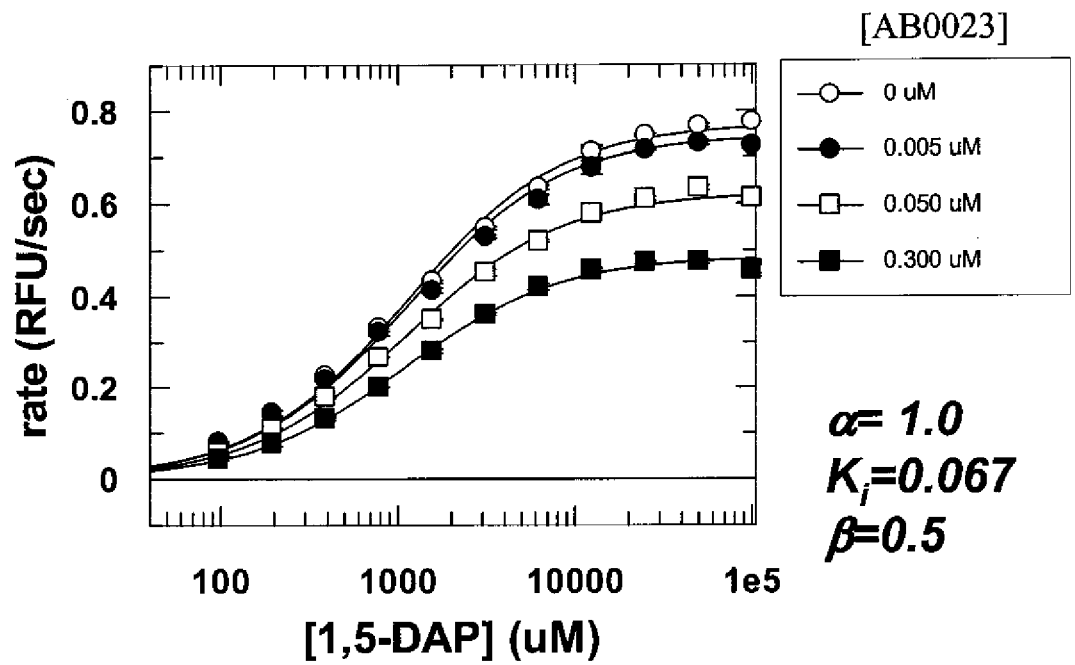
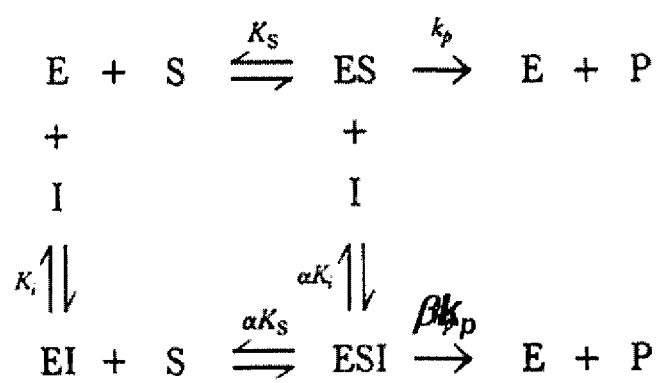

Anti-LOXL2 Antibody AB0023 : Binding Affinity and Off-Rate

*Analysis using the ProteOn*
*1 ug/mL AB0023 (M20) immobilized on chip*
*LOXL2 at varying concentrations was applied to chip*

- $k_{on} = 1.68 \times 10^6 \ M^{-1} s^{-1}$
- $k_{off} = 1.17 \times 10^{-4} \ s^{-1}$
- $K_D = 0.69 \ nM$
- $t_{1/2} = 98.7 \ min$

The antibody binds very tightly and releases very slowly
Kd estimate from various methods 0.1 – 1.0 nM

Figure 12
Anti-LOXL2 Antibody AB0023 Domain Mapping
AB0023 binds the SRCR 3-4 domain
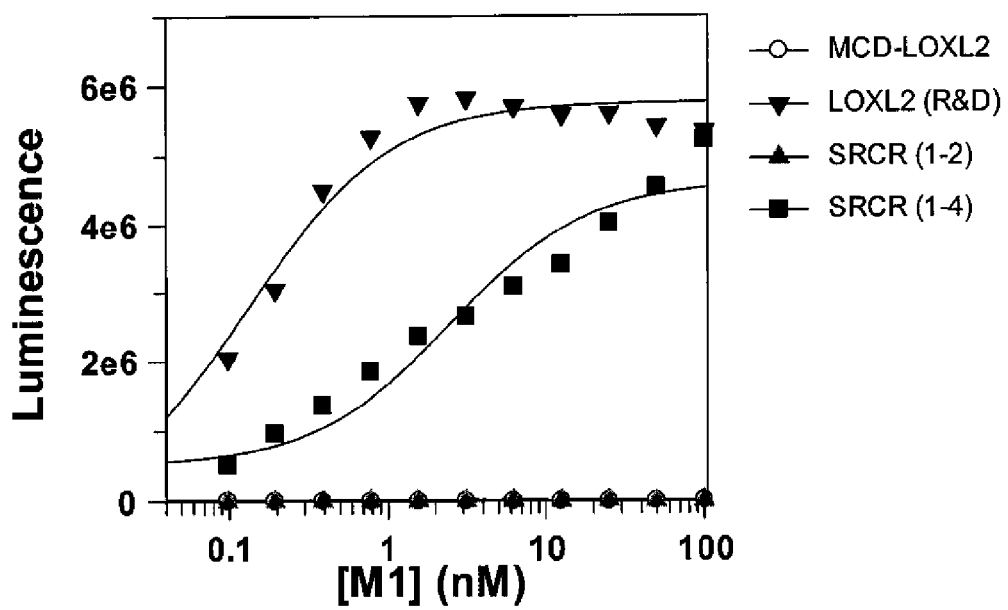
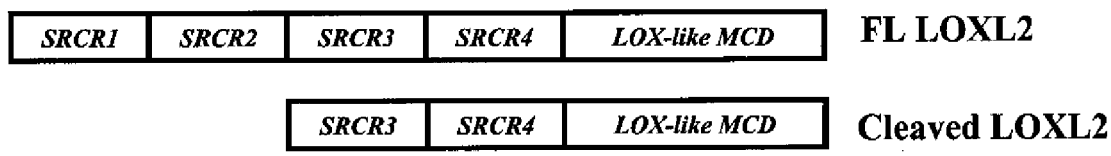
AB0023 binds the SRCR 3-4 domain

Anti-LOXL2 antibody AB0023: Cell-Based Assays

- Consistent inhibition of migration / invasion in collagen I and collagen IV, from supernatants through 10 ml prep material and scaled-up 100 ml prep and ascites material

- Partial inhibition also observed in cell adhesion assay

FIGURE 14

A.  AB0023 (hLOXL2 Protein Screen B clone M20) VH vs. Humanized Variants 1-4

```
                CDR1    GYAFTYYLIE
                CDR2    VINPGSGGTNYNEKFKG
                CDR3    NWMNFDY
```

Residues in Humanized AB0023 that Differ the Mouse mab (in *italicized underlining*):

```
M20 VH.pro        MEWSRVFIFLLSVTAGVHSQVQLQQSGAELVRPGTSVKVSCKASGYAFTYYLIEWVKQRPGQGLEWIGVI    70
VH variant 1.pro  ---------------QVQLVQSGAELKKPGASVKVSCKVSCKASGYAFTYYLIEWVKQAPGQGLEWIGVI    51
VH variant 2.pro  ---------------QVQLVQSGAEVKKPGASVKVSCKVSCKASGYAFTYYLIEWVRQAPGQGLEWIGVI    51
VH variant 3.pro  ---------------QVQLVQSGAEVKKPGASVKVSCKVSCKASGYAFTYYLIEWVRQAPGQGLEWIGVI    51
VH variant 4.pro  ---------------QVQLVQSGAEVKKPGASVKVSCKVSCKASGYAFTYYLIEWVRQAPGQGLEWIGVI    51

M20 VH.pro        NPGSGGTNYNEKFKGKATLTADKSSSTAYMQLSSLISDDSAVYFCARNWMNFDYWGQGTTLTVSS       135
VH variant 1.pro  NPGSGGTNYNEKFKGKGRATLTADKSTSTAYMELSSLRSEDSAVYFCARNWMNFDYWGQGTTVTVSS      116
VH variant 2.pro  NPGSGGTNYNEKFKGKGRATLTADKSTSTAYMELSSLRSEDTAVYFCARNWMNFDYWGQGTTVTVSS      116
VH variant 3.pro  NPGSGGTNYNEKFKGKGRATITADKSTSTAYMELSSLRSEDTAVYFCARNWMNFDYWGQGTTVTVSS      116
VH variant 4.pro  NPGSGGTNYNEKFKGGRVTITADKSTSTAYMELSSLRSEDTAVYFCARNWMNFDYWGQGTTVTVSS       116
```

B.  AB0023 (hLOXL2 Protein Screen B clone M20) VL (Vκ) vs. Humanized Variants 1-3

```
                CDR1    RSSKSLLHSNGNTYLY
                CDR2    RMSNLAS
                CDR3    MQHLEYPYT
```

Residues in Humanized AB0023 that Differ the Mouse mab (in *italicized underlining*):

```
M20 VL.pro        MRCLAEFLGLLVLWIPGAIGDIVMTQAAPSVSVTPGESVSISCRSSKSLLHSNGNTYLYWFLQRPGQSPQ    70
Vκ variant 1.pro  ----------------DIVMTQTPLSLSVTPGQPASISCRSSKSLLHSNGNTYLYWFLQKPGQSPQ      50
Vκ variant 2.pro  ----------------DIVMTQTPLSLSVTPGQPASISCRSSKSLLHSNGNTYLYWFLQKPGQSPQ      50
Vκ variant 3.pro  ----------------DIVMTQTPLSLSVTPGQPASISCRSSKSLLHSNGNTYLYWYLQKPGQSPQ      50

M20 VL.pro        FLIYRMSNLASGVPDRFSGSGSGTAFTLRISRVEAEDVGVYCMQHLEYPYTFGGGTKLEIK           132
Vκ variant 1.pro  FLIYRMSNLASGVPDRFSGSGSGTAFTLKISRVEAEDVGVYYCMQHLEYPYTFGGGTKVEIK           112
Vκ variant 2.pro  FLIYRMSNLASGVPDRFSGSGSGTDFTLKISRVEAEDVGVYYCMQHLEYPYTFGGGTKVEIK           112
Vκ variant 3.pro  FLIYRMSNLASGVPDRFSGSGSGTDFTLKISRVEAEDVGVYYCMQHLEYPYTFGGGTKVEIK           112
```

Binding of M64 to LOX

Cisplatin and Anti-LOX Synergy

IC50s

| Cell Line | Untreated (uM) | Anti-LOX (M64) (uM) |
|---|---|---|
| 231 | 261.8±72.3 | 242.2±14.4 |
| HT1080 | 207.5±6.9 | 194.2±22.7 |
| MiaPaCa 2 | 664.6±112.8 | 174.7±5.7 |
| BT549 | 384±244.3 | 197.3±28.5 |

LOX AND LOXL2 INHIBITORS AND USES THEREOF

CROSS-REFERENCE

This application claims the benefit of U.S. Provisional Application No. 60/963,282, entitled "Methods for Selecting Inhibitors of Tumor Invasion, Angiogenesis, and Metastasis," filed Aug. 2, 2007; U.S. Provisional Application No. 60/963,249, entitled "Treatment of Diseases With Inhibitors of Active Lysyl Oxidase," filed Aug. 2, 2007; U.S. Provisional Application No. 60/963,214, entitled "Treatment of Diseases Through Inhibition of Both Lysyl Oxidase and Lysyl Oxidase-Like Proteins," filed Aug. 2, 2007 U.S. Provisional Application No. 60/963,248, entitled "Diagnosis or Monitoring of Diseases by Assessing Active Lysyl Oxidase Levels or Activity," filed Aug. 2, 2007and U.S. Provisional Application No. 60/963,246, entitled "Combination Therapy Including Lysyl Oxidase Modulators," filed Aug. 2, 2007 and is related to co-pending U.S. Patent Application entitled, "Methods and Compositions for Treatment and Diagnosis of Fibrosis, Tumor Invasion, Angiogenesis and Metastasis," filed Aug, 1, 2008, Ser. No. 12/185,054, and PCT Patent Application entitled "Methods and Compositions for Treatment and Diagnosis of Fibrosis, Tumor Invasion, Angiogenesis and Metastasis," filed Aug. 1, 2008, Ser. No. PCT/US2008/009354, each of which applications is incorporated herein in its entirety by reference.

REFERENCE TO SEQUENCE LISTING

A sequence listing follows in Example 12 of this application.

BACKGROUND OF THE INVENTION

Cancer is a serious public health problem in the United States and other developed countries. Currently, one in four deaths in the United States is due to cancer. Cancer therapy involves treating patients with chemotherapeutic drugs to kill tumor cells. However, subsets of tumor cells are frequently resistant to drug therapy and survive to re-populate at sites of origin and at distant metastatic sites, leading to detectable disease recurrence and morbidity. Many carcinoma tumor cells that have the properties of increased invasive and metastatic capacity, and altered drag resistance, are thought to have undergone a morphological transformation encompassing or similar to EMT (epithelial-mesenchymal transition). Cells undergoing EMT lose the normal adhesive properties of epithelial cells and undergo a spectrum of changes including loss of E-cadherin expression and expression of mesenchymal markers, increased motility, increased invasiveness, and increased resistance to cell death.

The leading therapies for cancer are currently surgery, radiation and chemotherapy. Chemotherapeutic approaches such as anti-tumor antibiotics, alkylating agents, nitrosourea compounds, vinca alkaloids, steroid hormones, and anti-metabolites form the bulk of therapies available to oncologists. Despite advances in the field of cancer treatment, cancer remains a major health problem.

Angiogenesis, the formation of new blood vessels out of pre-existing capillaries, is a sequence of events that is of key importance in a broad array of physiologic and pathologic processes. Normal tissue growth, such as in embryonic development, wound healing, and the menstrual cycle, is characterized by dependence on new vessel formation for the supply of oxygen and nutrients as well as removal of waste products.

A large number of different and unrelated diseases are also associated with formation of new vasculature. Among certain pathologies are conditions in which angiogenesis is low, and should be enhanced to improve disease conditions. More frequently, however, excessive angiogenesis is an important characteristic of various pathologies, including pathologies characterized or associated with an abnormal or uncontrolled proliferation of cells. Pathologies which involve excessive angiogenesis include, for example, cancer (both solid and hematologic tumors), cardiovascular diseases (such as atherosclerosis and restenosis), chronic inflammation (rheumatoid arthritis, Crohn's disease), diabetes (diabetic retinopathy), psoriasis, endometriosis, neovascular glaucoma and adiposity (3). These conditions may benefit from chemotherapeutic inhibition of angiogenesis.

Generally speaking, the angiogenic process entails the proliferation and migration of a normally quiescent endothelium, the controlled proteolysis of the pericellular matrix, and the synthesis of new extracellular matrix components by developing capillaries. The establishment of new intra- and intercellular contacts and the morphological differentiation of endothelial cells to capillary-like tubular networks provide support for their subsequent maturation, branching, remodeling and selective regression to form a highly organized, functional microvascular network. The autocrine, paracrine and amphicrine interactions of the vascular endothelium with its surrounding stromal components, as well as with the pro-angiogenic and angiostatic cytokines and growth factors orchestrating physiologic angiogenesis, are normally tightly regulated both spatially and temporally.

Angiogenesis is crucial to the growth of neoplastic tissues. For more than 100 years, tumors have been observed to be more vascular than normal tissues. Several experimental studies have suggested that both primary tumor growth and metastasis require neovascularization. In contrast to the well orchestrated process described above for normal tissue growth, the pathologic angiogenesis necessary for active tumor growth is generally sustained and persistent, with the initial acquisition of the angiogenic phenotype being a common mechanism for the development of a variety of solid and hematopoietic tumor types. Tumors that are unable to recruit and sustain a vascular network typically remain dormant as asymptomatic lesions in situ. Metastasis is also angiogenesis-dependent: for a tumor cell to metastasize successfully, it generally must gain access to the vasculature in the primary tumor, survive the circulation, arrest in the microvasculature of the target organ, exit from this vasculature, grow in the target organ, and induce angiogenesis at the target site. Thus, angiogenesis appears to be necessary at the beginning as well as the completion of the metastatic cascade.

The criticality of angiogenesis to the growth and metastasis of neoplasms thus provides an optimal potential target for chemotherapeutic efforts. Appropriate anti-angiogenic agents may act directly or indirectly to influence tumor-associated angiogenesis either by delaying its onset (i.e., blocking an "angiogenic switch") or by blocking the sustained and focal neovascularization that is characteristic of many tumor types. Anti-angiogenesis therapies directed against the tumor-associated endothelium and the multiple molecular and cellular processes and targets implicated in sustained pathologic angiogenesis are being actively evaluated for their safety and efficacy in multiple clinical trials. However, there has been limited success to date with the discovery and/or identification of safe and/or effective anti-angiogenic agents.

Fibrosis is the abnormal accumulation of fibrous tissue that can occur as a part of the wound-healing process in damaged tissue. Such tissue damage may result from physical injury, inflammation, infection, exposure to toxins, and other causes.

Liver (hepatic) fibrosis, for example, occurs as a part of the wound-healing response to chronic liver injury. Fibrosis occurs as a complication of haemochromatosis, Wilson's disease, alcoholism, schistosomiasis, viral hepatitis, bile duct obstruction, exposure to toxins, and metabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

As summarized by Li and Friedman (Gastroenterol. Hepatol. 14:618-633, 1999), actual and proposed therapeutic strategies for liver fibrosis include removal of the underlying cause (e.g., toxin or infectious agent), suppression of inflammation (using, e.g., corticosteroids, IL-1 receptor antagonists, or other agents), down-regulation of stellate cell activation using, e.g., gamma interferon or antioxidants), promotion of matrix degradation, or promotion of stellate cell apoptosis. Despite recent progress, many of these strategies are still in the experimental stage, and existing therapies are aimed at suppressing inflammation rather than addressing the underlying biochemical processes. Thus, there remains a need in the art for materials and methods for treating fibrosis, including liver and lung fibrosis.

Fibrotic tissues accumulate in the heart and blood vessels as a result of hypertension, hypertensive heart disease, atherosclerosis, and myocardial infarction. High blood pressure, or hypertension, can be cause by a variety of factors and often leads to the development of Hypertensive Heart Disease (HHD) with progression to cardiac arrest and myocardial infarction. Similarly, atherosclerosis and other ischemic heart diseases often also result in cardiac arrest. These cardiovascular diseases all exhibit an accumulation of extra-cellular matrix or fibrotic deposition which results in stiffening of the vasculature and stiffening of the cardiac tissue itself. This deposition of fibrotic material is a response to the damage induced by the hypertensive and/or sclerotic state, but the effects of this response also result in the negative effects of vascular and cardiac stiffening as well as ventricle enlargement. Additionally, it is believed that the increased cardiac fibrosis seen in cardiovascular disease disrupts or alters the signals transmitted to cardiomyocytes via the tissue scaffolding of the heart, further leading to disruption of efficient cardiac function and promoting cardiac arrest and myocardial infarction.

SUMMARY OF THE INVENTION

Epithelial-to-Mesenchymal Transition (EMT) refers to the process whereby a cell with a gene expression/phenotype characteristic of epithelial cell (i.e., expressing specific proteins, factors, and molecules) changes or alters the genes or their level of expression which results in a change in the phenotype of the cell as exhibited by the alteration or change in the genes expressed.

Compositions are needed which prevent EMT and which are effective in blocking the activity of enzymes such as LOX and LOXL2. Such inhibitors are useful in treating diseases and disorders associated with aberrant levels of LOX and LOXL2.

Antibodies that bind to enzymes can be competitive inhibitors, uncompetitive inhibitors or non-competitive inhibitors. With respect to competitive inhibition, an inhibitor usually bears structural similarity to substrate. Inhibition will be noticeable at low substrate concentrations, but can be overcome at high substrate concentrations. With respect to uncompetitive inhibition, an inhibitor binds at a site that becomes available after substrate is bound at the active site. Inhibition will be most noticeable at high substrate concentration. With respect to non-competitive inhibition, an inhibitor binds at site away from substrate binding site and relative inhibition will generally be the same at all substrate concentrations. In one embodiment, an antibody or antigen binding fragment thereof, described herein specifically binds both full-length and processed LOX or LOXL2. In one aspect, both full-length and processed LOX or LOXL2 are active forms of the enzyme.

Provided herein is an isolated antibody or antigen binding fragment thereof, that specifically binds to an epitope having an amino acid sequence set forth as SEQ ID NO: 6. The antibody or antigen binding fragment thereof, comprises a variable heavy chain having at least 75% amino acid sequence identity to an amino acid sequence set forth as SEQ ID NO: 1 and a variable light chain having at least 75% amino acid sequence identity to an amino acid sequence set forth as SEQ ID NO: 2.

Provided herein is an isolated antibody or antigen binding fragment thereof, comprising a variable heavy chain having at least 75% amino acid sequence identity to an amino acid sequence set forth as SEQ ID NO: 1, and a variable light chain having at least 75% amino acid sequence identity to an amino acid sequence set forth as SEQ ID NO: 2. In one embodiment, an isolated antibody or antigen binding fragment thereof, comprises a variable heavy chain having at least 75% amino acid sequence identity to an amino acid sequence set forth as SEQ ID NO: 1. In another embodiment, an isolated antibody or antigen binding fragment thereof, comprises a variable light chain having at least 75% amino acid sequence identity to an amino acid sequence set forth as SEQ ID NO: 2. In yet another embodiment, an isolated antibody or antigen binding fragment thereof, competes with, or specifically binds to, any of the anti-LOXL2 antibodies or antigen binding fragments thereof described herein for binding to LOXL2. Antibodies or antigen binding fragments thereof can specifically bind to LOXL2 with a binding affinity of at least 2, 5, 10, 50, 100, 500 or 1000 times greater than to at least one of LOX, LOXL1, LOXL3 or LOXL4.

Provided herein are humanized anti-LOXL2 antibodies. A humanized antibody or antigen binding fragment thereof, can specifically binds to an epitope having an amino acid sequence set forth as SEQ ID NO: 6. In one embodiment, the humanized antibody or antigen binding fragment thereof, comprises a variable heavy chain having at least 75% amino acid sequence identity to an amino acid sequence set forth as SEQ ID NO: 25, 26, 27 or 28 and a variable light chain having at least 75% amino acid sequence identity to an amino acid sequence set forth as SEQ ID NO: 30, 31 or 32.

A humanized isolated antibody or antigen binding fragment thereof, can comprise a variable heavy chain having at least 75% amino acid sequence identity to an amino acid sequence set forth as SEQ ID NO: SEQ ID NO: 25, 26, 27 or 28, and a variable light chain having at least 75% amino acid sequence identity to an amino acid sequence set forth as SEQ ID NO: 30, 31 or 32.

A humanized antibody or antigen binding fragment thereof, can comprise a variable heavy chain having at least 75% amino acid sequence identity to an amino acid sequence set forth as SEQ ID NO: 25, 26, 27 or 28.

A humanized antibody or antigen binding fragment thereof, can comprise a variable light chain having at least 75% amino acid sequence identity to an amino acid sequence set forth as SEQ ID NO: 30, 31 or 32. Combinations of variable heavy chains and variable light chains can be made to assess binding affinity.

Provided herein is a humanized antibody or antigen binding fragment thereof, that competes with, or specifically binds to, an antibody or antigen binding fragment thereof described herein for binding to LOXL2.

Provided herein is a humanized antibody, or antigen-binding fragment thereof, which binds LOXL2, comprising a heavy chain variable region and a light chain variable region, wherein said heavy chain variable region comprises:
  (i) a heavy chain FR1 having the amino acid sequence of SEQ ID NO: 33 or the amino acid sequence of SEQ ID NO: 33 but for one or more substitutions selected from the group consisting of:
    (a) a substitution of glutamine (Q) by valine (V) or a conservative substitution thereof at position 24;
    (b) a substitution of leucine (L) by valine (V) or a conservative substitution thereof at position 30;
    (c) a substitution of valine (V) by lysine (K) or a conservative substitution thereof at position 31;
    (d) a substitution of arginine (R) by lysine (K) or a conservative substitution thereof at position 32; and
    (e) a substitution of threonine (T) by alanine (A) or a conservative substitution thereof at position 35; and a deletion of amino acid residues 1-19;
  (ii) a heavy chain FR2 having the amino acid sequence of SEQ ID NO: 34 or the amino acid sequence of SEQ ID NO: 34 but for one or more substitutions selected from the group consisting of:
    (a) a substitution of lysine (K) by arginine (R) or a conservative substitution thereof at position 3;
    (b) a substitution of arginine (R) by alanine (A) or a conservative substitution thereof at position 5, and
  (iii) a heavy chain FR3 having the amino acid sequence of SEQ ID NO: 35 or the amino acid sequence of SEQ ID NO: 35 but for one or more substitutions selected from the group consisting of:
    (a) a substitution of lysine (K) by arginine (R) or a conservative substitution thereof at position 1;
    (b) a substitution of alanine (A) by valine (V) or a conservative substitution thereof at position 2;
    (c) a substitution of leucine (L) by isoleucine (I) or a conservative substitution thereof at position 4;
    (d) a substitution of serine (S) by threonine (T) or a conservative substitution thereof at position 10;
    (e) a substitution of glutamine (Q) by glutamic acid (E) or a conservative substitution thereof at position 16;
    (f) a substitution of threonine (T) by arginine (R) or a conservative substitution thereof at position 21;
    (g) a substitution of aspartic acid (D) by glutamic acid (E) or a conservative substitution thereof at position 23;
    (h) a substitution of serine (S) by threonine (T) or a conservative substitution thereof at position 25; and
    (i) a substitution of phenylalanine (F) by tyrosine (Y) or a conservative substitution thereof at position 29; and
  (iv) a heavy chain FR4 having the amino acid sequence of SEQ ID NO: 36 or the amino acid sequence of SEQ ID NO: 36 but for a substitution of lysine (K) by valine (V) or a conservative substitution thereof at position 7,
and wherein said light chain variable region comprises:
  (i) a light chain FR1 having the amino acid sequence of SEQ ID NO: 49 or the amino acid sequence of SEQ ID NO: 49 but for one or more substitutions selected from the group consisting of:
    (a) a substitution of alanine (A) by threonine (T) or a conservative substitution thereof at position 27;
    (b) a substitution of alanine (A) by proline (P) or a conservative substitution thereof at position 28;
    (c) a substitution of proline (P) by leucine (L) or a conservative substitution thereof at position 29;
    (d) a substitution of valine (V) by leucine (L) or a conservative substitution thereof at position 31;
    (e) a substitution of glutamic acid (E) by glutamine (Q) or a conservative substitution thereof at position 37;
    (d) a substitution of serine (S) by proline (P) or a conservative substitution thereof at position 38;
    (f) a substitution of valine (V) by alanine (A) or a conservative substitution thereof at position 39; and a deletion of amino acid residues 1-20;
  (ii) a light chain FR2 having the amino acid sequence of SEQ ID NO: 50 or the amino acid sequence of SEQ ID NO: 50 but for one or more substitutions selected from the group consisting of:
    (a) a substitution of phenylalanine (F) by tyrosine (Y) or a conservative substitution thereof at position 2; and
    (b) a substitution of arginine (R) by lysine (K) or a conservative substitution thereof at position 5;
  (iii) a light chain FR3 having the amino acid sequence of SEQ ID NO: 51 or the amino acid sequence of SEQ ID NO: 51 but for one or more substitutions selected from the group consisting of:
    (a) a substitution of alanine (A) by aspartic acid (D) or a conservative substitution thereof at position 14; and
    (b) a substitution of arginine (R) by lysine (K) or a conservative substitution thereof at position 18; and
  (iv) a light chain FR4 having the amino acid sequence of SEQ ID NO: 52 or the amino acid sequence of SEQ ID NO: 52 but for a substitution of leucine (L) by valine (V) or a conservative substitution thereof at position 7;

In one embodiment, the antibody, or antigen-binding fragment thereof, comprises a heavy chain variable region FR1 having an amino acid sequence as set forth in SEQ ID NO: 33, 37 or 44; a heavy chain variable region FR2 having an amino acid sequence as set forth in SEQ ID NO: 34, 38 or 45; a heavy chain variable region FR3 having an amino acid sequence as set forth in SEQ ID NO: 35, 39, 46, 47 or 48; a heavy chain variable region FR4 having an amino acid sequence as set forth in SEQ ID NO: 36 or 40; a light chain variable region FR1 having an amino acid sequence as set forth in SEQ ID NO: 49 or 53; a light chain variable region FR2 having an amino acid sequence as set forth in SEQ ID NO: 50, 54 or 60; a light chain variable region FR3 having an amino acid sequence as set forth in SEQ ID NO: 51, 55 or 61; and a light chain variable region FR4 having an amino acid sequence as set forth in SEQ ID NO: 52 or 56.

Provided herein are antibodies that specifically bind to LOX. In one aspect, an isolated antibody or antigen binding fragment thereof, can comprise a variable heavy chain having at least 75% amino acid sequence identity to an amino acid sequence set forth as SEQ ID NO: 3 and a variable light chain having at least 75% amino acid sequence identity to an amino acid sequence set forth as SEQ ID NO: 4 or 5. In another aspect, an isolated antibody or antigen binding fragment thereof, can comprise a variable heavy chain having at least 75% amino acid sequence identity to an amino acid sequence set forth as SEQ ID NO: 3. In yet another aspect, an isolated antibody or antigen binding fragment thereof, can comprise a variable light chain having at least 75% amino acid sequence identity to an amino acid sequence set forth as SEQ ID NO: 4 or 5.

Provided herein is an isolated antibody or antigen binding fragment thereof, that competes with, or specifically binds to, an antibody or antigen binding fragment thereof of any one of the anti-LOX antibodies described herein for binding to LOX.

An anti-LOX antibody can specifically bind to LOX with a binding affinity of at least 2, 5, 10, 50, 100, 500 or 1000 times greater than to at least one of LOXL1, LOXL2, LOXL3 or LOXL4.

An isolated antibody or antigen binding fragment thereof can be labeled with a detectable label, a therapeutic label or both.

In one embodiment, an antigen binding fragment is, for example, a variable heavy chain, a variable light chain, a Fv, a scFv, a Fab, a F(ab')2, a genetically engineered antibody, a monoclonal antibody, or a humanized antibody.

Provided herein is a kit for treating a condition associated with LOX or LOXL2, comprising a composition of an antibody or antigen binding fragment thereof of any one of the preceding embodiments and a pharmaceutically acceptable carrier or excipient. A condition associated with LOX or LOXL2 can be, for example, a tumor, a metastasis, angiogenesis, or fibrosis. A kit can further comprise a detectable label, a therapeutic label or both. Kits can further comprise written instructions describing how to conjugate the antibody or antigen binding fragment thereof with the detectable label, a therapeutic label or both. Furthermore, written instructions can describe how to administer the antibody or antigen binding fragment thereof. In one embodiment, compositions in the kit are free of pyrogens and can, in some instances, is lyophilized.

Provided herein is a method of diagnosing a condition associated with LOX or LOXL2 comprising assessing a level of LOX and/or LOXL2 in a sample of a subject by contacting said sample with an antibody or antigen binding fragment thereof described herein, wherein a change in level of LOX and/or LOXL2 in the sample in comparison with a reference sample indicates the presence or increase of a tumor or metastasis. A condition associated with LOX or LOXL2 can be, for example, a tumor, a metastasis, angiogenesis, or a fibrotic condition. In one embodiment, an increase in LOX and/or LOXL2 levels in the sample in comparison with a reference sample indicates the presence of a tumor or metastasis or an increase in tumor or metastatic growth. A reference sample is a sample taken from the subject at an earlier time point or a sample from another individual. Levels of LOX and/or LOXL2 levels in the sample are detected by contacting the sample with any of the antibodies or antigen binding fragments thereof described herein. For detection purposes, an antibody or antigen binding fragment thereof is detectably labeled as needed depending upon the method used to assess binding.

Provided herein is a method of inhibiting LOXL2 by contacting a sample or a cellular tissue with an antibody or antigen binding fragment thereof, described herein. In one embodiment, binding of said antibody or antigen binding fragment thereof to LOXL2 inhibits enzymatic activity of LOXL2.

Provided herein is a method of inhibiting LOX by contacting a sample or cellular tissue with an antibody or antigen binding fragment thereof, described herein. In one embodiment, binding of said antibody or antigen binding fragment thereof to LOX inhibits enzymatic activity of LOX. Contacting can occur in vitro, in vivo or ex vivo. Inhibiting LOX or LOXL2 can reduce tumor growth in a subject either partially or completely. Inhibiting LOX or LOXL2 can reduce angiogenesis in a subject such that a therapeutic benefit occurs. Inhibiting LOX or LOXL2 can reduce fibrosis in a subject such that a therapeutic benefit occurs.

Provided herein is a method of reducing growth of a tumor in a subject, comprising administering an antibody or antigen binding fragment thereof, described herein. A tumor can be a primary tumor or a metastatic tumor. In one aspect, a tumor is, for example, Lung cancer (including lung adenocarcinoma, squamous cell carcinoma, large cell carcinoma, bronchioloalveolar carcinoma, non-small-cell carcinoma, small cell carcinoma, mesothelioma); breast cancer (including ductal carcinoma, lobular carcinoma, inflammatory breast cancer, clear cell carcinoma, mucinous carcinoma,); colorectal cancer (colon cancer, rectal cancer); anal cancer; pancreatic cancer (including pancreatic adenocarcinoma, islet cell carcinoma, neuroendocrine tumors); prostate cancer; ovarian carcinoma (ovarian epithelial carcinoma or surface epithelial-stromal tumour including serous tumour, endometrioid tumor and mucinous cystadenocarcinoma, sex-cord-stromal tumor); liver and bile duct carcinoma (including hepatocelluar carcinoma, cholangiocarcinoma, hemangioma); esophageal carcinoma (including esophageal adenocarcinoma and squamous cell carcinoma); non-Hodgkin's lymphoma; bladder carcinoma; carcinoma of the uterus (including endometrial adenocarcinoma, uterine papillary serous carcinoma, uterine clear-cell carcinoma, uterine sarcomas and leiomyosarcomas, mixed mullerian tumors); glioma, glioblastoma, medullablastoma, and other tumors of the brain; kidney cancers (including renal cell carcinoma, clear cell carcinoma, Wilm's tumor); cancer of the head and neck (including squamous cell carcinomas); cancer of the stomach (stomach adenocarcinoma, gastrointestinal stromal tumor); multiple myeloma; testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma. In one embodiment, a tumor is, for example, a colon tumor, an ovarian tumor, a lung tumor, an esophageal tumor, a breast tumor, a prostate tumor, a carcinoma. Tumor size in the subject can be reduced by at least 10%, 25%, 50%, 70%, 90%, 95%, or more following treatment as compared to the tumor in the subject prior to treatment. In one aspect, the survival of a subject with a tumor is increased by at least 10 days, 1 month, 3 months, 6 months, 1 year, 2 years, 5 years, 10 years, or more compared to a subject that is not administered the antibody or antigen binding fragment thereof. Metastatic tumor burden of a subject can be stabilized following administration of an antibody or antigen binding fragment thereof, described herein. For instance, metastatic tumor burden can be stabilized for at least 10 days, 1 month, 3 months, 6 months, 1 year, 2 years, 5 years, 10 years or more.

An antibody or antigen-binding fragment thereof described herein can specifically bind to a secreted or mature form of hLOX but not to a preproprotein of hLOX having an amino acid sequence of SEQ ID NO: 7. In one embodiment, secreted form of hLOX has an amino acid sequence of SEQ ID NO: 8, 62 or 63. In one embodiment, the mature form of hLOX has an amino acid sequence of SEQ ID NO: 9.

Provided herein is a method of inhibiting angiogenesis in a subject by an antibody or antigen binding fragment thereof, described herein.

Provided herein is a method of inhibiting a fibrotic disease in a subject by administering an antibody or antigen binding fragment thereof, described herein. Fibrotic diseases include, but are not limited to, liver fibrosis, lung fibrosis, kidney fibrosis, cardiac fibrosis and schleroderma. In one embodiment, kidney fibrosis includes, but is not limited to, diabetic nephropathy, vesicoureteral reflux, tubulointerstitial renal fibrosis; glomerulonephritis or glomerular nephritis, including focal segmental glomerulosclerosis and membranous glomerulonephritis, and Mesangiocapillary glomerular nephritis. In one embodiment, liver fibrosis results in cirrhosis, and associated conditions such as chronic viral hepatitis, non-alcoholic fatty liver disease (NAFLD), alcoholic steatohepantis (ASH), non-alcoholic steatohepatiris (NASH), primary biliary cirrhosis (PBC), biliary cirrhosis, and autoimmune hepatitis.

Provided herein is a method of decreasing extracellular matrix formation by contacting a sample or cellular tissue with an antibody or antigen binding fragment thereof, described herein. Administration or contacting can occur, in one example, by parenteral administration.

Provided herein is a method of monitoring a subject's response to administration of an antibody or antigen binding fragment thereof, described herein by detecting by detecting LOX and/or LOXL levels and/or activity.

In one embodiment, said antibody or antigen binding fragment thereof, is labeled with a therapeutic label.

Contemplated herein is combination therapy in which the methods further comprise co-administering a second therapeutic agent. In one embodiment, the second therapeutic agent is an antibody or a chemotherapeutic agent.

Provided herein is a use of an antibody or antigen binding fragment thereof, described herein in the preparation of a formulation for inhibiting LOXL2 or LOX, reducing tumor growth, inhibiting angiogenesis, inhibiting a fibrotic disease or decreasing extracellular matrix formation in a subject. In one embodiment, said antibody or antigen binding fragment thereof is labeled with a therapeutic label and, optionally, a diagnostic label.

Provided herein is a use of an antibody or antigen binding fragment thereof, described herein in the preparation of a formulation for diagnosing a tumor or metastasis comprising assessing LOX and/or LOXL2 levels in a sample of a patient, wherein a change in LOX and/or LOXL2 levels in the sample in comparison with a reference sample indicates the presence of a tumor or metastasis or an increase in tumor or metastatic growth. In one embodiment, said antibody or antigen binding fragment thereof is labeled with a diagnostic label.

INCORPORATION BY REFERENCE

All publications, patents, and patent applications mentioned in this specification are herein incorporated by reference to the same extent as if each individual publication, patent, or patent application was specifically and individually indicated to be incorporated by reference,

BRIEF DESCRIPTION OF THE DRAWINGS

Features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 2 illustrates common modes of enzymatic inhibition.

FIG. 3 illustrates βAPN is a competitive inhibitor of LOXL2.

FIG. 6A provides the amino acid sequences of a heavy chain variable region and FIG. 6B provides the amino acid sequences of a light chain variable region of an antibody that binds to the SRCR3-4 region of LOXL2. For each variable region, signal peptides are shown in italics, CDRs are underlined and the beginning of the constant framework is shown in bold font.

FIG. 7A provides the amino acid sequences of a heavy chain variable region and FIGS. 7B and 7C provide amino acid sequences of two light chain variable regions of antibodies that binds to LOX. For each variable region, signal peptides are shown in italics and CDRs are underlined.

FIG. 10 demonstrates that anti-LOXL2 antibody AB0023 is a non-competitive inhibitor.

FIG. 12 illustrates anti-LOXL2 antibody AB0023 domain mapping; AB0023 binds the SRCR 3-4 domain of LOXL2.

FIG. 14 provides amino acid sequences of the variable heavy (VH) (SEQ ID NO: 24) and variable light (VL) (SEQ ID NO: 29) chains of murine monoclonal antibody AB0023 (anti-hLOXL2). Complementarity determining regions (CDRs) (SEQ ID NOS 41-42, 70 and 57-59, respectively, in order of appearance) are shown by bold underlining. FIG. 14 also provides four humanized variants of the murine monoclonal antibody. Residues in the framework (FR) regions of the humanized variable heavy (SEQ ID NOS 25-28, respectively, in order of appearance) and light (SEQ ID NOS 30-32, respectively, in order of appearance) chains that differ from the murine monoclonal antibody are shown by dash marks (- - -) or by italicized underlining.

DETAILED DESCRIPTION OF THE INVENTION

Figure 1:
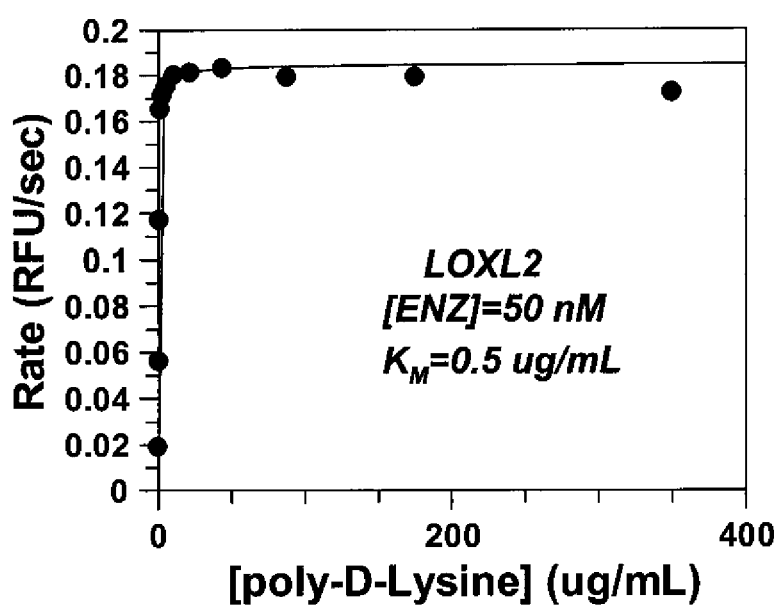
FIG. 1 illustrates Lysyl Oxidase Enzymology. LOX/L enzymes act via a ping-pong mechanism which can be described by Michaelis-Menten kinetics.

The present invention relates to the field of medicine, including cancer diagnosis and treatment. One aspect of the invention relates to LOX and LOXL2 as indicators of disease progression and a target for therapeutic agents.

The present invention provides innovative methodology and related composition and kits for diagnosing or monitoring various diseases associated with abnormal cell proliferation, angiogenesis and fibrosis, by using agents that specifically recognize active or mature forms of lysyl oxidase (LOX) or lysyl oxidase-like (LOXL) proteins.

Methods are provided for diagnosing or monitoring cancer metastasis in a subject, comprising: assessing active LOX or LOXL2 levels or activity in the blood or in a tumor, whereby a change in active LOX or LOXL2 levels or activity in the blood or in the tumor in comparison with a reference sample, indicates the presence of metastatic tumor growth.

As described in more detail below, levels of active LOX or LOXL2 can be assessed by various methods including but are not limited to immunohistochemistry by using antibodies that specifically bind to the active or mature form of LOX or LOXL2. Enzymatic activity of active LOX or LOXL2 can be measured by using various methods including but not limited to chromogenic and fluorometric assays.

Also provided herein are antibodies or antigen-binding fragments thereof, that specifically recognize active forms of LOX or LOXL2, methods for generating antibodies against active forms of LOX or LOXL2, and method of using the antibodies to treat abnormal cell proliferation, angiogenesis and fibrosis.

I. General Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference. The headings provided herein are for convenience only and do not limit the invention in any way.

As used herein, "a" or "an" means "at least one" or "one or more."

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:

(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Tip,
(v) a nitrogen ring group, consisting of His and Trp,
(vi) a large aliphatic non-polar group, consisting of Val, Leu and He,
(vii) a slightly-polar group, consisting of Met and Cys,
(viii) a small-residue group, consisting of Ser, Thr, Asp, Asn, Gly, Ala, Glu, Gin and Pro,
(ix) an aliphatic group consisting of Val, Leu, He, Met and Cys, and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art as described above.

A "conserved residue" is an amino acid that is relatively invariant across a range of similar proteins. Often conserved residues will vary only by being replaced with a similar amino acid, as described above for "conservative amino acid substitution".

The letter "x" or "xaa" as used in amino acid sequences herein is intended to indicate that any of the twenty standard amino acids may be placed at this position unless specifically noted otherwise. For the purposes of peptidomimetic design, an "x" or an "xaa" in an amino acid sequence may be replaced by a mimic of the amino acid present in the target sequence, or the amino acid may be replaced by a spacer of essentially any form that does not interfere with the activity of the peptidomimetic.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions snared by the compared sequences. A sequence which is "unrelated" or "non-homologous" shares less than 40% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid (nucleotide, oligonucleotide) and amino acid (protein) sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST amino acid searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used (see, ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). Methods to determine identify are designed to give the largest match between the sequences tested. Moreover, methods to determine identity are codified in publicly available computer programs. Computer program methods to determine identity between two sequences include, but are not Hmited to, the GCG program package (Devereux, J., et al, Nucleic Acids Research 12(1): 387 (1984)), BLASTP, BLASTN, and FASTA (Altschul, S. F. et al., J. Molec. Biol. 215:403-410 (1990) and Altschul et al. Nuc. Acids Res. 25: 3389-3402 (1997)). The BLAST X program is publicly available from NCBI and other sources (BLAST Manual, Altschul, S., et al, NCBI NLM NIH Bethesda, Md. 20894; Altschul, S., et al, J. Mol. Biol. 215:403-410 (1990). The well known Smith Waterman algorithm may also be used to determine identity.

The term "substantially identical" means identity between a first amino acid sequence that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences substantially identical to LOX contain a common structural domain having at least about 60%, or 65% identity, likely 75% identity, more likely 85%, 90%, 91%, 92%, 93%, 94%, 95%, 96%, 97%, 98% or 99% identity to LOX. For example, amino acid sequences that contain a common structural domain having at least about 60%, or 65% identity, likely 75% identity, more likely 85%, 90%, 91%, 92%, 93%, 94%, 95%, 96%, 97%, 98% or 99% identity to LOXL2 are termed sufficiently or substantially identical. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%, 91%, 92%, 93%, 94%, 95%, 96%, 97%, 98% or 99% identity to nucleic acid sequences provided herein are termed substantially identical.

II. Lysyl Oxidase (LOX) and Lysyl Oxidase-Like (LOXL) Proteins

Typically, solid tumors contain areas of low oxygen tension (hypoxia). Hypoxic cells present a great problem in the treatment of cancer because these cells are highly aggressive, metastatic and resistant to therapy. The underlying mechanisms contributing to these features are poorly understood. Metastasis poses a particular problem in breast cancer because there is no effective treatment for the majority of patients with detectable metastatic breast cancer (Steeg, P S, Br. Can. Res. 2(6): 396-9 (2000)).

The extracellular matrix (ECM) can have a major influence on tumor cells (Chang and Werb, Trends Cell. Biol. 11: S37-43 (2001); and Radisky et al, Semin. Cancer Bio. 11:87-95 (2001)). Mice exposed to hypoxia exhibit tissue specific increases in lysyl oxidase (LOX) activity, an amine oxidase that plays an essential role in the formation and maintenance of the ECM (Brody et al. Am. Rev. Respir, Dis. 120:1289-95 (2001)). A recent microarray study confirmed LOX to be a hypoxia-induced gene in a variety of cell lines (Denko, N.C. Oncogene 22:5907-14 (2003)). However, a biological role of LOX under hypoxic conditions was not identified. LOX initiates the covalent cross-linking of collagens and elastin in the ECM, increasing insoluble matrix deposition and tensile strength (Kagan and Li. J. Cell. Biochem. 88:660-72 (2003)). LOX expression is essential for wound healing and normal connective tissue function, and knock-out mice die soon after parturition due to cardiovascular instability (Hornstra et al. J. Biol. Chem. 278:14387-93 (2003)). Decreased LOX activity is associated with diseases such as Ehler-Danlos syndrome (Pinnell, S. R. J. Invest. Dermatol. 79(Supp 1): 90S-92S (1982); Royce et al. Biochem J. 192:579-86 (1980); and Khakoo et al. Clin. Genet. 51:109-14 (1997)). Increased LOX activity contributes to fibrotic and tissue remodeling diseases, such as liver cirrhosis (Kagan, H M. Pathol. Res. Pract. 190: 910-0 (1994); Chanki et al. Br. J. Dermatol. 133:710-5 (1995); and Ooshima and Midorikawa. Jpn. Circ. J. 41:1337-40 (1977)).

Elevated expression of LOX correlates with increased staging in renal cell cancer (Stassar et al. Br. J. Cancer, 85: 1372-82 (2001)), and increased LOX expression is observed in highly metastatic and/or invasive breast cancer cell lines (Kirschmann et al. Breast Cancer Res. Treat. 55:127-36 (1999); and Kirschmann et al. Cancer Res. 62:4478-83 (2002)). In contrast, LOX acts as a tumor suppressor in non-tumorgenic revertants of ras-transformed fibroblasts (Smith-Mungo and Kagan. Matrix Biol. 16:387-98 (1998)). Loss of LOX is associated with tumorigenesis in several cancer types such as gastric, colon and prostate cancers (Ren et al. Cancer Res. 58:1285-90 (1998); Cxiszar et al. Int. J. Cancer 97:636-42 (2002); and Kaneda et al. Cancer Res. 64:6410-5 (2004)). It would, thus, seem that LOX's tumor suppressive role depends on cell type and transformation status. The propeptide domain (and not the active enzyme) was recently shown to be responsible for the tumor suppressor activities. In breast cancer, increased LOX expression is associated with the early stromal reaction (Decitre et al. Lab. Invest. 78:143-51 (1998)), and treatment with antisense LOX in this cancer cell type prevents in vitro invasion (Kirschmann et al. Cancer Res. 62:4478-83 (2002)).

The amino acid sequence of LOXL2 shares extensive sequence homology with the conserved copper-binding and catalytic domains of both LOX and LOXL. These conserved domains are encoded by five consecutive exons within the LOX, LOXL, and LOXL2 genes that also maintain exon-intron structure conservation. Conservation of the nucleotide and deduced amino acid sequence within the carboxyl-terminal end of LOXL2, LOX, and LOXL include the copper-binding domain (WEWHSCHQHYH (SEQ ID NO: 66)) in LOX and LOXL and WIWHDCHRHYH (SEQ ID NO: 67) in LOXL2 with the four histidines that supply the nitrogen ligands for the copper coordination complex specific for lysyl oxidase proteins (Krebs and Krawetz, Biochim. Biophys. Acta 1202: 7-12 (1993)). The active site in LOX (DIDCQW-WIDITDVXPGNY (SEQ ID NO: 68)) and in LOXL2(DID-CQWVDITDVPPPGDY (SEQ ID NO: 69)) contains, in each, a Tyr residue (Y) at the COOH-terminal end, which participates together with a Lys residue in the formation of the quinone co-factor that is present in these proteins. Ten cysteines characteristic of LOX and LOXL are similarly conserved in LOXL2 (Kagan et al., (1994) in Molecular Biology and Pathology of Elastic Tissue (Mecham, R. P., and Roberts, L., eds), Ciba Foundation Symposium Series, Wiley, Chichester, UK). A growth factor and cytokine receptor domain present in the LOX and LOXL proteins has also been identified within the LOXL2-derived amino acid sequence. Four repeats of the scavenger receptor cysteine-rich domain are also present of LOXL2 (Saito et al., J. Biol. Chem. 272: 8157-8160 (1997), Resnick et al., Trends Biochem. Sci. 19: 5-8 (1994)).

Three major transcription termination sites have been noted within 3'-UTR domains of LOXL2 cDNA. The first termination site is 690 bp 3' of the termination codon, the second site is 740 bp, and the final transcription termination site is 900 bp 3' of the termination codon. These mRNAs all have 3'-UTRs differing slightly in size. Most exon-intron boundaries of the LOXL2 gene show the consensus sequence (C/T)AG-exon-GT(A/G). The sizes of the 11 exons of the LOXL2 gene range from 112 to 940 bp. Although the LOXL2 gene has 11 exons, five consecutive exons (exons 6-10), which encode the copper-binding and catalytic domains, exhibit 84% sequence similarity, and exon sizes are very similar to the corresponding exons of the LOX and LOXL genes. All the other exons in the LOXL2 gene are divergent in both sequence and size. LOXL2 has been identified in all tissues with the exception of blood leukocytes. LOXL2 mRNA has been detected in heart, liver, and pancreas; expression is significantly higher in placenta, prostate, uterus, and pancreas (ratios between 2 and 3) compared with lower expression in brain, lung, skeletal muscle, thymus, and kidney (ratios below 0.5). (Jourdan-Le Saux, et al. J. Biol. Chem., 274(18): 12939-12944 (1999)).

The expression of LOX and the different LOXL proteins varies in different diseases. This may be due to a number of reasons, such as the difference in tissue distribution, processing, domains, regulation of activity, as well as other differences between the proteins. For example, LOX and LOXL are implicated in fibrotic diseases as both LOX and LOXL are highly expressed in myo-fibroblasts around fibrotic areas (Kagen, Pathol. Res. Pract, 190:910-919 (1994); Murawaki et al, Hepatology 14:1167-1173 (1991); Siegel et al, Proc. Natl. Acad. Sci. USA 75:2945-2949 (1978); Jourdan Le-Saux et al, Biochem. Biophys. Res. Comm. 199:587-592 (1994); Kim et al, J. Cell Biochem. 72:181-188 (1999)). LOX and the various LOXL are also implicated in a number of cancers. For example, LOXL and LOXL4 have been shown to be epigenetically silenced and can inhibit ras/extracellular signal-regulated kinase signaling pathway in human bladder cancer (Wu et al. Cancer Res. 67:4123-4129 (2007)). Others have shown selective upregulation and amplification of the LOXL4 gene in head and neck squamous cell carcinoma (Gorough et al, J. Pathol. 212:74-82 (2007)). LOX and LOXL2 have also been implicated in a number of tumors, such as colon and esophageal cancers (Csiszar, Prog. Nucl. Acid Res. 70:1-32 (2001)), In breast cancer, LOX and the LOXL family members have been linked to the cancer (Kirschmann et al. Cancer Res. 62:448-4483 (2002)).

Lysyl oxidase catalyzes oxidative deamination of peptidyl lysine and hydroxylysine residues in collagens, and peptidyl lysine residues in elastin. The resulting peptidyl aldehydes spontaneously condense and undergo oxidation reactions to form the lysine-derived covalent cross-links required for the normal structural integrity of the extracellular matrix. In the reaction of lysyl oxidase with its substrates, hydrogen peroxide ($H_2O_2$) and ammonium are released in quantities stoichiometric with the peptidyl aldehyde product. See, e.g., Kagan et al., J. Cell. Biochem. 88:660-72 (2003).

Lysyl oxidase is secreted into the extracellular environment where it is then processed by proteolytic cleavage to a functional 30 kDa enzyme and an 18 kDa propeptide. The 30 kDa lysyl oxidase is enzymatically active whereas the 50 kDa proenzyme is not. Procollagen C-proteinases process pro-lysyl oxidase to its active form and are products of the Bmpl, Tll1 and Tll2 genes. The localization of the enzyme is mainly extracellular, although processed lysyl oxidase also localizes intracellularly and nuclearly. Sequence coding for the propeptide is moderately (60-70%) conserved among LOX and the LOXL proteins, whereas the sequence coding for the C-terminal 30 kDa region of the proenzyme in which the active site is located is highly conserved (approximately 95%). See Kagan et al., J. Cell Biochem. 59:329-38 (1995). LOX is induced by a number of growth factors and steroids such as TGF-β, TNF-α and interferon (Csiszar, Prog. Nucl. Acid Res. 70:1-32 (2001)).

Five different lysyl oxidases are known to exist in both humans and mice, LOX and four LOX related, or LOX-like proteins (LOXL, LOXL2, LOXL3, LOXL4). LOX and the LOX-like proteins are referred to collectively as "LOX/LOXL" for the purposes of the present disclosure. The five forms of lysyl oxidases reside on five different chromosomes. These family members show some overlap in structure and function, but appear to have distinct functions as well. For example, although the main activity of LOX is the oxidation of specific lysine residues in collagen and elastin outside of the cell, it may also act intracellularly, where it may regulate gene expression. In addition, LOX induces chemotaxis of monocytes, fibroblasts and smooth muscle cells. Further, a deletion of LOX in knockout mice appears to be lethal at parturition (Hornstra et al., J. Biol. Chem. 278:14387-14393 (2003)), whereas LOXL deficiency causes no severe developmental phenotype (Bronson et al., Neurosci. Lett. 390:118-122 (2005)).

The main activity of LOX is the oxidation of specific lysine residues in collagen and elastin outside of the cell, however, it may also act intracellularly, where it may regulate gene expression (Li et al., Proc. Natl. Acad. Sci. USA 94:12817-12822 (1997), Giampuzzi et al., J. Biol. Chem. 275:36341-36349 (2000)) In addition, LOX induces chemotaxis of monocytes, fibroblasts and smooth muscle cells (Lazarus et al., Matrix Biol. 14:727-731 (1995) Nelson et al., Proc. Soc. Exp. Biol. Med. 188:346-352 (1988)). LOX itself is induced by a number of growth factors and steroids such as TGF-β, TNF-α and interferon (Csiszar, Prog. Nucl. Acid Res. 70:1-32 (2001)). Recent studies have attributed other roles to LOX in diverse biological functions such as developmental regulation, tumor suppression, cell motility, and cellular senescence. The diverse role of LOX, and its recently discovered amino oxidase family, LOX-like (LOXL), may play important roles with their intracellular and extracellular localization.

As used herein, the term "lysyl oxidase" refers to an enzyme that catalyzes the following reaction: peptidyl-L-lysyl-peptide+$O_2$+$H_2O$→peptidyl-allysyl-peptide+$NH_3$+$H_2O_2$. Other synonyms for lysyl oxidase (EC 1.4.3.13) include protein-lysine 6-oxidase and protein-L-lysine:oxygen 6-oxidoreductase (deaminating). See, e.g., Harris et al., Biochim. Biophys. Acta 341:332-44 (1974); Rayton et al., J. Biol. Chem. 254:621-26 (1979); Stassen, Biophys. Acta 438: 49-60 (1976). A copper-containing quinoprotein with a lysyl adduct of tyrosyl quinone at its active center, LOX catalyzes the oxidation of peptidyl lysine to result in the formation of peptidyl alpha-aminoadipic-delta-semialdehyde. Once formed, this semialdehyde can spontaneously condense with neighboring aldehydes or with other lysyl groups to from intra- and interchain cross-links. See, e.g., Rucker et al., Am. J. Clin. Nutr. 67:996S-1002S (1998).

The term "LOX" refers to an enzyme having an amino acid sequence substantially identical to a polypeptide expressed or translated from one of the following sequences: EMBL/GenBank accession numbers: M94054 (SEQ ID NO: 10); AAA59525.1 (SEQ ID NO: 11)-mRNA; S45875 (SEQ ID NO: 12); AAB23549.1 (SEQ ID NO: 13)-mRNA; S78694 (SEQ ID NO: 14); AAB21243.1 (SEQ ID NO: 15)-mRNA; AF039291 (SEQ ID NO: 16); AAD02130.1 (SEQ ID NO: 17)-mRNA; BC074820 (SEQ ID NO: 18); AAH74820.1 (SEQ ID NO: 19)-mRNA; BC074872 (SEQ ID NO: 20); AAH74872.1 (SEQ ID NO: 21)-mRNA; M84150 (SEQ ID NO: 22); AAA5954L1 (SEQ ID NO: 23)-Genomic DNA. One embodiment of LOX is human lysyl oxidase (hLOX) preproprotein having an amino acid sequence (SEQ ID NO: 7), a secreted hLOX after cleavage of the signal peptide such as SEQ ID NO: 8 or a mature hLOX after proteolytic processing such as SEQ ID NO: 9.

LOX has highly conserved protein domains, conserved in several species including human, mouse, rat, chicken, fish and *Drosophila*. The human LOX family has a highly conserved C-terminal region containing the 205 amino acid LOX catalytic domain. The conserved region contains the copper binding (Cu), conserved cytokine receptor like domain (CRL), and the lysyl-tyrosylquinone cofactor site (LTQ). The predicted extracellular signal sequences are represented by the hatched boxes (See FIG. 7 of U.S. Provisional Application No. 60/963,249, which is incorporated herein by reference). Twelve cysteine residues are also similarly conserved, wherein two of them reside within the prepropepude region and ten are in the catalytically active processed form of LOX (Csiszar, Prog. Nucl. Acid Res. 70:1-32 (2001)). The conserved region also includes a fibronectin binding domain.

The prepropeptide region of LOX contains the signal peptide, and is cleaved, the cleavage site predicted to be between Cys21-Ala22, to generate a signal sequence peptide and a 48 kDa amino acid propeptide form of LOX, which is still inactive. The propeptide is N-glycosylated during passage through the Golgi that is secreted into the extracellular environment where the proenzyme, or propeptide, is cleaved between Gly168-Asp169 by a metalloendoprotease, a procollagen C-proteinase, which are products of the Bmpl, Tll1 and Tll2 genes. BMP I (bone morphogenetic protein I) is a procollagen C-proteinase that processes the propeptide to yield a functional 30 kDa enzyme and an 18 kDa propeptide. The sequence coding for the propeptide is moderately (60-70%) conserved, whereas the sequence coding for the C-terminal 30 kDa region of the proenzyme in which the active site is located is highly conserved (approximately 95%). (Kagan and Li, J. Cell. Biochem 88:660-672 (2003); Kagan et al, J. Cell Biochem 59:329-38 (1995)). The N-glycosyl units are also subsequently removed. LOX occurs in unprocessed and/or processed (mature) forms. The mature form of LOX is typically active although, in some embodiments, unprocessed LOX is also active.

Particular examples of a LOXL enzyme or protein are described in Molnar et al, Biochim Biophys Acta. 1647:220-24 (2003); Csiszar, Prog. Nucl. Acid Res. 70:1-32 (2001); and in WO 01/83702 published on Nov. 8, 2001, all of which are herein incorporated by reference. (It is noted that in these 3 publications, "LOXL1" was referred to as "LOXL" whereas in the present invention "LOXL" is used to refer to a lysyl oxidase-like proteins in general, not just LOXL1.) These enzymes include LOXL1, encoded by mRNA deposited at GenBank/EMBL BC015090; AAH15090.1; LOXL2, encoded by mRNA deposited at GenBank/EMBL U89942; LOXL3, encoded by mRNA deposited at GenBank/EMBL AF282619; AAK51671.1; and LOXL4, encoded by mRNA deposited at GenBank/EMBL AF338441; AAK71934.1.

Similar potential signal peptides as those described above for LOX have been predicted at the amino terminus of LOXL, LOXL2, LOXL3, and LOXL4. The predicted signal cleavage sites are between Gly25-Gln26 for LOXL, between Ala25-Gln26, for LOXL2, and between Gly25-Ser26 for LOXL3. The consensus for BMP-1 cleavage in pro-collagens and pro-LOX is between Ala/Gly-Asp, and often followed by an acidic or charged residue. A potential cleavage site to generate active LOXL is Gly303-Asp304, however, it is then followed by an atypical Pro. LOXL3 also has a potential cleavage site at Gly447-Asp448, which is followed by an Asp, processing at this site may yield an active peptide of similar size to active LOX. A potential cleavage site of BMP-1 was also identified within LOXL4, at residues Ala569-Asp570 (Kim et al., J. Biol. Chem. 278:52071-52074 (2003)). LOXL2 may also be proteolytically cleaved analogously to the other members of the LOXL family and secreted (Akiri et al., Cancer Res. 63:1657-1666 (2003)).

LOX and LOXL enzymes act via a ping-pong mechanism which can be described by Michaelis-Menten kinetics (see FIG. 1).

An example of LOX or LOXL protein include the enzyme having an amino acid sequence substantially identical to a polypeptide expressed or translated from one of the following sequences: EMBL/GenBank accessions: M94054; AAA59525.1-mRNA; S45875; AAB23549.1-mRNA; S78694; AAB21243.1-mRNA; AF039291; AAD02130.1-mRNA; BC074820; AAH74820.1-mRNA; BC074872; AAH74872.1-mRNA; M84150; AAA59541.1-Genomic DNA.

The terms "LOX" and "LOXL" also encompass functional fragments or derivatives that substantially retain enzymatic activity catalyzing the deamination of lysyl residues. Typically, a functional fragment or derivative retains at least 50% of 60%, 70%, 80%, 90%, 95%, 99% or 100% of its lysyl oxidation activity. It is also intended that a LOX or a LOXL2 protein can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity. See, e.g., Watson, et al., Molecular Biology of the Gene, 4th Edition, 1987, The Benjamin/Cummings Pub. Co., p. 224. Conservative and non-conservative amino acid substitutions have been described above.

A feature not known to be common amongst the LOX and LOXL proteins is the scavenger receptor cysteine rich (SRCR) domains. LOX and LOXL lack SRCR domains, whereas LOXL2, LOXL3, and LOXL4 each have four SRCR domains at the N-terminus. SRCR domains are found in secreted, transmembrane, or extracellular matrix proteins. SRCR domains are also known to mediate ligand binding in a number of secreted and receptor proteins (Hoheneste et al., Nat. Struct. Biol. 6:228-232 (1999); Sasaki et al., EMBO J. 17:1606-1613 (1998)). Another domain unique to LOXL is the presence of a proline rich domain (Molnar et al., Biochimica Biophsyica Acta 1647:220-224 (2003)).

Tissue distribution may also differ amongst LOX and the various LOXL. LOX is highly expressed in the heart, placenta, testis, lung, kidney and uterus, but marginally in the brain and liver. LOXL1 is expressed in the placenta, kidney, muscle, heart, lung, and pancreas, and as with LOX, has much lower expressing in the brain and liver (Kim et al., J. Biol. Chem. 270:7176-7182 (1995)). LOXL2 is highly expressed in the uterus, placenta, and other organs, but similar to LOX and LOXL, lowly expressed in the brain and liver (Jourdan Le-Saux et al., J. Biol. Chem. 274:12939:12944 (1999)). LOXL3 is highly expressed in the testis, spleen, and prostate, moderately in placenta, and not in the liver, whereas LOXL4 is highly expressed in the liver (Huang et al., Matrix Biol. 20:153-157 (2001); Maki and Kivirikko, Biochem. J. 355: 381-387 (2001); Jourdan Le-Saux et al., Genomics 74:211-218 (2001); Asuncion et al., Matrix Biol. 20:487-491 (2001)).

The expression, or implication of LOX and the different LOXL proteins, in diseases may also vary. This may be due to a number of reasons, such as the difference in tissue distribution, processing, domains, regulation of activity, as well as other differences between the proteins. For example, LOX and LOXL are implicated in fibrotic diseases as both LOX and LOXL are highly expressed in myo-fibroblasts around fibrotic areas (Kagen, Pathol. Res. Pract. 190:910-919 (1994); Murawaki et al, Hepatology 14:1167-1173 (1991); Siegel et al, Proc. Natl. Acad. Sci. USA 75:2945-2949 (1978); Jourdan Le-Saux et al, Biochem. Biophys. Res. Comm. 199: 587-592 (1994); Kim et al, J. Cell Biochem. 72:181-188 (1999)). LOX and the various LOXL are also implicated in a number of cancers. For example, LOXL and LOXL4 have been shown to be epigenetically silenced and can inhibit ras/extracellular signal-regulated kinase signaling pathway in human bladder cancer (Wu et al. Cancer Res. 67:4123-4129 (2007)). Others have shown selective upregulation and amplification of the LOXL4 gene in head and neck squamous cell carcinoma (Gorough et al, J. Pathol. 212:74-82 (2007)). LOX and LOXL2 have also been implicated in a number of tumors, such as colon and esophageal cancers (Csiszar, Prog. Nucl. Acid Res. 70:1-32 (2001)). In breast cancer, LOX and the LOXL family members have been linked to the cancer (Kirschmann et al. Cancer Res. 62:448-4483 (2002)).

III. Epithelial—Mesenchymal Transition

Epithelial-to-Mesenchymal Transition (EMT) refers to the process whereby a cell with a gene expression/phenotype characteristic of epithelial cell (i.e., expressing specific proteins, factors, and molecules) changes or alters the genes or their level of expression which results in a change in the phenotype of the cell as exhibited by the alteration or change in the genes expressed.

Epithelial and mesenchymal cells represent distinct lineages, each with a unique gene expression profile that imparts attributes specific to each cell type. Conversion of an epithelial cell into a mesenchymal cell requires alterations in morphology, cellular architecture, adhesion, and/or migration capacity. Advanced tumor cells frequently exhibit a conspicuous down-regulation of epithelial markers and a loss of intercellular junctions, resulting in a loss of epithelial polarity and reduced intercellular adhesion. The loss of epithelial features is often accompanied by increased cell motility and expression of mesenchymal genes. EMT can include loss of contact inhibition, altered growth control, and/or enhanced invasiveness (Christiansen and Rajasekaran, Cancer Res, 66(17): 8319-8326 (2006); and Thiery et al, Curr. Opin. Cell. Biol, 15:740-6 (2003)). Molecular and morphologic features indicative of EMT correlate with poor histologic differentiation, destruction of tissue integrity, and metastasis. EMT provides mechanisms for epithelial cells to overcome the physical constraints imposed on them by intercellular junctions and adopt a motile phenotype (Burdsal et al. Development, 118:829-44 (1993); and Nieto et al, Mech, Dev., 105:27-35 (2001)).

Commonly used molecular markers for EMT include increased expression of N-cadherin and vimentin, nuclear localization of β-catenin, and increased production of the transcription factors such as Snail1 (Snail), Snail2 (Slug), Twist, EF1/ZEB1, SIP1/ZEB2, and/or E47 that inhibit E-cadherin production. Phenotypic markers for an EMT include, but are not limited to, an increased capacity for migration and three-dimensional invasion, as well as resistance to apoptosis. These markers have further been correlated with induction of EMT and an association with cancerous phenotypes.

The occurrence of EMT during tumor progression allows tumor cells to acquire the capacity to infiltrate surrounding tissue and ultimately to metastasize to distant sites. Changes in gene expression within tumor cells can indicate a progression from epithelial or epithelial-like gene expression pattern to a mesenchymal or mesenchymal-like gene expression pattern. By way of example, the identification of loss of E-cadherin is correlated with metastatic carcinoma as well as resistance to cancer therapies such as EGFR inhibitors and IGF-R1 inhibitors. Analysis of many different types of cancer reveals that circulating tumor cells, or those found as micrometastases, evidence mesenchymal conversion based on changes of expression in a set of markers. These markers include, but are not limited to, EGFR, E-cadherin, ErbB3, RAB25, integrin beta 6, cadherin-2, fibroblast growth factor binding protein 1, distal-less homeo box 1, ZEB1 (transcription factor 8), SIP1, and vimentin.

By way of example, an epithelial-like gene expression profile includes expression, or increase expression of genes such as E-cadherin, ErbB3, or EGFR. An epithelial-like gene expression profile can include the expression of one or more of these genes, at least two, or at least three of these genes.

As with the previously described therapy-resistant cancers, the expression levels of E-cadherin, ErbB3, RAB25, integrin beta 6, cadherin-2, fibroblast growth factor binding protein 1, distal-less homeo box 1, ZEB1 (transcription factor 8), SIP1, TGF-β, FOXC2, GSK-3β, Smad-3, Pez, Snail1, Snail2, and ILK, and vimentin represent genes that are common to EMT characteristics as well as with those epithelial-based tumor cells/cancers that develop resistance to their respective therapies. The present invention also generally relates to a method to treat a patient with cancer, and particularly a cancer that has experienced EMT. The inventors have discovered that cancers that have experienced EMT or have switched from an epithelial-like gene expression pattern to a mesenchymal-like gene expression pattern are responsive to LOX/LOXL inhibitors.

For assessment of tumor cell epithelial or mesenchymal biomarker expression, patient samples containing tumor cells, or proteins or nucleic acids produced by these tumor cells, can be used in methods described, for example, in U.S.

patent application Publication Number 20070065858, which is incorporated in its entirety by reference herein. Briefly, the level of expression of the biomarker can be assessed by assessing the amount (e.g., absolute amount or concentration) of the marker in a tumor cell sample, e.g., a tumor biopsy obtained from a patient, or other patient sample containing material derived from the rumor (e.g., blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies can also be subjected to post-collection preparative and storage techniques, e.g., fixation.

One can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods can be used to detect such proteins on whole cells, or well known computer-based sequence analysis methods can be used to predict the presence of at least one extracellular domain (i.e., including both secreted proteins and proteins having at least one cell-surface domain). Expression of a marker protein having at least one portion which is displayed on the surface of a cell which expresses it can be detected without necessarily lysing the tumor cell (e.g., using a labeled antibody which binds specifically with a cell-surface domain of the protein).

Expression of biomarkers can be assessed by any of a wide variety of well known methods for detecting expression of a transcribed nucleic acid or protein. Non-limiting examples of such methods include, for example, immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

Expression of a biomarker can be assessed using an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair (e.g., biotin-streptavidin), or an antibody fragment (e.g., a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g., glycosylation, phosphorylation, methylation etc.).

Expression of a biomarker can also be assessed by preparing mRNA/cDNA (i.e., a transcribed polynucleotide) from cells in a patient sample, and by hybridizing the mRNA/cDNA with a reference polynucleotide which is a complement of a biomarker nucleic acid, or a fragment thereof. cDNA can, optionally, be amplified using any of a variety of polymerase chain reaction methods prior to hybridization with the reference polynucleotide. Expression of one or more biomarkers can likewise be detected using quantitative PCR to assess the level of expression of the biomarker(s). Alternatively, any of the many known methods of detecting mutations or variants (e.g., single nucleotide polymorphisms, deletions, etc.) of a biomarker can be used to detect occurrence of a biomarker in a patient.

A mixture of transcribed polynucleotides obtained from the sample can be contacted with a substrate having fixed thereto a polynucleotide complementary to or homologous with at least a portion (e.g., at least 7, 10, 15, 20, 25, 30, 40, 50, 100, 500, or more nucleotide residues) of a biomarker nucleic acid. If polynucleotides complementary to, or homologous with, are differentially detectable on the substrate (e.g., detectable using different chromophores or fluorophores, or fixed to different selected positions), then the levels of expression of a plurality of biomarkers can be assessed simultaneously using a single substrate (e.g., a "gene chip" microarray of polynucleotides fixed at selected positions). When a method of assessing biomarker expression is used which involves hybridization of one nucleic acid with another, hybridization can be performed under stringent hybridization conditions.

When a plurality of biomarkers of the invention are used in the methods of the invention, the level of expression of each biomarker in a patient sample can be compared with the normal level of expression of each of the plurality of biomarkers in non-cancerous samples of the same type, either in a single reaction mixture (i.e., using reagents, such as different fluorescent probes, for each biomarker) or in individual reaction mixtures corresponding to one or more of the biomarkers.

The level of expression of a biomarker in normal (i.e., non-cancerous) human tissue can be assessed in a variety of ways. This normal level of expression can be assessed by assessing the level of expression of the biomarker in a portion of cells which appears to be non-cancerous, and then comparing the normal level of expression with the level of expression in a portion of the tumor cells. As further information becomes available as a result of routine performance of the methods described herein, population-average values for normal expression of the biomarkers can be used. Alternatively, the normal level of expression of a biomarker can be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample (e.g., a tumor-associated body fluid) from a test subject and contacting the biological sample with a compound or an agent capable of detecting the polypeptide or nucleic acid (e.g., mRNA, genomic DNA, or cDNA). The detection methods can, thus, be used to detect mRNA, protein, cDNA, or genomic DNA, for example, in a biological sample in vitro as well as in vivo. In vitro techniques for detection of mRNA include, for example, Northern hybridizations and in situ hybridizations. In vitro techniques for detection of a biomarker protein include, but are not limited to, enzyme linked immunosorbent assays (ELISAs), Western blots, immunoprecipitation and immunofluorescence. In vitro techniques for detection of genomic DNA include, for example, Southern hybridizations. In vivo techniques for detection of mRNA include, for example, polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay involves anchoring the biomarker or probe onto a solid phase support, also referred to as a substrate, and detecting target biomarker/probe complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the probe can be anchored to a solid phase and a sample from a subject can be allowed to react as an unanchored component of the assay.

There are several established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored. Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite. In order to conduct assays with the above mentioned approaches, the non-immobilized component is added to the solid phase upon which the second component is anchored. After the reaction is complete, uncomplexed components can be removed (e.g., by washing) under conditions such that any complexes formed will remain immobilized upon the solid phase. The detection of biomarker/probe complexes anchored to the solid phase can be accomplished in a number of methods outlined herein. In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e., FET, see for example, Lakowicz et al., U.S. Pat. No. 5,631,169; Stavrianopoulos, et al., U.S. Pat. No. 4,868,103). A fluorophore label on the first, donor molecule is selected such that, upon excitation with incident light of appropriate wavelength, its emitted fluorescent energy will be absorbed by a fluorescent label on a second acceptor molecule, which in turn is able to fluoresce due to the absorbed energy. Alternately, the donor protein molecule can simply utilize the natural fluorescent energy of tryptophan residues. Labels are chosen that emit different wavelengths of light, such that the acceptor molecule label can be differentiated from that of the donor. Since the efficiency of energy transfer between the labels is related to the distance separating the molecules, spatial relationships between the molecules can be assessed. In a situation in which binding occurs between the molecules, the fluorescent emission of the acceptor molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S, and Urbaniczky, C, 1991, Anal. Chem. 63:2338-2345 and Szabo et al, 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes can be separated from uncomplexed assay components through a series of centrifugal steps, due to the different sedimentation equilibria of complexes based on their different sizes and densities (see, for example, Rivas, G, and Minton, A. P, 1993, Trends Biochem Sci. 18(8):284-7). Standard chromatographic techniques can also be utilized to separate complexed molecules from uncomplexed ones. For example, gel filtration chromatography separates molecules based on size, and through the utilization of an appropriate gel filtration resin in a column format; for example, the relatively larger complex can be separated from the relatively smaller uncomplexed components. Similarly, the relatively different charge properties of the biomarker/probe complex as compared to the uncomplexed components can be exploited to differentiate the complex from uncomplexed components, for example through the utilization of ion-exchange chromatography resins. Such resins and chromatographic techniques are well known to one skilled in the art (see, e.g., Heegaard, N. H, 1998, J. Mol. Recognit. Winter 11(1-6): 141-8; Hage, D. S, and Tweed, S. A. J. Chromatogr B Biomed Sci Appl Oct. 10, 1997; 699(1-2):499-525). Gel electrophoresis can also be employed to separate complexed assay components from unbound components (see, e.g., Ausubel et al, ed. Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically used. Appropriate conditions to the particular assay and components thereof will be well known to one skilled in the art.

In another embodiment, the level of biomarker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al. ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15,30,50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared and/or processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations can be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-tumor sample, or between samples from different sources.

Alternatively, the expression level can be provided as a relative expression level. To determine a relative expression level of a biomarker (e.g., a mesenchymal biomarker), the level of expression of the biomarker is determined for 10 or more, 20 or more, 30 or more, 40 or more, or 50 or more samples of normal versus cancer cell isolates prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. One type of agent for detecting biomarker protein of the invention is an antibody capable of binding to such a protein or a fragment thereof such as, for example, a detectably labeled antibody. Antibodies can be polyclonal or monoclonal. An intact antibody, or an antigen binding fragment thereof (e.g., Fab, F(ab')2, Fv, scFv, single binding chain polypeptide) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, either the antibody or proteins can be immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin B12, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional cross-linking, and heterobifunctional cross-linking. Carbodiimide coupling is an effective method of coupling carboxyl groups on one substance to amine groups on another. Carbodiimide coupling is facilitated by using the commercially available reagent 1-ethyl-3-(dimemyl-aminopropyl)-carbodhrnide (ED AC).

Homobifunctional cross-linkers, including the bifunctional imidoesters and bifunctional N-hydroxysuccmimide esters, are commercially available and are employed for coupling amine groups on one substance to amine groups on another. Heterobifunctional cross-linkers are reagents which possess different functional groups. The most common commercially available heterobifunctional cross-linkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chermluminescent or electrochemical materials. Two commonly used radioactive isotopes are 125I and 3H. Standard radioactive isotopic labeling procedures include the chloramine T, lactoperoxidase and Bolton-Hunter methods for 125I and reductive methylation for 3H. The term "detectably-labeled" refers to a molecule labeled in such a way that it can be readily detected by the intrinsic enzymatic activity of the label or by the binding to the label of another component, which can itself be readily detected.

Enzymes suitable for use in this invention include, but are not limited to, horseradish peroxidase, alkaline phosphatase, $\beta$-galactosidase, glucose oxidase, luciferases, including firefly and renilla, $\beta$-lactamase, urease, green fluorescent protein (GFP) and lysozyme. Enzyme labeling is facilitated by using dialdehyde, carbodiimide coupling, homobifunctional cross-linkers and heterobifunctional cross-linkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Temynck, Immunochemistry 8, 1175 (1975), Ishikawa et al, J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above. Thus, in one embodiment, biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used for chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g., aminated or carboxylated polystyrene, polyacrylamides, polyamides, polyvinylchloride, glass beads, agarose, or nitrocellulose.

IV. Anti-LOX Antibodies and Anti-LOXL2 Antibodies

Provided herein are antibodies that can be used to diagnose angiogenesis and associated diseases, fibrosis and associated diseases, tumors or metastasis. Provided herein are antibodies that inhibit angiogenesis and associated diseases, inhibit fibrosis and associated diseases, and treat tumors or metastasis. Provided herein are antibodies that can be used to monitor efficacy of treatment regimens and protocols and the like as described throughout the present application and known in the art. Antibodies and antigen binding fragments useful in such methods are those, for example, that specifically bind LOX or LOXL2.

The disclosure also describes cell lines which produce the antibodies or functional fragments thereof, methods for producing the cell lines, and methods for producing the antibodies or functional fragments thereof.

The term "antibody" or "antibody molecule" in the various grammatical forms is used herein as a collective noun that refers to a population of immunoglobulin molecules and/or immunologically active portions of immunoglobulin molecules, i.e., molecules that contain an antibody combining site or paratope. Thus, reference to an "antibody" also includes reference to any of the antigen binding fragments of antibodies.

As used herein, "immunoreactive" refers to antibodies or fragments thereof that are specific to a sequence of amino acid residues ("binding site" or "epitope"), yet if are cross-reactive to other peptides/proteins, are not toxic at the levels at which they are formulated for administration to human use. "Epitope" refers to that portion of an antigen capable of forming a binding interaction with an antibody or antigen binding fragment thereof. Such binding interaction can be manifested as an intermolecular contact with one or more amino acid residues of a CDR. Antigen binding can involve a CDR3 or a CDR3 pair. An epitope can be a linear peptide sequence (i.e., "continuous") or can be composed of noncontiguous amino acid sequences (i.e., "conformational" or "discontinuous"). The term "preferentially binds" means that the binding agent binds to the binding site with greater affinity than it binds unrelated amino acid sequences.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femromolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "antibody" also includes molecules which have been engineered through the use of molecular biological techniques to include only portions of the native molecule as long as those molecules have the ability to bind a particular antigen or sequence of amino acids with the required specificity. Such alternative antibody molecules include classically known portions of the antibody molecules, single chain antibodies, and single chain binding molecules.

An "antibody combining site" is that structural portion of an antibody molecule comprised of heavy and light chain variable and hypervariable regions that specifically binds antigen.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

"An inhibitor of LOX activity" or "an inhibitor of LOXL2 activity" can be an antibody or an antigen binding fragment thereof that directly or indirectly inhibits activity of lysyl oxidase, including but not limited to gene expression, post-translation modification, enzymatic processing or cleavage, binding to a modulator of LOX/LOXL2, enzymatic activity of LOX/LOXL2 or any other activity described herein.

As used herein, the term "antibody" refers to an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full length monoclonal antibodies), polyclonal antibodies, human antibodies, humanized antibodies, chimeric antibodies, diabodies, multispecific antibodies (e.g., bispecific antibodies), and antibody fragments including but not limited to single chain binding polypeptides, VH, VL, Fv, scFv, Fab, and Fab2, etc, so long as they exhibit the desired biological activity. The term "human antibody" therefore refers to antibodies containing sequences of human origin, except for possible non-human CDR regions, and does not imply that the full structure of an Ig molecule be present, only that the antibody has nnnimal immunogenicity in a human.

The term "binding" refers to a direct association between two molecules, due to, for example, covalent, electrostatic, hydrophobic, and ionic and/or hydrogen-bond interactions, including interactions such as salt bridges and water bridges. The term "specific binding" is applicable to a situation in which an antibody or antigen binding fragment thereof does not show any significant binding to molecules other than its epitope. In one embodiment, an antibody or antigen binding fragment thereof specifically binds to a human LOX or to human LOXL2 with a dissociation constant Kd equal to or lower than about 100 nM, lower than about 10 nM, lower than about 1 nM, lower than about 0.5 nM, lower than about 0.1 nM, lower than about 0.01 nM, or lower than about 0.005 nM measured at a temperature of about 4° C., 25° C., 37° C. or 42° C.

Conventional methods can be used to prepare antibodies. For example, by using a peptide or full length lysyl oxidase protein, polyclonal antisera or monoclonal antibodies can be made using standard methods. A mammal, (e.g., a mouse, hamster, or rabbit) can be immunized with an immunogenic form of the peptide that elicits an antibody response in the mammal. Techniques for conferring enhanced immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

The antibodies can be generated in cell culture, in phage, or in various animals, including but not limited to cows, rabbits, goats, mice, rats, hamsters, guinea pigs, sheep, dogs, cats, monkeys, chimpanzees, apes. Therefore, an antibody useful in the present methods is typically a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, Antibody Production: Essential Techniques (Wiley, 1997); Shephard, et al., Monoclonal Antibodies (Oxford University Press, 2000); and Goding, Monoclonal Antibodies: Principles and Practice (Academic Press, 1993).

Antibodies also can be made according to the protocol described by in Kenney, et al. ("Production of monoclonal antibodies using a secretion capture report web." Biotechnology 13:787-790, 1995). Briefly, mice are injected subcutaneously (s.c), with antigen in an adjuvant formulation. For peptide antigens, peptides are conjugated to bovine serum albumin and formulated in Freund's Adjuvant (FA) prior to immunization. For protein antigens, the protein is formulated in Alhydrogel-Muramyl Dipeptide (ALD/MDP) adjuvant. Cells from the spleen and lymph nodes of the mice are isolated and fused with appropriate cells and cultured. A hybridoma library of HAT-selected cells is isolated and is cloned. Cells are sorted and sera and supernatants are screened for the presence of antibodies.

"Antibody fragments" comprise a portion of an intact antibody, and can include the antigen binding or variable region of an intact antibody. Examples of antibody fragments include Fab, Fab', F(ab')2, Fv fragments, scFv fragments, diabodies, linear antibodies (Zapata et al., Protein Eng. 8(10): 1057-1062 (1995)), single-chain antibody molecules, single chain binding polypeptides, and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

A "single chain binding polypeptide" refers to a polypeptide having a heavy chain variable region, a light chain variable region and, optionally, an immunoglobulin Fc region. Such a molecule is a single chain variable fragment optionally having effector function through the presence of the immunoglobulin Fc region. Methods of preparing single chain binding polypeptides are known in the art (e.g., US. Patent Application 2005/0238646).

"Fv" refers to an antibody fragment which contains a complete antigen-recognition and -binding site. This region consists of a dimer of one heavy- and one light chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

A "Fab" fragment contains a "Fv" and also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

"Single-chain Fv" or "sFv" antibody fragments comprise the VH and VL domains of antibody, wherein these domains are present in a single polypeptide chain. A Fv polypeptide can further include, if needed, a polypeptide linker between the VH and VL domains, which enables the sFv to form a desired structure for antigen binding. For a review of sFv, see Pluckthun in The Pharmacology of Monoclonal Antibodies, vol. 113, Rosenburg and Moore eds, Springer-Verlag, New York, pp. 269-315(1994).

The term "diabodies" refers to small antibody fragments with two antigen-binding sites, which fragments contain a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al, Proc. Natl. Acad. Sci. USA, 90:6444-6448 (1993).

An antibody can also be a bispecific antibody. Bispecific antibodies are monoclonal, chimeric, human or humanized antibodies that have binding specificities for at least two different antigens. In the present case, one of the binding specificities is, for example, LOX or LOXL2, the other one is for any other antigen, such as, for example, a cell-surface protein or receptor or receptor subunit. In additional embodiments, a bispecific antibody is specific for LOX and LOXL2.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537 539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al, EMBO J, 10:3655-3659 (1991).

Antibody variable domains with the desired binding specificities (antibody-antigen combining sites) can be fused to immunoglobulin constant domain sequences using conventional methods known in the art. The fusion is, generally, with an immunoglobulin heavy-chain constant domain, containing at least part of the hinge, CH2, and CH3 regions. In one embodiment, the first heavy-chain constant region (CH1) containing the site necessary for light-chain binding is present in at least one of the fusions. DNAs encoding the immunoglobulin heavy-chain fusions and, if desired, the immunoglobulin light chain, can be inserted into separate expression vectors, and can be co-transfected into a suitable host organism. For further details of generating bispecific antibodies see, for example, Suresh et al. Methods in Enzymology, 121:210 (1986).

According to another approach described in WO 96/27011, the interface between a pair of antibody molecules can be engineered to maximize the percentage of heterodimers that are recovered from recombinant cell culture. The interface can comprise at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies can be prepared as full length antibodies or antibody fragments (e.g., F(ab')2 bispecific antibodies). Techniques for generating bispecific antibodies from antibody fragments have been described in the literature. For example, bispecific antibodies can be prepared can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with meTcaptoemylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells over-expressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain (VH) connected to a light-chain variable domain (VL) by a linker that is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies may bind to two different epitopes on a given LOX or LOXL2 polypeptide herein. Alternatively, an anti-LOX or anti-LOXL2 polypeptide arm may be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD 16) so as to focus cellular defense mechanisms to the cell expressing a particular target polypeptide. Bispecific antibodies can also be used to localize cytotoxic agents to cells that express a particular target polypeptide. These antibodies possess a target-binding arm and an arm that binds a cytotoxic agent or a radionuclide chelator, such as EOTUBE, DPT A, DOTA, or TETA. Another bispecific antibody of interest binds the target polypeptide and further binds tissue factor (TF).

The anti-LOX antibody or anti-LOXL2 antibody can also be a heteroconjugate antibody. Heteroconjugate antibodies are composed of two covalently joined antibodies. Such antibodies have, for example, been proposed to target immune system cells to unwanted cells (U.S. Pat. No. 4,676,980) and for treatment of HIV infection (WO 91/00360 and WO 92/200373). Antibodies can be prepared in vitro using known methods in synthetic protein chemistry, including those involving cross-linking agents. For example, immunotoxins can be constructed using a disulfide exchange reaction or by forming a thioether bond. Examples of suitable reagents for this purpose include, but are not limited to, iminothiolate and methyl-4-mercaptobulyrimidate and those disclosed, for example, in U.S. Pat. No. 4,676,980.

It may be desirable to modify an anti-LOX antibody or anti-LOXL2 antibody with respect to effector function, so as to enhance, e.g., the effectiveness of the antibody in treating or preventing cancer metastasis. For example, cysteine residue(s) may be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al, J. Exp Med, 176:1191-1195 (1992) and Shopes, J. Immunol, 148:2918-2922 (1992). Homodimeric antibodies with enhanced anti-tumor activity can also be prepared using heterobifunctional cross-linkers as described in Wolff et al. Cancer Research, 53:2560-2565 (1993). Alternatively, an antibody can be engineered that has dual Fc regions and may thereby have enhanced complement lysis and ADCC capabilities. See Stevenson et al, Anti-Cancer Drug Design, 3:219-230 (1989).

An "isolated antibody" is one that has been identified and separated and/or recovered from a component of its natural environment. Contaminant components of its natural environment are materials that would interfere with diagnostic or therapeutic uses for the antibody, and can include, for example, enzymes, hormones, and other proteinaceous or non-proteinaceous solutes. In one embodiment, an antibody will be purified (1) to greater than 80%, 85%, 90%, 95%, or 99% by weight of antibody as determined by the Lowry method, (2) to a degree sufficient to obtain at least 15 residues of N-terminal or internal amino acid sequence by use of a spinning cup sequenator, and/or (3) to homogeneity by SDS-PAGE under reducing or non-reducing conditions using Coomassie blue or silver stain. The term "isolated antibody" includes within its scope an antibody in situ within recombinant cells since at least one component of the antibody's natural environment will not be present. Generally, isolation of an antibody or antigen binding fragment thereof will include at least one purification step.

An antibody can be a humanized antibody or a human antibody. Humanized forms of non-human (e.g., murine) antibodies include, for example, chimeric immunoglobulins, immunoglobulin chains or fragments thereof (such as Fv, scFv, Fab, Fab', F(ab')2, single chain binding polypeptide, VH, VL, or other antigen-binding subsequences of antibodies) which contain minimal sequence derived from non-human immunoglobulin. Chimeric antibodies include those in which the heavy and light chain variable regions are combined with human constant regions (Fc). Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence.

A humanized antibody can also contain at least a portion of an immunoglobulin constant region (Fc), typically that of a human immunoglobulin (Jones et al., Nature, 321:522-525 (1986); Riechmann et al., Nature, 332:323-329(1988); and Presta, Curr. Op. Struct Biol. 2:593-596 (1992)).

Methods for humanizing non-human antibodies are well known in the art. Generally, a humanized antibody has one or more amino acid residues introduced into it from a source that is non-human. These non-human amino acid residues are often referred to as "import" or "donor" residues, which are typically taken from an "import" or "donor" variable domain. Humanization can be essentially performed following the method of Winter and co-workers (Jones et al., Nature, 321: 522 525 (1986); Riechmann et al., Nature, 332:323 327 (1988)); Verhoeyen et al. Science, 239:1534 1536 (1988)), by substituting rodent CDRs or CDR sequences for the corresponding sequences of a human antibody. Accordingly, such "humanized" antibodies include chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al., J. Mol. Biol., 222:581 (1991)). The techniques of Cole et al. and BoerneT et al. are also available for the preparation of human monoclonal antibodies (Cole et al., Monoclonal Antibodies and Cancer Therapy, Alan R Liss, p. 77 (1985) and Boerner et al., J. Immunol., 147(1):86-95 (1991)), Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812 13 (1994); Fishwald et al., Nature Biotechnology 14, 845-51 (1996); Neuberger, Nature Biotechnology 14, 826 (1996); Lonberg and Huszar, Intern. Rev. Immunol. 13:65-93 (1995).

Murine monoclonal antibodies have been developed that bind LOX or LOXL2 and block the enzymatic activity thereof. Humanized antibodies and antigen-binding fragments thereof described herein are created by humanization of the VL and VH sequences of the murine monoclonal anti-LOX and anti-LOXL2 antibodies.

Humanized immunoglobulins, including humanized antibodies, have been constructed by means of genetic engineering. Most humanized immunoglobulins that have been previously described have comprised a framework that is identical to the framework of a particular human immunoglobulin chain (i.e., an acceptor or recipient), and three CDRs from a non-human (donor) immunoglobulin chain. As described herein, humanization can also include criteria by which a limited number of amino acids in the framework of a humanized immunoglobulin chain are identified and chosen to be the same as the amino acids at those positions in the donor rather than in the acceptor, in order to increase the affinity of an antibody comprising the humanized immunoglobulin chain.

The present invention is based in part on the model that two contributing causes of the loss of affinity in prior means of producing humanized antibodies (using as examples mouse antibodies as the source of CDRs) are: (1) when the mouse CDRs are combined with a human framework, the amino acids in the frameworks close to the CDRs become human instead of mouse. Without intending to be bound by theory, these changed amino acids may slighdy distort the CDRs (e.g., they may create different electrostatic or hydrophobic forces than in the donor mouse antibody, and the distorted-CDRs may not make as effective contacts with the antigen as the CDRs did in the donor antibody); (2) also, amino acids in the original mouse antibody that are close to, but not part of, the CDRs (i.e., still part of the framework), may make contacts with the antigen that contribute to affinity. These amino acids are lost when the antibody is humanized because, generally, all framework amino acids are made human. To circumvent these issues, and to produce humanized antibodies that have a very strong affinity for a desired antigen, humanized antibodies and anugen-binging fragments thereof can be constructed using one or more of the following principles.

One principle is that as acceptor, a framework is used from a particular human immunoglobulin that is unusually homologous to the donor immunoglobulin to be humanized, or use a consensus framework from many human antibodies is used as an acceptor. For example, comparison of the sequence of a mouse heavy (or light) chain variable region against human heavy (or light) variable regions in a data bank (for example, the National Biomedical Research Foundation Protein Identification Resource or the protein sequence database of the National Center for Biotechnology Information—NCBI) shows that the extent of homology to different human regions can vary greatly, for example from about 40% to about 60%, about 70%, about 80%, or higher. By choosing as the acceptor immunoglobulin one of the human heavy chain variable regions that is most homologous to the heavy chain variable region of the donor immunoglobulin, fewer amino acids will be changed in going from the donor immunoglobulin to the humanized immunoglobulin. By choosing as the acceptor immunoglobulin one of the human light chain variable regions that is most homologous to the light chain variable region of the donor immunoglobulin, fewer amino acids will be changed in going from the donor immunoglobulin to the humanized immunoglobulin. Generally, using such techniques, there is a reduced chance of changing an amino acid near one or more of the CDRs that distorts their conformation. Moreover, the precise overall shape of a humanized antibody comprising the humanized immunoglobulin chain may more closely resemble the shape of the donor antibody, thereby also reducing the chance of distorting the CDRS.

One can also use light and heavy chains from the same human antibody as acceptor sequences, to improve the likelihood that the humanized light and heavy chains will make favorable contacts with each other. Alternatively, one can also use light and heavy chains from different human antibody germline sequences as acceptor sequences; when such combinations are used, one can readily determine whether the VH and VL bind an epitope of interest using conventional assays (e.g., an ELISA). In one example, the human antibody will be chosen in which the light and heavy chain variable regions sequences, taken together, are overall most homologous to the donor light and heavy chain variable region sequences. Sometimes greater weight will be given to the heavy chain sequence. Regardless of how the acceptor immunoglobulin is chosen, higher affinity can, in some cases, be achieved by selecting a small number of amino acids in the framework of the humanized immunoglobulin chain to be the same as the amino acids at those positions in the donor rather than in the acceptor. Methods of affinity maturation are known in the art.

Humanized antibodies generally have at least three potential advantages over mouse or chimeric antibodies for use in human therapy. Because the effector portion of an antibody is human, it is believed to interact better with the other parts of the human immune system (e.g., destroy the target cells more efficiently by complement-dependent cytotoxicity (CDC) or antibody-dependent cellular cytotoxicity (ADCC)). Additionally, the human immune system should not recognize the framework or constant region of the humanized antibody as foreign, and therefore the antibody response against such an injected antibody should be less than against a totally foreign mouse antibody or a partially foreign chimeric antibody. Finally, mouse antibodies are known to have a half-life in the human circulation that is much shorter than the half-life of human antibodies. Humanized antibodies can, presumably, have a half-life more similar to naturally-occurring human antibodies, allowing smaller and less frequent doses to be given.

Humanization of antibodies and antigen-binding fragments thereof, can be accomplished via a variety of methods known in the art and described herein. Similarly, production of humanized antibodies can also be accomplished via methods known in the art and described herein.

Methods for modifications of framework regions are known in the art and are contemplated herein. Selection of one or more relevant framework amino acid positions to be altered depends on a variety of criteria. One criterion for selecting relevant framework amino acids to change can be the relative differences in amino acid framework residues between the donor and acceptor molecules. Selection of relevant framework positions to alter using this approach has the advantage of avoiding any subjective bias in residue determination or any bias in CDR binding affinity contribution by the residue.

Another criterion that can be used for determining the relevant amino acid positions to change can be, for example, selection of framework residues that are known to be important or to contribute to CDR conformation. For example, canonical framework residues are important for CDR conformation and/or structure. Targeting of a canonical framework residue as a relevant position to change can be used to identify a more compatible amino acid residue in context with its associated donor CDR sequence.

The frequency of an amino acid residue at a particular framework position is another criterion which can be used for selecting relevant framework amino acid positions to change. For example, comparison of the selected framework with other framework sequences within its subfamily can reveal residues that occur at minor frequencies at a particular position or positions. Positions harboring less abundant residues are similarly applicable for selection as a position to alter in the acceptor variable region framework.

The relevant amino acid positions to change also can be selected, for example, based on proximity to a CDR. In certain contexts, FR residues can participate in CDR conformation and/or antigen binding. Moreover, this criterion can similarly be used to prioritize relevant positions selected by other criteria described herein. Therefore, differentiating between residues proximal and distal to one or more CDRs represents one way to reduce the number of relevant positions to change.

Other criteria for selecting relevant amino acid framework positions to alter include, for example, residues that are known or predicted to reside in a three dimensional space near the antigen-CDR interface or predicted to modulate CDR activity. Similarly, framework residues that are known to, or predicted to, form contacts between the heavy ($V_H$) and light ($V_L$) chain variable region interface can be selected. Such framework positions can affect the conformation and/or affinity of a CDR by modulating the CDR binding pocket, antigen (epitope) interaction or the $V_H$ and $V_L$ interaction. Therefore, selection of these amino acid positions for constructing a diverse population for screening of binding activity can be used to identify framework changes which replace residues having detrimental effects on CDR conformation or compensate for detrimental effects of residues occurring elsewhere in the framework.

Other framework residues that can be selected for alteration include amino acid positions that are inaccessible to solvent. Such residues are generally buried in the variable region and are, therefore, capable of influencing the conformation of the CDR or $V_H$ and $V_L$ interactions. Solvent accessibility can be predicted, for example, from the relative hydrophobicity of the environment created by the amino acid side chains of the polypeptide and/or by known three-dimensional structural data.

Following selection of relevant amino acid positions in the donor CDRs, as well as any relevant amino acid positions in the framework regions desired to be varied, amino acid changes at some or all of the selected positions can be incorporated into encoding nucleic acids for the acceptor variable region framework and donor CDRs. Altered framework or CDR sequences can be individually made and tested, or can be sequentially or simultaneously combined and tested.

The variability at any or all of the altered positions can range from a few to a plurality of different amino acid residues, including all twenty naturally occurring amino acids or functional equivalents and analogues thereof. In some cases, non-naturally occurring amino acids may also be considered and are known in the art.

Selection of the number and location of the amino acid positions to vary is flexible and can depend on the intended use and desired efficiency for identification of the altered variable region having a desirable activity such as substantially the same or greater binding affinity compared to the donor variable region. In this regard, the greater the number of changes that are incorporated into an altered variable region population, the more efficient it is to identify at least one species that exhibits a desirable activity, for example, substantially the same or greater binding affinity as the donor. Alternatively, where the user has empirical or actual data to the affect that certain amino acid residues or positions contribute disproportionately to binding affinity, then it can be desirable to produce a limited population of altered variable regions which focuses on changes within or around those identified residues or positions.

For example, if CDR grafted variable regions are desired, a large, diverse population of altered variable regions can include all the non-identical framework region positions between the donor and acceptor framework and all single CDR amino acid position changes. Alternatively, a population of intermediate diversity can include subsets, for example, of only the proximal non-identical framework positions to be incorporated together with all single CDR amino acid position changes to, for example, increase affinity of the humanized antibodies or antigen binding fragments. The diversity of the above populations can be further increased by, for example, additionally including all pair-wise CDR amino acid position changes. In contrast, populations focusing on predetermined residues or positions which incorporate variant residues at as few as one framework and/or one CDR amino acid position can similarly be constructed for screening and identification of an altered antibody variable region. As with the above populations, the diversity of such focused populations can be further increased by additionally expanding the positions selected for change to include other relevant positions in either or both of the framework and CDR regions. There are numerous other combinations ranging from few changes to many changes in either or both of the framework regions and CDRs that can additionally be employed, all of which will result in a population of altered variable regions that can be screened for the identification of at least one CDR grafted altered variable region having desired activity, for example, binding activity to LOX/LOXL2. Those skilled in the art will know, or can determine, which selected residue positions in the framework or donor CDRs, or subsets thereof, can be varied to produce a population for screening and identification of an altered antibody of the invention given the teachings and guidance provided herein. Codons encoding amino acids are known in the art.

Humanized antibodies and antigen-binding fragments can be made using conventional techniques known in the art. In addition, recombinantly prepared antibodies can often be produced in large quantities, particularly when utilizing high level expression vectors.

Antibodies can be sequenced using conventional techniques known in the art and the amino acid sequences of the complementarity determining regions (CDRs) determined. In one aspect, the amino acid sequences of one or more of the CDRs is inserted into a synthetic sequence of, for example, a human antibody (or antigen-binding fragment thereof) framework to create a human antibody that could limit adverse side reactions of treating a human patient with a non-human antibody. The amino acid sequences of one or more of the CDRs can also be inserted into a synthetic sequence of, for example, into a binding protein such as an Avimer™ to create a construct for administration to a human patient. Such techniques can be modified depending on the species of animal to be treated. For example, for veterinary uses, an antibody, antigen-binding fragment or binding protein can be synthesized for administration of a primate, a cow, a horse, etc.

In another aspect, using art-recognized techniques such as those provided and incorporated herein, nucleotides encoding amino acid sequences of one or more of the CDRs can inserted, for example, by recombinant techniques in restriction endonuclease sites of an existing polynucleotide that encodes an antibody, antigen-binding fragment or binding protein.

For high level production, the most widely used mammalian expression system is one which utilizes the gene amplification procedure offered by dihydrofolate reductase deficient ("dhfr−") Chinese hamster ovary cells. The system is well known to the skilled artisan. The system is based upon the dihydrofolate reductase "dhfr" gene, which encodes the DHFR enzyme, which catalyzes conversion of dihydrofolate to tetrahydrofolate. In order to achieve high production, dhfr-CHO cells are transfected with an expression vector containing a functional dhfr gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level and the stability of the cells being employed are taken into account. In long term culture, recombinant CHO cell populations lose homogeneity with respect to their specific antibody productivity during amplification, even though they derive from a single, parental clone.

The present application provides an isolated polynucleotide (nucleic acid) encoding an antibody or antigen-binding fragment as described herein, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody or antigen-binding fragments thereof described herein as provided itself forms an aspect of the present application, as does a method of production of the antibody or antigen-binding fragments thereof described herein which method comprises expression from encoding nucleic acid therefrom. Expression can conveniently be achieved by culturing under appropriate conditions recombinant host cells containing the nucleic acid. Following production by expression, an antibody or antigen-binding fragment can be isolated and/or purified using any suitable technique, then used as appropriate.

Specific antibodies, antigen-binding fragments, and encoding nucleic acid molecules and vectors described herein can be provided isolated and/or purified, e.g., from their natural environment, in substantially pure or homogeneous form, or, in the case of nucleic acid, free or substantially free of nucleic acid or genes origin other than the sequence encoding a polypeptide with the required function. Nucleic acid can comprise DNA or RNA and can be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is *E. coli*.

The expression of antibodies and antibody fragments in prokaryotic cells such as *E. coli* is well established in the art. For a review, see for example Pluckthun, A. Bio/Technology 9:545-551 (1991). Expression in eukaryotic cells in culture is also available to those skilled in the art as an option for production of the antibodies and antigen-binding fragments described herein, see for recent reviews, for example Raff, M. E. (1993) Curr. Opinion Biotech. 4:573-576; Trill J. J. et al. (1995) Curr. Opinion Biotech 6:553-560, each of which is which is incorporated herein by reference in its entirety.

Suitable vectors can be chosen or constructed, containing appropriate regulatory sequences, including promoter sequences, terminator sequences, polyadenylation sequences, enhancer sequences, marker genes and other sequences as appropriate. Vectors can be plasmids, viral e.g. 'phage, or phagemid, as appropriate. For further details see, for example, Molecular Cloning: a Laboratory Manual: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds, John Wiley & Sons, 1992. The disclosures of Sambrook et al. and Ausubel et al. are incorporated herein by reference in their entirety.

Thus, a further aspect provides a host cell containing nucleic acid as disclosed herein. A still further aspect provides a method comprising introducing such nucleic acid into a host cell. The introduction can employ any available technique. For eukaryotic cells, suitable techniques can include, for example, calcium phosphate transfection, DEAE Dextran, electroporation, biolistics, liposome-mediated transfection and transduction using retrovirus or other virus, e.g., vaccinia or, for insect cells, baculovirus. For bacterial cells, suitable techniques can include, for example, calcium chloride transformation, electroporation and transfection using bacteriophage.

The introduction can be followed by causing or allowing expression from the nucleic acid, e.g. by culturing host cells under conditions for expression of the gene.

In one embodiment, the nucleic acid is integrated into the genome (e.g. chromosome) of the host cell. Integration can be promoted by inclusion of sequences which promote recombination with the genome, in accordance with standard techniques.

The present application also provides a method which comprises using a construct as stated above in an expression system in order to express the antibodies or antigen-binding fragments thereof as above.

The present application also relates to isolated nucleic acids, such as recombinant DNA molecules or cloned genes, or degenerate variants thereof, mutants, analogs, or fragments thereof, which encode an antibody or antigen-binding sequence that binds LOX or LOXL2 described herein.

In one aspect, the present application provides a nucleic acid which codes for an antibody or antigen-binding fragment thereof which binds LOX or LOXL2 as described herein.

In a further embodiment, the full DNA sequence of the recombinant DNA molecule or cloned gene of an antibody or antigen-binding fragment described herein can be operatively linked to an expression control sequence which can be introduced into an appropriate host. The application accordingly extends to unicellular hosts transformed with the cloned gene or recombinant DNA molecule comprising a DNA sequence encoding the $V_H$ and/or $V_L$, or portions thereof, of the antibody.

Another feature is the expression of the DNA sequences disclosed herein. As is well known in the art, DNA sequences can be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

Polynucleotides and vectors can be provided in an isolated and/or a purified form (e.g., free or substantially free of polynucleotides of origin other than the polynucleotide encoding a polypeptide with the required function). As used herein, "substantially pure" and "substantially free," refer to a solution or suspension containing less than, for example, 20% or less extraneous material, 10% or less extraneous material, 5% or less extraneous material, 4% or less extraneous material, 3% or less extraneous material, 2% or less extraneous material, or 1% or less extraneous material.

A wide variety of host/expression vector combinations can be employed in expressing the DNA sequences of this invention. Useful expression vectors, for example, can consist of segments of chromosomal, non-chromosomal and synthetic DNA sequences. Suitable vectors include derivatives of SV40 and known bacterial plasmids, e.g., E. coli plasmids col El, PctI, Pbr322, Pmb9 and their derivatives, plasmids such as RP4; phage DNAs, e.g., the numerous derivatives of phage λ e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Also provided herein is a recombinant host cell which comprises one or more polynucleotide constructs. A polynucleotide encoding an antibody or antigen-binding fragment as provided herein forms an aspect of the present application, as does a method of production of the antibody or antigen-binding fragment which method comprises expression from the polynucleotide. Expression can be achieved, for example, by culturing under appropriate conditions recombinant host cells containing the polynucleotide. An antibody or antigen-binding fragment can then be isolated and/or purified using any suitable technique, and used as appropriate.

Any of a wide variety of expression control sequences—sequences that control the expression of a DNA sequence operatively linked to it—can be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary (CHO) cells, HeLa cells, baby hamster kidney cells, NSO mouse melanoma cells and many others. A common, bacterial host can be, for example, E. coli.

The expression of antibodies or antigen-binding fragments in prokaryotic cells, such as E. coli, is well established in the art. For a review, see for example Pluckthun, A. Bio/Technology 9:545-551 (1991). Expression in eukaryotic cells in culture is also available to those skilled in the art (Raff, M. E. (1993) Curr. Opinion Biotech. 4:573-576; Trill J. J. et al. (1995) Curr. Opinion Biotech 6:553-560).

A wide variety of unicellular host cells are also useful in expressing the DNA sequences. These hosts include well-known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present application also provides constructs in the form of plasmids, vectors, transcription or expression cassettes as described elsewhere herein which comprise at least one polynucleotide as above. Suitable vectors can be chosen or constructed, containing appropriate regulatory sequences, including promoter sequences, terminator sequences, polyadenylation sequences, enhancer sequences, selectable markers and other sequences as appropriate. Vectors can be plasmids, viral e.g., phage, phagemid, etc., as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

A further aspect provides a host cell containing one or more polynucleotides as disclosed herein. Yet a further aspect provides a method of introducing such one or more polynucleotides into a host cell, any available technique. For eukaryotic cells, suitable techniques can include, for example, calcium phosphate transfection, DEAEDextran, electroporation, liposome-mediated transfection and transduction using retrovirus or other virus (e.g. vaccinia) or, for insect cells, baculovirus. For bacterial cells, suitable techniques can include, for example calcium chloride transformation, electroporation and transfection using bacteriophages.

The introduction can be followed by causing or allowing expression from the one or more polynucleotides, e.g. by culturing host cells under conditions for expression of one or more polypeptides from one or more polynucleotides. Inducible systems can be used and expression induced by addition of an activator.

In one embodiment, the polynucleotides can be integrated into the genome (e.g., chromosome) of the host cell. Integration can be promoted by inclusion of sequences which promote recombination with the genome, in accordance with standard techniques. In another embodiment, the nucleic acid is maintained on an episomal vector in the host cell.

Methods are provided herein which include using a construct as stated above in an expression system in order to express a specific polypeptide.

Considering these and other factors, a person skilled in the art will be able to construct a variety of vector/expression control sequence/host combinations that will express the DNA sequences on fermentation or in large scale animal culture.

A polynucleotide encoding an antibody, antigen-binding fragment, or a binding protein can be prepared recombinantly/synthetically in addition to, or rather than, cloned. The polynucleotide can be designed with the appropriate codons for the antibody, antigen-binding fragment, or a binding protein. In general, one will select preferred codons for an intended host if the sequence will be used for expression. The complete polynucleotide can be assembled from overlapping oligonucleotides prepared by standard methods and assembled into a complete coding sequence. See, e.g., Edge, Nature, 292:756 (1981); Nambair et al. Science, 223:1299 (1984); Jay et al, J. Biol. Chem., 259:6311 (1984).

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method can be used to create analogs with unnatural amino acids.

As mentioned above, a DNA sequence encoding an antibody or antigen-binding fragment thereof can be prepared synthetically rather than cloned. The DNA sequence can be designed with the appropriate codons for the antibody or antigen-binding fragment amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al. Science, 223:1299 (1984); Jay et al, J. Biol. Chem., 259:6311 (1984), each of which is which is incorporated herein by reference in its entirety.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al. Immunology, Second Ed, 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant (CFA), incomplete Freund's adjuvant (IFA), saponin, mineral gels such as aluminum hydroxide, surface active substances such as lysolecithin, pluronic polyols, polyanions, peptides, oil or hydrocarbon emulsions, keyhole limpet hemocyanins, dinirrophenol, and potentially useful human adjuvant such as BCG (Bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

Antibodies can also be affinity matured using known selection and/or mutagenesis methods as described above. Affinity matured antibodies can have an affinity which is two times, five times, 10 times, 20 times, 30 times or more greater than the starting antibody (generally murine, rabbit, chicken, humanized or human) from which the matured antibody is prepared. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art. Another technique for measuring apparent binding affinity familiar to those of skill in the art is a surface plasmon resonance technique (analyzed on a BIACORE 2000 system) (Liljeblad, et al, Glyco. J. 2000, 17:323-329). Standard measurements and traditional binding assays are described by Heeley, R. P, Endocr. Res. 2002, 28:217-229.

In one embodiment, an antibody specifically and selectively binds to the mature or active form of LOX after proteolytic processing, with a greater binding affinity (e.g., at least about 5 times, at least about 10 times, at least about 50 times, at least about 100 times, at least about 500 times, or at least about 1000 times greater), than the binding affinity to at least one of: the preproprotein of human LOX, the secreted human LOX, or other lysyl oxidase-like or lysyl oxidase-related proteins (e.g., LOXL1, LOXL2, LOXL3, and LOXL4). In one embodiment, the antibody specifically and selectively binds to LOX in unprocessed and/or processed (mature) forms. The mature form of LOX is typically active although, in some embodiments, unprocessed LOX is also active.

In another embodiment, an antibody specifically and selectively binds to the secreted form of LOX, such as a secreted human LOX after cleavage of the signal peptide, with a greater binding affinity (e.g., at least about 5 times, at least about 10 times, at least about 50 times, at least about 100 times, at least about 500 times, or at least about 1000 times greater), than the binding affinity to at least one of: the preproprotein of human LOX, the mature or active human LOX, or other lysyl oxidase-like or lysyl oxidase-related proteins (e.g., LOXL1, LOXL2, LOXL3, and LOXL4).

In yet another embodiment, an antibody specifically and selectively binds to LOXL2 with a greater binding affinity (e.g., at least about 5 times, at least about 10 times, at least about 50 times, at least about 100 times, at least about 500 times, or at least about 1000 times greater) than the binding affinity to at least one of: human LOX, the mature or active human LOX, the secreted form of LOX or other lysyl oxidase-like (LOL) or lysyl oxidase-related proteins (e.g., LOXL1, LOXL3, and LOXL4) in unprocessed, mature, active and/or secreted products. In one embodiment, the antibody specifically and selectively binds to LOXL2 in unprocessed and/or processed (mature) forms. The mature form of LOXL2 is typically active although, in some embodiments, unprocessed LOXL2 is also active.

An antibody can bind to both human LOX or human LOXL2, with a greater binding affinity (e.g., at least about 5 times, at least about 10 times, at least about 50 times, at least about 100 times, at least about 500 times, or at least about 1000 times greater), than the binding affinity to at least one of: other lysyl oxidase-like or lysyl oxidase-related proteins (e.g., LOXL1, LOXL3, and LOXL4).

Figure 4:
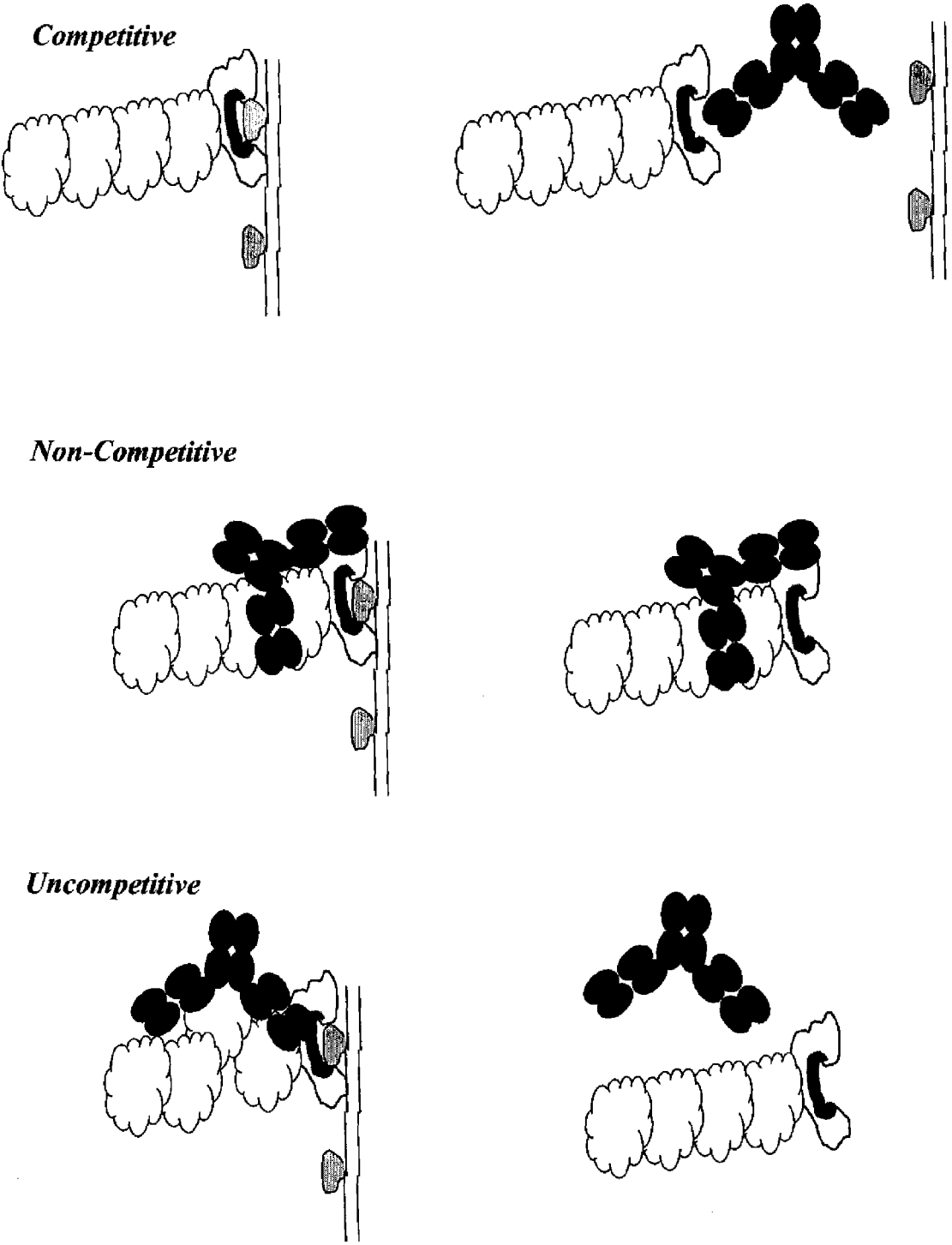
FIG. 4 illustrates modes of enzymatic inhibition: LOXL2.
Figure 5:
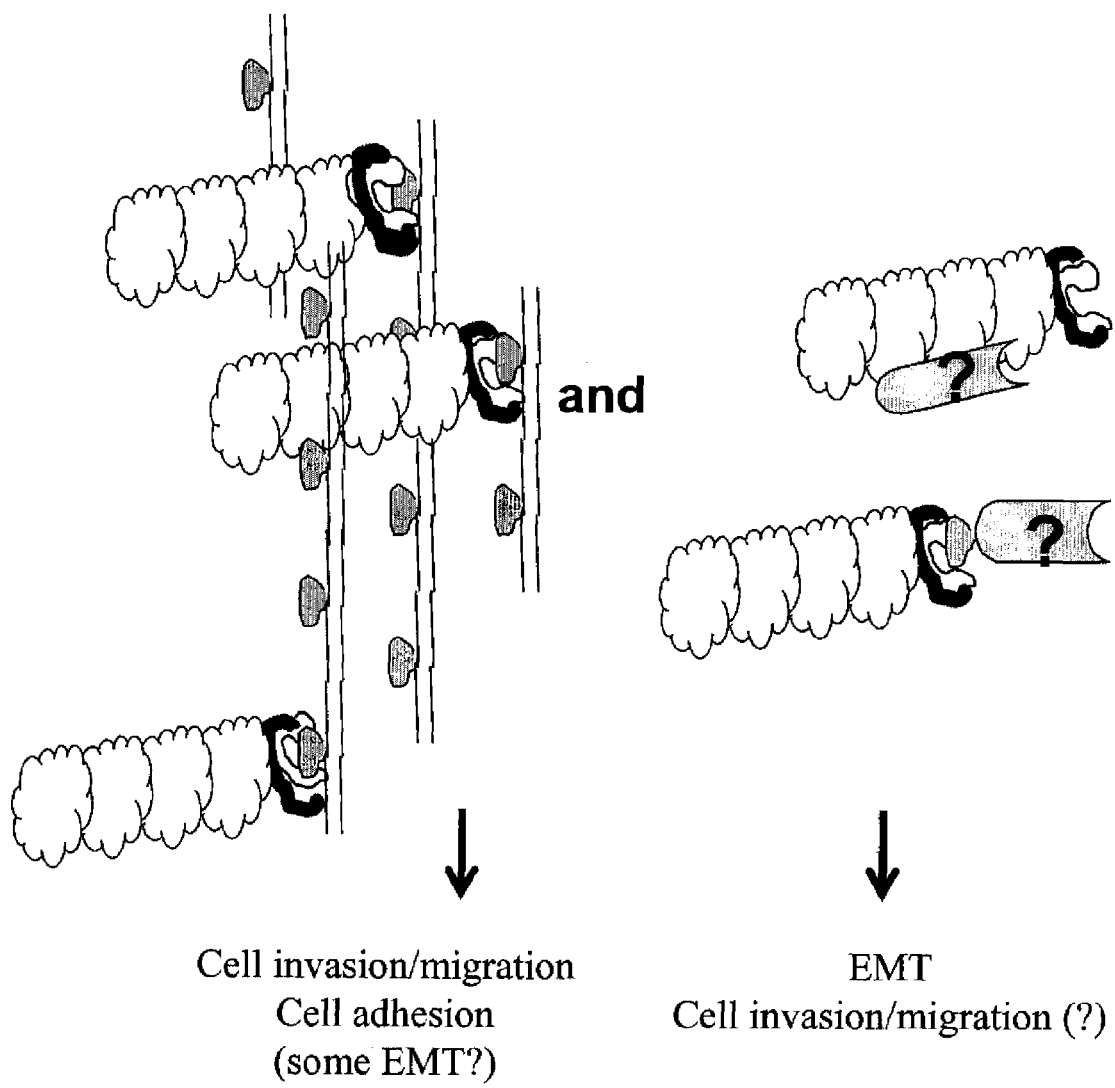
FIG. 5 illustrates extracellular LOXL2 localization and function of extracellular LOXL2.

Antibodies that bind to enzymes can be competitive inhibitors, uncompetitive inhibitors or non-competitive inhibitors. With respect to competitive inhibition, an inhibitor usually bears structural similarity to substrate. Inhibition will be noticeable at low substrate concentrations, but can be overcome at high substrate concentrations. With respect to uncompetitive inhibition, an inhibitor binds at site that becomes available after substrate is bound at the active site. Inhibition will be most noticeable at high substrate concentration. With respect to non-competitive inhibition, an inhibitor binds at site away from substrate binding site. Relative inhibition will generally be the same at all substrate concentrations. The mechanism of action antibodies that act as competitive inhibitors, uncompetitive inhibitors and non-competitive inhibitors is illustrated in FIG. 4. Antibodies described herein can be competitive inhibitors, uncompetitive inhibitors or non-competitive inhibitors. In one aspect, antibodies described herein can be non-competitive inhibitors.

In one aspect, antibodies described herein are non-competitive inhibitors; that is the antibodies block enzymatic activity of LOX or LOXL2 regardless of whether or not the enzymes are bound to substrate (collagen).

Binding of an antibody to LOX/LOXL2 can (1) reduce or inhibit uptake or internalization of LOX/LOXL2 (e.g., via integrin beta 1 or other cellular receptors or proteins) and/or (2) reduce or inhibit the enzymatic activity of LOX or LOXL2. It is believed that such an antibody could reduce EMT and thus is useful for the applications disclosed herein. An antibody described herein can bind to the proteolytic cleavage site of LOX or LOXL2, thereby effectively blocking (inhibiting) processing of the LOX or LOXL2 to reduce the level of active LOX or LOXL2. Such inhibition can occur through direct binding to LOX or LOXL2 or through indirect interference including steric hindrance, enzymatic alteration of LOX or LOXL2, inhibition of transcription or translation, destabilization of mRNA transcripts, impaired export, processing, or localization of LOX or LOXL2, and the like.

Binding of LOX/LOXL2 with other proteins, such as cellular receptors (e.g., uptake receptor integrin beta1), BTK (burton agammaglublinemia tyrosine kinase), or other integrins is also performed using the aforementioned assay, wherein instead of ECM proteins, cellular receptors (e.g., uptake receptor integrin beta1), BTK (burton agammagloublinemia tyrosine kinase), or other integrins are used.

Those anti-LOX/LOXL2 antibodies that inhibit LOX/LOXL2 binding to ECM proteins, cellular receptors, and integrins, are selected as candidates for further development. In one embodiment, anti-LOX/LOXL2 antibodies that inhibit LOX/LOXL2 binding to ECM proteins, cellular receptors, and integrins, are non-competitive inhibitors.

In one embodiment, an antibody described herein specifically binds to the catalytic domain of LOX. This domain, in the C-terminal region, contains the elements required for catalytic activity (the copper binding site, tyrosyl and lysyl residues that contribute to the carbonyl cofactor, and 10 cysteine residues. See, Thomassin et al. "The Pro-regions of lysyl oxidase and lysyl oxidase-like 1 are required for deposition onto elastic fibers," J. Biol. Chem. 2005 Dec. 30; 280 (52):42848-55 for further details.

Provided herein are antibodies or antigen binding fragments thereof that bind to LOX and/or inhibit the activity of LOX. Anti-LOX antibodies and antigen binding fragments thereof that bind and/or inhibit LOX have use in the purification, diagnostic, and therapeutic methods described herein. Antibodies can bind both full-length and/or processed LOX/LOXL2.

Provided herein is an isolated antibody or antigen binding fragment thereof, comprising a variable heavy chain having at least 75% amino acid sequence identity to an amino acid sequence set forth as SEQ ID NO: 3 and a variable light chain having at least 75% amino acid sequence identity to an amino acid sequence set forth as SEQ ID NO: 4 or 5.

In one aspect, provided herein is an isolated antibody or antigen binding fragment thereof, comprising a variable heavy chain having at least 75% amino acid sequence identity to an amino acid sequence set forth as SEQ ID NO: 3. In another aspect, provided herein is an isolated antibody or antigen binding fragment thereof, comprising a variable light chain having at least 75% amino acid sequence identity to an amino acid sequence set forth as SEQ ID NO: 4 or 5.

Further provided herein are antibodies or antigen binding fragments thereof, that compete with, or specifically bind to, an anti-LOX antibody or antigen binding fragment thereof described herein for binding to LOX. In one embodiment, anti-LOX antibodies described herein are non-competitive inhibitors.

Any of such antibodies or antigen binding fragments can specifically bind to LOX with a binding affinity of at least 2, 5, 10, 50, 100, 500 or 1000 times greater than to at least one of LOXL1, LOXL2, LOXL3 or LOXL4.

In one embodiment, an antibody or antigen binding fragment thereof, described herein specifically binds both full-length and processed LOX. In one aspect, both full-length and processed LOX are active forms of the enzyme.

Provided herein are antibodies or antigen binding fragments thereof that bind to LOXL2 and/or inhibit the activity of LOXL2. Anti-LOXL2 antibodies and antigen binding fragments thereof that bind and/or inhibit LOXL2 have use in the purification, diagnostic, and therapeutic methods described herein.

Provided herein is an isolated antibody or antigen binding fragment thereof, that specifically binds to an epitope having an amino acid sequence set forth as SEQ ID NO: 6. The antibody or antigen binding fragment thereof, can comprise a variable heavy chain having at least 75% amino acid sequence identity to an amino acid sequence set forth as SEQ ID NO: 1 and a variable light chain having at least 75% amino acid sequence identity to an amino acid sequence set forth as SEQ ID NO: 2.

Also provided herein is an isolated antibody or antigen binding fragment thereof, comprising a variable heavy chain having at least 75% amino acid sequence identity to an amino acid sequence set forth as SEQ ID NO: 1, and a variable light chain having at least 75% amino acid sequence identity to an amino acid sequence set forth as SEQ ID NO: 2.

In one aspect, provided herein is a variable heavy chain having at least 75% amino acid sequence identity to an amino acid sequence set forth as SEQ ID NO: 1. In another aspect, provided herein is a variable light chain having at least 75% amino acid sequence identity to an amino acid sequence set forth as SEQ ID NO: 2.

Further provided herein are antibodies or antigen binding fragments that compete with, or specifically bind to, any of the preceding antibodies or antigen binding fragments thereof for binding to LOXL2.

Any of such antibodies or antigen binding fragments can specifically bind to LOXL2 with a binding affinity of at least 2, 5, 10, 50, 100, 500 or 1000 times greater than to at least one of LOX, LOXL1, LOXL3 or LOXL4.

In one embodiment, an antibody or antigen binding fragment thereof, described herein specifically binds to the SRCR3-4 region of LOXL2 and, thus, binds both full-length and processed LOXL2. In one aspect, both full-length and processed LOXL2 are active forms of the enzyme. An antibody can, for example, specifically bind to an epitope having an amino acid sequence set forth as SEQ ID NO: 6. Such antibodies can serve as an uncompetitive partial inhibitor of enzymatic activity in vitro, inhibiting approximately half the enzymatic activity against a 1,5-diaminopentane substrate with an apparent $IC_{50}$ of 20-30 nM. Such antibodies can serve as non-competitive inhibitors.

When humanizing antibodies, simultaneous incorporation of all of the FR and/or CDR encoding nucleic acids and all of the selected amino acid position changes can be accomplished by a variety of methods known to those skilled in the art, including for example, recombinant and chemical synthesis. For example, simultaneous incorporation can be accomplished by, for example, chemically synthesizing the nucleotide sequence for the acceptor variable region, fused together with the donor CDR encoding nucleic acids, and incorporating at the positions selected for harboring variable amino acid residues a plurality of corresponding amino acid codons.

Provided herein are antibodies and antigen-binding fragments thereof that bind to LOX or LOXL2. Antibodies and antigen-binding fragments thereof that bind LOX or LOXL2 can inhibit (partially or fully) or manage/treat (partially or fully) symptoms associated with and/or caused by aberrant LOX or LOXL2 expression. The application also provides cell lines which can be used to produce the antibodies, methods for producing the cell lines, methods for expressing antibodies or antigen-binding fragments and purifying the same.

One can recognize that the antibodies and antigen-binding fragments thereof that specifically bind LOX or LOXL2 generated using the methods described herein can be tested using the assays provided herein or known in the art for the ability to bind to LOX or LOXL2 (e.g., ELISA) as well as affinity (e.g., Biacore or Surface Plasmon Resonance).

Humanized versions of anti-LOX and anti-LOXL2 antibodies have one or more of the following characteristics: retention of the inhibitory function of murine monoclonal antibodies, equivalent or increased binding affinity with a slow off rate (e.g., Kd 0.1-1 nM), binding to full length and/or processed LOX/LOXL2, non-competitive partial inhibition of enzymatic activity, equivalent or better Ic50 (e.g., about 30 nM), inhibitory activity in cell-based migration/invasion assays, inhibition of an EMT-like change induced by secreted LOX/LOXL2 in conditioned media of tumor cells, binding to matrix-associated LOX/LOXL2 generated by live human tumor cells, cross-reactivity of binding of human LOX/LOXL2 with murine LOX/LOXL2, therapeutic effectiveness (e.g., partial or reduction in tumor size and/or symptoms), reduced toxicity and reduced immunogenicity.

Provided herein are humanized antibodies that bind to hLOX, humanized antibodies that bind to hLOX and mLOX (murine LOX), humanized antibodies that bind to hLOXL2, and humanized antibodies that bind to hLOXL2 and mLOXL2 (murine LOXL2). In one aspect, the humanized antibodies are non-competitive inhibitors.

In one embodiment, a humanized anti-LOXL2 antibody has VH chain having an amino acid sequence of SEQ ID NO: 25, SEQ ID NO: 26, SEQ ID NO: 27 or SEQ ID NO: 28. One would understand that conservative amino acid modifications can be made using the methods described herein in one or more CDR or framework regions for affinity maturation of the antibody. Antibodies modified by such methods can be tested with respect to function using any of the assays described herein or known in the art.

In another embodiment, a humanized anti-LOXL2 antibody has VL chain having an amino acid sequence of SEQ ID NO: 30, SEQ ID NO: 31 or SEQ ID NO: 32. One would understand that conservative amino acid modifications can be made using the methods described herein in one or more CDR or framework regions for affinity maturation of the antibody. Antibodies modified by such methods can be tested with respect to function using any of the assays described herein or known in the art.

Provided herein is a humanized antibody, or antigen-binding fragment thereof, which binds LOXL2, comprising a heavy chain variable region and a light chain variable region, wherein said heavy chain variable region comprises:
(i) a heavy chain FR1 having the amino acid sequence of SEQ ID NO: 33 or the amino acid sequence of SEQ ID NO: 33 but for one or more substitutions selected from the group consisting of:
 (a) a substitution of glutamine (Q) by valine (V) or a conservative substitution thereof at position 24;
 (b) a substitution of leucine (L) by valine (V) or a conservative substitution thereof at position 30;
 (c) a substitution of valine (V) by lysine (K) or a conservative substitution thereof at position 31;
 (d) a substitution of arginine (R) by lysine (K) or a conservative substitution thereof at position 32; and
 (e) a substitution of threonine (T) by alanine (A) or a conservative substitution thereof at position 35; and a deletion of amino acid residues 1-19;
(ii) a heavy chain FR2 having the amino acid sequence of SEQ ID NO: 34 or the amino acid sequence of SEQ ID NO: 34 but for one or more substitutions selected from the group consisting of:
 (a) a substitution of lysine (K) by arginine (R) or a conservative substitution thereof at position 3;
 (b) a substitution of arginine (R) by alanine (A) or a conservative substitution thereof at position 5, and
(iii) a heavy chain FR3 having the amino acid sequence of SEQ ID NO: 35 or the amino acid sequence of SEQ ID NO: 35 but for one or more substitutions selected from the group consisting of:
 (a) a substitution of lysine (K) by arginine (R) or a conservative substitution thereof at position 1;
 (b) a substitution of alanine (A) by valine (V) or a conservative substitution thereof at position 2;

(c) a substitution of leucine (L) by isoleucine (I) or a conservative substitution thereof at position 4;
(d) a substitution of serine (S) by threonine (T) or a conservative substitution thereof at position 10;
(e) a substitution of glutamine (Q) by glutamic acid (E) or a conservative substitution thereof at position 16;
(f) a substitution of threonine (T) by arginine (R) or a conservative substitution thereof at position 21;
(g) a substitution of aspartic acid (D) by glutamic acid (E) or a conservative substitution thereof at position 23;
(h) a substitution of serine (S) by threonine (T) or a conservative substitution thereof at position 25; and
(i) a substitution of phenylalanine (F) by tyrosine (Y) or a conservative substitution thereof at position 29; and
(iv) a heavy chain FR4 having the amino acid sequence of SEQ ID NO: 36 or the amino acid sequence of SEQ ID NO: 36 but for a substitution of lysine (K) by valine (V) or a conservative substitution thereof at position 7, and wherein said light chain variable region comprises:
(i) a light chain FR1 having the amino acid sequence of SEQ ID NO: 49 or the amino acid sequence of SEQ ID NO: 49 but for one or more substitutions selected from the group consisting of:
(a) a substitution of alanine (A) by threonine (T) or a conservative substitution thereof at position 27;
(b) a substitution of alanine (A) by proline (P) or a conservative substitution thereof at position 28;
(c) a substitution of proline (P) by leucine (L) or a conservative substitution thereof at position 29;
(d) a substitution of valine (V) by leucine (L) or a conservative substitution thereof at position 31;
(e) a substitution of glutamic acid (E) by glutamine (Q) or a conservative substitution thereof at position 37;
(d) a substitution of serine (S) by proline (P) or a conservative substitution thereof at position 38;
(f) a substitution of valine (V) by alanine (A) or a conservative substitution thereof at position 39; and a deletion of amino acid residues 1-20;
(ii) a light chain FR2 having the amino acid sequence of SEQ ID NO: 50 or the amino acid sequence of SEQ ID NO: 50 but for one or more substitutions selected from the group consisting of:
(a) a substitution of phenylalanine (F) by tyrosine (Y) or a conservative substitution thereof at position 2; and
(b) a substitution of arginine (R) by lysine (K) or a conservative substitution thereof at position 5;
(iii) a light chain FR3 having the amino acid sequence of SEQ ED NO: 51 or the amino acid sequence of SEQ ID NO: 51 but for one or more substitutions selected from the group consisting of:
(a) a substitution of alanine (A) by aspartic acid (D) or a conservative substitution thereof at position 14; and
(b) a substitution of arginine (R) by lysine (K) or a conservative substitution thereof at position 18; and
(iv) a light chain FR4 having the amino acid sequence of SEQ ED NO: 52 or the amino acid sequence of SEQ ED NO: 52 but for a substitution of leucine (L) by valine (V) or a conservative substitution thereof at position 7;

In one embodiment, the antibody, or antigen-binding fragment thereof, comprises a heavy chain variable region FR1 having an amino acid sequence as set forth in SEQ ED NO: 33, 37 or 44; a heavy chain variable region FR2 having an amino acid sequence as set forth in SEQ ID NO: 34, 38 or 45; a heavy chain variable region FR3 having an amino acid sequence as set forth in SEQ ID NO: 35, 39, 46, 47 or 48; a heavy chain variable region FR4 having an amino acid sequence as set forth in SEQ ID NO: 36 or 40; a light chain variable region FR1 having an amino acid sequence as set forth in SEQ ID NO: 49 or 53; a light chain variable region FR2 having an amino acid sequence as set forth in SEQ ID NO: 50, 54 or 60; a light chain variable region FR3 having an amino acid sequence as set forth in SEQ ED NO: 51, 55 or 61; and a light chain variable region FR4 having an amino acid sequence as set forth in SEQ ID NO: 52 or 56.

Encompassed within the scope of the present application are variable heavy chains and variable light chains that are at least 50%, 60%, 70%, 75%, 80%, 85%, 90%, 95% or up to 100% identical to the variable heavy chains and variable light chains described herein.

Conservative substitutions are minor modification of these nucleotide sequences and/or amino acids are intended to be included as heavy and light chain encoding nucleic acids and their functional fragments. Such minor modifications include, for example, those which do not change the encoded amino acid sequence due to the degeneracy of the genetic code as well as those which result in only a conservative substitution of the encoded amino acid sequence or those that do not substantially alter the binding capacity of the antibody. Conservative substitutions of encoded amino acids include, for example, amino acids which belong within the following groups: (1) non-polar amino acids (Gly, Ala, Val, Leu, and He); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Tip, Tyr, and His). Other minor modifications are included within the nucleic acids encoding heavy and light chain polypeptides of the invention so long as the nucleic acid or encoded polypeptides retain some, or all, of their function as described herein and which have use in the methods described herein. Non-conservative substitutions are those that are not identified as conservative substitutions. Using the methods described herein, one can ascertain whether it would be possible to substitute a non-conservative amino acid for a framework amino acid residue and test the function of the modified antibody using the assays described elsewhere herein.

Modified variable heavy chains and variable light chains can be screened for binding and activity using methods known in the art and described herein.

A substantial portion of a variable domain will include three CDR regions, together with their intervening framework regions. The portion can also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of humanized anti-LOX or anti-LOXL2 antibodies and antigen-binding fragments described herein made by recombinant DNA techniques can result in the introduction of N- or C-terminal residues encoded by linkers introduced to facilitate cloning or other manipulation steps. Other manipulation steps include the introduction of linkers to join variable domains to further protein sequences including immunoglobulin heavy chains, other variable domains (for example in the production of diabodies) or protein labels as discussed in more detail below.

Antibodies encompassed within the present application, including, for example, those having variable heavy or light chains that have at least 50% identity to those described herein can be assessed for anti-LOX or anti-LOXL2 activity.

Provided herein is a method for identifying an antibody that inhibits metastatic tumor cell growth, comprising contacting LOX or LOXL2 or a cell expressing LOX or LOXL2 with a candidate antibody; and determining the expression or activity of the LOX or LOXL2, whereby the candidate antibody that reduces the expression or activity of LOX or LOXL2 compared to the expression or activity detected in the absence of the antibody is identified as the compound that inhibits metastatic tumor cell growth. In particular embodiments, the antibody is contacted with LOX or LOXL2 or a cell expressing LOX or LOXL2 under hypoxic conditions. In one aspect, antibodies described herein can be non-competitive inhibitors.

Also provided herein is method for identifying an antibody that increases the efficacy of chemotherapeutic agents, comprising contacting LOX or LOXL2 or a cell expressing LOX or LOXL2 with a candidate antibody; and determining the expression or activity of the LOX or LOXL2, whereby the candidate antibody that reduces the expression or activity of LOX or LOXL2 compared to the expression or activity detected in the absence of the antibody is identified as the antibody that increases the efficacy of chemotherapeutic agents in inhibiting or reducing metastatic tumor growth.

Any suitable source of LOX or LOXL2 can be employed as an antibody target in the present method. The enzyme can be derived, isolated, or recombinantly produced from any source known in the art, including yeast, microbial, and mammalian, that will permit the generation of a suitable product that can generate a detectable reagent or will be biologically active in a suitable assay.

The enzymatic activity of LOX or LOXL2 can be assessed by any suitable method described herein or known in the art. Exemplary methods of assessing LOX or LOXL2 activity include that of Trackman et al. Anal. Biochem. 113:336-342 (1981); Kagan, et al. Methods Enzymol. 82A:637-49 (1982); Palamakumbura et al. Anal. Biochem. 300:245-51 (2002); Albini et al. Cancer Res. 47:3239-45 (1987); Kamath et al, Cancer Res. 61:5933-40 (2001); U.S. Pat. No. 4,997,854; and U.S. Patent Application No. 2004/0248871. For example, enzymatic activity can be assessed by detecting and/or quantitating "lysyl oxidase byproducts," such as $H_2O_2$ production; collagen pyridinium residues, ammonium production; aldehyde product production; lysyl oxidation, deoxypyridinoline (Dpd)-discussed below. One may also detect and quanritate cellular invasive capacity in vitro; cellular adhesion and growth in vitro; and metastatic growth in vivo. In vivo models include, but are not limited to suitable syngeneic models, human tumor xenograft models, orthotopic models, metastatic models, transgenic models, and gene knockout models (see, e.g., Teicher, Tumors Models in Cancer Research (Humana Press 2001)).

Hypoxic conditions can be induced or naturally occurring. Hypoxic areas frequently occur in the interior of solid tumor. Hypoxia can also be induced in vivo, particularly in experimental animal models, using diminution or cessation of arterial blood flow to tumor or the administration of vasoconstrictive compounds. See, e.g., U.S. Pat. No. 5,646,185. Exemplary vasoconstrictive compounds include adrenergic direct and indirect agonists such as norepinephrine, epinephrine, phenylephrine, and cocaine. The presence of a hypoxic region in a solid tumor present in a subject can be observed by a number of methods currently known in the art, including nuclear magnetic resonance (NMR) and oxygen electrode $pO_2$ histography. Such methods may be used in the context of the present invention (as described below), to identify hypoxic treatment target regions and to guide in administering treatment compositions to such regions. In vitro, hypoxic conditions can be induced using any suitable method. For example, cells can be maintained under anoxic (<0.1% $O_2$) conditions at 37° C. within an anaerobic chamber or under hypoxic (1 to 2% $O_2$) conditions at 37° C. within a modular incubator chamber filled with 5% $CO_2$ and 1 to 2% $O_2$ balanced with N2. See, e.g., Erler et al, Mol. Cell. Biol. 24:2875-89 (2004).

The LOX or LOXL2 enzymes or LOX- or LOXL2-expressing cell can be contacted with a compound (e.g., a LOX/LOXL inhibitor such as an antibody) in any suitable manner for any suitable length of time. For tumor regions that are accessible to hypodermic delivery of agent, it may be desirable to inject the compound directly into the hypoxic region. The cells can be contacted with the compound more than once during incubation or treatment. Typically, the dose required for an antibody is in the range of about 1 micro-g/ml to 1000 micro-g/ml, more typically in the range of about 100 µg/ml to about 800 µg/ml. The exact dose can be readily determined from in vitro cultures of the cells and exposure of the cell to varying dosages of the compound. Typically, the length of time the cell is contacted with the compound is about 5 minutes, about 15 minutes, about 30 minutes, about 1 hour, about 4 hours, about 12 hours, about 36 hours, about 48 hours to about 3 days or more, even indefinitely, more typically for about 24 hours. For in vitro invasion assays, any suitable matrix may be used. In one embodiment, the matrix is reconstituted basement membrane Matrigel™ matrix (BD Sciences).

Screening methods can also include a step of measuring FAK levels. As described below, FAK (Focal Adhesion Kinase [p125FAK]) is activated as part of the cell motility process. When LOX is inhibited, FAK phosphorylation is not increased under hypoxic conditions. In a compound-screening assay, a secondary step can include the detection of phospho-FAK levels both with and without addition of the test antibody. A test inhibitory antibody will also reduce levels of phospho-FAK.

An antibody is an inhibitor of LOX or LOXL2 expression or biological activity when the antibody reduces the expression or activity or LOX or LOXL2 relative to that observed in the absence of the antibody. In one embodiment, an antibody is an inhibitor of LOX or LOXL2 when it reduces the incidence of metastasis relative to the observed in the absence of the antibody and, in further testing, inhibits metastatic tumor growth. In one aspect, antibodies described herein are non-competitive inhibitors. Tumor inhibition can be quantified using any convenient method of measurement. The incidence of metastasis can be assessed by examining relative dissemination (e.g., number of organ systems involved) and relative tumor burden in these sites. Metastatic growth can be ascertained by microscopic or macroscopic analysis, as appropriate. Tumor metastasis can be reduced by about 10%, 20%, 30%, 40%, 50%, 60%, 70%, 80%, 90%, 95% or greater. In some embodiments, the antibody can be assessed relative to other antibodies or compounds that do not impact LOX or LOXL2 expression or biological activity. The test antibodies can be administered at the time of tumor inoculation, after the establishment of primary tumor growth, or after the establishment of local and/or distant metastases. Single or multiple administration of the test antibody can be given using any convenient mode of administration including, but not limited to, intravenous, intraperitoneal, intratumoral, subcutaneous and intradermal.

Any suitable cell expressing LOX or LOXL2 can be employed with the present methods. As used herein, the term "cell" includes a biological cell (e.g., CHO, HeLa, etc.). The cell can be human or nonhuman. The cell can be freshly isolated (i.e., primary) or derived from a short term- or long term-established cell line. Exemplary biological cell lines include MDA-MB 231 human breast cancer cells, MDA-MB 435 human breast cancer cells, U-87 MG glioma, SCL1 squamous cell carcinoma cells, CEM, HeLa epithelial carcinoma, and Chinese hamster ovary (CHO) cells. Such cell lines are described, for example, in the Cell Line Catalog of the American Type Culture Collection (ATCC, Rockville, Md.).

A cell can express the LOX or LOXL2 or its promoter endogenously or exogenously (e.g., as a result of the stable transfer of genes). Endogenous expression by a cell as provided herein can result from constitutive or induced expression of endogenous genes.

Exogenous expression by a cell as provided herein can result from the introduction of the nucleic acid sequences encoding LOX or LOXL2 or a biologically active fragment thereof, or LOX or LOXL2 promoter nucleic acid sequence. Transformation may be achieved using viral vectors, calcium phosphate, DEAE-dextran, electroporation, biolistics, cationic lipid reagents, or any other convenient technique known in the art. The manner of transformation useful in the present invention is conventional and is exemplified in Current Protocols in Molecular Biology (Ausubel, et al., eds. 2000). Exogenous expression of the lysyl oxidase or its promoter can be transient, stable, or some combination thereof. Exogenous expression of the enzyme can be achieved using constitutive promoters, e.g., SV40, CMV, and the like, and inducible promoters known in the art. Suitable promoters are those that will function in the cell of interest.

The methods described herein are non-limiting and any other methods known in the art can also be used to test the activity of anti-LOX antibodies and anti-LOXL2 antibodies. Additional assays are described below in the Examples.

It may be necessary in some instances to introduce an unstructured polypeptide linker region between a label of the present invention and portions of the antibodies. The linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase a subunit. Other examples of naturally occurring linkers include linkers found in the 1CI and LexA proteins.

Within the linker, the amino acid sequence may be varied based on the preferred characteristics of the linker as determined empirically or as revealed by modeling. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. Ln some cases, particularly when it is necessary to span a longer distance between subunits or when the domains must be held in a particular configuration, the linker may optionally contain an additional folded domain.

In some embodiments it is preferable that the design of a linker involve an arrangement of domains which requires the linker to span a relatively short distance, preferably less than about 10 Angstroms (Å). However, in certain embodiments, linkers span a distance of up to about 50 Å.

Antibodies provided herein such that they are conjugated or linked to therapeutic and/or imaging/detectable moieties. Methods for conjugating or linking antibodies are well known in the art. Associations between antibodies and labels include any means known in the art including, but not limited to, covalent and non-covalent interactions.

In one non-limiting embodiment, antibodies can be associated with a toxin, a radionuclide, an iron-related compound, a dye, an imaging reagent, a fluorescent label or a chemotherapeutic agent that would be toxic when delivered to a cancer cell.

Alternatively, the antibodies can be associated with detectable label, such as a radionuclide, iron-related compound, a dye, an imaging agent or a fluorescent agent for immunodetection of target antigens.

Non-limiting examples of radiolabels include, for example, $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81M}Kr$, $^{87M}Sr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$.

Non-limiting examples of toxins include, for example, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, tricothecenes, *Clostridium perfringens* phospholipase C(PLC), bovine pancreatic ribonuclease (BPR), antiviral protein (PAP), abrin, cobra venom factor (CVF), gelonin (GEL), saporin (SAP) viscumin.

Non-limiting examples of iron-related compounds include, for example, magnetic iron-oxide particles, ferric or ferrous particles, $Fe^{203}$ and $Fe^{304}$. Iron-related compounds and methods of labeling polypeptides, proteins and peptides can be found, for example, in U.S. Pat. Nos. 4,101,435 and 4,452,773, and U.S. published applications 20020064502 and 20020136693, all of which are hereby incorporated by reference in their entirety.

In certain embodiments, the subject antibodies can be covalently or non-covalently coupled to a cytotoxin or other cell proliferation inhibiting compound, in order to localize delivery of that agent to a tumor cell. For instance, the agent can be selected from the group consisting agents, enzyme inhibitors, proliferation inhibitors, lytic agents, DNA or RNA synthesis inhibitors, membrane permeability modifiers, DNA metabolites, dichloroethylsulfide derivatives, protein production inhibitors, ribosome inhibitors, inducers of apoptosis, and neurotoxins.

In certain embodiments, the subject antibodies can be coupled with an agent useful in imaging tumors. Such agents include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many embodiments, such secondary functionality/moiety will be relatively large, e.g., at least 25 amu in size, and in many instances can be at least 50,100 or 250 amu in size.

In certain embodiments, the secondary functionality is a chelate moiety for chelating a metal, e.g., a chelator for a radiometal or paramagnetic ion. In additional embodiments, it is a chelator for a radionuclide useful for radiotherapy or imaging procedures.

Radionuclides useful within the present invention include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: $^{32}$P, $^{33}$P, $^{43}$K, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81}$MKr, $^{87}$MSr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{97}$Hg, $^{199}$Au, $^{203}$Pb, $^{211}$At, $^{212}$Pb, $^{212}$Bi and $^{213}$Bi. Preferred therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag, $^{166}$Ho or $^{177}$Lu. Conditions under which a chelator will coordinate a metal are described, for example, by Gasnow et al. U.S. Pat. Nos. 4,831,175, 4,454,106 and 4,472,509, each of which is incorporated herein by reference. Within the present invention, "radionuclide" and "radiolabel" are interchangeable.

$^{99}$Tc is a particularly attractive radioisotope for diagnostic applications, as it is readily available to all nuclear medicine departments, is inexpensive, gives minimal patient radiation doses, and has ideal nuclear imaging properties. It has a half-life of six hours which means that rapid targeting of a technetium-labeled antibody is desirable. Accordingly, in certain preferred embodiments, the modified antibodies include a chelating agent for technium.

In still other embodiments, the secondary functionality can be a radiosensitizing agent, e.g., a moiety that increases the sensitivity of cells to radiation. Examples of radiosensitizing agents include nifroimidazoles, metronidazole and misonidazole (see: DeVita, V. T. in Harrison's Principles of Internal Medicine, p. 68, McGraw-Hill Book Co., NY, 1983, which is incorporated herein by reference). The modified antibodies that comprise a radiosensitizing agent as the active moiety are administered and localize at the target cell. Upon exposure of the individual to radiation, the radiosensitizing agent is "excited" and causes the death of the cell.

There are a wide range of moieties which can serve as chelators and which can be derivatized to the antibodies of the present invention. For instance, the chelator can be a derivative of 1,4,7,10-tetraazacyclododecanetetraacetic acid (DOTA), emylenediaminetetraacetic acid (EDTA), diemylenefriaminepentaacetic acid (DTPA) and 1-p-Isothiocyanato-benzyl-memyl-diemylenetriaminepentaacetic acid (ITC-MX). These chelators typically have groups on the side chain by which the chelator can be used for attachment to subject antagonists. Such groups include, e.g., benzylisothiocyanate, by which the DOTA, DTPA or EDTA can be coupled to, e.g., an amine group.

In one embodiment, the chelate moiety is an "NxSy" chelate moiety. As defined herein, the "NxSy chelates" include bifunctional chelators that are capable of coordinately binding a metal or radiometal and, preferably, have N2S2 or N3S cores. Exemplary NxSy chelates are described, e.g., in Fritzberg et al. (1998) PNAS 85:4024-29; and Weber et al. (1990) Chem. 1:431-37; and in the references cited therein.

Jacobsen et al. (PCT application WO 98/12156) provides methods and compositions, i.e., synthetic libraries of binding moieties, for identifying compounds which bind to a metal atom. The approach described in that publication can be used to identify binding moieties which can subsequently be added to the antibodies to derive the modified antibodies.

One problem frequently encountered with the use of conjugated proteins in and radiodiagnostic applications is a potentially dangerous accumulation of the radiolabeled moiety fragments in the kidney. When the conjugate is formed using an acid- or base-labile linker, cleavage of the radioactive chelate from the protein can advantageously occur. If the chelate is of relatively low molecular weight, as most of the subject modified antibodies, antigen binding fragments and peptides are expected to be, it is not retained in the kidney and is excreted in the urine, thereby reducing the exposure of the kidney to radioactivity. However, in certain instances, it may be advantageous to utilize acid- or base-labile in the subject ligands for the same reasons they have been used in labeled proteins.

Accordingly, certain of the subject labeled/modified antibodies can be synthesized, by standard methods in the art, to provide reactive functional groups which can form acid-labile linkages with, e.g., a carbonyl group of the ligand. Examples of suitable acid-labile linkages include hydrazone and thiosemicarbazone functions. These are formed by reacting the oxidized carbohydrate with chelates bearing hydrazide, thiosemicarbazide, and functions, respectively.

Alternatively, base-cleavable which have been used for the enhanced clearance of the radiolabel from the kidneys, can be used. See, for example, Weber et al. 1990 Bioconjg. Chem. 1:431. The coupling of a bifunctional chelate to an antibody via a hydrazide linkage can incorporate base-sensitive ester moieties in a linker spacer arm. Such an ester-containing linker unit is exemplified by ethylene glycolbis (succinimidyl succinate), (EGS, available from Pierce Chemical Co, Rockford, Ill.), which has two terminal N-hydroxysuccinimide (NHS) ester derivatives of two 1,4-dibutyric acid units, each of which are linked to a single ethylene glycol moiety by two alkyl esters. One NHS ester may be replaced with a suitable amine-containing BFC (for example 2-aminobenzyl DTPA), while the other NHS ester is reacted with a limiting amount of hydrazine. The resulting hyrazide is used for coupling to the antagonists, forming an ligand-BFC linkage containing two alkyl ester functions. Such a conjugate is stable at physiological pH, but readily cleaved at basic pH.

Antibodies labeled by chelation of radioisotopes are subject to radiation-induced scission of the chelator and to loss of radioisotope by dissociation of the coordination complex. In some instances, metal dissociated from the complex can be re-complexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine.

In still other embodiments, the antibodies are coupled to a Boron addend, such as a carborane. For example, carboranes can be prepared with carboxyl functions on pendant side chains, as is well known in the art. Attachment of such carboranes to amine peptides can be achieved by activation of the carboxyl groups of the carboranes and condensation with the amine group to produce the conjugate. Such modified antibodies can be used for neutron capture therapy.

The present invention also contemplates the modification of the subject antagonists with dyes, for example, useful in therapy, and used in conjunction with appropriate non-ionizing radiation. The use of light and porphyrins in methods of the present invention is also contemplated and their use in cancer therapy has been reviewed by van den Bergh, Chemistry in Britain, 22:430-437 (1986), which is incorporated by reference herein in its entirety.

One embodiment of the present invention includes antagonists labeled with a fluorescent label. Common fluorescent labels include, for example, FITC, PE, Texas Red, cytochrome c, etc. Techniques for labeling polypeptides and fragments thereof, such as those provided herein, are well-known in the art.

The term "anticancer agent" also includes the chemotherapeutic agents described below. The term anticancer agent also includes treatment with a substance that reduces hypoxia in a cell, when such agent is combined with LOX inhibition. Such a substance may include, e.g., p53. See, e.g., Matoba et al., "p53 Regulates Mitochondrial Respiration," Science 16June 2006 312:1650-1653; published online 24 May 2006, and references cited there. A substance that drives cancer cells towards the respiratory pathway and away from the glycolytic pathway would be used advantageously with a LOX inhibitor insofar as LOX would not be up-regulated in this case.

Chemotherapeutics useful as active moieties which when conjugated to antagonists thereof of the present invention are specifically delivered to cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of known cytotoxic agents useful in the present invention are listed, for example, in Goodman et al., "The Pharmacological Basis of Therapeutics," Sixth Edition, A. B. Gilman et al., eds./Macmillan Publishing Co. New York, 1980. These include taxanes, such as paclitaxel and docetaxel; nitrogen such as mechlorthamine, melphalan, uracil mustard and chlorambucil; ethylenimine derivatives, such as thiotepa; alkyl sulfonates, such as busulfan; nitrosoureas, such as lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, and mitomycin; enzymes, such as platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, acetate and megestrol acetate), estrogens (diethylstilbestrol and ethinyl estradiol), and androgens (testosterone propionate and fluoxymesterone).

Drugs that interfere with protein synthesis can also be used; such drugs are known to those skilled in the art and include puromycin, cycloheximide, and ribonuclease.

Most of the chemotherapeutic agents currently in use in treating cancer possess functional groups that are amenable to chemical cross-linking directly with an amine or carboxyl group of an agent of the present invention. For example, free amino groups are available on methotrexate, doxorubicin, daunorubicin, cytosinarabinoside, bleomycin, fludarabine, and cladribine while free carboxylic acid groups are available on methotrexate, melphalan and chlorambucil.

These functional groups, that is free amino and carboxylic acids, are targets for a variety of homobifunctional and heterobifunctional chemical cross-linking agents which can crosslink these drugs directly to a free amino group of an antagonist.

Chemotherapeutic agents contemplated by the present invention also include other chemotherapeutic drugs that are commercially available. Merely to illustrate, the chemotherapeutic can be an inhibitor of chromatin function, a inhibitor, a inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), a DNA repair inhibitor.

Chemotherapeutic agents may be categorized by their mechanism of action into, for example, the following groups: anti-metabolites/anti-cancer agents, such as pyrimidine analogs floxuridine, capecitabine, and cytarabine) and purine analogs, folate antagonists and related inhibitors antiprobliferative/antimitotic agents including natural products such as vinca alkaloid (vinblastine, vincristine, and microtubule such as taxane (paclitaxel, docetaxel), vinblastin, nocodazole, epothilones and navelbine, epipidopodophyllotoxins (etoposide, teniposide), DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, triethylenethiophosphoramide and etoposide; antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, *Pseudomonas exotoxin, Bordetella pertussis* adenylate cyclase toxin, or diphtheria toxin, and caspase activators; and chromatin. Preferred dosages of the chemotherapeutic agents are consistent with currently prescribed dosages.

Additionally, other labels, such as biotin followed by streptavidin-alkaline phosphatase (AP), horseradish peroxidase are contemplated by the present invention.

As used herein, the terms "nucleic acid damaging treatment" and "nucleic acid damaging agent" refer to any treatment regimen that directly or indirectly damages nucleic acid (e.g., DNA, cDNA, genomic DNA, mRNA, tRNA or rRNA). Examples of such agents include alkylating agents, nitrosoureas, anti-metabolites, plant alkaloids, plant extracts and radioisotopes. Examples of agents also include nucleic acid damaging drugs, for example, 5-fluorouracil (5-FU), capecitabine, S-1 (Tegafur, 5-chlorO-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochloride (Gemzar), pentostatin, allopurinol, 2-fluoro-arabmosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubibcin (Cerubicine), idarubicin (Idamycin) and epirubicin (Ellence), anthracyclin analogues such as mitoxantrone, actinomycin D, non intercalating topoisomerase inhibitors such as epipodophyllotoxins (etoposide=VP16, teniposide=VM–26), podophylotoxin, bleomycin (Bleo), pepleomycin, compounds that form adducts with nucleic acid including platinum derivatives (e.g., cisplatin (CDDP), trans analogue of cisplatin, carboplatin, iproplatin, tetraplatin and oxaliplatin), camptothecin, topotecan, irinotecan (CPT-11), and SN-38. Specific examples of nucleic acid damaging treatments include radiation (e.g., focused microwaves, ultraviolet (UV), infrared (1R), or alpha-, beta- or gamma-radiation) and environmental shock (e.g., hyperthermia).

As used herein, the terms "anti-proliferative treatment" and "anti-proliferative agent" means any treatment regimen that directly or indirectly inhibits proliferation of a cell, virus, bacteria or other unicellular or multicellular organism regardless of whether or not the treatment or agent damages nucleic acid. Particular examples of anti-proliferative agents are anti-tumor and anti-viral drugs, which inhibit cell proliferation or virus proliferation or replication. Examples include, inter alia, cyclophosphamide, azathioprine, cyclosporin A, prednisolone, melphalan, chlorambucil, mechlorethamine, busulphan, methotrexate, 6-mercaptopurine, thioguanine, cytosine arabinoside, taxol, vinblastine, vincristine, doxorubicin, actinomycin D, mithramycin, carmustine, lomustine, semustine, streptozotocin, hydroxyurea, cisplatin, mitotane, procarbazine, dacarbazine and dibromomannitol. Anti proliferative agents that cause nucleic acid replication errors or inhibit nucleic acid replication are those such as nucleoside and nucleotide analogues (e.g., AZT or 5-AZC).

In another embodiment, the anti-LOX antibody can be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionuclide).

Methodology for labeling polypeptides and fragments thereof including, but not limited to, those provided herein are well known in the art. When the antibodies of the present invention are labeled with a radiolabel or toxin, the antibodies can be prepared as pharmaceutical compositions which are useful for therapeutic treatment of patients where the pharmaceutical compositions are administered to the patient in an effective amount. When the antibodies of the present invention are labeled with a label that can be visualized, the antibodies can be prepared as pharmaceutical compositions which are useful for diagnostic of patients where the pharmaceutical compositions are administered to the patient in an effective amount for in vivo imaging or where the pharmaceutical compositions are tested in an in vitro assay.

V. Compositions

Each of the antibodies of the present invention can be used as a composition when combined with a pharmaceutically acceptable carrier or excipient. Such pharmaceutical compositions are useful for administration to a subject in vivo or ex vivo, and for diagnosing and/or treating a subject with the disclosed antibodies, for example.

Pharmaceutically acceptable carriers are physiologically acceptable to the administered patient and retain the therapeutic properties of the antibodies or peptides with which it is administered. Pharmaceutically-acceptable carriers and their formulations are and generally described in, for example, Remington'pharmaceutical Sciences (18$^{th}$ Edition, ed. A. Gennaro, Mack Publishing Co., Easton, Pa. 1990). One exemplary pharmaceutical carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antibodies or peptides from the administration site of one organ, or portion of the body, to another organ, or portion of the body. Each carrier must be "acceptable" in the sense of being compatible with the other ingredients of the formulation and not injurious to the patient. Nor should a pharmaceutically acceptable carrier alter the specific activity of the antagonists. Exemplary carriers and excipients have been provided elsewhere herein.

In one aspect, the present invention provides pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. The pharmaceutical compositions and formulations include an amount of an invention compound, for example, an effective amount of an antagonist of the invention, and a pharmaceutically or physiologically acceptable carrier.

Pharmaceutical compositions can be formulated to be compatible with a particular route of administration, systemic or local. Thus, pharmaceutical compositions include carriers, diluents, or excipients suitable for administration by various routes.

In a further invention, the compositions of the present invention further comprise a pharmaceutically acceptable additive in order to improve the stability of the antagonist in composition and/or to control the release rate of the composition. Pharmaceutically acceptable additives of the present invention do not alter the specific activity of the subject antagonist. A preferable pharmaceutically acceptable additive is a sugar such as mannitol, sorbitol, glucose, xylitol, trehalose, sorbose, sucrose, galactose, dextran, dextrose, fructose, lactose and mixtures thereof. Pharmaceutically acceptable additives of the present invention can be combined with pharmaceutically acceptable carriers and/or excipients such as dextrose. Alternatively, a preferable pharmaceutically acceptable additive is a surfactant such as polysorbate 20 or polysorbate 80 to increase stability of the peptide and decrease gelling of the pharmaceutical solution. The surfactant can be added to the composition in an amount of 0.01% to 5% of the solution. Addition of such pharmaceutically acceptable additives increases the stability and half-life of the composition in storage.

The formulation and delivery methods will generally be adapted according to the site and the disease to be treated. Exemplary formulations include, but are not limited to, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. The dosage of the compounds of the invention will vary according to the extent and severity of the need for treatment, the activity of the administered composition, the general health of the subject, and other considerations well known to the skilled artisan.

Formulations or enteral (oral) administration can be contained in a tablet (coated or uncoated), capsule (hard or soft), microsphere, emulsion, powder, granule, crystal, suspension, syrup or elixir. Conventional nontoxic solid carriers which include, for example, pharmaceutical grades of mannitol, lactose, starch, magnesium stearate, sodium saccharin, talcum, cellulose, glucose, sucrose, magnesium carbonate, can be used to prepare solid formulations. Supplementary active compounds (e.g., preservatives, antibacterial, antiviral and antifungal agents) can also be incorporated into the formulations. A liquid formulation can also be used for enteral administration. The carrier can be selected from various oils including petroleum, animal, vegetable or synthetic, for example, peanut oil, soybean oil, mineral oil, sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Pharmaceutical compositions for enteral, parenteral, or transmucosal delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65 75; Warren (1997) J. Neurol. Sci. 152:31 38; and Tonegawa (1997) J. Exp. Med. 186:507 515. The parenteral preparation can be enclosed in ampules, disposable syringes or multiple dose vials made of glass or plastic.

Pharmaceutical compositions for intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be through nasal sprays or suppositories (see, e.g., Sayani (1996) "Systemic delivery of peptides and proteins across absorptive mucosae" Crit. Rev. Ther. Drug Carrier Syst. 13:85 184). For transdermal administration, the active compound can be formulated into ointments, salves, gels, or creams as generally known in the art. Transdermal delivery systems can also be achieved using patches.

For inhalation delivery, the pharmaceutical formulation can be administered in the form of an aerosol or mist. For aerosol administration, the formulation can be supplied in finely divided form along with a surfactant and propellant. In another embodiment, the device for delivering the formulation to respiratory tissue is in which the formulation vaporizes. Other delivery systems known in the art include dry powder aerosols, liquid delivery systems, inhalers, air jet nebulizers and propellant systems (see, e.g., Patton (1998) Biotechniques 16:141 143; Dura Pharmaceuticals, San Diego, Calif.; Aradigm, Hayward, Calif.; Aerogen, Santa Clara, Calif.; and Inhale Therapeutic Systems, San Carlos, Calif.).

Biodegradable, biocompatible polymers can be used, such as ethylene vinyl acetate, polyanhydrides, polyglycolic acid, collagen, polyorthoesters, andpolylactic acid. Methods for preparation of such formulations are known to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known in the art, for example, as described in U.S. Pat. Nos. 4,235,871; 4,501,728; 4,522,811; 4,837,028; 6,110,490; 6,096,716; 5,283,185; 5,279,833; Akimaru (1995) Cytokines Mol. Ther. 1:197 210; Alving (1995) Immunol. Rev. 145:5 31; and Szoka (1980) Ann. Rev. Biophys. Bioeng. 9:467). Biodegradable microspheres or capsules or other biodegradable polymer configurations capable of sustained delivery of small molecules including peptides are known in the art (see, e.g., Putney (1998) Nat. Biotechnol. 16:153 157). Compounds of the invention can be incorporated within micelles (see, e.g., Suntres (1994) J. Pharm. Pharmacol. 46:23 28; Woodle (1992) Pharm. Res. 9:260 265). Antagonists can be attached to the surface of the lipid monolayer or bilayer. For example, antagonists can be attached to hydrazide-PEG-(distearoylphosphatidy-1) ethanolamine-containing liposomes (see, e.g., Zalipsky (1995) Bioconjug. Chem. 6:705 708). Alternatively, any form of lipid membrane, such as a planar lipid membrane or the cell membrane of an intact cell, e.g., a red blood cell, can be used. Liposomal and lipid-containing formulations can be delivered by any means, including, for example, intravenous, transdermal (see, e.g., Vutla (1996) J. Pharm. Sci. 85:5 8), transmucosal, or oral administration.

Compositions of the present invention can be combined with other therapeutic moieties or imaging/diagnostic moieties as provided herein. Therapeutic moieties and/or imaging moieties can be provided as a separate composition, or as a conjugated moiety. Linkers can be included for conjugated moieties as needed and have been described elsewhere herein.

The antibodies disclosed herein may also be formulated as immunoliposomes. Liposomes containing the antibody are prepared by methods known in the art, such as described in Epstein et al, *Proc. Natl. Acad. Sci. USA*, 82:3688 (1985); Hwang et al, *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al, *J. Biol. Chem.*, 257: 286 288 (1982) via a disulfide-interchange reaction. A chemotherapeutic agent (such as Doxorubicin) is optionally contained within the liposome. See Gabizon et al, *J. National Cancer Inst*, 81(19): 1484 (1989).

Lipofections or liposomes can also be used to deliver the anti-LOX antibody, or an antibody fragment, into cells. Where antibody fragments are used, the smallest inhibitory fragment that specifically binds to the binding domain of the target protein can be used. For example, based upon the variable-region sequences of an antibody, peptide molecules can be designed that retain the ability to bind the target protein sequence. Such peptides can be synthesized chemically and/ or produced by recombinant DNA technology. See, e.g., Marasco et al., *Proc. Natl. Acad. Sci. USA*, 90:7889 7893 (1993). The formulation herein can also contain more than one active compound as necessary for the particular indication being treated, including, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended. The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra.

Formulations for in vivo administration are sterile. Sterilization can be readily accomplished via filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Various other pharmaceutical compositions and techniques for their preparation and use will be known to those of skill in the art in light of the present disclosure. For a detailed listing of suitable pharmacological compositions and associated administrative techniques one can refer to the detailed teachings herein, which can be further supplemented by texts such as Remington: The Science and Practice of Pharmacy 20th Ed. (Lippincott, Williams & Wilkins 2003).

Pharmaceutical compositions contemplated by the present invention have been described above. In one embodiment of the present invention, the pharmaceutical compositions are formulated to be free of pyrogens such that they are acceptable for administration to human patients. Testing pharmaceutical compositions for pyrogens and preparing pharmaceutical compositions free of pyrogens are well understood to one of ordinary skill in the art.

One embodiment of the present invention contemplates the use of any of the pharmaceutical compositions of the present invention to make a medicament for treating a disorder of the present invention. Medicaments can be formulated based on the physical characteristics of the patient/subject needing treatment, and can be formulated in single or multiple formulations based on the stage of the cancerous tissue. Medicaments of the present invention can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages and kits described below.

VI. Affinity Purification

Anti-LOX antibodies and anti-LOXL2 antibodies described herein are useful for affinity purification of LOX of LOXL2 from recombinant cell culture, natural sources or tissue biopsy samples (tissue and/or serum). In this process, antibodies against LOX or LOXL2 are immobilized on a suitable support, such a Sephadex resin or filter paper, using methods well known in the art. The immobilized antibody then is contacted with a sample containing the LOX or LOXL2 to be purified, and thereafter the support is washed with a suitable solvent that will remove substantially all the material in the sample except the LOX or LOXL2, which is bound to the immobilized antibody. Finally, the support is washed with another suitable solvent that will release the LOX or LOXL2 from the antibody.

VII. Packages and Kits

One embodiment of the present application includes a pharmaceutical package or kit useful for the methods provided herein. One embodiment of such pharmaceutical packages or kits includes preparations (compositions) of the antagonists as provided herein.

One aspect of the present invention relates to kits for carrying out the administration of a LOX/LOXL2 inhibitor. Another aspect of the present invention relates to kits for carrying out the combined administration of the LOX/LOXL2 inhibitor with one or more other therapeutic agent. In one embodiment, the kit comprises a LOX/LOXL2 inhibitor formulated in a pharmaceutical carrier or excipient, and at least one therapeutic agent that is not said LOX/LOXL2 inhibitor, formulated as appropriate, in one or more separate pharmaceutical preparations.

Pharmaceutical packages and kits can additionally include an excipient, a carrier, a buffering agent, a preservative or a stabilizing agent in a pharmaceutical formulation. Each component of the kit can be enclosed within an individual container and all of the various containers can be within a single package. Invention kits can be designed for room temperature or cold storage.

Additionally, the preparations can contain stabilizers to increase the shelf-life of the kits and include, for example, bovine serum albumin (BSA) or other known conventional stabilizers. Where the compositions are lyophilized, the kit can contain further preparations of solutions to reconstitute the preparations. Acceptable solutions are well known in the art and include, for example, pharmaceutically acceptable phosphate buffered saline (PBS).

Additionally, the pharmaceutical packages or kits provided herein can further include any of the other moieties provided herein such as, for example, a chemotherapeutic agent as described elsewhere in more detail.

Pharmaceutical packages and kits of the present invention can further include the components for an assay provided herein, such as, for example, an ELISA assay. Alternatively, preparations of the kits are used in immunoassays, such as immunohistochemistry to test patient tissue biopsy sections. Pharmaceutical packages and kits of the present invention can further include the components for collection of a sample.

Pharmaceutical packages and kits of the present invention can further include a label specifying, for example, a product description, mode of administration and indication of treatment. Pharmaceutical packages provided herein can include any of the compositions as described herein. The pharmaceutical package can further include a label for preventing, reducing the risk of, or treating any of the disease indications described herein.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions. Kits of the invention therefore can additionally include labels or instructions for using the kit components in any method of the invention. A kit can include an invention compound in a pack, or dispenser together with instructions for administering the compound in a method of the invention.

Instructions can include instructions for practicing any of the methods of the invention described herein including treatment, detection, monitoring or diagnostic methods. Instructions may additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

The compositions of the kit of the present invention can be formulated in single or multiple units for either a single test or multiple tests.

In preferred embodiments, the preparations of the kit are free of pyrogens. Methods for testing for the presence of, and/or specific levels of, pyrogens are routine in the art and kits are commercially available for such purpose.

Provided herein is a kit for treating a condition associated with LOX or LOXL2, containing a composition of an antibody or antigen binding fragment thereof described herein and a pharmaceutically acceptable carrier or excipient. A condition associated with LOX or LOXL2 can be, for example, a tumor, a metastasis, angiogenesis, or fibrosis. In one embodiment, antibodies in such kits can comprise a detectable label, a therapeutic label or both. In another embodiment, antibodies in such kits can be lyophilized.

Another aspect of the present invention relates to kits for carrying out the combined administration of the LOX or LOXL2 inhibitor with other therapeutic compounds. In one embodiment, the kit comprises a LOX or LOXL2 inhibitor formulated in a pharmaceutical carrier, and at least one cytotoxic agent, formulated as appropriate, in one or more separate pharmaceutical preparations.

VIII. Diagnostic Methods

The present invention also provides methods for diagnosing, monitoring, staging or detecting the diseases described above by using agents that recognize different forms of LOX or LOXL2. For example, as described above, antibodies against different forms of LOX or LOXL2, the preproprotein, secreted, mature or active form, can be used for these purposes. Methods of diagnosing, monitoring, staging or detecting the diseases described above by using agents that recognize different forms of LOX or LOXL2 are intended to encompass all of the diseases and indications described herein.

As described above, active LOX or LOXL2 is cleaved and can be detected by virtue of its change in molecular weight (immunoblot) or by use of antibodies that detect the uncleaved vs. cleaved form of LOX/LOXL, along with cellular localization by using various detection methods such as immunohistochemistry (IHC).

It is believed that the extracellular matrix and conditioned medium should contain proteolytically processed, active LOX or LOXL whereas uncleaved, inactive LOX/LOXL should be localized intracellularly. Some active, cleaved LOX/LOXL can also be detected inside the cell as a consequence of uptake from the extracellular space.

Samples from individuals can be collected and analyzed by determining inactive or active LOX levels. This analysis can be performed prior to the initiation of treatment using lysyl oxidase-specific therapy to identify tumors having elevated active LOX/LOXL expression or activity. Such diagnosis analysis can be performed using any sample, including but not limited to cells, protein or membrane extracts of cells, biological fluids such as sputum, blood, serum, plasma, or urine, or biological samples such as tissue samples, formalin-fixed or frozen tissue sections.

Any suitable method for detection and analysis of inactive and/or active LOX/LOXL can be employed. As used herein, the term "sample" refers to a sample from a human, animal, or to a research sample, e.g., a cell, tissue, organ, fluid, gas, aerosol, slurry, colloid, or coagulated material. Samples also include, but are not limited to, protein or membrane extracts of cells, biological fluids such as sputum, blood, serum, plasma, or urine, or biological samples such as formalin-fixed or frozen tissue sections employing antibodies described herein. The term "sample" can also refer to a cell, tissue, organ, or fluid that is freshly taken from a human or animal, or to a cell, tissue, organ, or fluid that is processed or stored. The sample can be tested in vivo, e.g., without removal from the human or animal, or it can be tested in vitro. The sample can be tested after processing, e.g., by histological methods.

Various diagnostic assay techniques known in the art can be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-158). The antibodies used in the diagnostic assays can be labeled with a detectable moiety. The detectable moiety directly or indirectly produces a detectable signal. For example, the detectable moiety can be any of those described herein such as, for example, a radio-isotope, such as $^3$H, $^{14}$C, $^{32}$P, $^{35}$S, or $^{125}$I, a fluorescent or chermluminescent compound, such as fluorescein isothiocyanate (FITC), Texas red, cyanin, photocyan, rhodamine, or luciferin, or an enzyme, such as alkaline phosphatase, β-galactosidase or horseradish peroxidase. Any method known in the art for conjugating the antibody to the detectable moiety can be employed, including those methods described by Hunter et al. Nature, 144:945 (1962); David et al. Biochemistry, 13:1014 (1974); Pain et al, J. Immunol. Meth, 40:219 (1981); and Nygren, J. Histochem. and Cytochem, 30:407 (1982).

Provided herein is a method of diagnosing a condition associated with LOX or LOXL2 comprising assessing a level of LOX and/or LOXL2 in a sample of a subject, wherein a change in level of LOX and/or LOXL2 in the sample in comparison with a reference sample indicates the presence or increase of a tumor or metastasis. In one aspect, the condition associated with LOX or LOXL2 is a tumor, a metastasis, angiogenesis, or fibrosis. An increase in LOX and/or LOXL2 levels in the sample in comparison with a reference sample can indicate the presence of a tumor or metastasis or an increase in tumor or metastatic growth. The reference sample can be a sample taken from the subject at an earlier time point or a sample from another individual. The level of LOX and/or LOXL2 levels in the sample can be detected by contacting the sample with an antibody or antigen binding fragment thereof described herein. In one embodiment, the antibody or antigen binding fragment thereof is detectably labeled.

In one embodiment, a method is provided for diagnosing cancer metastasis in a subject, comprising: assessing active LOX or LOXL2 levels or activity in the blood, whereby a change in active LOX or LOXL2 levels or activity (e.g., in gene expression, enzymatic activity, etc.) in the blood in comparison with a reference sample, indicates the presence of metastatic tumor growth. In some instances, the active LOX or LOXL2 levels or activities in the blood can be lower than those when measured earlier, which can indicate that the subject is at a greater risk of cancer metastasis; that the cancer has metastasized; or that cancer metastasis has increased. The reference sample may derive from the same subject, taken from the same tumor at a different time point or from other site of the body, or from another individual.

In another embodiment, a method is provided for diagnosing cancer metastasis in a subject having a tumor, comprising: assessing active LOX or LOXL2 levels or activity in the tumor, whereby a change in active LOX or LOXL2 levels or activity in the tumor in comparison with a reference sample indicates the presence of metastatic tumor growth. In some instances, the active LOX or LOXL2 levels or activities in the tumor can be higher than those when measured earlier, which can indicate that the subject is at a greater risk of cancer metastasis; that the cancer has metastasized; or that cancer metastasis has increased. The reference sample can derive from the same subject, taken from the same tumor at a different time point or from other site of the body, or from another individual.

Also provided herein is a method for staging tumor growth or metastasis in a subject, comprising assessing LOX and/or LOXL2 (e.g., hLOX or hLOXL2) levels in a tumor of the subject, whereby a change in LOX and/or LOXL2 level (e.g., in gene expression or enzymatic activity) in the tumor in comparison with a reference sample, indicates the presence of metastatic tumor growth. In some instances, the LOX and/or LOXL2 levels of activities in the tumor may be higher than those when measured earlier for the same subject, or higher than those in a reference sample taken from a normal tissue, which may indicate that the patient is at a greater risk of tumor metastasis; that the tumor has metastasized; or that tumor metastasis has increased.

Staging of solid tumor cancers is well known. The TNM system is one of the most commonly used staging systems. This system has been accepted by the International Union Against Cancer (UICC) and the American Joint Committee on Cancer (AJCC). Most medical facilities use the TNM system as their main method for cancer reporting. PDQ®, the NCI's comprehensive cancer database, also uses the TNM system The TNM system, referred to herein as "staging," is based on the extent of the tumor, the extent of spread to the lymph nodes, and the presence of metastasis.

Also provided here is a method for monitoring a subject's response to a therapy including a modulator of LOX/LOXL2 such as the treatment of cancer, tumors, and fibrotic diseases. The method comprises: detecting a change in the level of C-reactive protein in the subject after administration of a modulator of LOX or LOXL2 to the subject, wherein the change indicates that the LOX or LOXL2 modulator has a therapeutic effect on the subject. A C-reactive protein is an important pharmacodynamic marker for systemic inflammation. It is believed that a reduced level of C-reactive protein (e.g., in the blood sample of the subject) as compared to that prior to the administration of the LOX or LOXL2 inhibitor is indicative of the subject's response to the therapy using an inhibitor of LOX or LOXL2.

Measurement of active LOX or LOXL2 levels can take the form of an immunological assay, which detects the presence of an active LOX or LOXL2 protein with an antibody to the protein, preferably an antibody specifically binding to active LOX or LOXL2. Antigen-binding fragments of anti-LOX/LOXL antibodies can also be used.

Immunoassays also can be used in conjunction with laser induced fluorescence (see, for example, Schmalzing and Nashabeh, Electrophoresis 18:2184-93 (1997); and Bao, J. Chromatogr. B. Biomed. Sci. 699:463-80 (1997), each of which is incorporated herein by reference). Liposome immunoassays, such as flow-injection liposome immunoassays and liposome immunosensors also can be used to determine active LOX or LOXL levels according to a method of the invention (Rongen et al, J. Immunol. Methods 204:105-133 (1997). Immunoassays, such as enzyme-linked immunosorbent assays (ELISAs), can be particularly useful in a method of the invention. A radioimmunoassay also can be useful for determining whether a sample is positive for active LOX or LOXL2 or for determining the level of active LOX or LOXL2. A radioimmunoassay using, for example, an iodine-125 labeled secondary antibody, can be used.

In addition, one can measure the activity of active LOX or LOXL2, thus ignoring the amount of inactive enzyme. Enzymatic activity of active LOX or LOXL2 can be measured in a number of ways, using a soluble elastin or soluble collagen with labeled lysine as a substrate. Details of an activity assay are given in Royce et al, "Copper metabolism in mottled mouse mutants. The effect of copper therapy on lysyl oxidase activity in brindled (Mobr) mice," Biochem J. 1982Feb. 15; 202(2): 369-371. An exemplary assay is a chromogenic assay, such as that described by Palamakumbura, et al.

"A fluorometric assay for detection of lysyl oxidase enzyme activity in biological samples," Anal Biochem 2002 Jan. 15; 300(2):245-51.

In addition to measuring the level of LOX or LOXL2 in the blood (or urine), one can measure secondary products of LOX or LOXL2 activity. For example, deoxypyridinoline (Dpd) is formed by the enzymatic action of lysyl oxidase on lysine residues. Dpd is released into the circulation as a result of osteoclastic degradation of bone. It cannot be re-used, is cleared by the kidney and is excreted unchanged in urine. Thus, a test based on the Immunodiagnostic Systems (IDS) Gamma BCT Dpd assay, using a coated tube RIA using an anti-Dpd monoclonal antibody can be used to measure enzymatic activity.

Anti-LOX antibodies and anti-LOXL2 antibodies described herein can also be used in the diagnosis of diseases or conditions associated with aberrant collagen metabolism such as various fibrotic conditions, for example, lung fibrosis, as well as in proliferative vitreous retinopathy, surgical scarring, systemic sclerosis, scleroderma, wound contraction, hypertrophic scars, fibromatosis (especially Dupuytren's disease), and keloids.

IX. Therapeutic Methods

The pharmaceutical formulations according to the present invention can be used to treat a wide variety of diseases and disorders such as, for example, cancer, metastasis, fibrosis and aberrant angiogenesis.

Provided herein is a method of inhibiting LOXL2 by contacting a sample or a cellular tissue with any of the anti-LOXL2 antibodies or antigen binding fragments thereof described herein. Binding of said antibody or antigen binding fragment thereof to LOXL2 inhibits enzymatic activity of LOXL2.

Also provided herein is a method of inhibiting LOX by contacting a sample or cellular tissue with any of the anti-LOX antibodies or antigen binding fragments thereof described herein. Binding of said antibody or antigen binding fragment thereof to LOX inhibits enzymatic activity of LOX.

In either of such methods, contacting can occur in vitro, in vivo or ex vivo.

Inhibition of LOX or LOXL2 can have one or more effects in a subject such as, for example, reduction in tumor growth, reduction in angiogenesis, reduction in a fibrotic disease, and/or decreasing extracellular matrix formation. Fibrotic diseases include, but are not limited to liver fibrosis, lung fibrosis, kidney fibrosis, cardiac fibrosis, and scleroderma.

Provided herein are methods of treating diseases and disorders associated with aberrant expression of LOX or LOXL2. Diseases and disorder include, but are not limited to tumors (e.g., primary or metastatic), angiogenesis related conditions and fibrotic conditions.

As used herein, "prevention" refers to prophylaxis, prevention of onset of symptoms, prevention of progression of a disease or disorder associated with fibrosis or correlated with LOX/LOXL2 activity. As used herein, "treat" or "treatment" means stasis or a postponement of development of the symptoms associated a disease or disorder described herein. The terms further include ameliorating existing uncontrolled or unwanted symptoms, preventing additional symptoms, and ameliorating or preventing the underlying metabolic causes of symptoms. Thus, the terms denote that a beneficial result has been conferred on a mammalian subject with a disease or symptom, or with the potential to develop such disease or symptom. A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors. Prolonging survival includes without limitation times of at least 1 month (mo), about at least 2 months (mos.), about at least 3 mos., about at least 4 mos., about at least 6 mos., about at least 1 year, about at least 2 years, about at least 3 years, or more. Overall survival can also be measured in months to years. The patient's symptoms can remain static or can decrease.

Pharmaceutical compositions of the present invention are administered in therapeutically effective amounts which are effective for producing some desired therapeutic effect at a reasonable benefit/risk ratio applicable to any medical treatment. For the administration of the present pharmaceutical compositions to human patients, the pharmaceutical compositions of the present invention can be formulated by methodology known by one of ordinary skill in the art to be substantially free of pyrogens such that they do not induce an inflammatory response.

As used herein, the term "therapeutically effective amount" or "effective amount" refers to an amount of a therapeutic agent that when administered alone or in combination with another therapeutic agent to a cell, tissue, or subject is effective to prevent or ameliorate the disease condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. For example, when in vivo administration of an anti-LOX/anti-LOXL2 antibody is employed, normal dosage amounts can vary from about 10 ng/kg to up to 100 mg/kg of mammal body weight or more per day, preferably about 1 µg/kg/day to 50 mg/kg/day, optionally about 100 µg/kg/day to 20 mg/kg/day, 500 µg/kg/day to 10 mg/kg/day, or 1 mg/kg/day to 10 mg/kg/day, depending upon the route of administration.

An effective response of the present invention is achieved when the patient experiences partial or total alleviation or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month (mo), about at least 2 mos., about at least 3 mos., about at least 4 mos., about at least 6 mos., about at least 1 year, about at least 2 years, about at least 3 years, or more. Overall survival is also measured in months to years. The patient's symptoms may remain static, and the tumor burden may not increase.

A physician or veterinarian having ordinary skill in the art can readily determine and prescribe the effective amount (ED50) of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved.

As used herein, the term "subject" means mammalian subjects. Exemplary subjects include, but are not limited to humans, monkeys, dogs, cats, mice, rats, cows, horses, goats and sheep. In some embodiments, the subject has cancer and can be treated with the agent of the present invention as described below.

Regardless of the route of administration selected, the compounds of the present invention, which are used in a suitably hydrated form, and/or the pharmaceutical compositions of the present invention are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

In one aspect provided herein, administration of the antibodies results in an improvement the subject's condition. In another aspect, administration of the antibodies prevents the subject's condition from worsening and/or prolongs survival of the patient.

The patient can be a mammal such as a human or a non-human. Such a patient can be symptomatic or asymptomatic.

Compositions can be administered locally, regionally or systemically by any suitable route provided herein.

In one aspect, symptoms of the patient are ameliorated. Amelioration can be manifested as, for example, reduction in pain, reduced tumor size, elimination of tumors, prevention of increases in tumor size or progression or of disease, prevention of formation of metastasis, or inhibition of metastatic growth, inhibition of fibrosis, inhibition of angiogenesis, or a combination thereof.

If needed, for cancer treatments, methods can further include surgical removal of the cancer and/or administration of an anti-cancer agent or treatment. Administration of such an anti-cancer agent or treatment can be concurrent with administration of the compositions disclosed herein. Anti-cancer agents have been provided elsewhere herein.

In one aspect, administration of any of the antibodies provided herein reduces or eliminates the need for the patient to undergo surgery or treatment with one or more anti-cancer agents or treatments.

Indications that can be treated using the pharmaceutical formulations of the present invention include those involving undesirable or uncontrolled cell proliferation. Such indications include benign tumors, various types of cancers such as primary tumors and tumor metastasis, restenosis (e.g., coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, macular degeneration, glaucoma; age-related macular degeneration (wet AMD and dry AMD), atherosclerosis, rheumatoid arthritis, multiple sclerosis, liver fibrosis, kidney fibrosis, lung fibrosis, scleroderma, atherosclerosis, and Alzheimer's disease, repetitive motion disorders, disorders of tissues that are not highly vascularized, and proliferative responses associated with organ transplants.

Liver fibrosis includes, but is not limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, and autoimmune hepatitis.

Lung fibrosis includes, but is not limited to, idiopathic pulmonary fibrosis (IFF) or cryptogenic fibrosing alveolitis, chronic fibrosing interstitial pneumonia, interstitial lung disease (ILD), diffuse parenchymal lung disease (DPLD), emphysema and chronic obstructive pulmonary disease (COPD), and chronic asthma.

Cardiac fibrosis includes, but is not limited to, congestive heart failure, cardiomyopathy, and post-myocardial infarction defects in heart function.

Kidney fibrosis includes, but is not limited to, diabetic nephropathy, vesicoureteral reflux, tubulointerstitial renal fibrosis; glomerulonephritis or glomerular nephritis, including focal segmental glomerulosclerosis and membranous glomerulonephritis, and Mesangiocapillary glomerular nephritis.

Generally, cells in a benign tumor retain their differentiated features and do not divide in a completely uncontrolled manner. A benign tumor is usually localized and non-metastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas, and pituitary adenomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include, but are not limited to, lung cancer (including lung adenocarcinoma, squamous cell carcinoma, large cell carcinoma, bronchioloalveolar carcinoma, non-small-cell carcinoma, small cell carcinoma, mesothelioma); breast cancer (including ductal carcinoma, lobular carcinoma, inflammatory breast cancer, clear cell carcinoma, mucinous carcinoma,); colorectal cancer (colon cancer, rectal cancer); anal cancer; pancreatic cancer (including pancreatic adenocarcinoma, islet cell carcinoma, neuroendocrine tumors); prostate cancer; ovarian carcinoma (ovarian epithelial carcinoma or surface epithelial-stromal tumour including serous tumour, endometrioid tumor and mucinous cystadenocarcinoma, sex-cord-stromal tumor); liver and bile duct carcinoma (including hepatocelluar carcinoma, cholangiocarcinoma, hemangioma); esophageal carcinoma (including esophageal adenocarcinoma and squamous cell carcinoma); non-Hodgkin's lymphoma; bladder carcinoma; carcinoma of the uterus (including endometrial adenocarcinoma, uterine papillary serous carcinoma, uterine clear-cell carcinoma, uterine sarcomas and leiomyosarcomas, mixed mullerian tumors); glioma, glioblastoma, medullablastoma, and other tumors of the brain; kidney cancers (including renal cell carcinoma, clear cell carcinoma, Wilm's tumor); cancer of the head and neck (including squamous cell carcinomas); cancer of the stomach (stomach adenocarcinoma, gastrointestinal stromal tumor); multiple myeloma; testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

The term "metastasis" means the ability of tumor cells to invade host tissues and metastasize to distant, often specific organ sites. As is known, this is the salient feature of lethal tumor growths. Metastasis formation occurs via a complex series of unique interactions between tumor cells and normal host tissues and cells. In the context of the present invention, lysyl oxidase activity is critical in the metastatic growth of tumors, i.e., the growth of metastases, particularly under hypoxic conditions. As hypoxic tumors are also the most aggressive and resistant to traditional chemotherapy, agents modulating lysyl oxidase expression and/or function provide a novel therapy against metastatic tumors, particularly chemo-resistant tumors. "Metastasis" is distinguished from invasion. As described in "Understanding Cancer Series: Cancer," in the world wide web site: cancer.gov/cancertopics/understandingcancer/cancer; invasion refers to the direct migration and penetration by cancer cells into neighboring tissues.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocyte leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agarnmaglobulinemia.

Acute promyelocytic leukemia (APML) represents a distinct subgroup of AML. This subtype is characterized by promyelocytic blasts containing the 15; 17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9; 22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocyte series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Administration of LOX or LOX2 inhibitors has been found to reduce the size of existing tumors, to prevent metastases, and to reduce the size of (or even eliminate) existing metastases (see, e.g., Molnar et al. (2003) Biochim Biophys. Acta. 1647:220-224).

Provided herein is a method of reducing tumor growth in a subject, by administering any of the anti-LOX or anti-LOXL2 antibodies or antigen binding fragments thereof described herein. In one embodiment, a tumor is a primary tumor.

In another embodiment, a tumor is a metastatic tumor. Metastatic tumor burden of a subject can stabilized by administering antibodies as described herein. Tumor in the subject can be reduced by at least 10%, 25%, 50%, 70%, 90%, 95%, or more as compared to the tumor in the subject prior to treatment.

When an antibody or antigen binding fragment thereof specifically binds to LOXL2, examples of tumors include, but are not limited to, a colon tumor, an esophageal tumor, a breast tumor, a prostate tumor, a squamous carcinoma or a spindle cell carcinoma.

When an antibody or antigen binding fragment thereof specifically binds to LOX, examples of tumors include, but are not limited to, a breast tumor, a lung tumor, a kidney tumor, a uterine tumor, a liver tumor, or a head and neck tumor.

Provided herein is a method for preventing or reducing tumor growth, metastatic tumor growth, in a subject in vivo, comprising administering to a subject in need thereof an effective amount of an inhibitor of LOX or LOXL2 activity; and optionally, a pharmaceutically acceptable carrier or excipient, thereby preventing or reducing tumor growth, for example by at least 25%, 50%, 75%, 90%, or 95%, in the subject treated. A detailed description of suitable compositions for use in the present treatment methods is given above. Such methods are useful, for example, when the tumor is hypoxic. Hypoxic tumors can be readily identified using routine methods in the art. See, e.g., U.S. Pat. No. 5,674,693.

Also, provided herein is a method of treating metastasis in a subject with cancer in vivo, comprising administering to a subject in need thereof an effective amount of a LOX or LOXL2 inhibitor, thereby inhibiting metastasis, for example, by at least 25%, 50%, 75%, 90%, or 95%, in the subject treated. In one embodiment, inhibitors specifically inhibit human LOX or human LOXL2. Antibodies to be used in these methods have been described above. The antibody may be desirable to minimize cross-reactions with other members of the LOX or LOXL2 families and, thus, reduce the potential adverse side effects due to complications and normal tissue toxicity.

Also provided herein is a method of increasing or enhancing the chances of survival of a subject with metastatic tumor, comprising administering to a subject in need thereof an effective amount of an anti-LOX antibody or an anti-LOXL2 antibody, thereby increasing or enhancing the chances of survival of the subject treated by a certain period of time, for example, by at least 10 days, 1 month, 3 months, 6 months, 1 year, 1.5 years, 2 years, 3 years, 4 years, 5 years, 8 years, 10 years, or more. The increase in survival of a subject can be defined, for example, as the increase in survival of a preclinical animal model of cancer metastases (e.g., a mouse with metastatic cancer), by a certain period of time, for example, by at least 10 days, 1 month, 3 months, 6 months, or 1 year, or at least 2 times, 3 times, 4 times, 5 times, 8 times, or 10 times, more than a control animal model (that has the same type of metastatic cancer) without the treatment with the inventive method. Alternatively, the increase in survival of a mammal can also be defined, for example, as the increase in survival of a patient with cancer metastases by a certain period of time, for example, by at least 10 days, 1 month, 3 months, 6 months, 1 year, 1.5 years, 2 years, 3 years, 4 years, 5 years, 8 years, 10 years or more than a patient with the same type of metastatic cancer but without the treatment with the inventive method. The control patient may be on a placebo or treated with supportive standard care such as chemical therapy, biologies and/or radiation that do not include the inventive method as a part of the therapy.

Also provided herein is a method of stabilizing metastatic tumor burden of a subject, comprising administering to a subject in need thereof an effective amount of an anti-LOX antibody or an anti-LOXL2 antibody, thereby stabilizing metastatic tumor burden of a subject for a certain period of time, for example, for at least 10 days, 1 month, 3 months, 6 months, 1 year, 1.5 years, 2 years, 3 years, 4 years, 5 years, 8 years, 10 years or more. Stabilization of the metastatic tumor burden of a subject can be defined as stabilization of metastatic tumor burden of a preclinical animal model with metastatic tumor burden (e.g., a mouse with metastatic tumor) for a certain period of time, for example, for at least 10 days, 1 month, 3 months, 6 months, or 1 year more than a control animal model (that has the same type of metastatic tumor) without the treatment with the inventive method.

The present treatment methods also include a method to increase the efficacy of chemotherapeutic agents, comprising administering to a subject in need thereof an effective amount of an anti-LOX antibody or an anti-LOXL2 antibody; and optionally, a pharmaceutically acceptable carrier or excipient, thereby increasing the efficacy of chemotherapeutic agents (which are described in more detail above). Also contemplated are methods involving the delivery of LOX inhibitory formulations in combination with radiation therapy. Radiation therapy may be used to treat almost every type of solid tumor, including cancers of the brain, breast, cervix, larynx, lung, pancreas, prostate, skin, spine, stomach, uterus, or soft tissue sarcomas. Radiation can also be used to treat leukemia and lymphoma (cancers of the blood-forming cells and lymphatic system, respectively). Radiation dose to each site depends on a number of factors, including the type of cancer and whether there are tissues and organs nearby that may be damaged by radiation. Radiation will typically be delivered as X-rays, where the dosage is dependent on the tissue being treated. Radiopharmaceuticals, also known as radionucleotides, may also be used to treat cancer, including thyroid cancer, cancer that recurs in the chest wall, and pain caused by the spread of cancer to the bone (bone metastases). Radionuclides have been described in more detail above.

The subject to be treated or diagnosed by the present methods includes a subject having or being at risk of having metastatic tumor growth. Such tumors can be a in one aspect, a tumor is, for example, Lung cancer (including lung adenocarcinoma, squamous cell carcinoma, large cell carcinoma, bronchioloalveolar carcinoma, non-small-cell carcinoma, small cell carcinoma, mesothelioma); breast cancer (including ductal carcinoma, lobular carcinoma, inflammatory breast cancer, clear cell carcinoma, mucinous carcinoma,); colorectal cancer (colon cancer, rectal cancer); anal cancer; pancreatic cancer (including pancreatic adenocarcinoma, islet cell carcinoma, neuroendocrine tumors); prostate cancer; ovarian carcinoma (ovarian epithelial carcinoma or surface epithelial-stromal tumour including serous tumour, endometrioid tumor and mucinous cystadenocarcinoma, sex-cord-stromal tumor); liver and bile duct carcinoma (including hepatocelluar carcinoma, cholangiocarcinoma, hemangioma); esophageal carcinoma (including esophageal adenocarcinoma and squamous cell carcinoma); non-Hodgkin's lymphoma; bladder carcinoma; carcinoma of the uterus (including endometrial adenocarcinoma, uterine papillary serous carcinoma, uterine clear-cell carcinoma, uterine sarcomas and leiomyosarcomas, mixed mullerian tumors); glioma, glioblastoma, medullablastoma, and other tumors of the brain; kidney cancers (including renal cell carcinoma, clear cell carcinoma, Wilm's tumor); cancer of the head and neck (including squamous cell carcinomas); cancer of the stomach (stomach adenocarcinoma, gastrointestinal stromal tumor); multiple myeloma; testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma. In one non-limiting embodiment, the tumor is a breast rumor, a pancreas tumor, a lung tumor, a cervical tumor, a colon tumor or a head and neck tumor.

The present invention also provides a method for preventing or reducing the risk of tumor metastasis in a subject, comprising administering to a subject in need thereof an effective amount of an anti-LOX antibody or an anti-LOXL2 antibody; and optionally, a pharmaceutically acceptable carrier or excipient, thereby preventing or reducing preventing or reducing the risk of tumor metastasis. The inhibitor can be an antibody or an antigen binding fragment thereof. The subject in need of such a prophylactic can be an individual who is genetically predisposed to cancer or at a high risk of developing cancer due to various reasons such as family history of cancer and carcinogenic environment.

Examples of the human gene that is involved in the onset or development of cancer include, but are not limited to, VHL (the Von Hippon Landau gene involved in Renal Cell Carcinoma); P16/TNK4A (involved in lymphoma); E-cadherin (involved in metastasis of breast, thyroid, gastric cancer); hMLH1 (involved in DNA repair in colon, gastric, and endometrial cancer); BRCA1 (involved in DNA repair in breast and ovarian cancer); LKB1 (involved in colon and breast cancer); P15/INK4B (involved in leukemia such as AML and ALL); ER (estrogen receptor, involved in breast, colon cancer and leukemia); 06-MGMT (involved in DNA repair in brain, colon, lung cancer and lymphoma); GST-pi (involved in breast, prostate, and renal cancer); TIMP-3 (tissue metalloprotease, involved in colon, renal, and brain cancer metastasis); DAPK1 (DAP kinase, involved in apoptosis of B-cell lymphoma cells); P73 (involved in apoptosis of lymphomas cells); AR (androgen receptor, involved in prostate cancer); RAR-beta (retinoic acid receptor-beta, involved in prostate cancer); Endothelin-B receptor (involved in prostate cancer); Rb (involved in cell cycle regulation of retinoblastoma); p53 (an important tumor suppressor gene); P14ARF (involved in cell cycle regulation); RASSF1 (involved in signal transduction); APC (involved in signal transduction); Caspase-8 (involved in apoptosis); TERT (involved in senescence); TERC (involved in senescence); TMS-1 (involved in apoptosis); SOCS-1 (involved in growth factor response of hepatocarcinoma); PITX2 (hepatocarcinoma breast cancer); MTNT1; MTNT2; GPR37; SDC4; MY0D1; MDR1; THBS1; PTC1; andpMDR1, as described in Santini et al. (2001) Ann. of Intern. Med. 134:573-586, which is herein incorporated by reference in its entirety. Nucleotide sequences of these genes can be retrieved from the website of the National Center for Biotechnology Information (NCBI).

It should be noted that, although leukemia is a cancer of the blood, it might affect other organs, or, in effect, metastasize. In acute leukemias, the abnormal cells may collect in the central nervous system, the testicles, the skin and any other organ in the body. Because leukemia already involves all of the bone marrow in the body, and in many cases, has spread to other organs such as the liver, spleen, and lymph nodes, the staging of leukemia depends on other information that reflects the patient's outlook for survival. Leukemias include, for example, Acute lymphoblastic leukemia (ALL), Chronic lymphocytic leukemia (CLL), Acute myelogenous leukemia (AML), Chronic myelogenous leukemia (CML) and Hairy cell leukemia (HCL). Different staging systems are used for different types of chronic leukemia. Some types do not have any staging system Methods of staging are described in more detail below.

Treatment of abnormal cell proliferation due to insults to body tissue during surgery can be possible for a variety of surgical procedures, including joint surgery, bowel surgery, and keloid scarring. Diseases that produce fibrotic tissue include emphysema. Repetitive motion disorders that can be treated using the present invention include carpal tunnel syndrome. An example of cell proliferative disorders that can be treated using the invention is a bone tumor. Provided herein is a method for preventing or reducing the risk of abnormal cell proliferation due to insults to body tissue during surgery or a disease that produces fibrotic tissue in a subject, comprising administering to a subject in need thereof an effective amount of an anti-LOX antibody or an anti-LOXL2 antibody; and optionally, a pharmaceutically acceptable carrier or excipient, thereby preventing or reducing abnormal cell proliferation due to insults to body tissue during surgery. The inhibitor can be an antibody or an antigen binding fragment thereof. The subject in need of such a prophylactic can be an individual who is genetically predisposed to cancer or at a high risk of developing cancer due to various reasons such as family history of cancer and carcinogenic environment. In one embodiment, the disease can be, for example, joint surgery, bowel surgery, keloid scarring, a disease that produces fibrotic tissue, repetitive motion disorders of a bone tumor.

The proliferative responses associated with organ transplantation that can be treated using this invention include those proliferative responses contributing to potential organ rejections or associated complications. Specifically, these proliferative responses can occur during transplantation of the heart, lung, liver, kidney, and other body organs or organ systems. Provided herein is a method of treating an abnormal proliferative response associated with organ transplantation, comprising administering to a subject in need thereof an effective amount of an anti-LOX antibody or an anti-LOXL2 antibody; and optionally, a pharmaceutically acceptable carrier or excipient, thereby preventing or reducing abnormal cell proliferation due to organ transplantation. Transplantation can include, for example, transplant of heart, lung, liver, kidney, and other body organs or organ systems.

The indication for the inventive composition also includes fibrosis. Fibrosis results from abnormal accumulation of fibrous tissue that can occur as a part of the wound-healing process in damaged tissue. Such tissue damage may result from physical injury, inflammation, infection, exposure to toxins, and other causes. Examples of fibrosis include liver fibrosis, lung fibrosis, kidney fibrosis, cardiac fibrosis and scleroderma. The compounds and agents of the described invention are also contemplated for the treatment, prevention, and/or amelioration of fibrotic conditions.

Fibrotic tissues accumulate in the heart and blood vessels as a result of hypertension, hypertensive heart disease, atherosclerosis, and myocardial infarction. High blood pressure, or hypertension, can be cause by a variety of factors and often leads to the development of Hypertensive Heart Disease (HHD) with progression to cardiac arrest and myocardial infarction. Similarly, atherosclerosis and other ischemic heart diseases often also result in cardiac arrest. These cardiovascular diseases all exhibit an accumulation of extra-cellular matrix or fibrotic deposition which results in stiffening of the vasculature and stiffening of the cardiac tissue itself. This deposition of fibrotic material is a response to the damage induced by the hypertensive and/or sclerotic state, but the effects of this response also result in the negative effects of vascular and cardiac stiffening as well as ventricle enlargement. Additionally, it is believed that the increased cardiac fibrosis seen in cardiovascular disease disrupts or alters the signals transmitted to cardiomyocytes via the tissue scaffolding of the heart, further leading to disruption of efficient cardiac function and promoting cardiac arrest and myocardial infarction. Given the identified role of increased extracellular matrix deposition in cardiac fibroses, the compounds of the present invention are useful for the prevention, treatment, and/or amelioration of cardiac fibroses by the inhibition of LOX/LOXL2.

The prevent invention also provides compositions, methods, systems, medical devices or kits for the treatment or prevention of cardiac fibrosis associated with cardiovascular diseases such as hypertensive heart disease (HHD), myocardial infarction (MI), atherosclerosis, restenosis (e.g. coronary, carotid, and cerebral lesions), and heart disease associated with cardiac ischemic events.

The post MI-healing response can induce expression of LOX/LOXL2 but if this process continues unchecked, excessive cross-linking leads to extracellular matrix remodeling or fibrosis that results in cardiac dysfunction. The enzymes that break down matrices and cross-linked collagen or elastin appear to function more slowly or less efficiently and are outpaced by the cross-linking events. As LOX/LOXL2 also plays a role in epithelial-mesenchymal transition (EMT), this contributes further to cardiomyocyte remodeling and cardiomyocyte hypertrophy, in addition to matrix remodeling.

Initial reparative fibrosis induced by the MI may be helpful (e.g., prevents aneurysm and related damage) and can be allowed to proceed unhindered. However, while not wishing to be bound to a particular theory or mechanism of action, the inventors believe that anti-LOX/LOXL2 treatment initiated following this reparative fibrosis phase could attenuate reactive (mal-adaptive) fibrosis that leads to cardiac dysfunction. For example, anti-LOX/LOXL2 treatment can be initiated 2,4, 6, 8, 10, 12, 14, 16, 16, 20, 22, 24, 36, or 48 hours after MI, inclusive of all integers in-between. Additionally, anti-LOX/LOXL2 treatment can be initiated 2, 3, 4, 5, 6, 7, 8, 9, 10, 11, 12, 13, or 14 days after MI. Similarly, increases in blood pressure (hypertension) result in increased collagen deposition and reduced protein degradation in cardiac tissue. (Berk et al., J. Clin. Invest, 117(3): 568-575 (2007)). Anti-LOX/LOXL2 treatment initiated following diagnosis and/or establishment of Hypertensive Heart Disease or hypertension can prevent, reduce, or ameliorate fibrosis associated with hypertension. Such anti-LOX/LOXL2 treatment is initiated 2, 3, 4, 5, 6, 7, 8, 9, 10, 11, 12, 13 or 14 days after increases in hypertension or systemic blood pressure are diagnosed or detected.

As another example, biomarkers may be used to determine when an inappropriate level of cross-linking might be occurring: for example, LOX levels have been shown to correlate with C reactive protein (CRP), a commonly used biomarker, and treatment could begin when CRP levels are elevated above appropriate normal levels. More directly, methods and test kits exist to measure the release of cross-linked collagen telopeptides in urine or blood. Elevated levels of these collagen fragments could indicate a transition from reparative fibrosis to reactive (mal-adaptive) fibrosis. In addition, measures of cardiac function and output, including those associated with efficient contraction of the ventricle, can be made.

An inhibitor of LOX/LOXL2 can be delivered to a subject prior to, concurrently, or post a pathological cardiac condition or disease, such as hypertension, hypertensive heart disease (HHD), myocardial infarction (MI), atherosclerosis, and restenosis, to prevent the onset of, to reduce the risk of, or to retreat pathological fibrosis associated with such a pathological cardiac condition or disease. For example, an inhibitor of LOX/LOXL2 can be administered at least 1 hr, 2 hrs, 3 hrs, 5 hrs, or 10 hrs, or 1, 2, 3, 4, 5, 6, 7, 8, 9, 10, 11, 12, 13, or 14 days after the onset of such a pathological cardiac condition or disease.

Additionally, a limited duration of treatment is envisioned. Treatment should be sustained only long enough to prevent or attenuate reactive fibrosis to prevent or reduce cardiac dysfunction. For example, short-lived FAB antibody fragments are used when shorter durations of treatment are desired. Alternatively, full-length antibodies that have a longer half-life in serum can be used, with limited dosing over 1, 2, 3, 4, 5, 6, 7, 8, 9, 10, 11, or 12 weeks, inclusive of all days in-between. Standard tests of cardiac function can be used to monitor progress and adjust dosing as necessary, along with assessment of relevant biomarkers discussed above. Limited duration of treatment adds to the safety of this approach.

Fibrosis of the liver is implicated in the pathology of numerous hepatic diseases. As previously noted, fibrosis occurs as a complication of haemochromatosis, Wilson's disease, alcoholism, schistosomiasis, viral hepatitis, bile duct obstruction, exposure to toxins, and metabolic disorders. Left unchecked, hepatic fibrosis progresses to cirrhosis (defined by the presence of encapsulated nodules), liver failure, and death. The chronic insults to the liver from such sources as parasites and viral infection (e.g. HBV, HCV, HIV, schistosomiasis) or the long term stress from alcohol consumption inevitably result in remodeling of the liver, presumably to encapsulate the damaged area and protect the remaining liver tissue from damage. (Li and Friedman, Gastroenterol. Hepatol. 14:618-633, 1999). Liver fibrosis results in extracellular matrix changes, including 3-10 fold increases in total collagen content and replacement of the low density basement membrane with high-density matrix, which impair the metabolic and synthesis function of hepatocytes, hepatic stellate cells and endothelial cells. (Girogescu, M., Non-invasive Biochemical Markers of Liver Fibrosis, J. Gastrointestin. Liver Dis, 15(2): 149-159 (2006)). The compounds of the instant invention are thus useful for the prevention, treatment, and/or amelioration of fibrotic liver diseases, and such use is contemplated herein by inhibition of LOX/LOXL2.

Like liver fibrosis, kidney fibrosis can result from various diseases and insults to the kidneys. Examples of such diseases and insults include chronic kidney disease, metabolic syndrome, diabetes and resultant glomerular nephritis. It has become recognized that metabolic syndrome is a cluster of abnormalities including diabetic hallmarks such as insulin resistance as well as central or visceral obesity and hypertension. In nearly all cases, dysregulation of glucose results in the stimulation of cytokine release and upregulation of extracellular matrix deposition. Additional factors contributing to chronic kidney disease, diabetes, metabolic syndrome, and glomerular nephritis include hyperlipidemia, hypertension, and proteinuria, all of which result in further damage to the kidneys and further stimulate the extracellular matrix deposition. Thus, regardless of the primary cause, insults to the kidneys result in kidney fibrosis and the concomitant loss of kidney function. (Schena, F. and Gesualdo, L, Pathogenic Mechanisms of Diabetic Nephropathy, J. Am, Soc. Nephrol, 16: S30-33 (2005); Whaley-Connell, A, and Sower, J. R., Chronic Kidney Disease and the Cardiometabolic Syndrome, J. Clin. Hypert, 8(8): 546-48 (2006)). The compounds of the instant invention are thus useful for the prevention, treatment, and/or amelioration of fibrotic kidney diseases (chronic kidney disease, diabetic nephropathy, glomerular nephritis, metabolic syndrome), and such use is contemplated herein, Fibrosis of the lung includes many syndromes and diseases. Exemplary diseases include Idiopathic pulmonary fibrosis (IFF), Idiopathic Interstitial Pneumonia, and Acute Respiratory Distress Syndrome (ARDS). The pathogenesis of most lung fibroses, including the aforementioned diseases are not well understood, however all are characterized by an influx of inflammatory cells and a subsequent increase in the synthesis and deposition of collagen-rich extracellular matrix. (Chua et al. Am J. Respir. Cell. Mol. Biol, 33:9-13 (2005); Tzortzaki et al, J. Histochem. & Cytochem, 54(6): 693-700 (2006); Armstrong et al. Am. J. Respir. Crit. Care Med, 160:1910-1915 (1999)). Given the identified role of increased collagen and extracellular matrix deposition in lung fibroses, the compounds of the present invention are useful for the prevention, treatment, and/or amelioration of lung fibroses by the inhibition of LOX/LOXL2.

Scleroderma is an autoimmune disorder, in which there is an overproduction of abnormal collagen. This excess collagen accumulates throughout the body, causing hardening (sclerosis), scarring (fibrosis), and other damage. The damage may affect the appearance of the skin, or it may involve only the internal organs. The symptoms and severity of scleroderma vary from person to person. Given the identified role of increased collagen in scleroderma, the compounds of the present invention are useful for the prevention, treatment, and/or amelioration of scleroderma by the inhibition of LOX/LOXL2.

Abnormal angiogenesis that can be treated or prevented by using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopahy, and other ocular angiogenic diseases such as retinopathy of prematurity (retrolental fibroplastic), muscular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

Anti-LOX antibodies and anti-LOXL2 antibodies described herein can be used for treating diseases associated with undesired or abnormal angiogenesis. The method comprises administering to a patient suffering from undesired or abnormal angiogenesis a LOX/LOXL inhibitor in combination with anti-neoplastic agent or anti-angiogenic agent that is not said LOX/LOXL inhibitor. The particular dosage of these agents required to inhibit (partially or completely) angiogenesis and/or angiogenic diseases can depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the pharmaceutical formulations of the present invention can be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi sarcoma.

In yet another embodiment, the pharmaceutical formulations of the present invention can be used for treating chronic inflammatory diseases associated with abnormal angiogenesis. The method comprises administering to a patient suffering from a chronic inflammatory disease associated with abnormal angiogenesis a LOX/LOXL2 inhibitor in combination with anti-neoplastic agent or anti-angiogenic agent that is not said LOX/LOXL2 inhibitor. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the compounds described herein can prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present invention should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract. Inhibition of angiogenesis by the pharmaceutical formulations of the present invention should reduce the influx of inflammatory cells and prevent the lesion formation. Therefore, provided herein is a method of treating an inflammatory bowel disease, comprising administering to a subject in need thereof an effective amount of an anti-LOX antibody or an anti-LOXL2 antibody; and optionally, a pharmaceutically acceptable carrier or excipient.

Sarcoidois, another chronic inflammatory disease, is characterized as a multisystem granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the pharmaceutical formulations of the present invention to inhibit angiogenesis, such granulomas formation can be inhibited. Psoriasis, also a chronic and recurrent inflammatory disease, is characterized by papules and plaques of various sizes. Treatment using the pharmaceutical formulations of the present invention should prevent the formation of new blood vessels necessary to maintain the characteristic lesions and provide the patient relief from the symptoms. Therefore, provided herein is a method of prevent the formation of new blood vessels necessary to maintain the characteristic lesions and provide the patient relief from the symptoms, comprising administering to a subject in need thereof an effective amount of an anti-LOX antibody or an anti-LOXL2 antibody; and optionally, a pharmaceutically acceptable carrier or excipient.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis can actively contribute to, and help maintain, the chronically inflamed state of rheumatoid arthritis. Treatment using the pharmaceutical formulations of the present invention alone or in conjunction with other anti-RA agents may prevent the formation of new blood vessels necessary to maintain the chronic inflammation and provide the RA patient relief from the symptoms. Other anti-RA agents are conventional and known in the art. Therefore, provided herein is a method of preventing or treating RA, comprising administering to a subject in need thereof an effective amount of an anti-LOX antibody or an anti-LOXL2 antibody; and optionally, one or more other anti-RA agents.

In addition to the use of the anti-LOX antibodies or anti-LOXL2 antibodies alone in the treatment of the indications described above, combination therapy is also contemplated herein. The methods provided herein can further include administering an anti-cancer agent or treatment to the patient.

Provided herein is a method of treating any of the indications described above by administering an anti-LOX antibody and an anti-LOXL2 antibody.

In one aspect, this invention features methods for inhibiting the invasiveness and metastasis of tumor cells, by contacting the cells with at least one cytotoxic agent and at least one anti-LOX antibody or anti-LOX2 antibody. In general, the method includes a step of contacting metastatic tumor cells with an amount of at least one cytotoxic agent and at least one anti-LOX antibody or anti-LOX2 antibody, which, in combination, is effective to reduce or inhibit the invasiveness or metastatic potential of the cell. Alternatively, according to the present invention, an anti-LOX antibody or an anti-LOXL2 antibody can be combined with a chemotherapeutic agent to sensitize tumor cells (e.g., transition from the EMT state to the MET state) to killed by the chemotherapeutic agent, thus not only preventing or inhibiting tumor invasion and metastasis but also inhibiting primary tumor growth.

Any suitable anticancer agent may also be employed in the present methods.

As used herein the term "chemotherapeutic agent" or "chemotherapeutic" (or "chemotherapy," in the case of treatment with a chemotherapeutic agent) is meant to encompass any non-proteinaceous (i.e, non-peptidic) chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chrommomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin;

sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL™, Bristol Meyers Squibb Oncology, Princeton, N.J.) and docetaxel (TAXOTERE™., Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprohde, and goserelin; and pharmaceutically acceptable salts, acids or derivatives of any of the above.

Figure 18:
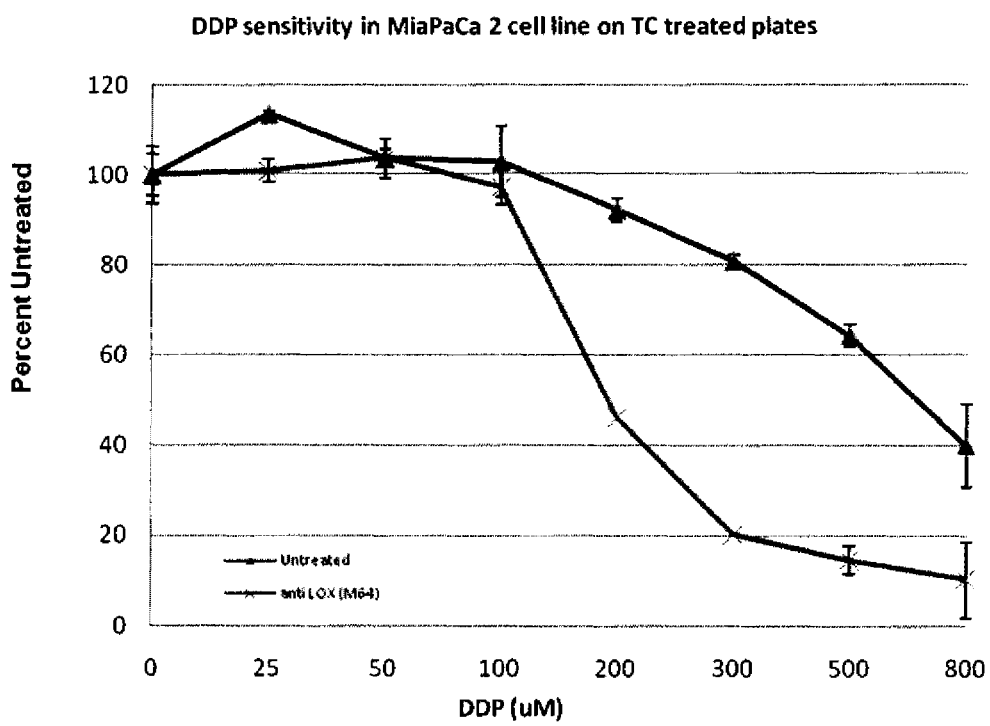
FIG. 18 demonstrates a synergistic effect of an anti-LOX antibody in combination with cisplatin. $IC_{50}$ values of M64 were also determined on four cell lines.

In one non-limiting example, this invention includes methods for synergistically inhibiting the invasiveness and metastasis of tumor cells, by contacting the cells with at least cisplatin and at least one anti-LOX antibody (see FIG. 18). One practicing methods described herein would understand that an anti-LOX2 antibody could be used in such methods.

In one embodiment, the anti-neoplastic agent in combination with the LOX/LOXL modulator is a tyrosine kinase inhibitor. For example, ZD 1839 (Iressa™ of AstraZeneca K.K.) shows a competitive effect for ATP in ATP binding site of EGFR (epidermal growth factor receptor) tyrosine kinase, and inhibits tyrosine kinase activity by inhibiting autophosphorylation of tyrosine kinase. As a result, the anticancer effect is expressed by blocking an EGFR-equipping signal transduction (ligands such as epidermal growth factor (EGF) are bound to the extracellular domain of EGFR, followed by activation of EGFR tyrosine kinase in the intracellular domain, causing not only autophosphorylation of EGFR but also phosphorylation of various intracellular target proteins, then transducing a proliferation signal from the cell surface to nucleus, then transducing the proliferation signals from the cancer cell surface to nucleus, and resulting in proliferation, infiltration, metastasis, angiogenesis of cancer cells) in association with proliferation, infiltration, differentiation and metastasis. IMC-C225 or cetuximab (Erbitux™) which is an EGFR-targeting monoclonal antibody) recognizes the receptor part of EGFR on a cell membrane surface and inhibits the autophosphorylation of EGFR thereby inhibiting the tyrosine kinase activity. Herceptin is a monoclonal antibody against Her2/Neu which is homologous to EGFR, and imatinib mesylate (GLEEVEC™, formerly STI-571) can inhibit both tyrosine kinase activities of BCR-Abl and c-kit (non-patent document No. 2). Sorafenib (Nexavar™) is a small molecular inhibitor of Raf kinase, PDGF (platelet-derived growth factor), VEGF receptor 2 & 3 kinases and c-Kit.

As used herein, monoclonal antibodies against tumor antigens are antibodies elicited against antigens expressed by tumors and leukemic cells, preferably tumor-specific antigens. The monoclonal antibody also includes fully human and humanized antibody.

Other examples of therapeutic antibodies for cancer therapy include Trastuzumab (HERCEPTIN™; Overexpression of HER2 protein is associated with more aggressive disease and poorer prognosis in the clinic); Rituximab (RITUXAN™) that is raised against CD20 on lymphoma cells and selectively deplete normal and maligant CD20+ pre-B and mature B cells; Alemtuzumab (CAMPATH™), a monoclonal antibody that specifically targets CD52 antigen that is found on B and T lymphocytes and used for the treatment of chronic lymphocytic leukemia (CLL) and lymphoma; and Gemtuzumab zogamicin (MYLOTARG™), an antibody conjugate that combines a specific antibody against CD33 with a chemotherapeutic drug (zogamicin) and is indicated for the treatment of relapsed adult acute myelocytic leukemia.

In another embodiment, anti-angiogenic agent is combined with a LOX/LOXL inhibitor to treat cancer and other diseases associated with abnormal or undesirable angiogenesis. Examples of anti-angiogenic agents include, but are not limited to, retinoid acid and derivatives thereof, 2-methoxyestradiol, ANGIOSTATIN™, ENDOSTATIN™, suramin, squalamine, tissue inhibitor of metalloproteinase-1, tissue inhibitor of metalloproternase-2, plasminogen activator inhibitor-1, plasminogen activator inbibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3, 4-dehydroproline, thiaproline, α-dipyridyl, β-aminopropionitrile fumarate, 4-propyl-5-(4-pyridinyl)-2(3 h)-oxazolone; methotrexate, mitoxantrone, heparin, interferons, 2 macroglobulin-serum, chimp-3, chymostatin, β-cyclodextrin tetradecasulfate, eponemycin; fumagillin, gold sodium thiomalate, d-penicillamine (CDPT), beta.-1-anticollagenase-serum, alpba.2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Exemplary anti-fibrotic agents include, but are not limited to the compounds such as β-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Antifibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456;

U.S. Pat. No. 5,5059,714; U.S. Pat. No. 5,120,764; U.S. Pat. No. 5,182,297; U.S. Pat. No. 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. In another embodiment, the anti-fibrotic agents are copper chelating agents, penetrating or not penetrating the cells. Additional exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The present methods can be performed on cells in culture, e.g., in vitro or ex vivo, or can be performed on cells present in a subject, e.g., as part of an in vivo therapeutic protocol. The therapeutic regimen can be carried out on a human or on other animal subjects. The anti-LOX antibody or anti-LOX2 antibody provided herein can be administered in any order relative to the chemotherapeutic agent. Sometimes, the anti-LOX antibody or anti-LOX2 antibody and the agent are administered simultaneously or sequentially. They can be administered at different sites and on different dosage regimens. The enhanced therapeutic effectiveness of the combination therapy of the present invention represents a promising alternative to conventional highly toxic regimens of anticancer agents. Chemotherapeutic agents to be employed in such methods have been described in more detail above.

EXAMPLES

The application may be better understood by reference to the following non-limiting examples, which are provided as exemplary embodiments of the application. The following examples are presented in order to more fully illustrate embodiments of the invention and should in no way be construed, however, as limiting the broad scope of the application. While certain embodiments of the present application have been shown and described herein, it will be obvious that such embodiments are provided by way of example only. Numerous variations, changes, and substitutions will now occur to those skilled in the art without departing from the invention. It should be understood that various alternatives to the embodiments described herein may be employed in practicing the methods described herein.

Example 1

Methods of Generating Murine Monoclonal Anti-LOX and Anti-LOXL2 Antibodies

Mice (BALB/c (00467)) were injected subcutaneously (s.c.), 5 times at 2-3 week intervals with 0.05 mg antigen (Ag) in an adjuvant formulation. For peptide Ags, peptides were conjugated to bovine serum albumin and formulated in Freunds Adjuvant (FA) prior to immunization. For protein Ags, the protein was formulated in Alhydrogel-Muramyl Dipeptide (ALD/MDP) adjuvant.

Mice were injected with Ag formulated in PBS, each day for 3 days via a combination of s.c, intraperitoneally (i.p.) and intravenous (i.v.) routes, 0.05 to 0.1 mg/route.

Cells from the spleen and lymph nodes of the mice were isolated and fused with P3X63-Ag8.653 myeloma cells using 50% polyethylene glycol.

Cells were cultured and a hybridoma library of HAT-selected cells was isolated essentially as described in Kenney, et al. ("Production of monoclonal antibodies using a secretion capture report web." Biotechnology 13:787-790, 1995).

The hybridoma library was cloned using a fluorescent activated cell sorter with automatic cell deposition unit.

Single viable cells were sorted into 96-well plates based upon the analysis criteria of forward-scatter, side-scatter and propidium iodide fluorescence as described by Kenney et al. Sera and supernatants were screened by enzyme linked immunosorbant assay (ELISA) using Ag-coated microtiter plate wells, which were then incubated with mouse plasma or hybridoma supernatant, followed by goat mouse IgG (Fc-specific) antibody-HRP conjugate, followed by TMB substrate solution and stop reagent.

The plate wells were washed to remove unbound antibody or antigen between all incubations and results determined.

VH and VL amino acid sequences of an anti-LOXL2 murine monoclonal antibody identified using the described methods are provided in FIG. 6A and FIG. 6B, respectively. For each variable region, signal peptides are shown in italics, CDRs are underlined and the beginning of the constant framework is shown in bold font.

A VH amino acid sequence of an anti-LOX murine monoclonal antibody identified using the described methods is provided in FIG. 7A. Two VL amino acid sequences of anti-LOX murine monoclonal antibodies identified using the described methods are provided in FIGS. 7B and 7C. For each variable region, signal peptides are shown in italics, CDRs are underlined.

Example 2

Anti-LOXL2 antibodies were screened using a protein screen B update to assess enzymatic activity of LOXL2.

Antibody candidates were initially chosen based on ELISA point tests. ELISA on multiple antigens was performed by Antibody Solutions and antibodies showing strong ELISA signal in the antigen of interest were selected for further characterization in enzymatic assays. LOXL2 produces hydrogen peroxide when the substrate 1,5-diaminopentane is deaminated and the enzyme regenerated.

Antibodies were assessed for their ability to inhibit enzymatic activity using a biochemical assay that couples the production of peroxide (liberated by LOXL2) to HRP and measuring the conversion of amplex red to a fluorescent product. Antibody hybridoma supernatant (10 μL) was added to 40 μL enzyme mixture (62.5 mM sodium borate pH 8.0, 5 units/mL HRP, 125 nM LOXL2, 10 ppm antifoam) and incubated at room temperature for 1 hour in a 96 well full area black plate. Enzymatic reaction was started with the addition of 50 μL of substrate solution (50 mM sodium borate, 100 μM amplex red reagent, 20 mM 1,5-diaminopentane (DAP), 10 ppm antifoam) and read in a Molecular Devices M5 plate Teader at 37° C. The plate reader was configured to read fluorescence (ex=544 ran, em=590 nm) in kinetics mode for 1 hour. Data was recorded as the slope of the fluorescence response to time. These slopes were compared to a control in which hydridoma media was added to the enzyme mixture. Slopes less than that of control were considered inhibitors.

Figure 8:
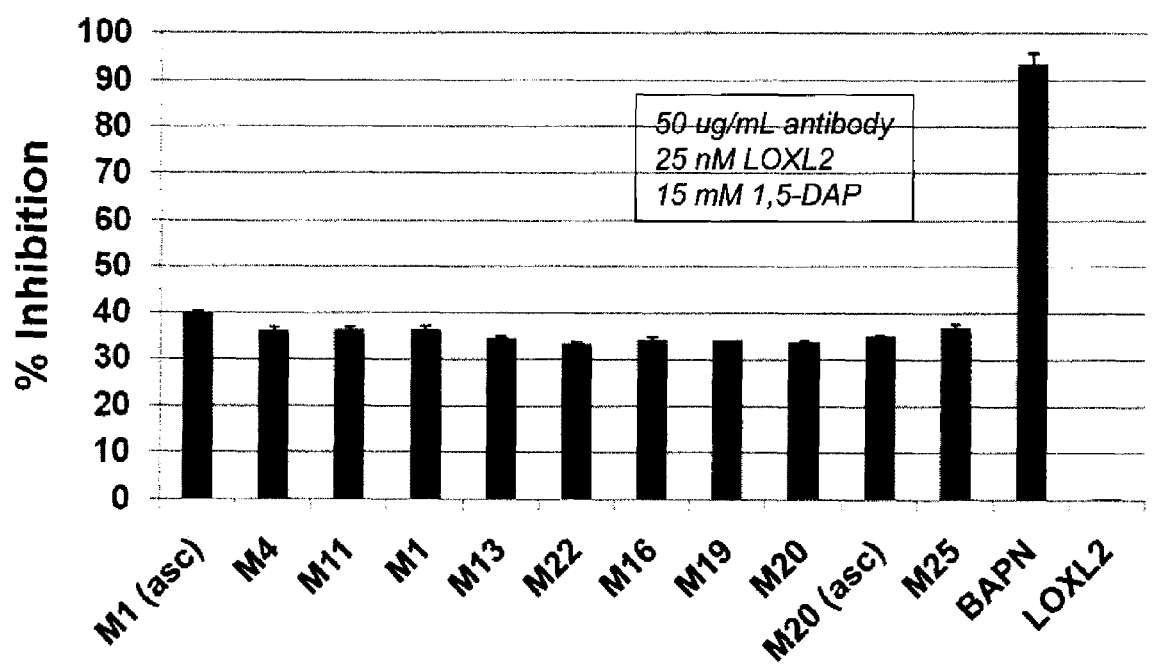
FIG. 8 provides a protein screen B update using anti-LOXL2 antibodies. LOXL2 enzymatic activity was assessed.

Antibodies M1 (asc), M4, M11, M1, M13, M22, M16, M19, M20, M20 (asc) and M25 test antibodies were tested against BAPN (a competitive inhibitor of LOXL2) as a positive control and LOXL2 as a negative control (see FIG. 8).

One anti-LOXL2 antibody was designated AB0023. Anti-LOXL2 antibodies repeated inhibitory activity observed in 10 ml preparation materials in the enzymatic assay. Inhibition was also repeated in cell-based assays (see below). Sequence analysis confirmed that the amino acid sequences of M01, M16, M19 and M20 are identical.

Example 3

Anti-LOXL2 Antibody AB0023 and Enzymatic Activity

Enzymatic Activity of anti-LOXL2 antibodies can be assessed and IC50s determined.

M1, M1 (asc), M20 and M20 (asc) were assessed in the presence of 25 nM LOXL2 and 15 mM 1,5 DAP over increasing concentrations of antibody.

$IC_{50}$ Determinations

Dose responses on selected antibodies were carried out against LOXL2 using the coupled enzymatic assay described above. A dilution series of antibody was created in PBST (0.01% tween-20) and 10 µL of this was added to 40 µL of enzyme mixture (62.5 mM sodium borate pH 8.0, 5 units/mL HRP, 125 nM LOXL2, 10 ppm antifoam) and incubated at room temperature for 1 hour in a 96 well full area black plate. Enzymatic reaction was started with the addition of 50 µL of substrate solution (50 mM sodium borate, 100 µM amplex red reagent, 20 mM 1,5-diaminopentane, 10 ppm antifoam) and read in an M5 plate reader using conditions described above. The slopes of the fluorescence response as a function of time were plotted against antibody concentration and the data was fit to a four parameter fit using GraFit. The midpoint of this plot is the apparent IC50 and is the concentration at which fifty percent of the total response is inhibited.

Figure 9:
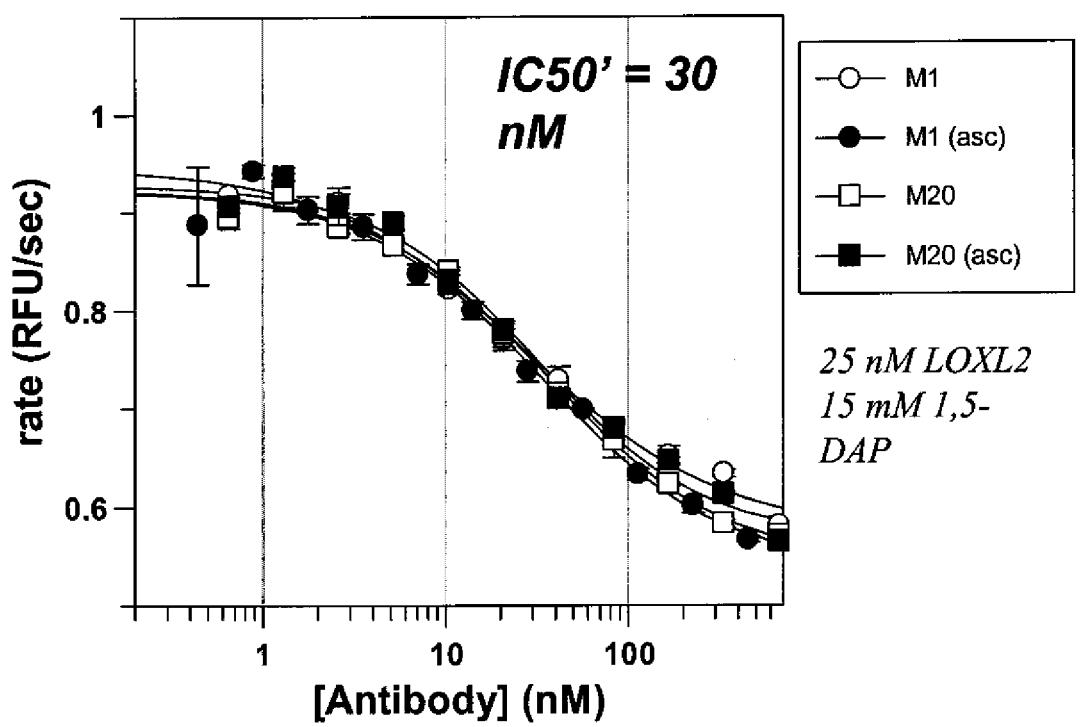
FIG. 9 illustrates enzymatic activity of anti-LOXL2 antibody AB0023.

Ab0023 was found to be a partial inhibitor of LOXL2 enzymatic activity with an apparent IC50 of approximately 30 nM (see FIG. 9).

Based upon the use of a partial inhibitor in clinic for therapeutic treatment (i.e., Nevirapine—an approved HIV-1 drug described by Spence et al. (1995) Science 267), a partial inhibitor of LOXL2 can also be used in therapeutic applications.

Example 4

Anti-LOXL2 Antibody AB0023 is a Non-Competitive Inhibitor

The activity of anti-LOXL2 antibody AB0023 was assessed over increasing concentrations of 1,5 DAP and over increasing concentrations of antibody (1 µM, 0.005 µM, 0.050 µM, and 0.300 µM).

Mode of Inhibition

Mode of inhibition of antibodies against LOXL2 was conducted using the model described below. In these experiments, the dependence of the steady state rate on the concentration of 1,5-diaminopentane was monitored under increasing concentrations of antibody. The purpose was to assess whether the $K_m$ for substrate, $k_{cat}$ or both change in the presence of antibody. Collected data was analyzed globally with Grafit using the model shown in figure below. E represents enzyme, S represents substrate, A represents antibody, and P represents product. Parameter a describes the effect of the compound on substrate affinity. An α value equal to one describes a situation in which the compound binds equally well the free enzyme and the enzyme-substrate complex (non-competitive inhibition like). Values less than one describe an interaction in which the compound binds the enzyme-substrate complex (uncompetitive inhibition like). Values greater than one correspond to the compound binding the free enzyme better than the enzyme-substrate complex (competitive inhibition like). The β value describes the effect of the modulator on the rate of the enzyme. Inhibitors have values less than one (for a complete inhibitor β=0) and activators have values greater than one. $K_A$ is the dissociation constant of the compound, $K_s$ is the Michaelis constant for the substrate and k is the catalytic rate of the enzyme. The steady state rates were determined from the slope of the fluorescence response as a function of time as described above (IC50 determination). Data was plotted as the dependence of steady state rate on the concentration of substrate (1,5-diaminopentane) at several fixed concentrations of antibody and analyzed with GraFit.

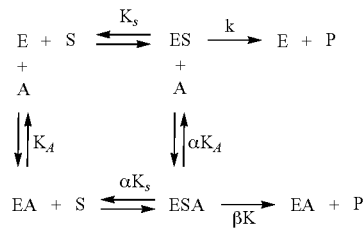

Anti-LOXL2 antibody AB0023 was determined to be a non-competitive inhibitor based on the following results: α=1, $K_r$=0.067 and β=0.5 (see FIG. 10).

Example 5

Kinetic Measurement of AB0023 Antibody Binding to LOXL2 by Surface Plasmon Resonance Binding affinity and off-rate of AB0023 were assessed via Surface Plasmon Resonance (SPR).

Binding affinities were measured using a Bio-Rad ProteOn instrument thermostated to 25° C. The binding affinities were determined using two methods, using amine coupling; one in which the antibody was immobilized and the antigen (LOXL2) was added, and another in which the antigen (LOXL2) was immobilized and antibody was added. Antibody or antigen was immobilized on a GLC chip using at 1:1 ratio of NHS to EDC provided with the ProteOn immobilization kit. Chip was first activated with NHS/EDC a mixture and then antigen or antibody at 1 µg/mL in acetate buffer pH 4.5 was flowed over activated surface to couple. This typically yielded a coupling of about 500 RU's. The activated chip surface was then capped with the addition of 1M ethanolamine. Coupled chips were stored at 4° C. and regenerated with 50 mM sodium hydroxide.

Dissociation constants were determined by probing the coupled chip with a dilution series of antibody or antigen in PBST (0.05% Tween-20). Data was acquired on all six channels available on the ProteOn using a non-coupled channel as a reference. Collected data was analyzed using ProteOn manager software from Bio-Rad.

Figure 11:
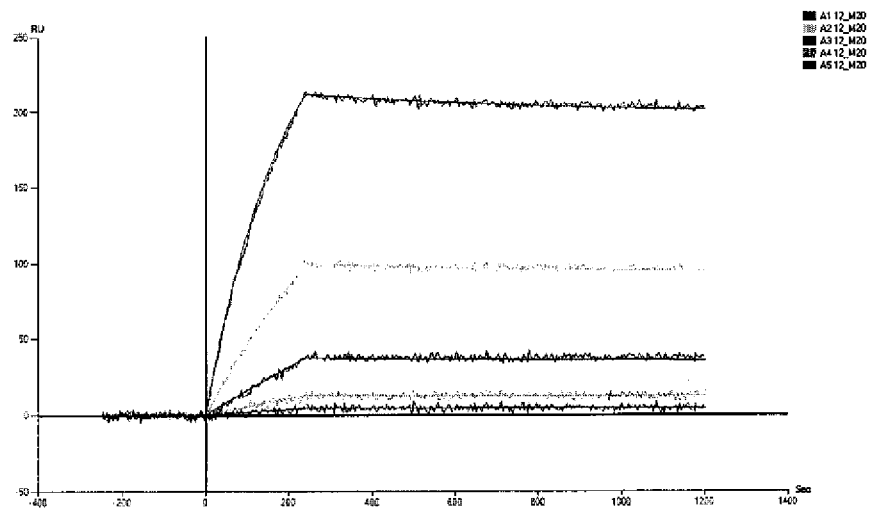
FIG. 11 illustrates the binding affinity and off-rate of anti-LOXL2 antibody AB0023.

AB0023 was found to bind tightly to LOXL2 and release slowly. Kd was estimated to be 0.1-1.0 nM. Furthermore, AB0023 was found to have the following characteristics: $k_{on}=1.68\times10^6$ $M^{-1}s^{-1}$, $k_{off}=1.17\times10^{-4}s^{-1}$, $K_D=0.69$ nM and $t_{1/2}=98.7$ minutes. See FIG. 11.

Example 6

Domain mapping was conducted and AB0023 was found to bind to the SRCR3-4 domain.

Materials and Methods

All plates were obtained from Corning. Secondary antibody and Pico substrate were obtained from Pierce. Horse radish peroxidase (HRP) was obtained from Sigma. All ProteOn reagents were obtained from Bio-Rad. LOXL2 was obtained from R&D systems. Antibodies used in this study were produced at Antibody Solution or via ascites from Aragen Biosciences. All other reagents were of the highest quality possible.

Binding via ELISA

Binding of antibody to LOXL2 was determined using a luminescence based ELISA. White Corning plates were coated with 0.1 µg/mL of LOXL2 or antigen of interest in 50 mM borate buffer (pH 8.0) overnight at 4° C. Plates were washed using BioTek plate washer and blocked with 5% skim milk in PBST (0.05% tween-20) for 1 hour at room temperature. Plates were washed with PBST (0.05% tween-20) and then used immediately or stored at 4° C. in dessicator for future use. The antibody body to be tested was serially diluted in PBST (0.01% tween-20) and 100 µL of each dilution was added per well. Plates were incubated with test article for 1 hour at room temperature and then washed with PBST (0.05% Tween-20). Detection antibody (anti-mouse HRP conjugate) was diluted 16,000 fold in 5% skim milk in PBST (0.05% Tween-20) and 100 µL was applied per well. Plates were incubated for 1 hour with detection antibody and then washed with PBST (0.05% PBST). Signal was detected using the SuperSignal ELISA pico chemiluminescent substrate from Pierce following the manufacturer's instructions. Luminescence was measure using a Molecular Devices M5 plate reader with an integration time of 500 ms capturing all wavelengths. Data was background corrected and the dependence of luminescence signal to antibody concentration was fit using the Langmuir isotherm equation using the GraFit program In instances where the antigen concentration was similar to the dissociation constant the quadratic equation of tight binding was used. Reported dissociation values were obtained from the fits to these equations; were PL represents the signal of the bound complex, $B_{max}$ is that maximal binding, $K_D$ is the dissociation constant and L is the ligand concentration.

Langmuir Isotherm equation:

$$[PL] = \frac{B_{max} * [L]}{K_D * [L]}.$$

Tight binding equation:

$$[PL] = B_{max} * \frac{([P]_T + [L]_T + K_D) - \sqrt{([P]_T + [L]_T + K_D)^2 - 4[P]_T[L]_T}}{2[P]_T}.$$

AB0023 was tested against MCD-LOXL2, LOXL2 (R&D), SRCR1-2 and SRCR 1-4. AB0023 was found to bind to the SRCR3-4 domain (see FIG. 12).

Example 7

Inhibition of Migration/Invasion in Collagen I and Collagen IV and Inhibition of Cell Growth Cell based assays were conducted to assess binding of AB0023 to bind substrate (i.e., collagen).

Briefly, AB0023 was scaled up from various samples prior to testing.

Cultrex 96-well collagen I and collagen IV cell invasion kits (Trevigen, Gaithersburg, Md.) were used for anti-sera/antibody supernatant screenings. MDA MB 231 cells were serum-deprived 24 hours prior to assay set up. On day of set up, collagen I and collagen IV coated plates were made at least 4 hours prior to invasion assay set up (not longer than 8 hours prior). Collagen I and collagen IV plates were coated according to manufacturer's instructions. Cells were plated at 20,000 cells per well in 95 µls serum-free media in the upper chamber of the plate. One hundred fifty (150) µls of media containing 10% FBS and 1×L-glutamine was aliquoted into the lower chambers of the plate. Using a multi-channel pipette, 5 µls of each anti-sera was placed in the upper chambers of the plate. The anti-sera and cell mixture was carefully mixed up and down once with the pipette. Plates were incubated at 37° C. with 5% $CO_2$ for 48 hours.

After 48 hours, the plates were ready to be read. The cell dissociation solution containing calcein AM was made according to manufacturer's instructions. The plates were also washed and disassembled according to manufacturer's instructions. 125 µls of cell dissociation solution containing calcein AM was added to the lower chambered wells and the plates were placed at 37° C. for 30 minutes. After 30 minutes the sides of the plates were tapped to loosen the cells, and the plates were placed in incubator for another 30 minutes at 37° C. The plates were then disassembled and the lower plate was placed into the plate reader (SpectraMax M5, Molecular Devices, Sunnyvale, Calif.) with settings: Flourescence, 485-520 emission, top read, black opaque plate, sensitivity at 30.

Figure 13:
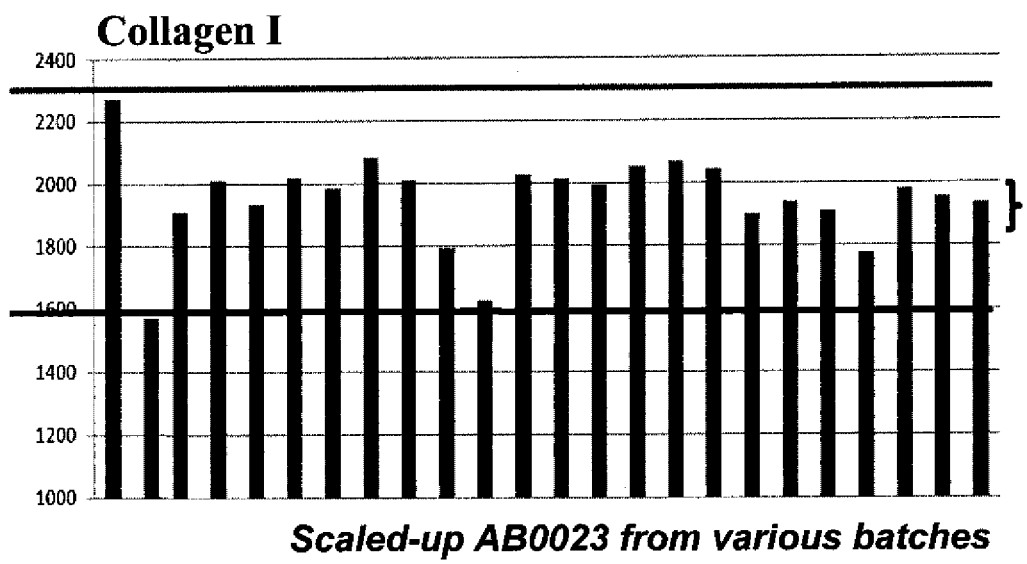
FIG. 13 shows that anti-LOXL2 antibody AB0023 demonstrates consistent inhibition of migration/invasion in collagen I and collagen IV, from supernatants through 10 ml prep material and scaled-up 100 ml prep and ascites material. Partial inhibition also observed in cell adhesion assays. In test samples, cells in the assay migrate toward serum and fluorescence is measured to determine cell count and migration. The far left bar is a control sample in which no antibody is present and the bottom layer contains serum (positive control for cell invasion). The second bar from left is a negative control in which no antibody is present and the bottom layer does not contain serum.

Consistent inhibition of migration/invasion was observed in collagen I (FIG. 13) and collagen IV, from supernatents through 10 mL preparation material and scaled up 100 mL preparations and ascites.

Cell Adhesion Assays

MDA-MB231 cells were plated in 15 $cm^2$ plates and grown in 4.5 g/L glucose containing DMEM (10% FBS and 2 mM L-Glutamine) so that they were confluent on the day of the assay. The media was aspirated and the cells were washed 2 times with 10 ml 1 mM EDTA PBS per plate. Cells were removed from plates by incubating with another 10 ml 1 mM EDTA PBS for 5 minutes at 37° C. in a biosafety cabinet and subsequently pipetting the cells off of the plate in the EDTA PBS solution. Cell concentration was determined and enough cells for assay (50k/well plus extra for pipetting) were spun-down in 15 ml conical tube. Cell pellet was dispersed in pre-warmed serum-free DMEM to 500K cells/ml and $CuCl_2$ was added to 1 µM final concentration. One hundred (100) µl/well of cell suspension was pipetted into a U-bottom style 96 well tissue culture plate containing 10 µl of appropriate mAb dilution. The cell suspension/mAb mixture was left to incubate for 10 minutes at room temperature in the dark. One hundred (100) μl/well of re-suspended cells/mAb mixture was then transferred to collagen IV coated 96 well plates (BD Biocoat, BD Biosciences). Plates were incubated at 37° C. in a biosafety cabinet for 1 hour. Wells were then aspirated and washed gently two times with 200 μl DPBS (Mediatech) to remove cell that had not adhered. One hundred (100) μl of 10 μM final concentration Calcein-AM (BD Biosciences) in DPBS was then added to each well to stain the cells that remained. Plates were incubated at 37° C. in a biosafety cabinet for 1 hour. Plates were read on a Molecular Devices M5 plate reader at 494/517 (excitation/emission). Percent (%) adhesion was calculated by normalizing to PBS or un-related antibody controls.

Figure 17:
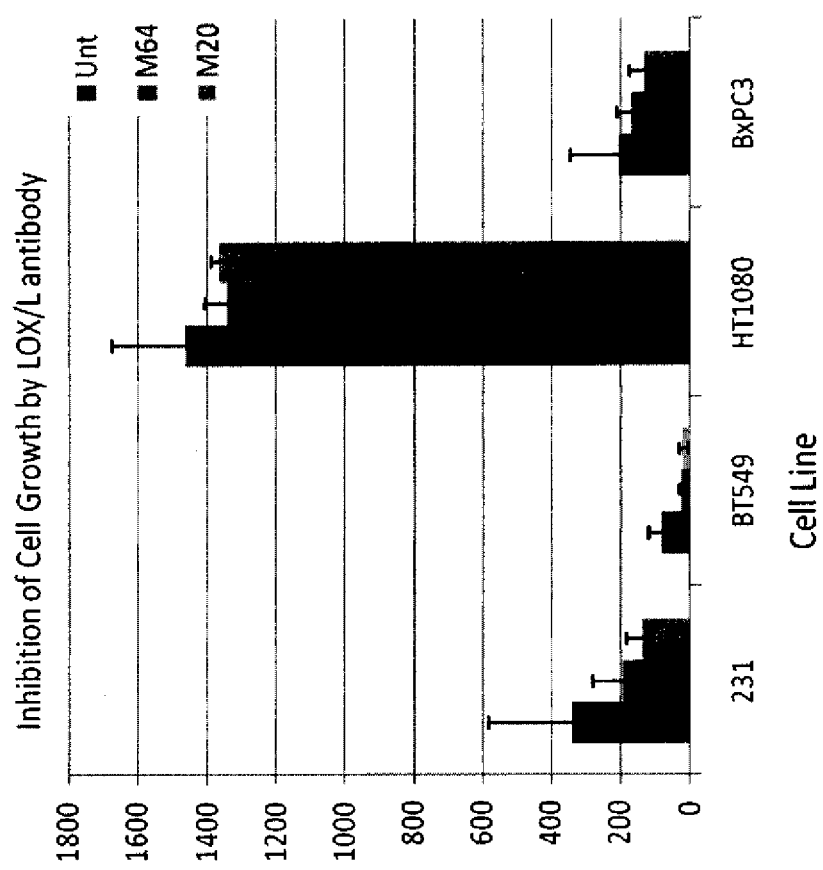
FIG. 17 demonstrates that anti-LOXL2 antibodies inhibited cell growth of four cancer derived cell lines.

Using this assay, partial inhibition of adhesion was observed upon exposure of cells to AB0023 antibody.
Cell Growth Anti-LOXL2 antibodies inhibited cell growth of four cell lines: 231 is a breast cancer cell line, BT549 is a breast cancer cell line, HT1080 is a fibrosacrcoma, and BxPC3 is a prostate cancer cell line (FIG. 17). Thus, the antibody is effective in inhibiting growth of cancers of different origins.

Example 8

AB0023 Inhibition of EMT-Like Change

Epithelial to Mesenchymal changes were assessed using immunohistochemistry.

To detect whether a cell is in an EMT or mesenchymal-to-epithelial transition (MET) state, cells were stained with antibodies specific to cellular protein markers for epithelial of mesenchymal states such as E-cadherin, vimentin, fibronectin, and phalloidin to detect F-actin.
Rhodamine Phalloidin Staining Protocol Cells were seeded 24 hours prior to day of staining; cells were approximately 80% confluent 24 hours later in an 8-chambered slide. The next day, the media was aspirated and the chambers were rinsed with 1×PBS. Cells were then fixed with 4% Parafomaldehyde (PFA) for 20 minutes at room temperature and then rinsed once with 1× Phosphate Buffered Saline (PBS). For permeabilization, the cells were treated with 0.5% Saponin (J T Baker, Phillipsburg, N.J.) in PBS for 5 minutes at room temperature. The chambers were carefully rinsed once with 1×PBS, and a 1:100 dilution of rhodamine phalloidin (Invitrogen, Carlsbad, Calif.) in PBS was added to the cells and incubated for 15 minutes at room temperature. The chambers were rinsed two times with 1×PBS and the slides were mounted with Vectashield (Vector Laboratories, Burlingame, Calif.).
E-Cadherin Staining Protocol Cells were seeded 24 hours prior to day of staining; cells were approximately 80% confluent the next day in an 8-chambered slide. The next day, the media was aspirated and the chambers were rinsed with 1×PBS. Cells were then fixed with ice cold methanol and then incubated for 2 minutes in −20° C. The cells were rinsed once with 1×PBX and 1 μg/ml of E-cadherin Ab (Calbiochem, Gibbstown, N.J.) was added to the slide chambers. The slides were then incubated at 37° C. for 1 hour. After carefully rinsing the chambers one time with 1×PBS, the secondary Ab (anti-mouse IgG cy3 conjugated, Jackson Immuno Research, West Grove, Pa.) was added and incubated at room temperature for 30-45 minutes. The chambers were rinsed two times with 1×PBS and mounted with Vectashield (Vector Laboratories, Burlingame, Calif.).

Conditioned media from HS-578t cells (LOXL2 high) applied to MCF-7 cells (LOXL2 low/negative). Cells were stained with rhoformine-phalloidin (F-actin, red) and Dapi (nuclei, blue).

AB0023 was found to inhibit EMT-like changes induced by conditioned media from tumor cells that express LOXL2 (data not shown).

Example 9

Anti-LOXL2 Antibody AB0023 binds matrix-Associated LOXL2

Internalization and Ab uptake studies in Hs578t cells.

Hs578t cells were cultured in DMEM containing 10% FBS and 1× glutamine. The cells were seeded in an 8 chamber glass slide (B D Falcon, Franklin Lakes, N.J.) and allowed to adhere overnight. For low confluency, cells were seeded at 30-40,000 cells per slide. Low confluency was used for detection of Lox in the cytosol 24 hours later. For high confluency, cells were seeded at 100,000 cells per slide. High confluency was used for detection of Lox associated with the matrix and collagen approximately 48-72 hours later.

The following day, 1 μg/ml (final concentration in regular growth medium) of anti-Lox M64 or anti-Loxl2 M20 monoclonal Ab (mAb) was added to the chambers. For continuous uptake, the mAbs were incubated with cells at different time points: for example, 3 hours, 8 hours, or 24 hours (overnight). After appropriate amount of continuous uptake, the media was removed and the chambers were rinsed with 1×PBS. The cells were fixed in 4% PFA (paraformaldehyde) at room temperature for 20 minutes. After fixation, the cells were washed with 1×PBS at room temperature for 5 minutes and then quenched in 50 mM ammonium chloride at room temperature for 10 minutes. The cells were washed again with 1×PBS at room temperature for 5 minutes.

The cells were permeabilized by adding saponin buffer (0.5% Saponin/1% BSA in PBS) at room temperature for 20 minutes. The secondary detection Ab (Alexa Fluor 488 donkey anti-mouse IgG, Invitrogen, Carlsbad, Calif.) was added at room temperature in saponin buffer and the cells were incubated for 30-45 minutes. The cells were then washed 3× in saponin buffer. The slides were mounted with vectashield (Vector Laboratories, Burlingame, Calif.).

For detection of collagen detection, cells were incubated with anti-collagen antibody (1:50, Calbiochem anti-collagen type I Rabbit polyclonal, Gibbstown, NX), one hour prior to fixing the cells with 4% PFA. Secondary Ab for collagen used is donkey anti-rabbit Cy3 (ImmunoJackson Labs, West Grove, Pa.).

Analysis by immunoblotting and immunofluorescence (data not shown) indicated that LOXL2 was predominantly intracellular at low density but was secreted at high cell density (confluent cells). LOXL2 was detected in the media of confluent cells and also on the extracellular matrix. Immunofluorescence on live cells indicated that AB0023 bound LOXL2 associated with the collagen matrix.

Example 10

Anti-LOX Antibody M64 Binds LOX

Figure 15:
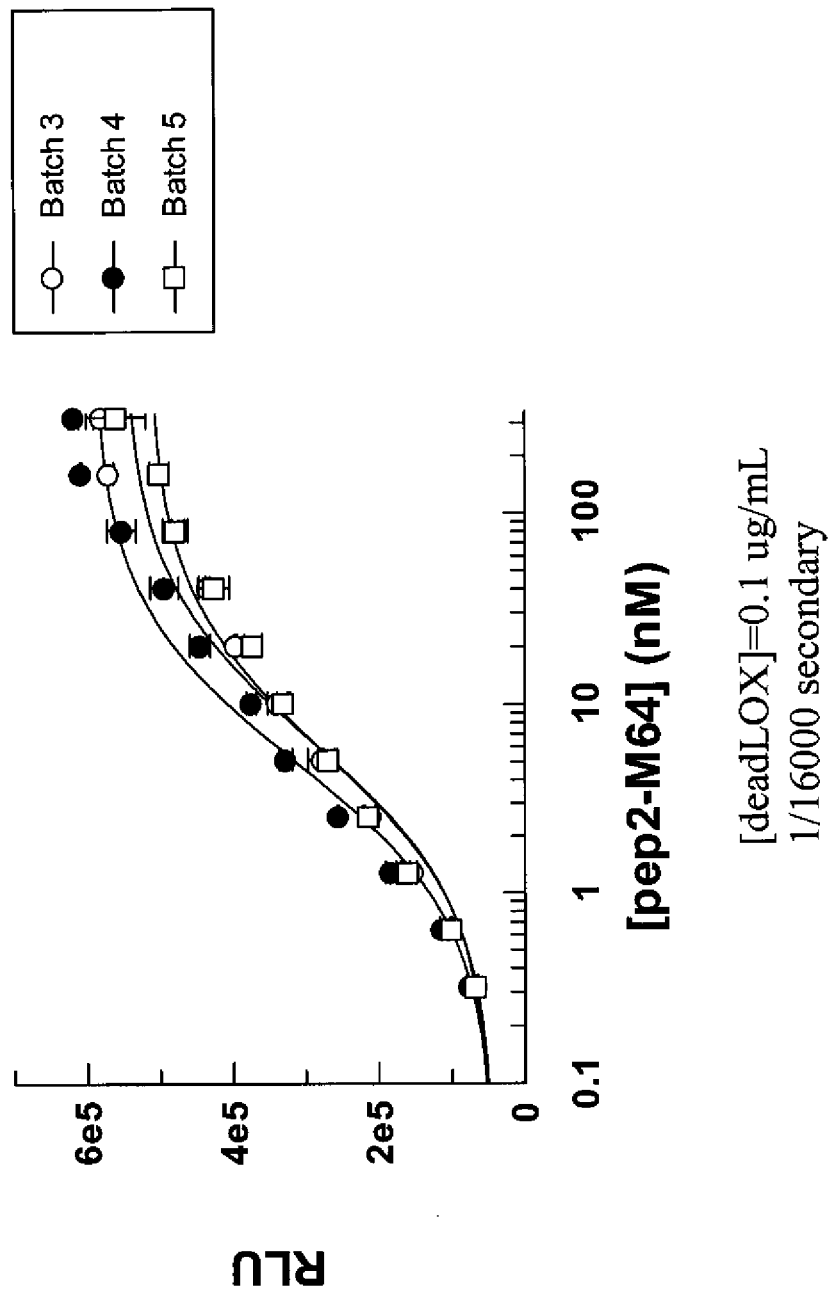
FIG. 15 demonstrates that M64 binds to LOX in a dose dependent manner. Batch 3 has a $K_D$ of 6.6 nM, Batch 4 has a $K_D$ of 5.0 nM and Batch 5 has a $K_D$ of 5.7 nM.

The activity of anti-LOX antibody M64 was assessed over increasing concentrations of 1,5 DAP and over increasing concentrations of antibody (see FIG. 15).

Materials and Methods

All plates were obtained from Corning. Secondary antibody and Pico substrate were from Pierce. Amplex red reagent was from Invitrogen. Horse radish peroxidase (HRP), 1,5-diaminopentane, antifoam were from Sigma. All ProteOn reagents were from Bio-Rad. LOX was produced in house at Arresto Biosciences. Antibodies used in this study were produced at Antibody Solution or via ascites (asc) from Aragen Biosciences. All other reagents were of the highest quality possible.

Binding via ELISA

Binding of antibody to LOX was determined using a luminescence based ELISA. White Corning plates were coated with 0.1 ug/mL of LOX or antigen of interest in 50 mM borate buffer (pH 8.0) overnight at 4° C. Plates were washed using a BioTek plate washer and blocked with 5% skim milk in PBST (0.05% tween-20) for 1 hour at room temperature. Plates were washed with PBST (0.05% tween-20) and then used immediately or stored at 4° C. in a dessicator for future use. The antibody to be tested was serially diluted in PBST (0.01% tween-20) and 100 uL of each dilution was added per well. Plates were incubated with test material for 1 hour at room temperature and then washed with PBST (0.05% tween-20). Detection antibody (anti-mouse HRP conjugate) was diluted 16000 fold in 5% skim milk in PBST (0.05% tween-20) and 100 uL was applied per well. Plates were incubated for 1 hour with detection antibody and then washed with PBST (0.05% PBST). Signal was detected using the SuperSignal ELISA pico chemiluminescent substrate from Pierce following the manufacturer's instructions. Luminescence was measured using a Molecular Devices M5 plate reader with an integration time of 500 ms capturing all wavelengths. Data was background corrected and the dependence of luminescence signal to antibody concentration was fit using the Langmuir isotherm equation using the GraFit program. In instances where the antigen concentration was similar to the dissociation constant the quadratic equation of tight binding was used. Reported dissociation values were obtained from the fits to these equations; were PL represents the signal of the bound complex, $B_{max}$ is that maximal binding, $K_D$ is the dissociation constant and L is the ligand concentration.

Langmuir Isotherm Equation

Langmuir Isotherm equation:

$$[PL] = \frac{B_{max} * [L]}{K_D * [L]}.$$

Tight binding equation:

$$[PL] = B_{max} * \frac{([P]_T + [L]_T + K_D) - \sqrt{([P]_T + [L]_T + K_D)^2 - 4[P]_T[L]_T}}{2[P]_T}.$$

Anti-LOX antibody M64 was tested in three batches and was found to have a KD of 6.6 nM, 5.0 nM and 5.7 nM for Batch 3, Batch 4 and Batch 5, respectively (FIG. 15).

Example 11

Kinetic Measurement of M64 Antibody Binding to LOX by Surface Plasmon Resonance Binding affinity of M64 was assessed via Surface Plasmon Resonance (SPR).

Binding affinities were measured using a Bio-Rad ProteOn instrument thermostated to 25° C. The binding affinities were determined using two methods, using amine coupling; one in which the antibody was immobilized and the antigen (LOX) was added, and another in which the antigen (LOX) was immobilized and antibody was added. Antibody or antigen was immobilized on a GLC chip using at 1:1 ratio of NHS to EDC provided with the ProteOn immobilization kit. Chip was first activated with NHS/EDC a mixture and then antigen or antibody at 1 µg/mL in acetate buffer pH 4.5 was flowed over activated surface to couple. This typically yielded a coupling of about 500 RU's. The activated chip surface was then capped with the addition of 1M ethanolamine. Coupled chips were stored at 4° C. and regenerated with 50 mM sodium hydroxide.

Dissociation constants were determined by probing the coupled chip with a dilution series of antibody or antigen in PBST (0.05% tween-20). Data was acquired on all six channels available on the ProteOn using a non-coupled channel as a reference. Collected data was analyzed using ProteOn manager software from Bio-Rad.

Figure 16:
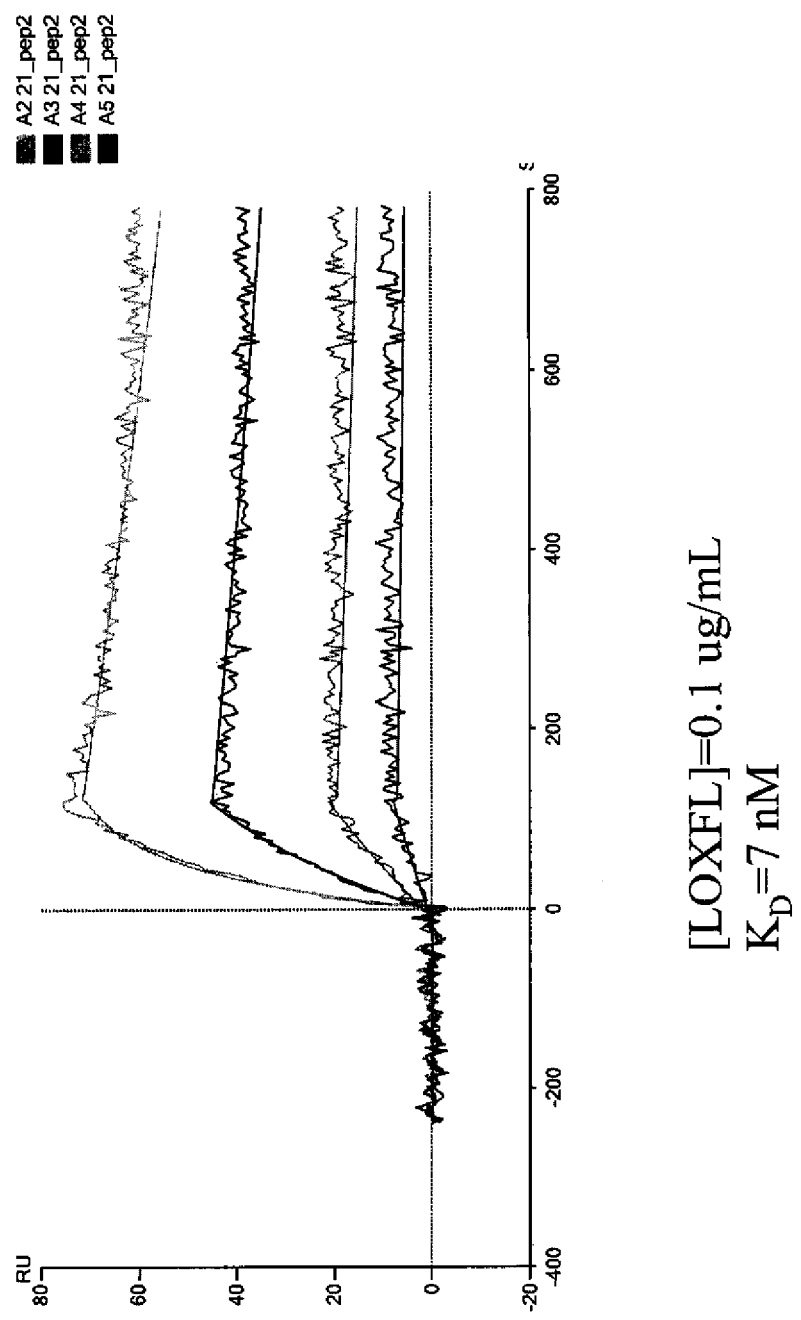
FIG. 16 illustrates the binding affinity of anti-LOX antibody M64.

M64 was found to have a $K_D$ of 7 nM (FIG. 16).

Example 12

Below is a listing of sequences described throughout the specification.

| SEQ ID NO | Sequence |
|---|---|
| 1. | MEWSRVFIFLLSVTAGVHSQVQLQQSGAELVRPGTSVKVSCKAS<u>GY AFTYYLIE</u>WVKQRPGQGLEWIG<u>VINPGSGGTNYNEKFKG</u>KATLTAD KSSSTAYMQLSSLTSDDSAVYFCAR<u>NWMNFDY</u>WGQGTTLTVSS |
| 2. | MRCLAEFLGLLVLWIPGAIGDIVMTQAAPSVSVTPGESVSISC<u>RSS KSLLHSNGNTYLY</u>WFLQRPGQSPQFLI<u>YRMSNLAS</u>GVPDRFSGSGS GTAFTLRISRVEAEDVGVYYC<u>MQHLEYPYT</u>FGGGTKLEIK |
| 3. | MGWSWVFLFLLSVTAGVHSQVQLQQSGAELVKPGASVKLSCKAS<u>GY TFRSYDIN</u>WVRQRPEQGLEWIG<u>WIFPGDGSTKYNEKFKG</u>KAILTTD KSSSTAYMQLSRLTSEDSAVYFCAR<u>VYYAMDY</u>WGQGTSVTVSS |
| 4. | MKLPVRLLVMFRIPASSSDVLLTQTPLSLPVSLGDQASISC<u>RSSQS IVHSNGNTYLE</u>WYLQKPGQSPKLLIY<u>KVSNRFS</u>GVPDRFGGSGSGT DFTLKINRVEAEDLGIYYC<u>FQSSHIPLT</u>FGAGTKLELKRAD |
| 5. | MKLPVRLLVMFWIPASSSDVLLTQTPFLSLPVSLGDQASISC<u>RSSQS IVHSNGNTYLE</u>WYLQKPGQSPKLLIY<u>KVSIRFS</u>GVPDRFGGSGSGT DFTLKINRVEAEDLGIYYC<u>FQSSHIPLT</u>FGAGTKLELKRAD |
| 6. | VRLRGGAYIGEGRVEVLKNGEWGTVCDDKWDLVSASVVCRELGFGS AKEAVTGSRLGQGIGPIHLNEIQCTGNEKSIIDCKFNAESQGCNHE EDAGVRCNTPAMGLQKKLRLNGGRNPYEGRVEVLVERNGSLVWGMV CGQNWGIVEAMVVCRQLGLGFASNAFQETWYHGDVNSNKVVMSGVK CSGTELSLAHCRHDGEDVACPQGGVQYGAGVACS |
| 7. | MRFAWTVLLLGPLQL<u>CA</u>LVHCAPPAAGQQQPPREPPAAPGAWRQQI QWENNGQVFSLLSLGSQYQPQRRRDPGAAVPGAANASAQQPRTPIL LIRDNRTAAARTRTAGSSGVTAGRPRPTARHWFQAGYSTSRAREAG ASRAENQTAFGEVPALSNLRPPSRVDGMV<u>GDD</u>PYNPYKYSDDNPYY NYYDTYERPRPGGRYRPGYGTGYFQYGLPDLVADPYYIQASTYVQK MSMYNLRCAAEENCLASTAYRADVRDYDHRVLLRFPQRVKNQGTSD |

| SEQ ID NO | Sequence |
|---|---|
| | FLPSRPRYSWEWHSCHQHYHSMDEFSHYDLLDANTQRRVAEGHKAS FCLEDTSCDYGYHRRFACTAHTQGLSPGCYDTYGADIDCQWIDITD VKPGNYILKVSVNPSYLVPESDYTNNVVRCDIRYTGHHAYASGCTI SPY |
| 8. | ALVHCAPPAAGQQQPPREPPAAPGAWRQQIQWENNGQVFSLLSLGS QYQPQRRRDPGAAVPGAANASAQQPRTPILLIRDNRTAAARTRTAG SSGVTAGRPRPTARHWFQAGYSTSRAREAGASRAENQTAPGEVPAL SNLRPPSRVDGMVGDDPYNPYKYSDDNPYYNYYDTYERPRPGGRYR PGYGTGYFQYGLPDLVADPYYIQASTYVQKMSMYNLRCAAEENCLA STAYRADVRDYDHRVLLRFPQRVKNQGTSDFLPSRPRYSWEWHSCH QHYHSMDEFSHYDLLDANTQRRVAEGHKASFCLEDTSCDYGYHRRF ACTAHTQGLSPGCYDTYGADIDCQWIDITDVKPGNYILKVSVNPSY LVPESDYTNNVVRCDIRYTGHHAYASGCTISPY |
| 9. | DDPYNPYKYSDDNPYYNYYDTYERPRPGYGTGYFQYGLPD LVADPYYIQASTYVQKMSMYNLRCAAEENCLASTAYRADVRDYDHR VLLRFPQRVKNQGTSDFLPSRPRYSWEWHSCHQHYHSMDEFSHYDL LDANTQRRVAEGHKASFCLEDTSCDYGYHRRFACTAHTQGLSPGCY DTYGADIDCQWIDITDVKPGNYILKVSVNPSYLVPESDYTNNVVRC DIRYTGHHAYASGCTISPY |
| 10. | gggcgtgatttgagcccgttttattttctgtgagccacgtcctc ctcgagggggtcaatctggccaaaaggagtgatgcgcttcgcctgg accgtgctcctgctcgggcctttgcagctctgcgcgctagtgcact gcgccccctcccgccgccggccaacagcagccccgcgccgagccgc ggcggctccgggcgcctggcgccagcagatccaatgggagaacaac gggcaggtgttcagcttgctgagcctgggctcacagtaccagcctc agcgccgccgggacccgggcgccgccgtccctggtgcagccaacgc ctccgcccagcagccccgcactccgatcctgctgatccgcgacaac cgcaccgcggccgacgcggcggcggctcatctggagtca ccgctggccgccccaggccaccgccgtcactggttccaagctgg ctactcgacatctagagcccgcgaacgtggcgcctcgcgcgcggag aaccagacagcgccgggagaagttcctgcgtcagtaacctgcggc cgcccagccgcgtggacggcatggtgggcgacgaccttacaaccc ctacaagtactctgacgacaacccttattacaactactacgatact tatgaaaggcccagacctgggggcaggtaccggcccggatacggca ctggcctacttccagtacggtctcccagacctggtggccgacccct actacatccaggcgtccacgtacgtgcagaagatgtccatgtacaac ctgagatgcgcggcggaggaaaactgtctggccagtacagcataca gggcagatgtcagagattatgatcacagggtgctgctcagatttcc ccaaagagtgaaaaaccaaggacatcagatttcttacccagccga ccaagatattcctgggaatggcacagttgtcatcaacattaccaca gtatggatgagtttagccactatgacctgcttgatgccaacaccca gaggagagtggctgaaggccacaaagcaagtttctgtcttgaagac acatcctgctgatggctaccacaggcgattgagtcctggctgttatga tacctatggtgcagacatagactgccagtggattgatattacagat gtaaaacctggaaactatatcctaaaggtcagtgtaaacccagct acctggttcctgaatctgactataccaacaatgttgtgcgctgtga cattcgctacacaggacatcatgcgtatgcctcaggctgcacaattt tcaccgtattagaaggcaaagcaaaactcccaatggataaatcagt gctcggtgttctgaagtgggaaaaaatagactaacttcagtaggat ttatgtattttgaaaagagaacagaaaacaacaaaagaattttttg tttggactgttttcaataacaaagcacataacttaggattttgaacgc ttaagtcatcattacttgggaaatttttaatgttattatttcat cacttgtgaattaacacagtgtttcaattctgtaatttcatatttgactcttt |
| 11. | MRFAWTVLLLGPLQLCALVHCAPPAAGQQQPPREPPAAPGAWRQQI QWENNGQVFSLLSLGSQYQPQRRRDPGAAVPGAANASAQQPRTPIL LIRDNRTAAARTRTAGSSGVTAGRPRPTARHWFQAGYSTSRARERG ASRAENQTAPGEVPALSNLRPPSRVDGMVGDDPYNPYKYSDDNPYY NYYDTYERPRPGGRYRPGYGTGYFQYGLPDLVADPYYIQASTYVQK MSMYNLRCAAEENCLASTAYRADVRDYDHRVLLRFPQRVKNQGTSD FLPSRPRYSWEWHSCHQHYHSMDEFSHYDLLDANTQRRVAEGHKAS FCLEDTSCDYGYHRRFACTAHTQGLSPGCYDTYGADIDCQWIDITD VKPGNYILKVSVNPSYLVPESDYTNNVVRCDIRYTGHHAYASGCTI SPY |
| 12. | atgcgcttcgcctggaccgtgctcctgctcgggcctttgcagctct gcgcgctagtgcactgcgccccctcccgccgccggccaacagcagcc cccgcgccgagccgccggcggctccgggcgcctggcgccagcagatc caatgggagaacaacgggcaggtgttcagcttgctgagcctggct cacagtaccagcctcagcgccgccgggacccgggcgccgccgtccc tggtgcagccaacgcctccgcccagcagccccgcactccgatcctg ctgatccgcgacaaccgcaccgccgcggggcgaacgcggacggccg gctcatctggagtcaccgctggccgccccaggccaccgccgtca ctggttccaagctggctactcgacatctagagcccgcgaacgtggc gcctcgcgcgcggagaaccagacagcgccgggagaagttcctgcgc tcagtaacctgcggccgcccagccgcgtggacggcatggtgggcga cgaccttacaaccctacaagtactctgacgacaacccttattac aactactacgatacttatgaaaggcccagacctgggggcaggtacc ggcccggatacggcactggctacttccagtacggtctcccagacct ggtggccgacccctactacatccaggcgtccacgtacgtgcagaag atgtccatgtacaacctgagatgcgcggcggaggaaaactgtctgg ccagtacagcatacagggcagatgtcagagattatgatcacaggt gctgctcagatttcccccaaagagtgaaaaaccaaggacatcagat ttcttacccagccgaccaagatattcctgggaatggcacagttgtc atcaacattaccacagtatggatgagtttagccactgtacctgct tgatgccaacaccagaggagagtggctgaaggccacaaagcaagt ttctgtcttgaagacacatcctgtgactatggctaccacaggcgat ttgcatgtactgcacacacacagggattgagtcctggctgttatga tacctatggtgcagacatagactgccagtggattgatattacagat gtaaaacctggaaactatatcctaaaggtcagtgtaaacccagct acctggttcctgaatctgactataccaacaatgttgtgcgctgtga cattcgctacacaggacatcatgcgtatgcctcaggctgcacaatt tcaccgtattag |
| 13. | MRFAWTVLLLGPLQLCALVHCAPPAAGQQQPPREPPAAPGAWRQQI QWENNGQVFSLLSLGSQYQPQRRRDPGAAVPGAANASAQQPRTPIL LIRDNRTAAARTRTAGSSGVTAGRPRPTARHWFQAGYSTSRARERG ASRAENQTAPGEVPALSNLRPPSRVDGMVGDDPYNPYKYSDDNPYY NYYDTYERPRPGGRYRPGYGTGYFQYGLPDLVADPYYIQASTYVQK MSMYNLRCAAEENCLASTAYRADVRDYDHRVLLRFPQRVKNQGTSD FLPSRPRYSWEWHSCHQHYHSMDEFSHYDLLDANTQRRVAEGHKAS FCLEDTSCDYGYHRRFACTAHTQGLSPGCYDTYGADIDCQWIDITD VKPGNYILKVSVNPSYLVPESDYTNNVVRCDIRYTGHHAYASGCTI SPY |
| 14. | gggcaggactgagaaagggaaagggaagggtgccacgtccgagc agccgccttgactggggaagggtctgaatcccaccttggcattgc ttggtggagactgagatacccgtgctccgctcgcctccttggttga agatttctccttccctcacgtgatttgagcccgttttatttct gtgagccacgtcctcctcgagggggtcaatctggccaaaaggagtg atgcgcttcgcctggaccgtgctcctgctcgggcctttgcagctct gcgcgctagtgcactgcgccccctcccgccgccggccaacagcagcc cccgcgccgagccgccggcggctccgggcgcctggcgccagcagatc caatgggagaacaacgggcaggtgttcagcttgctgagcctggct cacagtaccagcctcagcgccgccgggacccgggcgccgccgtccc tggtgcagccaacgcctccgcccagcagccccgcactccgatcctg ctgatccgcgacaaccgcaccgccgcgggggcgaacgcggacggccg gctcatctggagtcaccgctggccgccccaggccaccgccgtca ctggttccaagctggctactcgacatctagagcccgcgaagctggg ccctcgcgcgcggagaaccagacagcgccgggagaagttcctgctc tcagtaacctgcggccgcccagccgcgtggacggcatggtgggcga cgaccttacaaccctacaagtactctgacgacaacccttattac aactactacgatacttatgaaaggcccagacctgggggcaggtacc ggcccggatacggcactggctacttccagtacggtctcccagacct ggtggccgacccctactacatccaggcgtccacgtacgtgcagaag atgtccatgtacaacctgagatgcgcggcggaggaaaactgtctgg ccagtacagcatacagggcagatgtcagagattatgatcacaggt gctgctcagatttcccccaaagagtgaaaaaccaaggacatcagat ttcttacccagccgaccaagatattcctgggaatggcacagttgtc atcaacattaccacagtatggatgagtttagccacttgtacctgct tgatgccaacaccagaggagagtggctgaaggccacaaagcaagt ttctgtcttgaagacacatcctgtgactatggctaccacaggcgat ttgcatgtactgcacacacacagggattgagtcctggctgttatga tacctatggtgcagacatagactgccagtggattgatattacagat gtaaaacctggaaactatatcctaaaggtcagtgtaaacccagct acctggttcctgaatctgactataccaacaatgttgtgcgctgtga cattcgctacacaggacatcatgcgtatgcctcaggctgcacaatt tcaccgtattagaaggcaaagcaaaactcccaatggataaatcagt gctcggtgttctgaagtgggaaaaaatagactaacttcagtaggat ttatgtattttgaaaagagaacagaaaacaacaaaagaattttttg tttggactgttttcaataacaaagcacataacttggattttgaacgc ttaagtcatcattacttgggaaatttttaatgttattatttcat cacttgtgaattaacacagtgtttcaattctgtaatttacatatttt gactctttcaaaaaaaaaaaaaaaaaaaa |
| 15. | MRFAWTVLLLGPLQLCALVHCAPPAAGQQQPPREPPAAPGAWRQQI QWENNGQVFSLLSLGSQYQPQRRRDPGAAVPGAANASAQQPRTPIL LIRDNRTAAGRTRTAGSSGVTAGRPRPTARHWFQAGYSTSRAREAG |

| SEQ ID NO | Sequence |
|---|---|
| | PSRAENQTAPGEVPALSNLRPPSRVDGMVGDDPYNPYKYSDDNPYY<br>NYYDTYERPRPGGRYRPGYGTGYFQYGLPDLVADPYYIQASTYVQK<br>MSMYNLRCAAEENCLASTAYRADVRDYDHRVLLRFPQRVKNQGTSD<br>FLPSRPRYSWEWHSCHQHYHSMDEFSHLYLLDANTQRRWAEGHKAS<br>FCLEDTSCDYGYHRRFACTAHTQGLSPGCYDTYGADIDCQWIDITD<br>VKPGNYILKVSVNPSYLVPESDYTNNVVRCDIRYTGHHAYASGCTI<br>SPY |
| 16. | ccgcgccgctccccgttgccttccaggactgagaaaggggaaggg<br>aagggtgccacgtccgagcagccgccttgactggggaagggtctga<br>atcccaccttggcattgctggtggagactgagatacccgtgctc<br>cgctcgcctccttggtgaagatttctccttccctcacgtgatttg<br>agcccgttttttatttctgtgagccacgtcctcctcgagcgggt<br>caatctggcaaaaggagtgatgcgcttcgcctggaccgtgctcctg<br>ctcgggccttttgcagctctgcgcgctagtgcactgcgcccctccg<br>ccgccgccaacagcagccccgcgcgagccgccggcggctccggg<br>cgcctggcgccagcagatccaatggggagaacaacgggcaggtgttc<br>agcttgctgagcctgggctcacagtaccagcctcagcgccgccggg<br>acccggggccgccgtccctggtgcagcaacgcctccgcccagca<br>gccccgcactccgatcctgctgatccgcgacaaccgcaccgccgcg<br>gcgcgaacgcggacggccggctcatctggagtcaccgctggcc<br>ccaggcccaccgcccgtcactggttccaagctggctactcgacatc<br>tagagcccgcgaagctggcgcctcgcgcgggagaaccagacagcc<br>cggggagaagttcctgcgctcagtaacctgcggccgcccagccgcg<br>tggacggcatggtgggcgacgacccttacaaccctacaagtactc<br>tgacgacaacccttattacaactactacgatacttatgaaaggccc<br>agacctgggggcaggtaccggcccggatacggcactggctacttcc<br>agtacggtctcccagacctggtggccgaccctactacatccaggc<br>gtccacgtacgtgcagaagatgtccatgtacaacctgagatgcgcg<br>gcggcggaggaaaactgtctggccagtacagcatacagggcagatg<br>tcagagattatgatcacagggtgctgctcagatttcccaaagagt<br>aaaaaccaagggacatcagatttcttacccagccgaccaagatatt<br>cctgggaatggcacagttgtcatcaacattaccacagtatggatgagt<br>ttagccactatgacctgcttgatgccaacacccagaggagagt<br>ggctgaaggccacaaagcaagtttctgtcttgaagacacatcctgt<br>gactatggctaccacaggcgatttgcatgtactgcacacacacaggat<br>tgagtcctggctgttatgatacctatggtgcagacatagactgcca<br>gtggattgatattacagatgtaaaacctggaaactatatcctaaag<br>gtcagtgtaaaccccagctacctggttcctgaatctgactataccaa<br>caatgttgtgcgctgtgacattcgctacacaggacatcatgcgta<br>tgcctcaggctgcacaatttcaccgtattagaaggcaaagcaaaac<br>tcccaatggataaatcagtgcctggtgttctgtcgtgggaaaaat<br>agactaacttcagtaggatttatgtattttgaaaaagaaacagaa<br>aacaacaaaagaattttttgtttggactgttttcaataacaaagcac<br>ataactggattttgaacgcttaagtcatcattacttgggaaatttt<br>taatgttttattatttacatcactttgtaattaacacagtgtttca<br>attctgtaattacatatttgactctttcaaagaaaatccaaatttct<br>catgttccttttgaaattgtagtgcaaaatggtcagtattatctaa<br>atgaatgagccaaaatgactttgaactgaaacttttctaaagtgct<br>ggaactttagtgaaacataataataatgggtttatacgacagcaac<br>gga |
| 17. | MRFAWTVLLLGPLQLCALVHCAPPAAGQQQPPREPPAAPGAWRQQI<br>QWENNGQVFSLLSLGSQYQPQRRDPGAAVPGAANASAQQPRTPIL<br>LIRDNRTAAARTRTAGSSGVTAGRPRPTARHWFQAGYSTSRAREAG<br>ASRAENQTAPGEVPALSNLRPPSRVDGMVGDDPYNPYKYSDDNPYY<br>NYYDTYERPRPGGRYRPGYGTGYFQYGLPDLVADPYYIQASTYVQK<br>MSMYNLRCAAEENCLASTAYRADVRDYDHRVLLRFPQRVKNQGTSD<br>FLPSRPRYSWEWHSCHQHYHSMDEFSHYDLLDANTQRRVAEGHKAS<br>FCLEDTSCDYGYHRRFACTAHTQGLSPGCYDTYGADIDCQWIDITD<br>VKPGNYILKVSVNPSYLVPESDYTNNVVRCDIRYTGHHAYASGCTI<br>SPY |
| 18. | ggtcaatctggcaaaaggagtgatgcgcttcgcctggaccgtgctc<br>ctgctcgggcctttgcagctctgcgcgctagtgcactgcgcccctc<br>cgccgccggcaacagcagccccgcgcgagccgccggcggctcc<br>gggcgcctggcgccagcagatccaatggggagaacaacgggcaggtg<br>ttcagcttgctgagcctgggctcacagtaccagcctcagcgccgc<br>gggacccggggccgccgtccctggtgcagcaacgcctccgccca<br>gcagccccgcactccgatcctgctgatccgcgacaaccgcaccgcc<br>gcggcgcgaacgcggacggccggctcatctggagtcaccgctggcc<br>gccccaggcccaccgcccgtcactggttccaagctggctactcgac<br>atctagagcccgcgaagctggcgcctcgcgcgggagaaccagaca<br>gcgccgggagaagttcctgcgctcagtaacctgcggccgcccagcc<br>gcgtggacggcatggtgggcgacgacccttacaaccctacaagta<br>ctctgacgacaacccttattacaactactacgatacttatgaaagg |

| SEQ ID NO | Sequence |
|---|---|
| | cccagacctgggggcaggtaccggcccggatacggcactggctact<br>tccagtacggtctcccagacctggtggccgaccctactacatcca<br>ggcgtccacgtacgtgcagaagatgtccatgtacaacctgagatgc<br>gcggcggaggaaaactgtctggccagtacagcatacagggcagatg<br>tcagagattatgatcacagggtgctgctcagatttccccaaagagt<br>gaaaaaccaagggacatcagatttcttacccagccgaccaagatat<br>tcctgggaatggcacagttgtcatcaacattaccacagtatggatg<br>agtttagccactatgacctgcttgatgccaacacccagaggagagt<br>ggctgaaggccacaaagcaagtttctgtcttgaagacacatcctgt<br>gactatggctaccacaggcgatttgcatgtactgcacacacacagg<br>gattgagtcctggctgttatgatacctatggtgcagacatagactg<br>ccagtggattgatattacagatgtaaaacctggaaactatatccta<br>aaggtcagtgtaaaccccagctacctggttcctgaatctgactata<br>ccaacaatgttgtgcgctgtgacattcgctacacaggacatcatgc<br>gtatgcctcaggctgcacaatttcaccgtattagaaggcaaagcaa<br>aactcccaatggataaatcagtgcctggtgttct |
| 19. | MRFAWTVLLLGPLQLCALVHCAPPAAGQQQPPREPPAAPGAWRQQI<br>QWENNGQVFSLLSLGSQYQPQRRDPGAAVPGAANASAQQPRTPIL<br>LIRDNRTAAARTRTAGSSGVTAGRPRPTARHWFQAGYSTSRAREAG<br>ASRAENQTAPGEVPALSNLRPPSRVDGMVGDDPYNPYKYSDDNPYY<br>NYYDTYERPRPGGRYRPGYGTGYFQYGLPDLVADPYYIQASTYVQK<br>MSMYNLRCAAEENCLASTAYRADVRDYDHRVLLRFPQRVKNQGTSD<br>FLPSRPRYSWEWHSCHQHYHSMDEFSHYDLLDANTQRRVAEGHKAS<br>FCLEDTSCDYGYHRRFACTAHTQGLSPGCYDTYGADIDCQWIDITD<br>VKPGNYILKVSVNPSYLVPESDYTNNVVRCDIRYTGHHAYASGCTI<br>SPY |
| 20. | ggtcaatctggcaaaaggagtgatgcgcttcgcctggaccgtgctc<br>ctgctcgggcctttgcagctctgcgcgctagtgcactgcgcccctc<br>cgccgccggcaacagcagccccgcgcgagccgccggcggctcc<br>gggcgcctggcgccagcagatccaatggggagaacaacgggcaggtg<br>ttcagcttgctgagcctgggctcacagtaccagcctcagcgccgc<br>gggacccggggccgccgtccctggtgcagcaacgcctccgccca<br>gcagccccgcactccgatcctgctgatccgcgacaaccgcaccgcc<br>gcggcgcgaacgcggacggccggctcatctggagtcaccgctggcc<br>gccccaggcccaccgcccgtcactggttccaagctggctactcgac<br>atctagagcccgcgaagctggcgcctcgcgcgggagaaccagaca<br>gcgccgggagaagttcctgcgctcagtaacctgcggccgcccagcc<br>gcgtggacggcatggtgggcgacgacccttacaaccctacaagta<br>ctctgacgacaacccttattacaactactacgatacttatgaaagg<br>cccagacctgggggcaggtaccggcccggatacggcactggctact<br>tccagtacggtctcccagacctggtggccgaccctactacatcca<br>ggcgtccacgtacgtgcagaagatgtccatgtacaacctgagatgc<br>gcggcggaggaaaactgtctggccagtacagcatacagggcagatg<br>tcagagattatgatcacagggtgctgctcagatttccccaaagagt<br>gaaaaaccaagggacatcagatttcttacccagccgaccaagatat<br>tcctgggaatggcacagttgtcatcaacattaccacagtatggatg<br>agtttagccactatgacctgcttgatgccaacacccagaggagagt<br>ggctgaaggccacaaagcaagtttctgtcttgaagacacatcctgt<br>gactatggctaccacaggcgatttgcatgtacgcacacacacagg<br>gattgagtcctggctgttatgatacctatggtgcagacatagactg<br>ccagtggattgatattacagatgtaaaacctggaaactatatccta<br>aaggtcagtgtaaaccccagctacctggttcctgaatctgactata<br>ccaacaatgttgtgcgctgtgacattcgctacacaggacatcatgc<br>gtatgcctcaggctgcacaatttcaccgtattagaaggcaaagcaa<br>aactcccaatggataaatcagtgcctggtgttctgaa |
| 21. | MRFAWTVLLLGPLQLCALVHCAPPAAGQQQPPREPPAAPGAWRQQI<br>QWENNGQVFSLLSLGSQYQPQRRDPGAAVPGAANASAQQPRTPIL<br>LIRDNRTAAARTRTAGSSGVTAGRPRPTARHWFQAGYSTSRAREAG<br>ASRAENQTAPGEVPALSNLRPPSRVDGMVGDDPYNPYKYSDDNPYY<br>NYYDTYERPRPGGRYRPGYGTGYFQYGLPDLVADPYYIQASTYVQK<br>MSMYNLRCAAEENCLASTAYRADVRDYDHRVLLRFPQRVKNQGTSD<br>FLPSRPRYSWEWHSCHQHYHSMDEFSHYDLLDANTQRRVAEGHKAS<br>FCLEDTSCDYGYHRRFACTAHTQGLSPGCYDTYGADIDCQWIDITD<br>VKPGNYILKVSVNPSYLVPESDYTNNVVRCDIRYTGHHAYASGCTI<br>SPY |
| 22. | Gttcagcttgctgagcctgggctcacagtaccagcctcagcgccgc<br>cgggacccggggccgccgtccctggtgcagcaacgcctccgccca<br>agcagccccgcactccgatcctgctgatccgcgacaaccgcaccgcc<br>gcggcgcgaacgcggacggccggctcatctggagtcaccgctggcc<br>gccccaggcccaccgcccgtcactggttccaagctggctactcga<br>catctagagcccgcgaagctggcgcctcgcgcgggagaaccagaca<br>gcgccgggagaagttcctgcgctcagtaacctgcggccgcccagc |

| SEQ ID NO | Sequence |
|---|---|
| | cgcgtggacggcatggtgggcgacgaccttacaacccctacaagt actctgacgacaaccctttattacaaccactacgatacttatgaaag gcccagacctgggggcaggtaccggcccggatacggcactggctac ttccagtacggtaagtaccccaagtccgctggaagcacccgtgca cctggtcccagctatgtggcttcttctcgacgtggctgcctggc gcggcgggccccggtcctcgcagatccgaccctcccacgcgcct gcagtggcagccctggaatccagtgcaaaccgcgcgtctggcccct cctgcttccttttcacattgctttgcagtcccggggtcccagtt ctcttgctgtcctccgctccactctgcagtcccggtgggcgaaggg tgaggagtaagggacctagagggtagggagttggagcggggcg ccggggttgtttcactgctgcgcccgtcgcctgctgacgtttaggtc tcccagacctggtg |
| 23. | FSLLSLGSQYQPRRRDPGAAVPGAANASAQQPRTPILLIRDNRTA AARTRTAGSSGVTAGRPRPTARHWFQAGYSTSRAREAGASRAENQT APGEVPALSNLRPPSRVDGMVGDDPYNPYKYSDDNPYYNYYDTYER PRPGGRYRPGYGTGYFQYGLPDLV |
| 24. | MEWSRVFIFLLSVTAGVHSQVQLQQSGAELVRPGTSVKVSCKASGY AFTYYLIEWVKQRPGQGLEWIGVINPGSGGTNYNEKFKGKATLTAD KSSSTAYMQLSSLTSDDSAVYFCARNWMNFDYWGQGTTLTVSS |
| 25. | QVQL*V*QSGAEL*KK*PG*A*SVKVSCKASGYAFTYYLIEWVK*Q*APGQGLE WIGVINPGSGGTNYNEKFKG*R*ATLTADKS*T*STAYM*E*LSSL*RS*E*D*SA VYFCARNWMNFDYWGQGTT*V*TVSS |
| 26. | QVQL*V*QSGAE*VKK*PG*A*SVKVSCKASGYAFTYYLIEWV*RQ*APGQGLE WIGVINPGSGGTNYNEKFKG*R*ATLTADKS*T*STAYM*E*LSSL*RS*E*D*TA* VYFCARNWMNFDYWGQGTT*V*TVSS |
| 27. | QVQL*V*QSGAE*VKK*PG*A*SVKVSCKASGYAFTYYLIEWV*RQ*APGQGLE WIGVINPGSGGTNYNEKFKG*RAT I*TADKS*T*STAYM*E*LSSL*RS*E*D*TA* VYFCARNWMNFDYWGQGTT*V*TVSS |
| 28. | QVQL*V*QSGAE*VKK*PG*A*SVKVSCKASGYAFTYYLIEWV*RQ*APGQGLE WIGVINPGSGGTNYNEKFK*GRVT I*TADKS*T*STAYM*E*LSSL*RS*E*D*TA* VY*Y*CARNWMNFDYWGQGTT*V*TVSS |
| 29. | MRCLAEFLGLLVLWIPGAIGDIVMTQAAPSVSVTPGESVSISCRSS KSLLHSNGTYLYWFLQRPGQSPQFLIYRMSNLASGVPDRFSGSGSG TAFTLRISRVEAEDVGVYYCMQHLEYPYTFGGGTKLEIK |
| 30. | DIVMTQ*TPLSL*SVTPG*QPAS*ISCRSSKSLLHSNGNTYLYWFLQ*K*PG QSPQFLIYRMSNLASGVPDRFSGSGSGTAFTL*KI*SRVEAEDVGVYY CMQHLEYPYTFGGGTK*V*EIK |
| 31. | DIVMTQ*TPLSL*SVTPG*QPAS*ISCRSSKSLLHSNGNTYLYWFLQ*K*PG QSPQFLIYRMSNLASGVPDRFSGSGSGT*DFTLKI*SRVEAEDVGVYY CMQHLEYPYTFGGGTK*V*EIK |
| 32. | DIVMTQ*TPLSL*SVTPG*QPAS*ISCRSSKSLLHSNGNTYLYW*YLQKPG QSPQFLIYRMSNLASGVPDRFSGSGSGT*DFTLKI*SRVEAEDVGVYY CMQHLEYPYTFGGGTK*V*EIK |
| 33. | MEWSRVFIFLLSVTAGVHSQVQLQQSGAELVRPGTSVKVSCKAS |
| 34. | WVKQRPGQGLEWIG |
| 35. | KATLTADKSSTAYMQLSSLTSDDSAVYFCAR |
| 36. | WGQGTTLTVSS |
| 37. | QVQL*V*QSGAEL*KK*PG*A*SVKVSCKAS |
| 38. | WV*KQ*APGQGLEWIG |
| 39. | *R*ATLTADKS*T*STAYM*E*LSSL*RS*E*DSAVYFCAR |
| 40. | WGQGTT*V*TVSS |
| 41. | GYAFTYYLIE |
| 42. | VINPGSGGTNYNEKFKG |
| 43. | NWMNFDY |
| 44. | QVQL*V*QSGAE*VKK*PG*A*SVKVSCKAS |
| 45. | WV*RQ*APGQGLEWIG |
| 46. | *R*ATLTADKS*T*STAYM*E*LSSL*RS*E*D*T*AVYFCAR |
| 47. | *R*AT*I*TADKS*T*STAYM*E*LSSL*RS*E*D*T*AVYFCAR |
| 48. | *RVT I*TADKS*T*STAYM*E*LSSL*RS*E*D*T*AVY*Y*CAR |
| 49. | MRCLAEFLGLLVLWIPGAIGDIVMTQAAPSVSVTPGESVSISC |
| 50. | WFLQRPGQSPQFLIY |
| 51. | GVPDRFSGSGSGTAFTLRISRVEAEDVGVYYC |
| 52. | FGGGTKLEIK |
| 53. | DIVMTQ*TPLSL*SVTPG*QPAS*ISC |
| 54. | WFLQ*K*PGQSPQFLIY |
| 55. | GVPDRFSGSGSGTAFTL*KI*SRVEAEDVGVYYC |
| 56. | FGGGTK*V*EIK |
| 57. | RSSKSLLHSNGNTYLY |
| 58. | RMSNLAS |
| 59. | MQHLEYPYT |
| 60. | GVPDRFSGSGSGT*DFTLKI*SRVEAEDVGVYYC |
| 61. | W*YLQKPGQSPQFLIY |
| 62. | Alternative cleavage sites can be between amino acids 21 and 22 of preprotein compared to SEQ ID NO: 8 APPAAGQQQPPREPPAAPGAWRQQIQWENNGQVFSLLSLGSQYQPQ RRRDPGAAVPGAANASAQQPRTPILLIRDNRTAAARTRTAGSSGVT AGRPRPTARHWFQAGYSTSRAREAGASRAENQTAPGEVPALSNLRP PSRVDGMVGDDPYNPYKYSDDNPYYNYYDTYERPRPGGRYRPGYGT GYFQYGLPDLVADPYYIQASTYVQKMSMYNLRCAAEENCLASTAYR ADVRDYDHRVLLRFPQRVKNQGTSDFLPSRPRYSWEWHSCHQHYHS MDEFSHYDLLDANTQRRVAEGHKASFCLEDTSCDYGYHRRFACTAH TQGLSPGCYDTYGADIDCQWIDITDVKPGNYILKVSVNPSYLVPES DYTNNVVRCDIRYTGHHAYASGCTISPY |
| 63. | Alternative cleavage sites can be between amino acids 27 and 28 of preprotein compared to SEQ ID NO: 8 QQQPPREPPAAPGAWRQQIQWENNGQVFSLLSLGSQYQPQRRRDPG AAVPGAANASAQQPRTPILLIRDNRTAAARTRTAGSSGVTAGRPRP TARHWFQAGYSTSRAREAGASRAENQTAPGEVPALSNLRPPSRVDG MVGDDPYNPYKYSDDNPYYNYYDTYERPRPGGRYRPGYGTGYFQYG LPDLVADPYYIQASTYVQKMSMYNLRCAAEENCLASTAYRADVRDY DHRVLLRFPQRVKNQGTSDFLPSRPRYSWEWHSCHQHYHSMDEFSH YDLLDANTQRRVAEGHKASFCLEDTSCDYGYHRRFACTAHTQGLSP GCYDTYGADIDCQWIDITDVKPGNYILKVSVNPSYLVPESDYTNNV VRCDIRYTGHHAYASGCTISPY |
| 64. | Human LOX mRNA sequence ATGCGCTTCGCCTGGACCGTGCTCCTGCTCGGCCTTTGCAGCTCT GCGCGCTAGTGCACTGCGCCCCTCCGCCGCCGGCCAACAGCAGCC CCCGCGAGCCGCCGGCGGCTCCGGGCGCCTGGCGCCAGCAGATC CAATGGGAGAACAACGGGCAGGTGTTCAGCTTGCTGAGCCTGGGCT CACAGTACCAGCCTCAGCGCCGCCGGGACCCGGGCGCCGCCGTCCC TGGTGCAGCCAACGCCTCCGCCCAGCAGCCCCGCACTCCGATCCTG CTGATCCGCGACAACCGCACCGCCGCGGCGCGAACGCGGACGGCG GCTCATCTGGAGTCACCGCTGGCGCCCCAGGCCCACCGCCCGTCA CTGGTTCCAAGCTGGCTACTCGACATCTAGAGCCCGCGAAGCTGGC GCCTCGCGCGCGGAGAACCAGACAGCGCCGGGAGAAGTTCCTGCGC TCAGTAACCTGCGGCCGCCCAGCCGCGTGGACGGCATGGTGGGCGA CGACCCTTACAACCCCTACAAGTACTCTGACGACAACCCTTATTAC |

| SEQ ID NO | Sequence |
|---|---|
| | AACTACTACGATACTTATGAAAGGCCCAGACCTGGGGGCAGGTACC GGCCCGGATACGGCACTGGCTACTTCCAGTACGGTCTCCCAGACCT GGTGGCCGACCCCTACTACATCCAGGCGTCCACGTACGTGCAGAAG ATGTCCATGTACAACCTGCGATGCGCGGCGGAGGAAAACTGTCTGG CCAGTACAGCATACAGGGCAGATGTCAGAGATTATGATCACAGGGT GCTGCTCAGATTTCCCCAAAGAGTGAAAAACCAAGGGACATCAGAT TTCTTACCCAGCCGACCAAGATATTCCTGGGAATGGCACAGTTGTC ATCAACATTACCACAGTATGGATGAGTTTAGCCACTATGACCTGCT TGATGCCAACACCCAGAGGAGAGTGGCTGAAGGCCACAAAGCAAGT TTCTGTCTTGAAGACACATCCTGTGACTATGGCTACCACAGGCGAT TTGCATGTACTGCACACACAGGGATTGAGTCCTGGCTGTTATGA TACCTATGGTGCAGACATAGACTGCCAGTGGATTGATATTACAGAT GTAAAACCTGGAAACTATATCCTAAAGGTCAGTGTAAACCCCAGCT ACCTGGTTCCTGAATCTGACTATACCAACAATGTTGTGCGCTGTGA CATTCGCTACACAGGACATCATGCGTATGCCTCAGGCTGCACAATT TCACCGTAT |
| 65. | Human LOX Protein Sequence MRFAWTVLLLGPLQLCALVHCAPPAAGQQQPPREPPAAPGAWRQQI QWENNGQVFSLLSLGSQYQPQRRRDPGAAVPGAANASAQQPRTPIL LIRDNRTAAARTRTAGSSGVTAGRPRPTARHWFQAGYSTSRAREAG ASRAENQTAPGEVPALSNLRPPSRVDGMVGDDPYNPYKYSDDNPYY NYYDTYERPRPGGRYRPGYGTGYFQYGLPDLVADPYYIQASTYVQK MSMYNLRCAAEENCLASTAYRADVRDYDHRVLLRFPQRVKNQGTSD FLPSRPRYSWEWHSCHQHYHSMDEFSHYDLLDANTQRRVAEGHKAS FCLEDTSCDYGYHRRFACTAHTQGLSPGCYDTYGADIDCQWIDITD VKPGNYILKVSVNPSYLVPESDYTNNVVRCDIRYTGHHAYASGCTI SPY |

While preferred embodiments of the present invention have been shown and described herein, it will be clear to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. An isolated antibody or antigen binding fragment thereof, comprising a heavy chain variable region comprising the amino acid sequence set forth as SEQ ID NO: 25, 26, 27, or 28, and a light chain variable region comprising the amino acid sequence set forth as SEQ ID NO: 30, 31, or 32, wherein the isolated antibody or antigen binding fragment thereof specifically binds a lysyl oxidase-like 2 (LOXL2) protein.

2. An isolated antibody or antigen binding fragment thereof, comprising a heavy chain variable region comprising the amino acid sequence set forth as SEQ ID NO: 25, 26, 27, or 28, wherein the isolated antibody or antigen binding fragment thereof specifically binds a lysyl oxidase-like 2(LOXL2) protein.

3. An isolated antibody or antigen binding fragment thereof, comprising a light chain variable region comprising the amino acid sequence set forth as SEQ ID NO: 30, 31, or 32, wherein the isolated antibody or antigen binding fragment thereof specifically binds a lysyl oxidase-like 2 (LOXL2) protein.

4. An isolated antibody or antigen binding fragment thereof, comprising the complementarity determining regions (CDRs), CDR1, CDR2, and CDR3, of a heavy chain variable region comprising the amino acid sequence set forth as SEQ ID NO: 25, 26, 27, or 28, and the CDRs, CDR1, CDR2, and CDR3, of a light chain variable region comprising the amino acid sequence set forth as SEQ ID NO: 30, 31, or 32, wherein the isolated antibody or antigen binding fragment thereof specifically binds a lysyl oxidase-like 2(LOXL2) protein.

5. The isolated antibody or antigen binding fragment thereof of claim 1, wherein the heavy chain variable region comprises the amino acid sequence set forth as SEQ ID NO: 25.

6. The isolated antibody or antigen binding fragment thereof of claim 1, wherein the heavy chain variable region comprises the amino acid sequence set forth as SEQ ID NO: 26.

7. The isolated antibody or antigen binding fragment thereof of claim 1, wherein the heavy chain variable region comprises the amino acid sequence set forth as SEQ ID NO: 27.

8. The isolated antibody or antigen binding fragment thereof of claim 1, wherein the heavy chain variable region comprises the amino acid sequence set forth as SEQ ID NO: 28.

9. The isolated antibody or antigen binding fragment thereof of claim 1, wherein the light chain variable region comprises the amino acid sequence set forth as SEQ ID NO: 30.

10. The isolated antibody or antigen binding fragment thereof of claim 1, wherein the light chain variable region comprises the amino acid sequence set forth as SEQ ID NO: 31.

11. The isolated antibody or antigen binding fragment thereof of claim 1, wherein the light chain variable region comprises the amino acid sequence set forth as SEQ ID NO: 32.

12. The isolated antibody or antigen binding fragment thereof of claim 1, wherein the heavy chain variable region comprises the amino acid sequence set forth as SEQ ID NO:27 and the light chain variable region comprises the amino acid sequence set forth as SEQ ID NO:31.

13. The isolated antibody or antigen binding fragment thereof of claim 2, wherein, the heavy chain variable region comprises the amino acid sequence set forth as SEQ ID NO: 25.

14. The isolated antibody or antigen binding fragment thereof of claim 2, wherein, the heavy chain variable region comprises the amino acid sequence set forth as SEQ ID NO: 26.

15. The isolated antibody or antigen binding fragment thereof of claim 2, wherein the heavy chain variable region comprises the amino acid sequence set forth as SEQ ID NO: 27.

16. The isolated antibody or antigen binding fragment thereof of claim 2, wherein the heavy chain variable region comprises the amino acid sequence set forth as SEQ ID NO: 28.

17. The isolated antibody or antigen binding fragment thereof of claim 3, wherein, the light chain variable region comprises the amino acid sequence set forth as SEQ ID NO: 30.

18. The isolated antibody or antigen binding fragment thereof of claim 3, wherein the light chain variable region comprises the amino acid sequence set forth as SEQ ID NO: 31.

19. The isolated antibody or antigen binding fragment thereof of claim 3, wherein, the light chain variable region comprises the amino acid sequence set forth as SEQ ID NO: 32.

20. The isolated antibody or antigen binding fragment thereof of claim 1, wherein the antibody or fragment is labeled with a detectable label, a therapeutic agent or both.

21. The isolated antibody or antigen binding fragment thereof of claim 1, wherein the antibody or fragment is a Fv, a scFv, a Fab, a F(ab')$_2$, or monoclonal.

22. The isolated antibody or antigen binding fragment thereof of claim 4, wherein the CDR1, CDR2, and CDR3 of the heavy chain variable region comprise the amino acid sequences set forth as SEQ ID NOs: 41, 42, and 70, respectively, and the CDR1, CDR2, and CDR3 of the light chain variable region comprise the amino acid sequences set forth as SEQ ID NOs: 57, 58, and 59, respectively.

23. The isolated antibody or antigen binding fragment thereof of claim 1, wherein the antibody or fragment is labeled with a therapeutic agent.

24. The isolated antibody or antigen binding fragment thereof of claim 2, wherein the antibody or fragment is labeled with a detectable label, a therapeutic agent or both.

25. The isolated antibody or antigen binding fragment thereof of claim 2, wherein the antibody or fragment is labeled with a therapeutic agent.

26. The isolated antibody or antigen binding fragment thereof of claim 2, wherein the antibody or fragment is a Fv, a scFv, a Fab, a F(ab')$_2$, or monoclonal.

27. The isolated antibody or antigen binding fragment thereof of claim 3, wherein the antibody or fragment is labeled with a detectable label, a therapeutic agent or both.

28. The isolated antibody or antigen binding fragment thereof of claim 3, wherein the antibody or fragment is labeled with a therapeutic agent.

29. The isolated antibody or antigen binding fragment thereof of claim 3, wherein the antibody or fragment is a Fv, a scFv, a Fab, a F(ab')$_2$, or monoclonal.

30. The isolated antibody or antigen binding fragment thereof of claim 4, wherein the antibody or fragment is humanized.

* * * * *

SEQUENCE LISTING

<160> NUMBER OF SEQ ID NOS: 70

<210> SEQ ID NO 1
<211> LENGTH: 135
<212> TYPE: PRT
<213> ORGANISM: Mus sp.

<400> SEQUENCE: 1

```
Met Glu Trp Ser Arg Val Phe Ile Phe Leu Leu Ser Val Thr Ala Gly
1               5                   10                  15

Val His Ser Gln Val Gln Leu Gln Ser Gly Ala Glu Leu Val Arg
                20                  25                  30

Pro Gly Thr Ser Val Lys Val Ser Cys Lys Ala Ser Gly Tyr Ala Phe
            35                  40                  45

Thr Tyr Tyr Leu Ile Glu Trp Val Lys Gln Arg Pro Gly Gln Gly Leu
    50                  55                  60

Glu Trp Ile Gly Val Ile Asn Pro Gly Ser Gly Gly Thr Asn Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Asp Asp Ser Ala Val
            100                 105                 110

Tyr Phe Cys Ala Arg Asn Trp Met Asn Phe Asp Tyr Trp Gly Gln Gly
        115                 120                 125

Thr Thr Leu Thr Val Ser Ser
    130                 135
```

<210> SEQ ID NO 2
<211> LENGTH: 132
<212> TYPE: PRT
<213> ORGANISM: Mus sp.

<400> SEQUENCE: 2

```
Met Arg Cys Leu Ala Glu Phe Leu Gly Leu Leu Val Leu Trp Ile Pro
1               5                   10                  15
```

```
Gly Ala Ile Gly Asp Ile Val Met Thr Gln Ala Ala Pro Ser Val Ser
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Phe Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
            115                 120                 125

Leu Glu Ile Lys
        130

<210> SEQ ID NO 3
<211> LENGTH: 135
<212> TYPE: PRT
<213> ORGANISM: Artificial Sequence
<220> FEATURE:
<223> OTHER INFORMATION: Synthetic polypeptide

<400> SEQUENCE: 3

Met Gly Trp Ser Trp Val Phe Leu Phe Leu Leu Ser Val Thr Ala Gly
1               5                   10                  15

Val His Ser Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Thr Phe
        35                  40                  45

Arg Ser Tyr Asp Ile Asn Trp Val Arg Gln Arg Pro Glu Gln Gly Leu
    50                  55                  60

Glu Trp Ile Gly Trp Ile Phe Pro Gly Asp Gly Ser Thr Lys Tyr Asn
65                  70                  75                  80

Glu Lys Phe Lys Gly Lys Ala Ile Leu Thr Thr Asp Lys Ser Ser Ser
                85                  90                  95

Thr Ala Tyr Met Gln Leu Ser Arg Leu Thr Ser Glu Asp Ser Ala Val
            100                 105                 110

Tyr Phe Cys Ala Arg Val Tyr Tyr Ala Met Asp Tyr Trp Gly Gln Gly
            115                 120                 125

Thr Ser Val Thr Val Ser Ser
        130                 135

<210> SEQ ID NO 4
<211> LENGTH: 133
<212> TYPE: PRT
<213> ORGANISM: Artificial Sequence
<220> FEATURE:
<223> OTHER INFORMATION: Synthetic polypeptide

<400> SEQUENCE: 4

Met Lys Leu Pro Val Arg Leu Leu Val Met Phe Trp Ile Pro Ala Ser
1               5                   10                  15

Ser Ser Asp Val Leu Leu Thr Gln Thr Pro Leu Ser Leu Pro Val Ser
            20                  25                  30

Leu Gly Asp Gln Ala Ser Ile Ser Cys Arg Ser Ser Gln Ser Ile Val
        35                  40                  45
```

```
His Ser Asn Gly Asn Thr Tyr Leu Glu Trp Tyr Leu Gln Lys Pro Gly
    50                  55                  60

Gln Ser Pro Lys Leu Leu Ile Tyr Lys Val Ser Asn Arg Phe Ser Gly
65                  70                  75                  80

Val Pro Asp Arg Phe Gly Gly Ser Gly Ser Gly Thr Asp Phe Thr Leu
                85                  90                  95

Lys Ile Asn Arg Val Glu Ala Glu Asp Leu Gly Ile Tyr Tyr Cys Phe
                100                 105                 110

Gln Ser Ser His Ile Pro Leu Thr Phe Gly Ala Gly Thr Lys Leu Glu
            115                 120                 125

Leu Lys Arg Ala Asp
        130

<210> SEQ ID NO 5
<211> LENGTH: 133
<212> TYPE: PRT
<213> ORGANISM: Artificial Sequence
<220> FEATURE:
<223> OTHER INFORMATION: Synthetic polypeptide

<400> SEQUENCE: 5

Met Lys Leu Pro Val Arg Leu Leu Val Met Phe Trp Ile Pro Ala Ser
1               5                   10                  15

Ser Ser Asp Val Leu Leu Thr Gln Thr Pro Leu Ser Leu Pro Val Ser
                20                  25                  30

Leu Gly Asp Gln Ala Ser Ile Ser Cys Arg Ser Ser Gln Ser Ile Val
            35                  40                  45

His Ser Asn Gly Asn Thr Tyr Leu Glu Trp Tyr Leu Gln Lys Pro Gly
    50                  55                  60

Gln Ser Pro Lys Leu Leu Ile Tyr Lys Val Ser Ile Arg Phe Ser Gly
65                  70                  75                  80

Val Pro Asp Arg Phe Gly Gly Ser Gly Ser Gly Thr Asp Phe Thr Leu
                85                  90                  95

Lys Ile Asn Arg Val Glu Ala Glu Asp Leu Gly Ile Tyr Tyr Cys Phe
                100                 105                 110

Gln Ser Ser His Ile Pro Leu Thr Phe Gly Ala Gly Thr Lys Leu Glu
            115                 120                 125

Leu Lys Arg Ala Asp
        130

<210> SEQ ID NO 6
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 6

Val Arg Leu Arg Gly Gly Ala Tyr Ile Gly Glu Gly Arg Val Glu Val
1               5                   10                  15

Leu Lys Asn Gly Glu Trp Gly Thr Val Cys Asp Asp Lys Trp Asp Leu
                20                  25                  30

Val Ser Ala Ser Val Val Cys Arg Glu Leu Gly Phe Gly Ser Ala Lys
            35                  40                  45

Glu Ala Val Thr Gly Ser Arg Leu Gly Gln Gly Ile Gly Pro Ile His
    50                  55                  60

Leu Asn Glu Ile Gln Cys Thr Gly Asn Glu Lys Ser Ile Ile Asp Cys
65                  70                  75                  80
```

```
Lys Phe Asn Ala Glu Ser Gln Gly Cys Asn His Glu Glu Asp Ala Gly
                85                  90                  95

Val Arg Cys Asn Thr Pro Ala Met Gly Leu Gln Lys Lys Leu Arg Leu
            100                 105                 110

Asn Gly Gly Arg Asn Pro Tyr Glu Gly Arg Val Glu Val Leu Val Glu
            115                 120                 125

Arg Asn Gly Ser Leu Val Trp Gly Met Val Cys Gly Gln Asn Trp Gly
130                 135                 140

Ile Val Glu Ala Met Val Val Cys Arg Gln Leu Gly Leu Gly Phe Ala
145                 150                 155                 160

Ser Asn Ala Phe Gln Glu Thr Trp Tyr Trp His Gly Asp Val Asn Ser
                165                 170                 175

Asn Lys Val Val Met Ser Gly Val Lys Cys Ser Gly Thr Glu Leu Ser
            180                 185                 190

Leu Ala His Cys Arg His Asp Gly Glu Asp Val Ala Cys Pro Gln Gly
            195                 200                 205

Gly Val Gln Tyr Gly Ala Gly Val Ala Cys Ser
        210                 215

<210> SEQ ID NO 7
<211> LENGTH: 417
<212> TYPE: PRT
<213> ORGANISM: Homo sapiens

<400> SEQUENCE: 7

Met Arg Phe Ala Trp Thr Val Leu Leu Leu Gly Pro Leu Gln Leu Cys
1               5                   10                  15

Ala Leu Val His Cys Ala Pro Ala Ala Gly Gln Gln Gln Pro Pro Pro
            20                  25                  30

Arg Glu Pro Pro Ala Ala Pro Gly Ala Trp Arg Gln Gln Ile Gln Trp
        35                  40                  45

Glu Asn Asn Gly Gln Val Phe Ser Leu Leu Ser Leu Gly Ser Gln Tyr
    50                  55                  60

Gln Pro Gln Arg Arg Arg Asp Pro Gly Ala Ala Val Pro Gly Ala Ala
65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
            100                 105                 110

Thr Ala Gly Arg Pro Arg Pro Thr Ala Arg His Trp Phe Gln Ala Gly
            115                 120                 125

Tyr Ser Thr Ser Arg Ala Arg Glu Ala Gly Ala Ser Arg Ala Glu Asn
130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Pro Tyr Asn Pro Tyr Lys
            165                 170                 175

Tyr Ser Asp Asp Asn Pro Tyr Tyr Asn Tyr Asp Thr Tyr Glu Arg
            180                 185                 190

Pro Arg Pro Gly Gly Arg Tyr Arg Pro Gly Tyr Gly Thr Gly Tyr Phe
            195                 200                 205

Gln Tyr Gly Leu Pro Asp Leu Val Ala Asp Pro Tyr Tyr Ile Gln Ala
        210                 215                 220

Ser Thr Tyr Val Gln Lys Met Ser Met Tyr Asn Leu Arg Cys Ala Ala
225                 230                 235                 240
```

```
Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
            260                 265                 270

Gly Thr Ser Asp Phe Leu Pro Ser Pro Arg Tyr Ser Trp Glu Trp
        275                 280                 285

His Ser Cys His Gln His Tyr His Ser Met Asp Glu Phe Ser His Tyr
290                 295                 300

Asp Leu Leu Asp Ala Asn Thr Gln Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
            340                 345                 350

Asp Thr Tyr Gly Ala Asp Ile Asp Cys Gln Trp Ile Asp Ile Thr Asp
        355                 360                 365

Val Lys Pro Gly Asn Tyr Ile Leu Lys Val Ser Val Asn Pro Ser Tyr
    370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 8
<211> LENGTH: 401
<212> TYPE: PRT
<213> ORGANISM: Homo sapiens

<400> SEQUENCE: 8

Ala Leu Val His Cys Ala Pro Pro Ala Ala Gly Gln Gln Gln Pro Pro
1               5                   10                  15

Arg Glu Pro Pro Ala Ala Pro Gly Ala Trp Arg Gln Gln Ile Gln Trp
                20                  25                  30

Glu Asn Asn Gly Gln Val Phe Ser Leu Leu Ser Leu Gly Ser Gln Tyr
            35                  40                  45

Gln Pro Gln Arg Arg Arg Asp Pro Gly Ala Ala Val Pro Gly Ala Ala
        50                  55                  60

Asn Ala Ser Ala Gln Gln Pro Arg Thr Pro Ile Leu Leu Ile Arg Asp
65                  70                  75                  80

Asn Arg Thr Ala Ala Ala Arg Thr Arg Thr Ala Gly Ser Ser Gly Val
                85                  90                  95

Thr Ala Gly Arg Pro Arg Pro Thr Ala Arg His Trp Phe Gln Ala Gly
                100                 105                 110

Tyr Ser Thr Ser Arg Ala Arg Glu Ala Gly Ala Ser Arg Ala Glu Asn
            115                 120                 125

Gln Thr Ala Pro Gly Glu Val Pro Ala Leu Ser Asn Leu Arg Pro Pro
        130                 135                 140

Ser Arg Val Asp Gly Met Val Gly Asp Pro Tyr Asn Pro Tyr Lys
145                 150                 155                 160

Tyr Ser Asp Asp Asn Pro Tyr Tyr Asn Tyr Asp Thr Tyr Glu Arg
                165                 170                 175

Pro Arg Pro Gly Gly Arg Tyr Arg Pro Gly Tyr Gly Thr Gly Tyr Phe
            180                 185                 190
```

```
Gln Tyr Gly Leu Pro Asp Leu Val Ala Asp Pro Tyr Tyr Ile Gln Ala
        195                 200                 205
Ser Thr Tyr Val Gln Lys Met Ser Met Tyr Asn Leu Arg Cys Ala Ala
210                 215                 220
Glu Glu Asn Cys Leu Ala Ser Thr Ala Tyr Arg Ala Asp Val Arg Asp
225                 230                 235                 240
Tyr Asp His Arg Val Leu Leu Arg Phe Pro Gln Arg Val Lys Asn Gln
                245                 250                 255
Gly Thr Ser Asp Phe Leu Pro Ser Arg Pro Arg Tyr Ser Trp Glu Trp
            260                 265                 270
His Ser Cys His Gln His Tyr His Ser Met Asp Glu Phe Ser His Tyr
        275                 280                 285
Asp Leu Leu Asp Ala Asn Thr Gln Arg Arg Val Ala Glu Gly His Lys
290                 295                 300
Ala Ser Phe Cys Leu Glu Asp Thr Ser Cys Asp Tyr Gly Tyr His Arg
305                 310                 315                 320
Arg Phe Ala Cys Thr Ala His Thr Gln Gly Leu Ser Pro Gly Cys Tyr
                325                 330                 335
Asp Thr Tyr Gly Ala Asp Ile Asp Cys Gln Trp Ile Asp Ile Thr Asp
            340                 345                 350
Val Lys Pro Gly Asn Tyr Ile Leu Lys Val Ser Val Asn Pro Ser Tyr
        355                 360                 365
Leu Val Pro Glu Ser Asp Tyr Thr Asn Asn Val Val Arg Cys Asp Ile
370                 375                 380
Arg Tyr Thr Gly His His Ala Tyr Ala Ser Gly Cys Thr Ile Ser Pro
385                 390                 395                 400
Tyr

<210> SEQ ID NO 9
<211> LENGTH: 249
<212> TYPE: PRT
<213> ORGANISM: Homo sapiens

<400> SEQUENCE: 9

Asp Asp Pro Tyr Asn Pro Tyr Lys Tyr Ser Asp Asp Asn Pro Tyr Tyr
1               5                   10                  15
Asn Tyr Tyr Asp Thr Tyr Glu Arg Pro Arg Pro Gly Gly Arg Tyr Arg
            20                  25                  30
Pro Gly Tyr Gly Thr Gly Tyr Phe Gln Tyr Gly Leu Pro Asp Leu Val
        35                  40                  45
Ala Asp Pro Tyr Tyr Ile Gln Ala Ser Thr Tyr Val Gln Lys Met Ser
50                  55                  60
Met Tyr Asn Leu Arg Cys Ala Ala Glu Glu Asn Cys Leu Ala Ser Thr
65                  70                  75                  80
Ala Tyr Arg Ala Asp Val Arg Asp Tyr Asp His Arg Val Leu Leu Arg
                85                  90                  95
Phe Pro Gln Arg Val Lys Asn Gln Gly Thr Ser Asp Phe Leu Pro Ser
            100                 105                 110
Arg Pro Arg Tyr Ser Trp Glu Trp His Ser Cys His Gln His Tyr His
        115                 120                 125
Ser Met Asp Glu Phe Ser His Tyr Asp Leu Leu Asp Ala Asn Thr Gln
    130                 135                 140
Arg Arg Val Ala Glu Gly His Lys Ala Ser Phe Cys Leu Glu Asp Thr
145                 150                 155                 160
Ser Cys Asp Tyr Gly Tyr His Arg Arg Phe Ala Cys Thr Ala His Thr
```

```
                     165                 170                 175
Gln Gly Leu Ser Pro Gly Cys Tyr Asp Thr Tyr Gly Ala Asp Ile Asp
            180                 185                 190

Cys Gln Trp Ile Asp Ile Thr Asp Val Lys Pro Gly Asn Tyr Ile Leu
        195                 200                 205

Lys Val Ser Val Asn Pro Ser Tyr Leu Val Pro Glu Ser Asp Tyr Thr
    210                 215                 220

Asn Asn Val Val Arg Cys Asp Ile Arg Tyr Thr Gly His His Ala Tyr
225                 230                 235                 240

Ala Ser Gly Cys Thr Ile Ser Pro Tyr
            245
```

<210> SEQ ID NO 10
<211> LENGTH: 1604
<212> TYPE: DNA
<213> ORGANISM: Homo sapiens
<220> FEATURE:
<221> NAME/KEY: misc_difference
<222> LOCATION: 1530
<223> OTHER INFORMATION: n = a, c, g, t, unknown or other

<400> SEQUENCE: 10

```
gggcgtgatt tgagccccgt ttttattttc tgtgagccac gtcctcctcg agggggtcaa      60
tctggccaaa aggagtgatg cgcttcgcct ggaccgtgct cctgctcggg cctttgcagc     120
tctgcgcgct agtgcactgc gcccctcccg ccgccggcca acagcagccc ccgcgcgagc     180
cgccggcggc tccgggcgcc tggcgccagc agatccaatg ggagaacaac gggcaggtgt     240
tcagcttgct gagcctgggc tcacagtacc agcctcagcg ccgccgggac ccgggcgccg     300
ccgtccctgg tgcagccaac gcctccgccc agcagcccccg cactccgatc ctgctgatcc     360
gcgacaaccg caccgccgcg gcgcgaacgc ggacggccgg ctcatctgga gtcaccgctg     420
gccgccccag gcccaccgcc cgtcactggt tccaagctgg ctactcgaca tctagagccc     480
gcgaacgtgg cgcctcgcgc gcggagaacc agacagcgcc gggagaagtt cctgcgctca     540
gtaacctgcg gccgcccagc cgcgtggacg gcatggtggg cgacgaccct acaaccccct     600
acaagtactc tgacgacaac ccttattaca actactacga tacttatgaa aggcccagac     660
ctggggggcag gtaccggccc ggatacggca ctggctactt ccagtacggt ctcccagacc     720
tggtggccga ccctactac atccaggcgt ccacgtacgt gcagaagatg tccatgtaca     780
acctgagatg cgcggcggag gaaaactgtc tggccagtac agcatacagg gcagatgtca     840
gagattatga tcacagggtg ctgctcagat tcccccaaag agtgaaaaac caagggacat     900
cagatttctt acccagccga ccaagatatt cctgggaatg gcacagttgt catcaacatt     960
accacagtat ggatgagttt agccactatg acctgcttga tgccaacacc cagaggagag    1020
tggctgaagg ccacaaagca gtttctgtc ttgaagacac atcctgtgac tatggctacc    1080
acaggcgatt tgcatgtact gcacacacac agggattgag tcctggctgt tatgatacct    1140
atggtgcaga catagactgc cagtggatta atattacaga tgtaaaacct ggaaactata    1200
tcctaaaggt cagtgtaaac cccagctacc tggttcctga atctgactat accaacaatg    1260
ttgtgcgctg tgacattcgc tacacaggac atcatgcgta tgcctcaggc tgcacaattt    1320
caccgtatta gaaggcaaag caaaactccc aatggataaa tcagtgcctg gtgttctgaa    1380
gtgggaaaaa atagactaac ttcagtagga tttatgtatt tgaaaaagaa gaacagaaaa    1440
caacaaaaga attttgtttt ggactgtttt caataacaaa gcacataact ggattttgaa    1500
cgcttaagtc aatcattact tggaaatttn taatgtttat tatttacatc aactttgtga    1560
```
attaacacag tgtttcaatt ctgtaatttc atatttgact cttt    1604

<210> SEQ ID NO 11
<211> LENGTH: 417
<212> TYPE: PRT
<213> ORGANISM: Homo sapiens

<400> SEQUENCE: 11

Met Arg Phe Ala Trp Thr Val Leu Leu Gly Pro Leu Gln Leu Cys
1               5                   10                  15

Ala Leu Val His Cys Ala Pro Pro Ala Gly Gln Gln Pro Pro
            20                  25                  30

Arg Glu Pro Pro Ala Ala Pro Gly Ala Trp Arg Gln Gln Ile Gln Trp
            35                  40                  45

Glu Asn Asn Gly Gln Val Phe Ser Leu Leu Ser Leu Gly Ser Gln Tyr
            50                  55                  60

Gln Pro Gln Arg Arg Asp Pro Gly Ala Ala Val Pro Gly Ala Ala
65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
                100                 105                 110

Thr Ala Gly Arg Pro Arg Pro Thr Ala Arg His Trp Phe Gln Ala Gly
            115                 120                 125

Tyr Ser Thr Ser Arg Ala Arg Glu Arg Gly Ala Ser Arg Ala Glu Asn
            130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Pro Tyr Asn Pro Tyr Lys
                165                 170                 175

Tyr Ser Asp Asp Asn Pro Tyr Tyr Asn Tyr Tyr Asp Thr Tyr Glu Arg
                180                 185                 190

Pro Arg Pro Gly Gly Arg Tyr Arg Pro Gly Tyr Gly Thr Gly Tyr Phe
            195                 200                 205

Gln Tyr Gly Leu Pro Asp Leu Val Ala Asp Pro Tyr Tyr Ile Gln Ala
            210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
                260                 265                 270

Gly Thr Ser Asp Phe Leu Pro Ser Arg Pro Arg Tyr Ser Trp Glu Trp
            275                 280                 285

His Ser Cys His Gln His Tyr His Ser Met Asp Glu Phe Ser His Tyr
            290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
                340                 345                 350

Asp Thr Tyr Gly Ala Asp Ile Asp Cys Gln Trp Ile Asp Ile Thr Asp
            355                 360                 365

```
Val Lys Pro Gly Asn Tyr Ile Leu Lys Val Ser Val Asn Pro Ser Tyr
        370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 12
<211> LENGTH: 1254
<212> TYPE: DNA
<213> ORGANISM: Homo sapiens

<400> SEQUENCE: 12
atgcgcttcg cctggaccgt gctcctgctc gggcctttgc agctctgcgc gctagtgcac      60
tgcgcccctc ccgccgccgg ccaacagcag ccccgcgcg agccgccggc ggctccgggc       120
gcctggcgcc agcagatcca atgggagaac aacgggcagg tgttcagctt gctgagcctg     180
ggctcacagt accagcctca gccgccgcgg acccgggcg ccgccgtccc tggtgcagcc      240
aacgcctccg cccagcagcc ccgcactccg atcctgctga tccgcgacaa ccgcaccgcc     300
gcggcgcgaa cgcggacggc cggctcatct ggagtcaccg ctggccgccc caggcccacc     360
gcccgtcact ggttccaagc tggctactcg acatctagag cccgcgaacg tggcgcctcg     420
cgcgcggaga accagacagc gccgggagaa gttcctgcgc tcagtaacct gcggccgccc     480
agccgcgtgg acgcatggt gggcgacgac ccttacaacc cctacaagta ctctgacgac      540
aacccttatt acaactacta cgatacttat gaaaggccca gacctggggg caggtaccgg    600
cccggatacg gcactggcta cttccagtac ggtctcccag acctggtggc cgacccctac     660
tacatccagg cgtccacgta cgtgcagaag atgtccatgt acaacctgag atgcgcggcg     720
gaggaaaact gtctggccag tacagcatac agggcagatg tcagagatta tgatcacagg    780
gtgctgctca gatttccca aagagtgaaa aaccaaggga catcagattt cttacccagc      840
cgaccaagat attcctggga atggcacagt tgtcatcaac attaccacag tatggatgag    900
tttagccact atgacctgct tgatgccaac acccagagga gagtggctga aggccacaaa    960
gcaagtttct gtcttgaaga cacatcctgt gactatggct accacaggcg atttgcatgt   1020
actgcacaca cacagggatt gagtcctggc tgttatgata cctatggtgc agacatagac   1080
tgccagtgga ttgatattac agatgtaaaa cctggaaact atatcctaaa ggtcagtgta   1140
aaccccagct acctggttcc tgaatctgac ataccaaca atgttgtgcg ctgtgacatt    1200
cgctacacag acatcatgc gtatgcctca ggctgcacaa tttcaccgta ttag           1254

<210> SEQ ID NO 13
<211> LENGTH: 417
<212> TYPE: PRT
<213> ORGANISM: Homo sapiens

<400> SEQUENCE: 13

Met Arg Phe Ala Trp Thr Val Leu Leu Leu Gly Pro Leu Gln Leu Cys
1               5                   10                  15

Ala Leu Val His Cys Ala Pro Pro Ala Ala Gly Gln Gln Gln Pro Pro
            20                  25                  30

Arg Glu Pro Pro Ala Ala Pro Gly Ala Trp Arg Gln Gln Ile Gln Trp
        35                  40                  45

Glu Asn Asn Gly Gln Val Phe Ser Leu Leu Ser Leu Gly Ser Gln Tyr
    50                  55                  60
```

```
Gln Pro Gln Arg Arg Arg Asp Pro Gly Ala Ala Val Pro Gly Ala Ala
 65                  70                  75                  80

Asn Ala Ser Ala Gln Gln Pro Arg Thr Pro Ile Leu Leu Ile Arg Asp
             85                  90                  95

Asn Arg Thr Ala Ala Ala Arg Thr Arg Thr Ala Gly Ser Ser Gly Val
            100                 105                 110

Thr Ala Gly Arg Pro Arg Pro Thr Ala Arg His Trp Phe Gln Ala Gly
        115                 120                 125

Tyr Ser Thr Ser Arg Ala Arg Glu Arg Gly Ala Ser Arg Ala Glu Asn
    130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Pro Tyr Asn Pro Tyr Lys
                165                 170                 175

Tyr Ser Asp Asp Asn Pro Tyr Tyr Asn Tyr Tyr Asp Thr Tyr Glu Arg
                180                 185                 190

Pro Arg Pro Gly Gly Arg Tyr Arg Pro Gly Tyr Gly Thr Gly Tyr Phe
            195                 200                 205

Gln Tyr Gly Leu Pro Asp Leu Val Ala Asp Pro Tyr Tyr Ile Gln Ala
    210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
            260                 265                 270

Gly Thr Ser Asp Phe Leu Pro Ser Arg Pro Arg Tyr Ser Trp Glu Trp
        275                 280                 285

His Ser Cys His Gln His Tyr His Ser Met Asp Glu Phe Ser His Tyr
    290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
            340                 345                 350

Asp Thr Tyr Gly Ala Asp Ile Asp Cys Gln Trp Ile Asp Ile Thr Asp
        355                 360                 365

Val Lys Pro Gly Asn Tyr Ile Leu Lys Val Ser Val Asn Pro Ser Tyr
    370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 14
<211> LENGTH: 1780
<212> TYPE: DNA
<213> ORGANISM: Homo sapiens

<400> SEQUENCE: 14
gggccaggac tgagaaaggg gaaagggaag ggtgccacgt ccgagcagcc gccttgactg      60
gggaagggtc tgaatcccac ccttggcatt gcttggtgga gactgagata cccgtgctcc     120
```

```
gctcgcctcc ttggttgaag atttctcctt ccctcacgtg atttgagccc cgttttattt      180
ttctgtgagc cacgtcctcc tcgagcgggg tcaatctggc aaaaggagtg atgcgcttcg      240
cctggaccgt gctcctgctc gggcctttgc agctctgcgc gctagtgcac tgcgcccctc      300
ccgccgccgg ccaacagcag cccccgcgcg agccgccggc ggctccgggc gcctggcgcc      360
agcagatcca atgggagaac aacgggcagg tgttcagctt gctgagcctg gctcacagt       420 accagcctca gcgccgccgg gacccgggcg ccgccgtccc tggtgcagcc aacgcctccg      480
cccagcagcc ccgcactccg atcctgctga tccgcgacaa ccgcaccgcc gcggggcgaa      540
cgcggacggc cggctcatct ggagtcaccg ctggccgccc caggcccacc gcccgtcact      600
ggttccaagc tggctactcg acatctagag cccgcgaagc tgggccctcg cgcgcggaga      660
accagacagc gccgggagaa gttcctgctc tcagtaacct gcggccgccc agccgcgtgg      720
acggcatggt gggcgacgac ccttacaacc cctacaagta ctctgacgac aacccttatt      780
acaactacta cgatacttat gaaaggccca gacctggggg caggtaccgg cccggatacg      840
gcactggcta cttccagtac ggtctcccag acctggtggc cgacccctac tacatccagg      900
cgtccacgta cgtgcagaag atgtccatgt acaacctgag atgcgcggcg gaggaaaact      960
gtctggccag tacagcatac agggcagatg tcagagatta tgatcacagg gtgctgctca     1020
gatttcccca aagagtgaaa aaccaaggga catcagattt cttacccagc cgaccaagat     1080
attcctggga atggcacagt tgtcatcaac attaccacag tatggatgag tttagccact     1140
tgtacctgct tgatgccaac acccagagga gatgggctga aggccacaaa gcaagtttct     1200
gtcttgaaga cacatcctgt gactatggct accacaggcg atttgcatgt actgcacaca     1260
cacagggatt gagtcctggc tgttatgata cctatggtgc agacatagac tgccagtgga     1320
ttgatattac agatgtaaaa cctggaaact atatcctaaa ggtcagtgta aaccccagct     1380
acctggttcc tgaatctgac ataccaacaa tgttgtgcg ctgtgacatt cgctacacag      1440
gacatcatgc gtatgcctca ggctgcacaa tttcaccgta ttagaaggca agcaaaact      1500 cccaatggat aaatcagtgc ctggtgttct gaagtgggaa aaaatagact aacttcagta     1560
ggatttatgt attttgaaaa agagaacaga aaacaacaaa agaattttttg tttggactgt    1620 tttcaataac aaagcacata actggatttt gaacgcttaa gtcatcatta cttgggaaat     1680
ttttaatgtt tattatttac atcactttgt gaattaacac agtgtttcaa ttctgtaatt     1740
acatatttga ctctttcaaa aaaaaaaaaa aaaaaaaaa                            1780
```

<210> SEQ ID NO 15
<211> LENGTH: 417
<212> TYPE: PRT
<213> ORGANISM: Homo sapiens

<400> SEQUENCE: 15

```
Met Arg Phe Ala Trp Thr Val Leu Leu Leu Gly Pro Leu Gln Leu Cys
1               5                   10                  15

Ala Leu Val His Cys Ala Pro Pro Ala Ala Gly Gln Gln Gln Pro Pro
            20                  25                  30

Arg Glu Pro Pro Ala Ala Pro Gly Ala Trp Arg Gln Gln Ile Gln Trp
        35                  40                  45

Glu Asn Asn Gly Gln Val Phe Ser Leu Leu Ser Leu Gly Ser Gln Tyr
    50                  55                  60

Gln Pro Gln Arg Arg Arg Asp Pro Gly Ala Ala Val Pro Gly Ala Ala
65                  70                  75                  80
```

```
Asn Ala Ser Ala Gln Gln Pro Arg Thr Pro Ile Leu Leu Ile Arg Asp
                85                  90                  95
Asn Arg Thr Ala Ala Gly Arg Thr Arg Thr Ala Gly Ser Ser Gly Val
            100                 105                 110
Thr Ala Gly Arg Pro Arg Pro Thr Ala Arg His Trp Phe Gln Ala Gly
        115                 120                 125
Tyr Ser Thr Ser Arg Ala Arg Glu Ala Gly Pro Ser Arg Ala Glu Asn
    130                 135                 140
Gln Thr Ala Pro Gly Glu Val Pro Ala Leu Ser Asn Leu Arg Pro Pro
145                 150                 155                 160
Ser Arg Val Asp Gly Met Val Gly Asp Pro Tyr Asn Pro Tyr Lys
                165                 170                 175
Tyr Ser Asp Asp Asn Pro Tyr Tyr Asn Tyr Tyr Asp Thr Tyr Glu Arg
                180                 185                 190
Pro Arg Pro Gly Gly Arg Gly Tyr Arg Pro Gly Tyr Gly Thr Gly Tyr Phe
                195                 200                 205
Gln Tyr Gly Leu Pro Asp Leu Val Ala Asp Pro Tyr Tyr Ile Gln Ala
    210                 215                 220
Ser Thr Tyr Val Gln Lys Met Ser Met Tyr Asn Leu Arg Cys Ala Ala
225                 230                 235                 240
Glu Glu Asn Cys Leu Ala Ser Thr Ala Tyr Arg Ala Asp Val Arg Asp
                245                 250                 255
Tyr Asp His Arg Val Leu Leu Arg Phe Pro Gln Arg Val Lys Asn Gln
                260                 265                 270
Gly Thr Ser Asp Phe Leu Pro Ser Arg Pro Arg Tyr Ser Trp Glu Trp
                275                 280                 285
His Ser Cys His Gln His Tyr His Ser Met Asp Glu Phe Ser His Leu
            290                 295                 300
Tyr Leu Leu Asp Ala Asn Thr Gln Arg Arg Trp Ala Glu Gly His Lys
305                 310                 315                 320
Ala Ser Phe Cys Leu Glu Asp Thr Ser Cys Asp Tyr Gly Tyr His Arg
                325                 330                 335
Arg Phe Ala Cys Thr Ala His Thr Gln Gly Leu Ser Pro Gly Cys Tyr
                340                 345                 350
Asp Thr Tyr Gly Ala Asp Ile Asp Cys Gln Trp Ile Asp Ile Thr Asp
                355                 360                 365
Val Lys Pro Gly Asn Tyr Ile Leu Lys Val Ser Val Asn Pro Ser Tyr
                370                 375                 380
Leu Val Pro Glu Ser Asp Tyr Thr Asn Asn Val Val Arg Cys Asp Ile
385                 390                 395                 400
Arg Tyr Thr Gly His His Ala Tyr Ala Ser Gly Cys Thr Ile Ser Pro
                405                 410                 415
Tyr

<210> SEQ ID NO 16
<211> LENGTH: 1935
<212> TYPE: DNA
<213> ORGANISM: Homo sapiens

<400> SEQUENCE: 16
ccgcgccgct ccccgttgcc ttccaggact gagaaagggg aaagggaagg gtgccacgtc    60
cgagcagccg ccttgactgg ggaagggtct gaatcccacc cttggcattg cctggtggag   120
actgagatac ccgtgctccg ctcgcctcct tggttgaaga tttctccttc cctcacgtga   180
tttgagcccc gtttttattt tctgtgagcc acgtcctcct cgagcggggt caatctggca   240
```

```
aaaggagtga tgcgcttcgc ctggaccgtg ctcctgctcg ggcctttgca gctctgcgcg      300
ctagtgcact gcgcccctcc cgccgccggc aacagcagc cccgcgcga gccgccggcg        360
gctccgggcg cctggcgcca gcagatccaa tgggagaaca cgggcaggt gttcagcttg       420
ctgagcctgg gctcacagta ccagcctcag cgccgccggg accgggcgc cgccgtccct      480
ggtgcagcca cgcctccgc ccagcagccc cgcactccga tcctgctgat ccgcgacaac       540
cgcaccgccg cggcgcgaac gcggacggcc ggctcatctg gagtcaccgc tggccgcccc     600
aggcccaccg cccgtcactg gttccaagct ggctactcga catctagagc ccgcgaagct      660
ggcgcctcgc gcgcggagaa ccagacagcg ccgggagaag ttcctgcgct cagtaacctg     720
cggccgccca gccgcgtgga cggcatggtg ggcgacgacc cttacaaccc ctacaagtac      780
tctgacgaca accettatta caactactac gatacttatg aaaggcccag acctgggggc      840
aggtaccggc ccggatacgg cactggctac ttccagtacg gtctcccaga cctggtggcc     900
gaccectact acatccaggc gtccacgtac gtgcagaaga tgtccatgta caacctgaga     960
tgcgcggcgg aggaaaactg tctggccagt acagcataca gggcagatgt cagagattat   1020
gatcacaggg tgctgctcag atttcccca agagtgaaaa accaagggac atcagatttc    1080
ttacccagcc gaccaagata ttcctgggaa tggcacagtt gtcatcaaca ttaccacagt    1140
atggatgagt ttagccacta tgacctgctt gatgccaaca cccagaggag agtggctgaa  1200
ggccacaaag caagtttctg tcttgaagac acatcctgtg actatggcta ccacaggcga   1260
tttgcatgta ctgcacacac acaggggattg agtcctggct gttatgatac ctatggtgca   1320
gacatagact gccagtggat tgatattaca gatgtaaaac ctggaaacta tatcctaaag    1380
gtcagtgtaa accccagcta cctggttcct gaatctgact ataccaacaa tgttgtgcgc    1440
tgtgacattc gctacacagg acatcatgcg tatgcctcag gctgcacaat ttcaccgtat   1500
tagaaggcaa agcaaaactc caatggata aatcagtgcc tggtgttctg aagtgggaaa   1560
aaatagacta acttcagtag gatttatgta ttttgaaaaa gagaacagaa acaacaaaa    1620
gaattttgt ttggactgtt tcaataaca aagcacataa ctggattttg aacgcttaag     1680
tcatcattac ttgggaaatt tttaatgttt attatttaca tcactttgtg aattaacaca   1740
gtgtttcaat tctgtaatta catatttgac tctttcaaag aaatccaaat ttctcatgtt    1800
ccttttgaaa ttgtagtgca aaatggtcag tattatctaa atgaatgagc caaaatgact   1860
ttgaactgaa acttttctaa agtgctggaa ctttagtgaa acataataat aatgggttta   1920
tacgacagca acgga                                                     1935
```

<210> SEQ ID NO 17
<211> LENGTH: 417
<212> TYPE: PRT
<213> ORGANISM: Homo sapiens

<400> SEQUENCE: 17

Met Arg Phe Ala Trp Thr Val Leu Leu Gly Pro Leu Gln Leu Cys
1               5                   10                  15

Ala Leu Val His Cys Ala Pro Pro Ala Ala Gly Gln Gln Gln Pro Pro
                20                  25                  30

Arg Glu Pro Pro Ala Ala Pro Gly Ala Trp Arg Gln Gln Ile Gln Trp
            35                  40                  45

Glu Asn Asn Gly Gln Val Phe Ser Leu Leu Ser Leu Gly Ser Gln Tyr
        50                  55                  60

Gln Pro Gln Arg Arg Arg Asp Pro Gly Ala Ala Val Pro Gly Ala Ala

```
              65                  70                  75                  80
Asn Ala Ser Ala Gln Gln Pro Arg Thr Pro Ile Leu Leu Ile Arg Asp
                    85                  90                  95
Asn Arg Thr Ala Ala Ala Arg Thr Arg Thr Ala Gly Ser Ser Gly Val
                100                 105                 110
Thr Ala Gly Arg Pro Arg Pro Thr Ala Arg His Trp Phe Gln Ala Gly
                115                 120                 125
Tyr Ser Thr Ser Arg Ala Arg Glu Ala Gly Ala Ser Arg Ala Glu Asn
                130                 135                 140
Gln Thr Ala Pro Gly Glu Val Pro Ala Leu Ser Asn Leu Arg Pro Pro
145                 150                 155                 160
Ser Arg Val Asp Gly Met Val Gly Asp Pro Tyr Asn Pro Tyr Lys
                    165                 170                 175
Tyr Ser Asp Asp Asn Pro Tyr Tyr Asn Tyr Tyr Asp Thr Tyr Glu Arg
                180                 185                 190
Pro Arg Pro Gly Gly Arg Tyr Arg Pro Gly Tyr Gly Thr Gly Tyr Phe
                195                 200                 205
Gln Tyr Gly Leu Pro Asp Leu Val Ala Asp Pro Tyr Tyr Ile Gln Ala
                210                 215                 220
Ser Thr Tyr Val Gln Lys Met Ser Met Tyr Asn Leu Arg Cys Ala Ala
225                 230                 235                 240
Glu Glu Asn Cys Leu Ala Ser Thr Ala Tyr Arg Ala Asp Val Arg Asp
                    245                 250                 255
Tyr Asp His Arg Val Leu Leu Arg Phe Pro Gln Arg Val Lys Asn Gln
                260                 265                 270
Gly Thr Ser Asp Phe Leu Pro Ser Arg Pro Arg Tyr Ser Trp Glu Trp
                275                 280                 285
His Ser Cys His Gln His Tyr His Ser Met Asp Glu Phe Ser His Tyr
290                 295                 300
Asp Leu Leu Asp Ala Asn Thr Gln Arg Arg Val Ala Glu Gly His Lys
305                 310                 315                 320
Ala Ser Phe Cys Leu Glu Asp Thr Ser Cys Asp Tyr Gly Tyr His Arg
                    325                 330                 335
Arg Phe Ala Cys Thr Ala His Thr Gln Gly Leu Ser Pro Gly Cys Tyr
                340                 345                 350
Asp Thr Tyr Gly Ala Asp Ile Asp Cys Gln Trp Ile Asp Ile Thr Asp
                355                 360                 365
Val Lys Pro Gly Asn Tyr Ile Leu Lys Val Ser Val Asn Pro Ser Tyr
                370                 375                 380
Leu Val Pro Glu Ser Asp Tyr Thr Asn Asn Val Val Arg Cys Asp Ile
385                 390                 395                 400
Arg Tyr Thr Gly His His Ala Tyr Ala Ser Gly Cys Thr Ile Ser Pro
                    405                 410                 415
Tyr

<210> SEQ ID NO 18
<211> LENGTH: 1322
<212> TYPE: DNA
<213> ORGANISM: Homo sapiens

<400> SEQUENCE: 18
ggtcaatctg gcaaaaggag tgatgcgctt cgcctggacc gtgctcctgc tcgggccttt      60
gcagctctgc gcgctagtgc actgcgcccc tcccgccgcc ggccaacagc agccccgcg     120 cgagccgccg gcggctccgg gcgcctggcg ccagcagatc caatgggaga acaacgggca    180
```

```
ggtgttcagc ttgctgagcc tgggctcaca gtaccagcct cagcgccgcc gggacccggg    240
cgccgccgtc cctggtgcag ccaacgcctc cgcccagcag ccccgcactc cgatcctgct    300
gatccgcgac aaccgcaccg ccgcggcgcg aacgcggacg gccggctcat ctggagtcac    360
cgctggccgc cccaggccca ccgcccgtca ctggttccaa gctggctact cgacatctag    420
agcccgcgaa gctggcgcct cgcgcgcgga gaaccagaca gcgccgggag aagttcctgc    480
gctcagtaac ctgcggccgc ccagccgcgt ggacggcatg gtgggcgacg acccttacaa    540
cccctacaag tactctgacg acaacccctta ttacaactac tacgatactt atgaaaggcc    600
cagacctggg ggcaggtacc ggcccggata cggcactggc tacttccagt acggtctccc    660
agacctggtg gccgaccccct actacatcca ggcgtccacg tacgtgcaga agatgtccat    720
gtacaacctg agatgcgcgg cggaggaaaa ctgtctggcc agtacagcat acagggcaga    780
tgtcagagat tatgatcaca gggtgctgct cagatttccc caaagagtga aaaaccaagg    840
gacatcagat ttcttaccca gccgaccaag atattcctgg gaatggcaca gttgtcatca    900
acattaccac agtatggatg agtttagcca ctatgacctg cttgatgcca cacccagag    960 gagagtggct gaaggccaca agcaagtttt ctgtcttgaa gacacatcct gtgactatgg   1020
ctaccacagg cgatttgcat gtactgcaca cacagggga ttgagtcctg ctgttatga   1080 tacctatggt gcagacatag actgccagtg gattgatatt acagatgtaa aacctggaaa   1140
ctatatccta aaggtcagtg taaaccccag ctacctggtt cctgaatctg actataccaa   1200
caatgttgtg cgctgtgaca ttcgctacac aggacatcat gcgtatgcct caggctgcac   1260
aatttcaccg tattagaagg caaagcaaaa ctcccaatgg ataaatcagt gcctggtgtt   1320
ct                                                                  1322
```

```
<210> SEQ ID NO 19
<211> LENGTH: 417
<212> TYPE: PRT
<213> ORGANISM: Homo sapiens

<400> SEQUENCE: 19

Met Arg Phe Ala Trp Thr Val Leu Leu Leu Gly Pro Leu Gln Leu Cys
 1               5                  10                  15

Ala Leu Val His Cys Ala Pro Ala Ala Gly Gln Gln Gln Pro Pro
             20                  25                  30

Arg Glu Pro Pro Ala Ala Pro Gly Ala Trp Arg Gln Gln Ile Gln Trp
         35                  40                  45

Glu Asn Asn Gly Gln Val Phe Ser Leu Leu Ser Leu Gly Ser Gln Tyr
     50                  55                  60

Gln Pro Gln Arg Arg Arg Asp Pro Gly Ala Ala Val Pro Gly Ala Ala
 65                  70                  75                  80

Asn Ala Ser Ala Gln Gln Pro Arg Thr Pro Ile Leu Leu Ile Arg Asp
                 85                  90                  95

Asn Arg Thr Ala Ala Ala Arg Thr Arg Thr Ala Gly Ser Ser Gly Val
            100                 105                 110

Thr Ala Gly Arg Pro Arg Pro Thr Ala Arg His Trp Phe Gln Ala Gly
        115                 120                 125

Tyr Ser Thr Ser Arg Ala Arg Glu Ala Gly Ala Ser Arg Ala Glu Asn
    130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Asp Pro Tyr Asn Pro Tyr Lys
```

```
              165                 170                 175
Tyr Ser Asp Asp Asn Pro Tyr Tyr Asn Tyr Tyr Asp Tyr Glu Arg
            180                 185                 190

Pro Arg Pro Gly Gly Arg Tyr Arg Pro Gly Tyr Gly Thr Gly Tyr Phe
            195                 200                 205

Gln Tyr Gly Leu Pro Asp Leu Val Ala Asp Pro Tyr Tyr Ile Gln Ala
            210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
            260                 265                 270

Gly Thr Ser Asp Phe Leu Pro Ser Arg Pro Arg Tyr Ser Trp Glu Trp
            275                 280                 285

His Ser Cys His Gln His Tyr His Ser Met Asp Glu Phe Ser His Tyr
            290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
            340                 345                 350

Asp Thr Tyr Gly Ala Asp Ile Asp Cys Gln Trp Ile Asp Ile Thr Asp
            355                 360                 365

Val Lys Pro Gly Asn Tyr Ile Leu Lys Val Ser Val Asn Pro Ser Tyr
370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 20
<211> LENGTH: 1325
<212> TYPE: DNA
<213> ORGANISM: Homo sapiens

<400> SEQUENCE: 20
ggtcaatctg gcaaaaggag tgatgcgctt cgcctggacc gtgctcctgc tcgggccttt      60
gcagctctgc gcgctagtgc actgcgcccc tcccgccgcc ggccaacagc agccccgcg     120 cgagccgccg gcggctccgg gcgcctggcg ccagcagatc caatgggaga caacgggca     180 ggtgttcagc ttgctgagcc tgggctcaca gtaccagcct cagcgccgcc gggacccggg     240
cgccgccgtc cctggtgcag ccaacgcctc cgcccagcag ccccgcactc cgatcctgct     300
gatccgcgac aaccgcaccg ccgcggcgcg aacgcggacg gccggctcat ctggagtcac     360
cgctggccgc cccaggccca ccgcccgtca ctggttccaa gctggctact cgacatctag     420
agcccgcgaa gctggcgcct cgcgcgcgga gaaccagaca cgccgggag aagttcctgc      480 gctcagtaac ctgcggccgc ccagccgcgt ggacggcatg gtgggcgacg acccttacaa     540 ccctacaag tactctgacg acaaccctta ttacaactac tacgatactt atgaaaggcc      600
cagacctggg ggcaggtacc ggcccggata cggcactggc tacttccagt acggtctccc     660
agacctggtg gccgacccct actacatcca ggcgtccacg tacgtgcaga agatgtccat     720
```

```
gtacaacctg agatgcgcgg cggaggaaaa ctgtctggcc agtacagcat acagggcaga    780
tgtcagagat tatgatcaca gggtgctgct cagatttccc caaagagtga aaaccaagg    840 gacatcagat ttcttaccca gccgaccaag atattcctgg aatggcaca gttgtcatca    900 acattaccac agtatggatg agtttagcca ctatgacctg cttgatgcca acacccagag    960
gagagtggct gaaggccaca agcaagttt ctgtcttgaa gacacatcct gtgactatgg   1020
ctaccacagg cgatttgcat gtactgcaca cacacaggga ttgagtcctg gctgttatga   1080
tacctatggt gcagacatag actgccagtg gattgatatt acagatgtaa aacctggaaa   1140
ctatatccta aaggtcagtg taaaccccag ctacctggtt cctgaatctg actataccaa   1200
caatgttgtg cgctgtgaca ttcgctacac aggacatcat gcgtatgcct caggctgcac   1260
aatttcaccg tattagaagg caaagcaaaa ctcccaatgg ataaatcagt gcctggtgtt   1320
ctgaa                                                              1325

<210> SEQ ID NO 21
<211> LENGTH: 417
<212> TYPE: PRT
<213> ORGANISM: Homo sapiens

<400> SEQUENCE: 21

Met Arg Phe Ala Trp Thr Val Leu Leu Leu Gly Pro Leu Gln Leu Cys
1               5                   10                  15

Ala Leu Val His Cys Ala Pro Pro Ala Ala Gly Gln Gln Gln Pro Pro
                20                  25                  30

Arg Glu Pro Pro Ala Ala Pro Gly Ala Trp Arg Gln Gln Ile Gln Trp
            35                  40                  45

Glu Asn Asn Gly Gln Val Phe Ser Leu Leu Ser Leu Gly Ser Gln Tyr
        50                  55                  60

Gln Pro Gln Arg Arg Arg Asp Pro Gly Ala Ala Val Pro Gly Ala Ala
65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
            100                 105                 110

Thr Ala Gly Arg Pro Arg Pro Thr Ala Arg His Trp Phe Gln Ala Gly
        115                 120                 125

Tyr Ser Thr Ser Arg Ala Arg Glu Ala Gly Ala Ser Arg Ala Glu Asn
    130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Pro Tyr Asn Pro Tyr Lys
                165                 170                 175

Tyr Ser Asp Asp Asn Pro Tyr Tyr Asn Tyr Asp Thr Tyr Glu Arg
            180                 185                 190

Pro Arg Pro Gly Gly Arg Tyr Arg Pro Gly Tyr Gly Thr Gly Tyr Phe
        195                 200                 205

Gln Tyr Gly Leu Pro Asp Leu Val Ala Asp Pro Tyr Tyr Ile Gln Ala
    210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
```

```
                 260                 265                 270
Gly Thr Ser Asp Phe Leu Pro Ser Arg Pro Arg Tyr Ser Trp Glu Trp
            275                 280                 285

His Ser Cys His Gln His Tyr His Ser Met Asp Glu Phe Ser His Tyr
        290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
            340                 345                 350

Asp Thr Tyr Gly Ala Asp Ile Asp Cys Gln Trp Ile Asp Ile Thr Asp
        355                 360                 365

Val Lys Pro Gly Asn Tyr Ile Leu Lys Val Ser Val Asn Pro Ser Tyr
    370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 22
<211> LENGTH: 842
<212> TYPE: DNA
<213> ORGANISM: Homo sapiens

<400> SEQUENCE: 22
gttcagcttg ctgagcctgg gctcacagta ccagcctcag cgccgccggg acccgggcgc    60
cgccgtccct ggtgcagcca acgcctccgc ccagcagccc cgcactccga tcctgctgat   120
ccgcgacaac cgcaccgccg cggcgcgaac gcggacggcc ggctcatctg gagtcaccgc   180
tggccgcccc aggcccaccg cccgtcactg gttccaagct ggctactcga catctagagc   240
ccgcgaagct ggcgcctcgc gcgcggagaa ccagacagcg ccgggagaag ttcctgcgct   300
cagtaacctg cggccgccca ccgcgcgtgga cggcatggtg ggcgacgacc cttacaaccc   360
ctacaagtac tctgacgaca acccttatta caactactac gatacttatg aaaggcccag   420 acctggggc aggtaccggc ccggatacgg cactggctac ttccagtacg gtaagtaccc   480
ccaagtccgc tggaagcacc cgtgcacctg gtccccagct atgtggcttc ttctcgacgt   540
ggctgcctgg gcgcggcggg ccccggtcct cgcagatccg acccctcccc acgcgcctgc   600
agtggcagcc ctggaatcca gtgcaaaccg cgcgtctggc ccctcctgct tccttttcac   660
attgctttgc agtcccgggg gtccccagtt ctcttgctgt cctccgctcc actctgcagt   720
cccggtgggc gaagggtgag gagtaaggga cctagagggg tagggagttg gagcgggggg   780 cgccggggttg tttcactgct gcgcccgtcg cctgctgacg tttaggtctc ccagacctgg   840
tg                                                                  842

<210> SEQ ID NO 23
<211> LENGTH: 162
<212> TYPE: PRT
<213> ORGANISM: Homo sapiens

<400> SEQUENCE: 23

Phe Ser Leu Leu Ser Leu Gly Ser Gln Tyr Gln Pro Gln Arg Arg Arg
1               5                   10                  15
```

```
Asp Pro Gly Ala Ala Val Pro Gly Ala Ala Asn Ala Ser Ala Gln Gln
         20                  25                  30

Pro Arg Thr Pro Ile Leu Leu Ile Arg Asp Asn Arg Thr Ala Ala Ala
         35                  40                  45

Arg Thr Arg Thr Ala Gly Ser Ser Gly Val Thr Ala Gly Arg Pro Arg
 50                  55                  60

Pro Thr Ala Arg His Trp Phe Gln Ala Gly Tyr Ser Thr Ser Arg Ala
 65                  70                  75                  80

Arg Glu Ala Gly Ala Ser Arg Ala Glu Asn Gln Thr Ala Pro Gly Glu
                 85                  90                  95

Val Pro Ala Leu Ser Asn Leu Arg Pro Pro Ser Arg Val Asp Gly Met
            100                 105                 110

Val Gly Asp Asp Pro Tyr Asn Pro Tyr Lys Tyr Ser Asp Asp Asn Pro
            115                 120                 125

Tyr Tyr Asn Tyr Tyr Asp Thr Tyr Glu Arg Pro Arg Pro Gly Gly Arg
        130                 135                 140

Tyr Arg Pro Gly Tyr Gly Thr Gly Tyr Phe Gln Tyr Gly Leu Pro Asp
145                 150                 155                 160

Leu Val

<210> SEQ ID NO 24
<211> LENGTH: 135
<212> TYPE: PRT
<213> ORGANISM: Mus sp.

<400> SEQUENCE: 24

Met Glu Trp Ser Arg Val Phe Ile Phe Leu Leu Ser Val Thr Ala Gly
 1               5                  10                  15

Val His Ser Gln Val Gln Leu Gln Gln Ser Gly Ala Glu Leu Val Arg
             20                  25                  30

Pro Gly Thr Ser Val Lys Val Ser Cys Lys Ala Ser Gly Tyr Ala Phe
         35                  40                  45

Thr Tyr Tyr Leu Ile Glu Trp Val Lys Gln Arg Pro Gly Gln Gly Leu
 50                  55                  60

Glu Trp Ile Gly Val Ile Asn Pro Gly Ser Gly Gly Thr Asn Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Asp Asp Ser Ala Val
            100                 105                 110

Tyr Phe Cys Ala Arg Asn Trp Met Asn Phe Asp Tyr Trp Gly Gln Gly
            115                 120                 125

Thr Thr Leu Thr Val Ser Ser
        130                 135

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Leu Lys Lys Pro Gly Ala
 1               5                  10                  15

Ser Val Lys Val Ser Cys Lys Ala Ser Gly Tyr Ala Phe Thr Tyr Tyr
             20                  25                  30
```

```
Leu Ile Glu Trp Val Lys Gln Ala Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Arg Ala Thr Leu Thr Ala Asp Lys Ser Thr Ser Thr Ala Tyr
 65                  70                  75                  80

Met Glu Leu Ser Ser Leu Arg Ser Glu Asp Ser Ala Val Tyr Phe Cys
                85                  90                  95

Ala Arg Asn Trp Met Asn Phe Asp Tyr Trp Gly Gln Gly Thr Thr Val
            100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Tyr Tyr
            20                  25                  30

Leu Ile Glu Trp Val Arg Gln Ala Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Asn Trp Met Asn Phe Asp Tyr Trp Gly Gln Gly Thr Thr Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Tyr Tyr
            20                  25                  30

Leu Ile Glu Trp Val Arg Gln Ala Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Arg Ala Thr Ile Thr Ala Asp Lys Ser Thr Ser Thr Ala Tyr
 65                  70                  75                  80
```

```
Met Glu Leu Ser Ser Leu Arg Ser Glu Asp Thr Ala Val Tyr Phe Cys
                85                  90                  95

Ala Arg Asn Trp Met Asn Phe Asp Tyr Trp Gly Gln Gly Thr Thr Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Tyr Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Met Asn Phe Asp Tyr Trp Gly Gln Gly Thr Thr Val
            100                 105                 110

Thr Val Ser Ser
        115

<210> SEQ ID NO 29
<211> LENGTH: 132
<212> TYPE: PRT
<213> ORGANISM: Mus sp.

<400> SEQUENCE: 29

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Ser
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Phe Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys
    130
```

```
<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Phe Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Val Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Phe Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Val Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30
```

```
Asn Gly Asn Thr Tyr Leu Tyr Trp Tyr Leu Gln Lys Pro Gly Gln Ser
            35                  40                  45

Pro Gln Phe Leu Ile Tyr Arg Met Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                 85                  90                  95

Leu Glu Tyr Pro Tyr Thr Phe Gly Gly Gly Thr Lys Val Glu Ile Lys
            100                 105                 110

<210> SEQ ID NO 33
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Glu Trp Ser Arg Val Phe Ile Phe Leu Leu Ser Val Thr Ala Gly
 1               5                  10                  15

Val His Ser Gln Val Gln Leu Gln Gln Ser Gly Ala Glu Leu Val Arg
            20                  25                  30

Pro Gly Thr Ser Val Lys Val Ser Cys Lys Ala Ser
        35                  40

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Val Lys Gln Arg Pro Gly Gln Gly Leu Glu Trp Ile Gly
 1               5                  10

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Ala Thr Leu Thr Ala Asp Lys Ser Ser Thr Ala Tyr Met Gln
 1               5                  10                  15

Leu Ser Ser Leu Thr Ser Asp Asp Ser Ala Val Tyr Phe Cys Ala Arg
            20                  25                  30

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Gly Gln Gly Thr Thr Leu Thr Val Ser Ser
 1               5                  10
```

-continued

```
<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Val Gln Leu Val Gln Ser Gly Ala Glu Leu Lys Lys Pro Gly Ala
1               5                   10                  15

Ser Val Lys Val Ser Cys Lys Ala Ser
            20                  25

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Val Lys Gln Ala Pro Gly Gln Gly Leu Glu Trp Ile Gly
1               5                   10

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ala Thr Leu Thr Ala Asp Lys Ser Thr Ser Thr Ala Tyr Met Glu
1               5                   10                  15

Leu Ser Ser Leu Arg Ser Glu Asp Ser Ala Val Tyr Phe Cys Ala Arg
            20                  25                  30

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Gly Gln Gly Thr Thr Val Thr Val Ser Ser
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Tyr Ala Phe Thr Tyr Tyr Leu Ile Glu
1               5                   10

<210> SEQ ID NO 42
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 42

Val Ile Asn Pro Gly Ser Gly Gly Thr Asn Tyr Asn Glu Lys Phe Lys
1               5                   10                  15

Gly

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Trp Met Asn Phe Asp Tyr
1               5

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Val Arg Gln Ala Pro Gly Gln Gly Leu Glu Trp Ile Gly
1               5                   10

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Thr Leu Thr Ala Asp Lys Ser Thr Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 47
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 47

Arg Ala Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 49
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Ser
            20                  25                  30

Val Thr Pro Gly Glu Ser Val Ser Ile Ser Cys
            35                  40

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Phe Leu Gln Arg Pro Gly Gln Ser Pro Gln Phe Leu Ile Tyr
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Val Pro Asp Arg Phe Ser Gly Ser Gly Ser Gly Thr Ala Phe Thr
1               5                   10                  15

Leu Arg Ile Ser Arg Val Glu Ala Glu Asp Val Gly Val Tyr Tyr Cys
            20                  25                  30
```

```
<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Gly Gly Gly Thr Lys Leu Glu Ile Lys
1               5                   10

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Phe Leu Gln Lys Pro Gly Gln Ser Pro Gln Phe Leu Ile Tyr
1               5                   10                  15

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Val Pro Asp Arg Phe Ser Gly Ser Gly Ser Gly Thr Ala Phe Thr
1               5                   10                  15

Leu Lys Ile Ser Arg Val Glu Ala Glu Asp Val Gly Val Tyr Tyr Cys
            20                  25                  30

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Gly Gly Gly Thr Lys Val Glu Ile Lys
1               5                   10

<210> SEQ ID NO 57
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 57

Arg Ser Ser Lys Ser Leu Leu His Ser Asn Gly Asn Thr Tyr Leu Tyr
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Met Ser Asn Leu Ala Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Gln His Leu Glu Tyr Pro Tyr Thr
1               5

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Tyr Leu Gln Lys Pro Gly Gln Ser Pro Gln Phe Leu Ile Tyr
1               5                   10                  15

<210> SEQ ID NO 62
<211> LENGTH: 396
<212> TYPE: PRT
<213> ORGANISM: Homo sapiens

<400> SEQUENCE: 62

Ala Pro Pro Ala Ala Gly Gln Gln Gln Pro Pro Arg Glu Pro Pro Ala
1               5                   10                  15

Ala Pro Gly Ala Trp Arg Gln Gln Ile Gln Trp Glu Asn Asn Gly Gln
```

```
            20                  25                  30
Val Phe Ser Leu Leu Ser Leu Gly Ser Gln Tyr Gln Pro Gln Arg Arg
        35                  40                  45

Arg Asp Pro Gly Ala Ala Val Pro Gly Ala Ala Asn Ala Ser Ala Gln
    50                  55                  60

Gln Pro Arg Thr Pro Ile Leu Leu Ile Arg Asp Asn Arg Thr Ala Ala
65                  70                  75                  80

Ala Arg Thr Arg Thr Ala Gly Ser Ser Gly Val Thr Ala Gly Arg Pro
                85                  90                  95

Arg Pro Thr Ala Arg His Trp Phe Gln Ala Gly Tyr Ser Thr Ser Arg
            100                 105                 110

Ala Arg Glu Ala Gly Ala Ser Arg Ala Glu Asn Gln Thr Ala Pro Gly
        115                 120                 125

Glu Val Pro Ala Leu Ser Asn Leu Arg Pro Pro Ser Arg Val Asp Gly
    130                 135                 140

Met Val Gly Asp Asp Pro Tyr Asn Pro Tyr Lys Tyr Ser Asp Asp Asn
145                 150                 155                 160

Pro Tyr Tyr Asn Tyr Tyr Asp Thr Tyr Glu Arg Pro Arg Pro Gly Gly
                165                 170                 175

Arg Tyr Arg Pro Gly Tyr Gly Thr Gly Tyr Phe Gln Tyr Gly Leu Pro
            180                 185                 190

Asp Leu Val Ala Asp Pro Tyr Tyr Ile Gln Ala Ser Thr Tyr Val Gln
        195                 200                 205

Lys Met Ser Met Tyr Asn Leu Arg Cys Ala Ala Glu Glu Asn Cys Leu
210                 215                 220

Ala Ser Thr Ala Tyr Arg Ala Asp Val Arg Asp Tyr Asp His Arg Val
225                 230                 235                 240

Leu Leu Arg Phe Pro Gln Arg Val Lys Asn Gln Gly Thr Ser Asp Phe
                245                 250                 255

Leu Pro Ser Arg Pro Arg Tyr Ser Trp Glu Trp His Ser Cys His Gln
            260                 265                 270

His Tyr His Ser Met Asp Glu Phe Ser His Tyr Asp Leu Leu Asp Ala
        275                 280                 285

Asn Thr Gln Arg Arg Val Ala Glu Gly His Lys Ala Ser Phe Cys Leu
    290                 295                 300

Glu Asp Thr Ser Cys Asp Tyr Gly Tyr His Arg Arg Phe Ala Cys Thr
305                 310                 315                 320

Ala His Thr Gln Gly Leu Ser Pro Gly Cys Tyr Asp Thr Tyr Gly Ala
                325                 330                 335

Asp Ile Asp Cys Gln Trp Ile Asp Ile Thr Asp Val Lys Pro Gly Asn
            340                 345                 350

Tyr Ile Leu Lys Val Ser Val Asn Pro Ser Tyr Leu Val Pro Glu Ser
        355                 360                 365

Asp Tyr Thr Asn Asn Val Val Arg Cys Asp Ile Arg Tyr Thr Gly His
    370                 375                 380

His Ala Tyr Ala Ser Gly Cys Thr Ile Ser Pro Tyr
385                 390                 395

<210> SEQ ID NO 63
<211> LENGTH: 390
<212> TYPE: PRT
<213> ORGANISM: Homo sapiens

<400> SEQUENCE: 63

Gln Gln Gln Pro Pro Arg Glu Pro Pro Ala Ala Pro Gly Ala Trp Arg
```

```
               1               5              10              15
            Gln Gln Ile Gln Trp Glu Asn Asn Gly Gln Val Phe Ser Leu Leu Ser
                            20                  25                  30

Leu Gly Ser Gln Tyr Gln Pro Gln Arg Arg Arg Asp Pro Gly Ala Ala
                        35                  40                  45

Val Pro Gly Ala Ala Asn Ala Ser Ala Gln Gln Pro Arg Thr Pro Ile
             50                  55                  60

Leu Leu Ile Arg Asp Asn Arg Thr Ala Ala Arg Thr Arg Thr Ala
             65                  70                  75                  80

Gly Ser Ser Gly Val Thr Ala Gly Arg Pro Arg Pro Thr Ala Arg His
                            85                  90                  95

Trp Phe Gln Ala Gly Tyr Ser Thr Ser Arg Ala Arg Glu Ala Gly Ala
                            100                 105                 110

Ser Arg Ala Glu Asn Gln Thr Ala Pro Gly Glu Val Pro Ala Leu Ser
                        115                 120                 125

Asn Leu Arg Pro Pro Ser Arg Val Asp Gly Met Val Gly Asp Pro
             130                 135                 140

Tyr Asn Pro Tyr Lys Tyr Ser Asp Asp Asn Pro Tyr Tyr Asn Tyr Tyr
            145                 150                 155                 160

Asp Thr Tyr Glu Arg Pro Arg Pro Gly Gly Arg Tyr Arg Pro Gly Tyr
                            165                 170                 175

Gly Thr Gly Tyr Phe Gln Tyr Gly Leu Pro Asp Leu Val Ala Asp Pro
                        180                 185                 190

Tyr Tyr Ile Gln Ala Ser Thr Tyr Val Gln Lys Met Ser Met Tyr Asn
                        195                 200                 205

Leu Arg Cys Ala Ala Glu Glu Asn Cys Leu Ala Ser Thr Ala Tyr Arg
                        210                 215                 220

Ala Asp Val Arg Asp Tyr Asp His Arg Val Leu Leu Arg Phe Pro Gln
            225                 230                 235                 240

Arg Val Lys Asn Gln Gly Thr Ser Asp Phe Leu Pro Ser Arg Pro Arg
                            245                 250                 255

Tyr Ser Trp Glu Trp His Ser Cys His Gln His Tyr His Ser Met Asp
                            260                 265                 270

Glu Phe Ser His Tyr Asp Leu Leu Asp Ala Asn Thr Gln Arg Arg Val
                        275                 280                 285

Ala Glu Gly His Lys Ala Ser Phe Cys Leu Glu Asp Thr Ser Cys Asp
                        290                 295                 300

Tyr Gly Tyr His Arg Arg Phe Ala Cys Thr Ala His Thr Gln Gly Leu
            305                 310                 315                 320

Ser Pro Gly Cys Tyr Asp Thr Tyr Gly Ala Asp Ile Asp Cys Gln Trp
                            325                 330                 335

Ile Asp Ile Thr Asp Val Lys Pro Gly Asn Tyr Ile Leu Lys Val Ser
                        340                 345                 350

Val Asn Pro Ser Tyr Leu Val Pro Glu Ser Asp Tyr Thr Asn Asn Val
                        355                 360                 365

Val Arg Cys Asp Ile Arg Tyr Thr Gly His His Ala Tyr Ala Ser Gly
                        370                 375                 380

Cys Thr Ile Ser Pro Tyr
            385                 390

<210> SEQ ID NO 64
            <211> LENGTH: 1251
            <212> TYPE: DNA
            <213> ORGANISM: Homo sapiens
```

<400> SEQUENCE: 64

```
atgcgcttcg cctggaccgt gctcctgctc gggcctttgc agctctgcgc gctagtgcac      60
tgcgccctc cgccgccgg ccaacagcag ccccgcgcg agccgccggc ggctccgggc     120
gcctggcgcc agcagatcca atgggagaac aacgggcagg tgttcagctt gctgagcctg     180
ggctcacagt accagcctca gcgccgccgg gacccgggcg ccgccgtccc tggtgcagcc     240
aacgcctccg cccagcagcc ccgcactccg atcctgctga tccgcgacaa ccgcaccgcc     300
gcggcgcgaa cgcggacggc cggctcatct ggagtcaccg ctggccgccc caggcccacc     360
gcccgtcact ggttccaagc tggctactcg acatctagag cccgcgaagc tggcgcctcg     420
cgcgcggaga accagacagc gccgggagaa gttcctgcgc tcagtaacct gcggccgccc     480
agccgcgtgg acggcatggt gggcgacgac ccttacaacc cctacaagta ctctgacgac     540
aacccttatt acaactacta cgatacttat gaaaggccca gacctggggg caggtaccgg     600
cccggatacg gcactggcta cttccagtac ggtctcccag acctggtggc cgaccccta    660
tacatccagg cgtccacgta cgtgcagaag atgtccatgt acaacctgag atgcgcggcg     720
gaggaaaact gtctggccag tacagcatac agggcagatg tcagagatta tgatcacagg     780
gtgctgctca gatttcccca aagagtgaaa aaccaaggga catcagattt cttacccagc     840
cgaccaagat attcctggga atggcacagt tgtcatcaac attaccacag tatggatgag     900
tttagccact atgacctgct tgatgccaac acccagagga gagtggctga aggccacaaa     960
gcaagtttct gtcttgaaga cacatcctgt gactatggct accacaggcg atttgcatgt    1020
actgcacaca cacagggatt gagtcctggc tgttatgata cctatggtgc agacatagac    1080
tgccagtgga ttgatattac agatgtaaaa cctggaaact atatcctaaa ggtcagtgta    1140
aaccccagct acctggttcc tgaatctgac tataccaaca atgttgtgcg ctgtgacatt    1200
cgctacacag acatcatgc gtatgcctca ggctgcacaa tttcaccgta t             1251
```

<210> SEQ ID NO 65
<211> LENGTH: 417
<212> TYPE: PRT
<213> ORGANISM: Homo sapiens

<400> SEQUENCE: 65

```
Met Arg Phe Ala Trp Thr Val Leu Leu Gly Pro Leu Gln Leu Cys
 1               5                   10                  15

Ala Leu Val His Cys Ala Pro Pro Ala Ala Gly Gln Gln Gln Pro Pro
                20                  25                  30

Arg Glu Pro Pro Ala Ala Pro Gly Ala Trp Arg Gln Gln Ile Gln Trp
            35                  40                  45

Glu Asn Asn Gly Gln Val Phe Ser Leu Leu Ser Leu Gly Ser Gln Tyr
        50                  55                  60

Gln Pro Gln Arg Arg Arg Asp Pro Gly Ala Ala Val Pro Gly Ala Ala
    65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
            100                 105                 110

Thr Ala Gly Arg Pro Arg Pro Thr Ala Arg His Trp Phe Gln Ala Gly
            115                 120                 125

Tyr Ser Thr Ser Arg Ala Arg Glu Ala Gly Ala Ser Arg Ala Glu Asn
        130                 135                 140

Gln Thr Ala Pro Gly Glu Val Pro Ala Leu Ser Asn Leu Arg Pro Pro
```

```
                145                 150                 155                 160
Ser Arg Val Asp Gly Met Val Gly Asp Pro Tyr Asn Pro Tyr Lys
                    165                 170                 175

Tyr Ser Asp Asp Asn Pro Tyr Tyr Asn Tyr Tyr Asp Thr Tyr Glu Arg
                180                 185                 190

Pro Arg Pro Gly Gly Arg Tyr Arg Pro Gly Tyr Gly Thr Gly Tyr Phe
                195                 200                 205

Gln Tyr Gly Leu Pro Asp Leu Val Ala Asp Pro Tyr Tyr Ile Gln Ala
                210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
                260                 265                 270

Gly Thr Ser Asp Phe Leu Pro Ser Arg Pro Arg Tyr Ser Trp Glu Trp
                275                 280                 285

His Ser Cys His Gln His Tyr His Ser Met Asp Glu Phe Ser His Tyr
                290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
                340                 345                 350

Asp Thr Tyr Gly Ala Asp Ile Asp Cys Gln Trp Ile Asp Ile Thr Asp
                355                 360                 365

Val Lys Pro Gly Asn Tyr Ile Leu Lys Val Ser Val Asn Pro Ser Tyr
                370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 66
<211> LENGTH: 11
<212> TYPE: PRT
<213> ORGANISM: Artificial Sequence
<220> FEATURE:
<223> OTHER INFORMATION: Synthetic peptide

<400> SEQUENCE: 66

Trp Glu Trp His Ser Cys His Gln His Tyr His
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic peptide

<400> SEQUENCE: 67

Trp Ile Trp His Asp Cys His Arg His Tyr His
1               5                   10

<210> SEQ ID NO 68
```

```
-continued

<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 14
<223> OTHER INFORMATION: Xaa = any amino acid

<400> SEQUENCE: 68

Asp Ile Asp Cys Gln Trp Trp Ile Asp Ile Thr Asp Val Xaa Pro Gly
1               5                   10                  15

Asn Tyr

<210> SEQ ID NO 69
<211> LENGTH: 18
<212> TYPE: PRT
<213> ORGANISM: Artificial Sequence
<220> FEATURE:
<223> OTHER INFORMATION: Synthetic peptide

<400> SEQUENCE: 69

Asp Ile Asp Cys Gln Trp Val Asp Ile Thr Asp Val Pro Pro Pro Gly
1               5                   10                  15

Asp Tyr

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide

<400> SEQUENCE: 70

Asn Trp Met Asn Phe Asp Tyr
1               5
```